US011077210B2

(12) United States Patent
Frangioni et al.

(10) Patent No.: US 11,077,210 B2
(45) Date of Patent: Aug. 3, 2021

(54) NEAR-INFRARED FLUORESCENT CONTRAST BIOIMAGING AGENTS AND METHODS OF USE THEREOF

(71) Applicants: Beth Israel Deaconess Medical Center, Boston, MA (US); Georgia State University Research Foundation Inc.

(72) Inventors: John V. Frangioni, Wayland, MA (US); Hak Soo Choi, Needham, MA (US); Maged M. Henary, Atlanta, GA (US)

(73) Assignees: Beth Israel Deaconess Medical Center, Boston, MA (US); Georgia State University Research Foundation Inc., Atlanta, GA (US)

( * ) Notice: Subject to any disclaimer, the term of this patent is extended or adjusted under 35 U.S.C. 154(b) by 736 days.

(21) Appl. No.: 15/033,337

(22) PCT Filed: Oct. 30, 2014

(86) PCT No.: PCT/US2014/063097
§ 371 (c)(1),
(2) Date: Apr. 29, 2016

(87) PCT Pub. No.: WO2015/066290
PCT Pub. Date: May 7, 2015

(65) Prior Publication Data
US 2016/0263249 A1   Sep. 15, 2016

Related U.S. Application Data

(60) Provisional application No. 61/929,916, filed on Jan. 21, 2014, provisional application No. 61/898,424, filed on Oct. 31, 2013.

(51) Int. Cl.
| | |
|---|---|
| *A61B 5/00* | (2006.01) |
| *A61B 8/00* | (2006.01) |
| *A61B 10/00* | (2006.01) |
| *A61K 49/00* | (2006.01) |
| *C09B 23/08* | (2006.01) |
| *C09B 23/01* | (2006.01) |
| *C09B 69/00* | (2006.01) |
| *C09B 19/00* | (2006.01) |
| *C09B 17/00* | (2006.01) |
| *C09B 23/04* | (2006.01) |
| *C09B 57/10* | (2006.01) |
| *G01N 33/483* | (2006.01) |

(52) U.S. Cl.
CPC ........ *A61K 49/0021* (2013.01); *A61K 49/003* (2013.01); *A61K 49/0028* (2013.01); *A61K 49/0032* (2013.01); *A61K 49/0041* (2013.01); *C09B 17/00* (2013.01); *C09B 19/00* (2013.01); *C09B 23/0016* (2013.01); *C09B 23/0025* (2013.01); *C09B 23/0033* (2013.01); *C09B 23/0041* (2013.01); *C09B 23/0066* (2013.01); *C09B 23/04* (2013.01); *C09B 23/083* (2013.01); *C09B 23/086* (2013.01); *C09B 57/10* (2013.01); *C09B 69/008* (2013.01); *G01N 33/4833* (2013.01); *A61K 49/0017* (2013.01)

(58) Field of Classification Search
None
See application file for complete search history.

(56) References Cited

U.S. PATENT DOCUMENTS

| | | | |
|---|---|---|---|
| 6,083,485 A | 7/2000 | Licha et al. | |
| 6,258,340 B1 | 7/2001 | Licha et al. | |
| 6,440,389 B1 * | 8/2002 | Rabito | A61K 49/0028 424/9.6 |
| 6,913,743 B2 | 7/2005 | Licha et al. | |
| 6,926,885 B2 | 8/2005 | Licha et al. | |
| 7,025,949 B2 | 4/2006 | Licha et al. | |
| 7,445,767 B2 | 11/2008 | Licha et al. | |
| 7,582,483 B2 | 9/2009 | Mizutani et al. | |
| 7,655,217 B2 | 2/2010 | Licha et al. | |
| 7,682,603 B2 * | 3/2010 | Hammer | A61K 49/0021 424/9.61 |
| 8,173,819 B2 | 5/2012 | Rajopadhye et al. | |
| 8,268,014 B2 | 9/2012 | Frohling | |
| 8,460,639 B2 | 6/2013 | Nomoto et al. | |
| 2001/0055567 A1 | 12/2001 | Licha et al. | |
| 2003/0026762 A1 | 2/2003 | Malmros et al. | |
| 2003/0026763 A1 | 2/2003 | Licha et al. | |
| 2003/0170179 A1 | 9/2003 | Licha et al. | |
| 2004/0028611 A1 | 2/2004 | Frangioni | |

(Continued)

FOREIGN PATENT DOCUMENTS

| | | |
|---|---|---|
| JP | H5-150395 A | 6/1993 |
| JP | 2000-95758 A | 4/2000 |

(Continued)

OTHER PUBLICATIONS

Ghanadzadeh et al. (Spectrochimica Acta Part A 2009, 73, 324-329).*
Dao et al. (Australas. Phys. Eng. Sci. Med. 2004, 27, 224-229).*
Sloviter (Cancer Res. 1949, 9, 677-680).*
Ciba-Geigy AG, "Use of dyes for shading during optical brightening of polyester and polyacrylonitrile substrates", Research Disclosure, 1982, vol. 216, Article No. 21611, pp. 107-109.
Yuan, L. et al. "A unique class of near-infrared functional fluorescent dyes with carboxylic-acid-modulated fluorescence on/off switching rational design, synthesis, optical properties, theoretical calculations, and applications for fluorescence imaging in living animals", Journal of the American Chemical Society, 2012, vol. 134, No. 2, pp. 1200-1211.

(Continued)

*Primary Examiner* — Michael G. Hartley
*Assistant Examiner* — Melissa J Perreira
(74) *Attorney, Agent, or Firm* — Locke Lord LLP; Nicholas J. DiCeglie, Jr.

(57) ABSTRACT

The instant invention provides near-infrared fluorescent biological contrast agents and methods of using them.

7 Claims, 20 Drawing Sheets

(56) References Cited

U.S. PATENT DOCUMENTS

| | | | |
|---|---|---|---|
| 2004/0029837 A1* | 2/2004 | Fries | C07D 265/34 514/100 |
| 2004/0062713 A1 | 4/2004 | Matsuo et al. | |
| 2005/0106106 A1 | 5/2005 | Licha et al. | |
| 2005/0169844 A1 | 8/2005 | Licha et al. | |
| 2006/0040400 A1 | 2/2006 | Mizutani et al. | |
| 2006/0165598 A1 | 7/2006 | Licha et al. | |
| 2006/0165599 A1 | 7/2006 | Licha et al. | |
| 2006/0275209 A1 | 12/2006 | Schweiger et al. | |
| 2007/0292883 A1* | 12/2007 | Ossovskaya | C12Q 1/6886 435/6.14 |
| 2008/0308744 A1 | 12/2008 | Frangioni et al. | |
| 2008/0318336 A1 | 12/2008 | Scherninski et al. | |
| 2009/0269277 A1* | 10/2009 | Chang | A61K 47/48746 424/1.49 |
| 2010/0035871 A1* | 2/2010 | Stack | C07D 265/36 514/230.5 |
| 2010/0129293 A1 | 5/2010 | Licha et al. | |
| 2010/0323389 A1 | 12/2010 | Xu et al. | |
| 2012/0017931 A1 | 1/2012 | Frohling | |
| 2012/0045851 A1 | 2/2012 | Scherninski et al. | |
| 2013/0030282 A1 | 1/2013 | Margel et al. | |
| 2014/0063097 A1 | 3/2014 | Liu et al. | |
| 2015/0209451 A1 | 7/2015 | Frangioni et al. | |
| 2017/0290927 A1 | 10/2017 | Frangioni et al. | |

FOREIGN PATENT DOCUMENTS

| | | |
|---|---|---|
| JP | 2005-524072 A | 8/2005 |
| JP | 2007-508282 A | 4/2007 |
| JP | 2009-507035 A | 2/2009 |
| JP | 2010-169677 A | 8/2010 |
| JP | 2011-503067 A | 1/2011 |
| JP | 2012-524153 A | 10/2012 |
| JP | 2013-523725 A | 6/2013 |
| JP | 2013-199477 A | 10/2013 |
| WO | 2005/082423 A2 | 9/2005 |
| WO | 2007/017602 A2 | 2/2007 |
| WO | 2009/061473 A2 | 5/2009 |
| WO | 2010/091243 A1 | 8/2010 |
| WO | 2010/121163 A2 | 10/2010 |
| WO | 2012/063028 A1 | 5/2012 |

OTHER PUBLICATIONS

James, N.S. et al., "Evaluation of polymethine dyes as potential probes for near infrared fluorescence imaging of tumors: Part 1", Theranostics, Aug. 2013, vol. 3, No. 9, pp. 692-702.

Quek, C.-H. et al. "Near-infrared fluorescent nanoprobes for in vivo optical imaging", Nanomaterials, 2012, vol. 2, No. 2, pp. 92-112.

Ashitate, Y., et al. "Simultaneous mapping of pan and sentinel lymph nodes for real-time image guided surgery", Theranostics, Apr. 2014, vol. 4, No. 7, pp. 693-700.

Amiot, C. L. et al., "Near-infrared fluorescent materials for sensing of biological targets", Sensors, 2008, vol. 8, No. 5, pp. 3082-3105.

Tibbe, A. G. J. et al., "Imaging technique implemented in CellTracks system," Cytometry, 2002, vol. 47, No. 4, pp. 248-255.

International Search Report issued in PCT/US2014/063104, dated Feb. 26, 2015.

International Search Report issued in PCT/US2014/063097, dated Apr. 10, 2015.

Chemical Physics Letters, Mar. 1996, vol. 250 pp. 261-265.

Gibbs "Near infrared fluorescence for image-guided surgery" Quant Imaging Med Surg, Jan. 1, 2012, pp. 177-187.

Journal of Photopolymer Science and Technology, 2000, vol. 13, No. 2, pp. 183-186.

Proceedings of SPIE, 2011, vol. 8114, pp. 81140 T-1 to 81140 T-9.

Sano, K. "Short PEG-linkers improve the performance of targeted, activatable monoclonal antibody-indocyanine green optical imaging probes" Bioconjugate Chemistry, 2013 24(5), pp. 811-816.

European Journal of Medicinal Chemistry, 2012, vol. 54, pp. 647-659.

Office Action issued in Japanese Patent Application No. JP 2016-552234, dated Oct. 21, 2020.

* cited by examiner

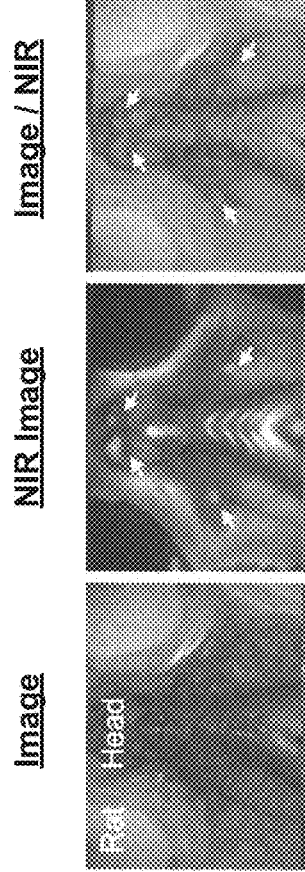
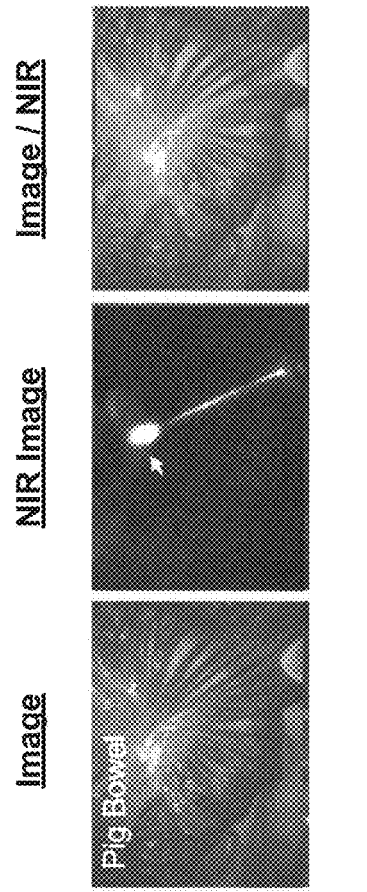
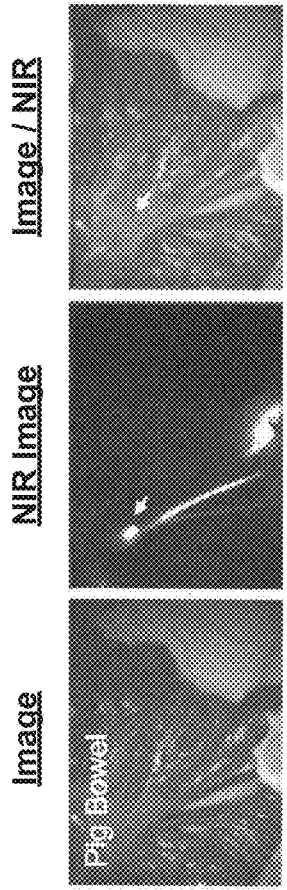
Fig. 4
Fig. 5
Fig. 6

| Target | Name | Chemical Structure | Image | NIR Image | Image / NIR |
|---|---|---|---|---|---|
| Cartilage 800 | LN50 |  | | |  |

| Target | Name | Chemical Structure | Image | NIR Image | Image / NIR |
|---|---|---|---|---|---|
| Cartilage 700 | SP56 |  | | |  |

| Target | Name | Chemical Structure | Image | NIR Image | Image / NIR |
|---|---|---|---|---|---|
| Neuro-endocrine 800 | AL20 |  | | |  |

| Target | Name | Chemical Structure | Image | NIR Image | Image / NIR |
|---|---|---|---|---|---|
| Neuro-endocrine 700 | ESS61 | 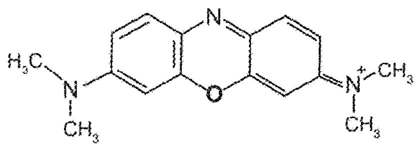 | Insulinoma mouse | | |

Fig. 10

| Target | Name | Chemical Structure | Image | NIR Image | Image / NIR |
|---|---|---|---|---|---|
| Bone 800 | P800SO3 | 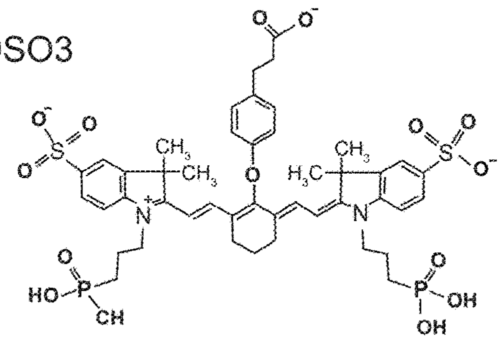 | Pig Spine | | |

Fig. 11

| Target | Name | Chemical Structure | Image | NIR Image | Image / NIR |
|---|---|---|---|---|---|
| Bone 700 | P700SO3 | 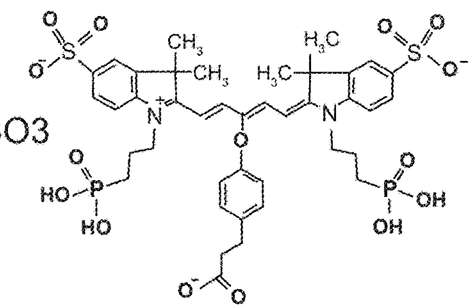 | Pig Spine | | |

Fig. 12

| Target | Name | Chemical Structure | Image | NIR Image | Image / NIR |
|---|---|---|---|---|---|
| Salivary Glands 800 | ZK211 | 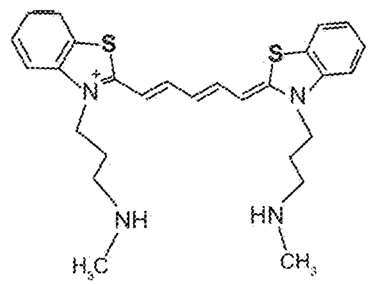 | |  | |

| Target | Name | Chemical Structure | Image | NIR Image | Image / NIR |
|---|---|---|---|---|---|
| Salivary Glands 700 | NRB1 | 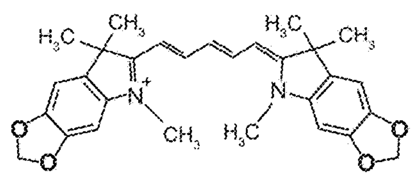 | |  | |

| Target | Name | Chemical Structure | Image | NIR Image | Image / NIR |
|---|---|---|---|---|---|
| White Adipose 800 | AH34 | 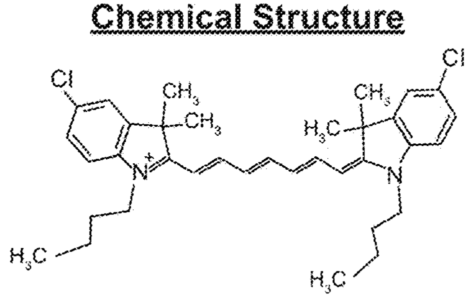 | |  | |

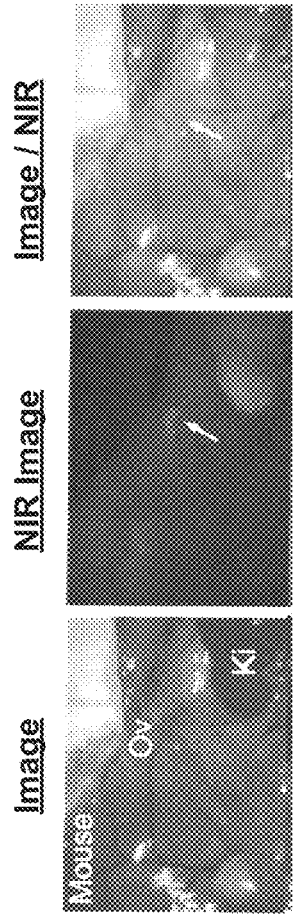
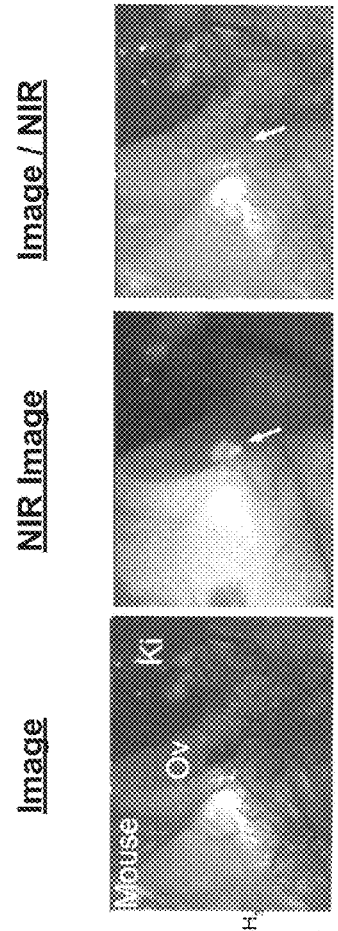
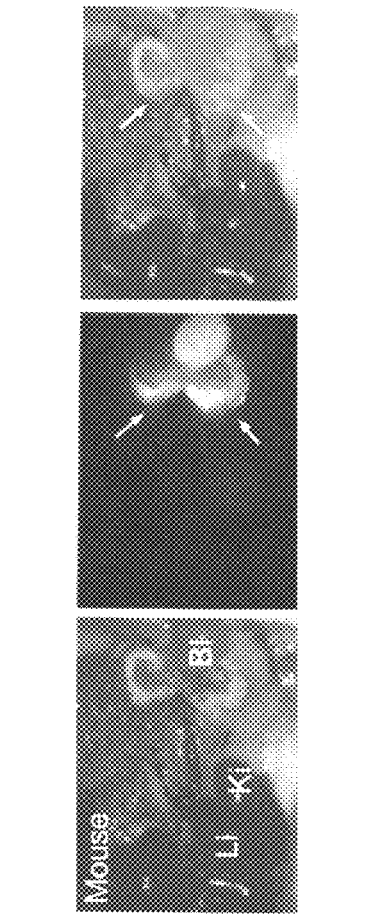
| Target | Name | Chemical Structure | Mouse Image | NIR Image | Image / NIR |
|---|---|---|---|---|---|
| Ovaries 800 | AL27 | 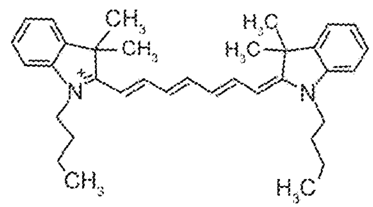 | | | |
Fig. 25
| Target | Name | Chemical Structure | Mouse Image | NIR Image | Image / NIR |
|---|---|---|---|---|---|
| Ovaries 700 | PS62 | 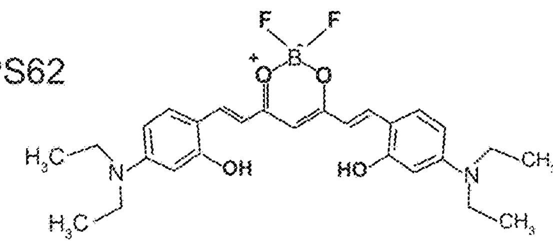 | | | |
Fig. 26
| Target | Name | Chemical Structure | Mouse Image | NIR Image | Image / NIR |
|---|---|---|---|---|---|
| Seminal Vesicles 800 | CNN2 | 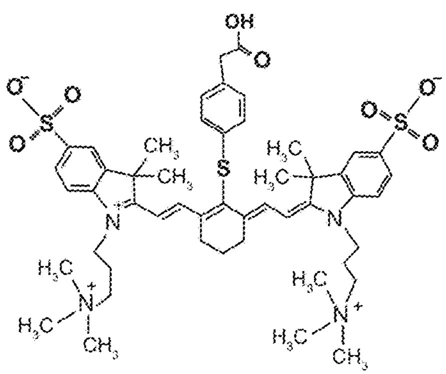 | | | |
Fig. 27

| Target | Name | Chemical Structure | Image | NIR Image | Image / NIR |
|---|---|---|---|---|---|
| Bile Ducts 800 | ZK198 | 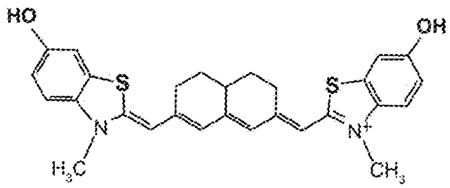 | Pig, GB, Li, Du, St | | |

Fig. 37

| Target | Name | Chemical Structure | Image | NIR Image | Image / NIR |
|---|---|---|---|---|---|
| Bile Ducts 700 | A106 | 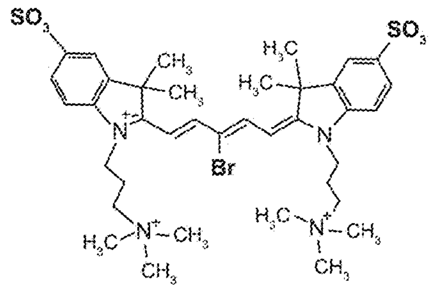 | Pig, Li, GB, Du | | |

Fig. 38

| Target | Name | Chemical Structure | Image | NIR Image | Image / NIR |
|---|---|---|---|---|---|
| Peyer's Patches 800 | AL30 | 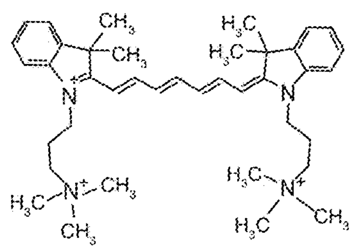 | Rat, Ln | | |

Fig. 39

| Target | Name | Chemical Structure | Image | NiR Image | Image / NiR |
|---|---|---|---|---|---|
| Brain Vasculature Agents 700 | ZK214 | 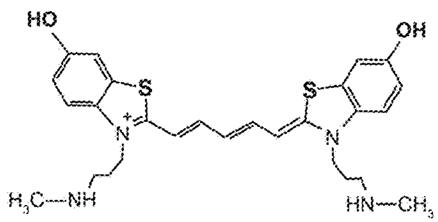 | Mouse Brain Dorsal | | |

| Target | Name | Chemical Structure | Image | NiR Image | Image / NiR |
|---|---|---|---|---|---|
| Brain Grey Matter 800 | ZK189 | 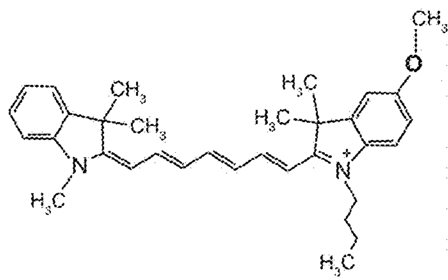 | Mouse Brain Dorsal | | |

| Target | Name | Chemical Structure | Image | NiR Image | Image / NiR |
|---|---|---|---|---|---|
| Brain Grey Matter 700 | WuA96 | 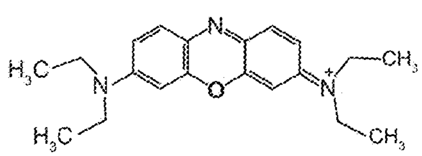 | Mouse Brain Dorsal | | |

| Target | Name | Chemical Structure | Image | NIR Image | Image / NIR |
|---|---|---|---|---|---|
| Choroid Plexus 800 | ZK208 | 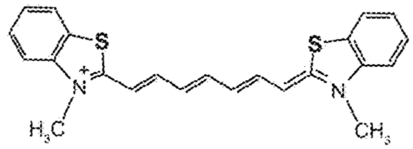 |  |  |  |

| Target | Name | Chemical Structure | Image | NIR Image | Image / NIR |
|---|---|---|---|---|---|
| Choroid Plexus 700 | SP28 | 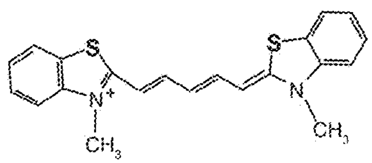 |  |  |  |

| Target | Name | Chemical Structure | Image | NIR Image | Image / NIR |
|---|---|---|---|---|---|
| CSF 800 | AL20 | 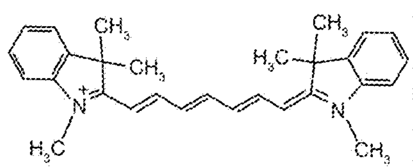 |  |  | |

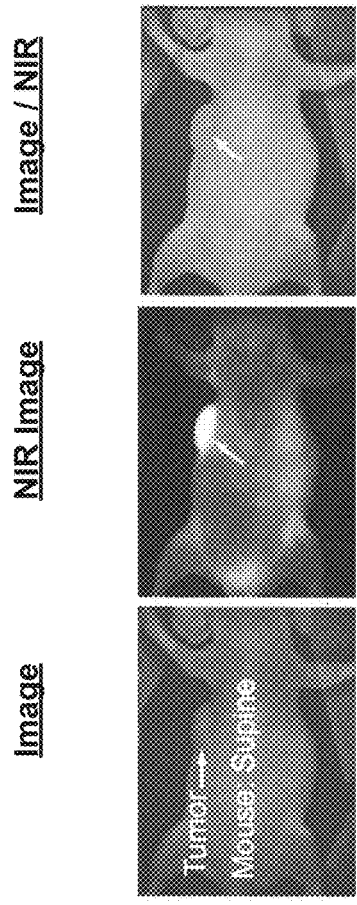
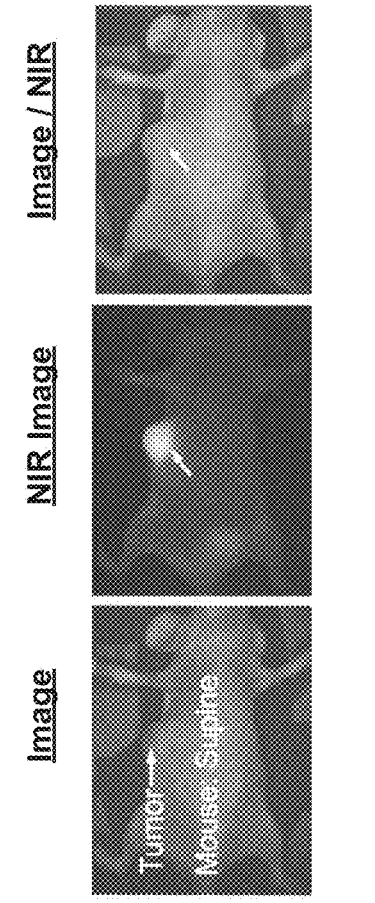
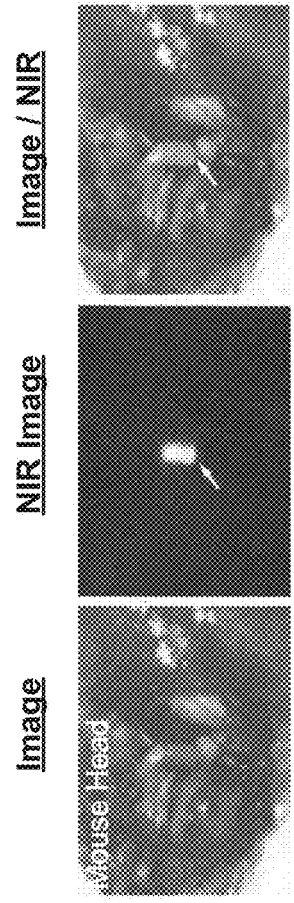
Fig. 49
| Target | Name | Chemical Structure |
|---|---|---|
| PEGylated Agents 800 | PEG60k-ZW800-1 | 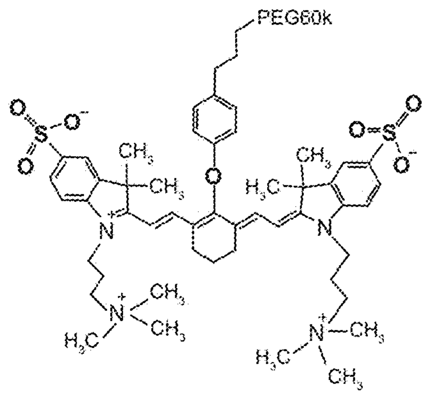 |
Fig. 50
| Target | Name | Chemical Structure |
|---|---|---|
| PEGylated Agents 700 | PEG60k-LN15 | 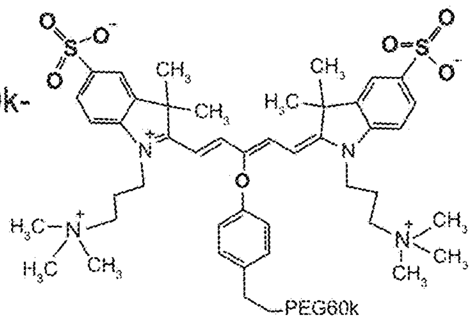 |
Fig. 51
| Target | Name | Chemical Structure |
|---|---|---|
| Pituitary Gland 800 | AL22 | 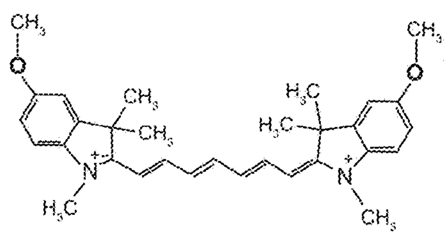 |

| Target | Name | Chemical Structure | Image | NIR Image | Image / NIR |
|---|---|---|---|---|---|
| Pituitary Gland 700 | SP60 | 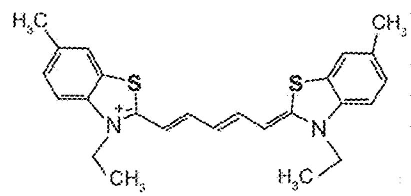 |  |  |  |

| Target | Name | Chemical Structure | Image | NIR Image | Image / NIR |
|---|---|---|---|---|---|
| Stem Cell Tracking 800 | PS126 | 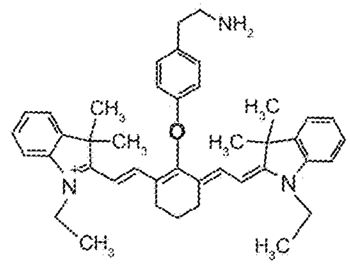 |  |  |  |

| Target | Name | Chemical Structure | Image | NIR Image | Image / NIR |
|---|---|---|---|---|---|
| Stem Cell Tracking 700 | PS127 | 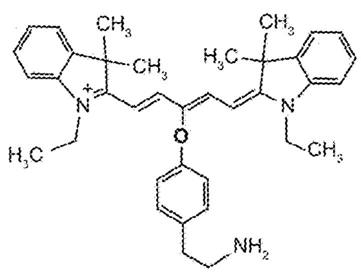 | | | |

| Target | Name | Chemical Structure | Image | NIR Image | Image / NIR |
|---|---|---|---|---|---|
| Intravital Microscopy 800 | Dex70k-ZW800-1 | 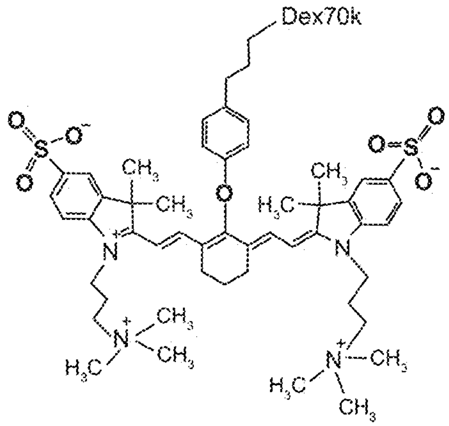 | Vasculature | Tumor | |

Fig. 57

| Target | Name | Chemical Structure | Image | NIR Image | Image / NIR |
|---|---|---|---|---|---|
| Intravital Microscopy 700 | Dex70k-LN15 | 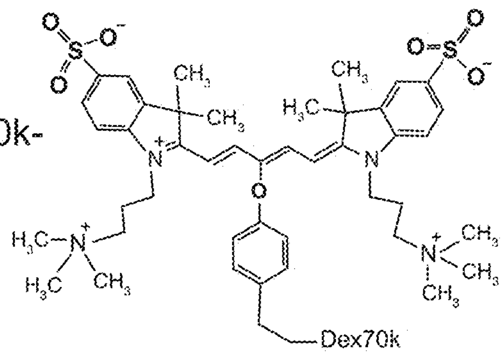 | Vasculature | Tumor | |

Fig. 58

NEAR-INFRARED FLUORESCENT CONTRAST BIOIMAGING AGENTS AND METHODS OF USE THEREOF

RELATED APPLICATIONS

This application is a 35 U.S.C. § 371 National Phase Application of International PCT Patent Application no. PCT/US2014/063097, filed Oct. 30, 2014 which application claims the benefit of and priority to U.S. Provisional Patent Applications No. 61/929,916 filed Oct. 31, 2013 and 61/929,916 filed Jan. 21, 2014, the contents of which are incorporated herein by reference in their entirety.

GOVERNMENT SUPPORT

This invention was made with government support under CA115296, EB010022, and EB011523 awarded by NIH. The government has certain rights in the invention.

BACKGROUND

Near infrared (NIR) fluorescence has potential importance in the medical field, particularly in in vitro diagnostics, in vivo diagnostics, and image-guided surgery. However, the availability of suitable fluorophores as imaging agents has been a primary hindrance. To be viable, ideal NIR fluorophores should have good optical properties as well as superior physicochemical properties with respect to solubility, biodistribution, targeting, and clearance. Most current fluorophores contemplated for use as imaging agents fail in connection with their physicochemical properties. For example, known fluorophores suffer from failure to adequately accumulate at the target to be imaged (i.e., low signal), resulting in a low signal-to-background ratio (SBR), or exhibit significant non-specific background uptake in normal tissues (i.e., high background), also resulting in a low SBR.

Accordingly, there is a current need for new and improved NIR fluorescent imaging agents, particularly those that equilibrate rapidly between the intravascular and extravascular spaces, target various cells, tissues, or organs with high sensitivity and specificity, and are eliminated efficiently from the body if not targeted. The imaging agents of the invention are directed toward these and other needs.

SUMMARY

The present invention is directed, at least in part, to near-infrared fluorescent contrast agents and methods of using them.

In one aspect, the near-infrared fluorescent contrast is a compound of Formula (I):

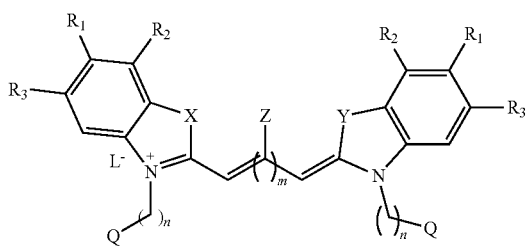

(Formula I)

Wherein for Formula (I)
Each $R_1$ is independently H, OR', halogen, sulfonato, substituted or unsubstituted amino, C(O)NH— $C_1$-$C_6$ alkyl, $C_1$-$C_6$ alkyl, $C_1$-$C_6$ alkoxy or phenyl;
Each $R_2$ is independently H, OR', halogen, sulfonato, substituted or unsubstituted amino, C(O)NH— $C_1$-$C_6$ alkyl, $C_1$-$C_6$ alkyl, $C_1$-$C_6$ alkoxy or phenyl;
Or $R^1$ and $R^2$ can be taken together with the carbon atoms to which they are attached to form a 5-6 membered aryl or heteroaryl ring, optionally substituted with halogen, alkyl, alkoxy, hydroxyl, —$SO_2OH$, or —$CO_2H$;
Each $R_3$ is independently H, OR', halogen, sulfonato, substituted or unsubstituted amino, C(O)NH— $C_1$-$C_6$ alkyl, $C_1$-$C_6$ alkyl, $C_1$-$C_6$ alkoxy or phenyl;
Q is H, alkyl optionally substituted with alkoxy, cycloalkyl, heterocycloalkyl, aryl, arylalkyl, heteroaryl, heteroarylalkyl, —$N^+(alkyl)_3$, —OCO-alkyl, —$SO_2OH$, phenyl, sulfonato, phosphates, KUE, GPI, —or —$NR_3R_4R_5$, wherein $R_3$, $R_4$ and $R_5$ are each independently for each occurrence H or $C_1$-$C_4$ alkyl, or $R_4$ and $R_5$, taken together with the nitrogen atom to which they are attached, form a heterocyclic ring;
X and Y are each independently O, S, Se, C(R")$_2$, NR'";
Z is H, halogen, CN, $R_6$, $OR_6$, $SR_6$, $NHR_6$ or $CH_2R_6$, in which $R_6$ is optionally substituted $C_1$-$C_6$ alkyl, optionally substituted aryl, or optionally substituted heteroaryl, alkyl-$N_3$, aryl-$N_3$, aryl-halogen;
Each R' is independently H, alkyl or aryl;
Each R" is independently H or alkyl;
Each R'" is independently H, akyl, akyl-$SO_3H$, or akyl-COOH;
m and n are independently an integer from 0-3; and
L is an anion;
or a salt, solvate, hydrate, polymorph, prodrug, or stereoisomer thereof.

In another aspect, the near-infrared fluorescent contrast is a compound of Formula (II):

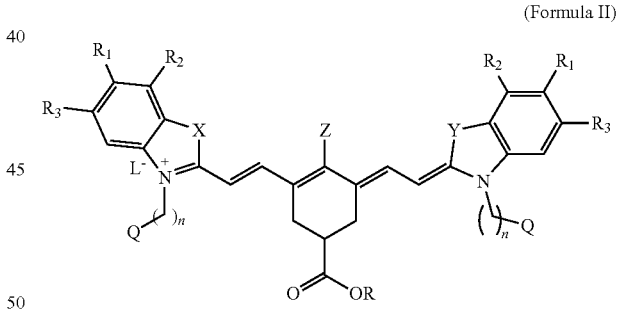

(Formula II)

Wherein for Formula (II)
Each $R_1$ is independently H, OR', halogen, sulfonato, substituted or unsubstituted amino, C(O)NH— $C_1$-$C_6$ alkyl, $C_1$-$C_6$ alkyl, $C_1$-$C_6$ alkoxy or phenyl;
Each $R_2$ is independently H, OR', halogen, sulfonato, substituted or unsubstituted amino, C(O)NH— $C_1$-$C_6$ alkyl, $C_1$-$C_6$ alkyl, $C_1$-$C_6$ alkoxy or phenyl;
Or $R^1$ and $R^2$ can be taken together with the carbon atoms to which they are attached to form a 5-6 membered aryl or heteroaryl ring, optionally substituted with halogen, alkyl, alkoxy, hydroxyl, —$SO_2OH$, or —$CO_2H$;
Each $R_3$ is independently H, OR', halogen, sulfonato, substituted or unsubstituted amino, C(O)NH— $C_1$-$C_6$ alkyl, $C_1$-$C_6$ alkyl, $C_1$-$C_6$ alkoxy or phenyl;
Q is H, alkyl optionally substituted with alkoxy, cycloalkyl, heterocycloalkyl, aryl, arylalkyl, heteroaryl, heteroarylalkyl, —N⁺(alkyl)₃, —OCO-alkyl, —SO₂OH, phenyl, sulfonato, phosphates, KUE, GPI, — or —NR₃R₄R₅, wherein R₃, R₄ and R₅ are each independently for each occurrence H or C₁-C₄ alkyl, or R₄ and R₅, taken together with the nitrogen atom to which they are attached, form a heterocyclic ring;
X and Y are each independently O, S, Se, C(R")₂, NR;
Z is H, halogen, CN, R₆, OR₆, SR₆, NHR₆ or CH₂R₆, in which R₆ is optionally substituted C₁-C₆ alkyl, optionally substituted aryl, or optionally substituted heteroaryl, alkyl-N₃, aryl-N₃, aryl-halogen;
R is independently H, OR"" (where R=H, akyl, or aryl, NH₂, NHR, alkyl NH₂, alkyl COOH),
L is an anion;
Each R' is independently H, alkyl or aryl;
Each R" is independently H or alkyl;
Each R'" is independently H, akyl, akyl-SO₃H, or akyl-COOH;
Each R"" is independently H, akyl, or aryl, NH₂, NHR, alkyl-NH₂, or alkyl-COOH; m and n are independently an integer from 0-3; and
L is an anion;
or a salt, solvate, hydrate, polymorph, prodrug, or stereoisomer thereof.

In still another aspect, the near-infrared fluorescent contrast is a compound of Formula (III):

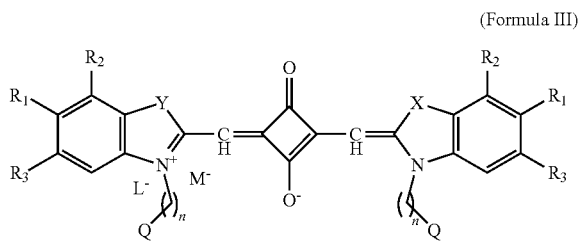

(Formula III)

wherein For Formula (III)
Each R₁ is independently H, OR', halogen, sulfonato, substituted or unsubstituted amino, C(O)NH— C₁-C₆ alkyl, C₁-C₆ alkyl, C₁-C₆ alkoxy or phenyl;
Each R₂ is independently H, OR', halogen, sulfonato, substituted or unsubstituted amino, C(O)NH— C₁-C₆ alkyl, C₁-C₆ alkyl, C₁-C₆ alkoxy or phenyl;
Or R¹ and R² can be taken together with the carbon atoms to which they are attached to form a 5-6 membered aryl or heteroaryl ring, optionally substituted with halogen, alkyl, alkoxy, hydroxyl, —SO₂OH, or —CO₂H;
Each R₃ is independently H, OR', halogen, sulfonato, substituted or unsubstituted amino, C(O)NH— C₁-C₆ alkyl, C₁-C₆ alkyl, C₁-C₆ alkoxy or phenyl;
Q is H, alkyl optionally substituted with alkoxy, cycloalkyl, heterocycloalkyl, aryl, arylalkyl, heteroaryl, heteroarylalkyl, —N⁺(alkyl)₃, —OCO-alkyl, —SO₂OH, phenyl, sulfonato, phosphates, KUE, GPI, — or —NR₃R₄R₅, wherein R₃, R₄ and R₅ are each independently for each occurrence H or C₁-C₄ alkyl, or R₄ and R₅, taken together with the nitrogen atom to which they are attached, form a heterocyclic ring;
X and Y are each independently O, S, Se, C(R")₂, NR'"; Z is H, halogen, CN, R₆, OR₆, SR₆, NHR₆ or CH₂R₆, in which R₆ is optionally substituted C₁-C₆ alkyl, optionally substituted aryl, or optionally substituted heteroaryl, alkyl-N₃ (for click chemistry), aryl-N₃ (for click chemistry), aryl-halogen (only for palladium catalyzed reactions);
Each R' is independently H, alkyl or aryl;
Each R" is independently H or alkyl;
Each R'" is independently H, akyl, akyl-SO₃H, or akyl-COOH;
m and n are independently an integer from 0-3; and
L is an anion;
or a salt, solvate, hydrate, polymorph, prodrug, or stereoisomer thereof.

In another aspect, the near-infrared fluorescent contrast is a compound of Formula (IV):

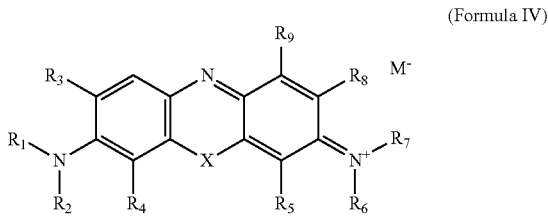

(Formula IV)

wherein
R₁, R₂, R₃, R₄, R₆ and R₇ are each independently H or C₁-C₆ alkyl;
R₅, R₈ and R₉ are each independently H, CN, OH, or C₁-C₆ alkyl;
or R₁ and R₃, taken together with the atoms to which they are connected, form a 5- to 6-membered heterocylic ring;
or R₂ and R₄, taken together with the atoms to which they are connected, form a 5- to 6-membered heterocylic ring;
or R₅ and R₆, taken together with the atoms to which they are connected, form a 5- to 6-membered heterocylic ring;
or R₇ and R₈, taken together with the atoms to which they are connected, form a 5- to 6-membered heterocylic ring;
or R₈ and R₉, taken together with the atoms to which they are connected, form an aryl or heteroaryl ring;
X is O, S, Se, N—R; where R=H or C₁-C₆ alkyl; and
M⁻ is an anion
or a salt, solvate, hydrate, polymorph, prodrug, or stereoisomer thereof.

In still another aspect, the near-infrared fluorescent contrast is a compound of Formula (V):

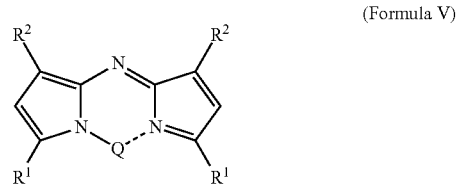

(Formula V)

Wherein:
Q is —B(R³)₂—; Si(R³)₂
Each R¹ is independently H, alkyl, aryl, or heteroaryl, wherein each alkyl, aryl, or heteroaryl is optionally substituted with alkoxy, alkoxy-N⁺(alkyl)₃, alkoxy-OH, halogen, or COOH; and
Each R² is independently H, alkyl, aryl, or heteroaryl, wherein each alkyl, aryl, or heteroaryl is optionally substituted with alkoxy, alkoxy-N⁺(alkyl)₃, alkoxy-OH, halogen, or COOH; and
Each R³ is independently H, F, or alkyl; OH
or a salt, solvate, hydrate, polymorph, prodrug, or stereoisomer thereof.

In one aspect, the near-infrared fluorescent contrast is:

| Name | Structure |
|------|-----------|
| AL22 | 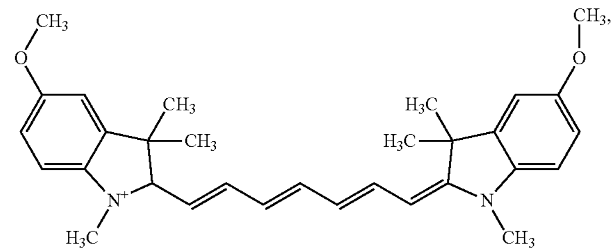 [SMILES: COc1ccc2c(c1)C(C)(C)\C(=C/C=C/C=C/C=C/C1[NH+](C)c3ccc(OC)cc3C1(C)C)N2C] |
| SP64 | 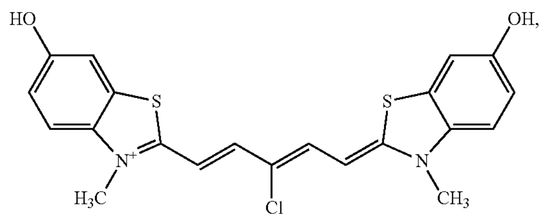 [SMILES: CN1/C(=C/C=C(Cl)/C=C/c2sc3cc(O)ccc3[n+]2C)Sc2cc(O)ccc21] |
| SP60 | 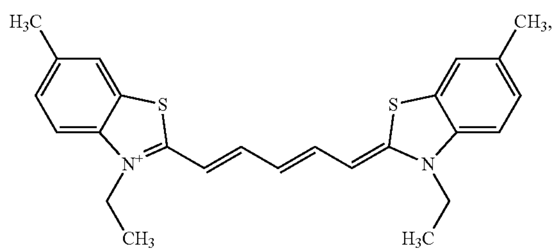 [SMILES: CCN1/C(=C/C=C/C=C/c2sc3cc(C)ccc3[n+]2CC)Sc2cc(C)ccc21] |
| PTN1 | 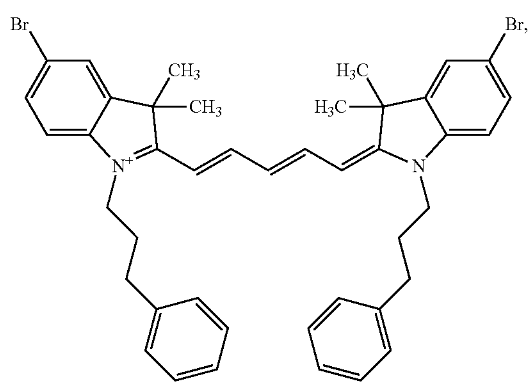 [SMILES: CC1(C)C(/C=C/C=C/C=C2/N(CCCc3ccccc3)c3ccc(Br)cc3C2(C)C)=[N+](CCCc2ccccc2)c2ccc(Br)cc21] |
| SP56 | 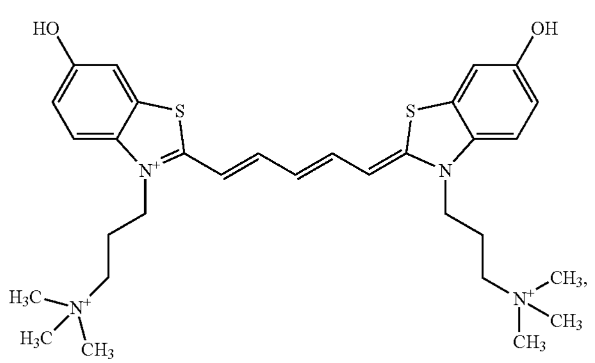 [SMILES: C[N+](C)(C)CCCN1/C(=C/C=C/C=C/c2sc3cc(O)ccc3[n+]2CCC[N+](C)(C)C)Sc2cc(O)ccc21] |

-continued
| Name | Structure |
|---|---|
| QBN1 | 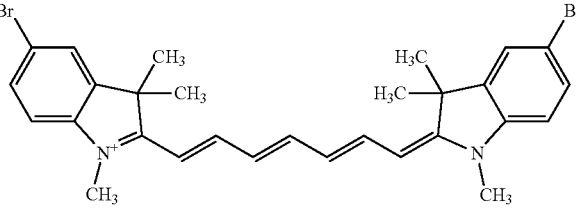 |
| TG18 | 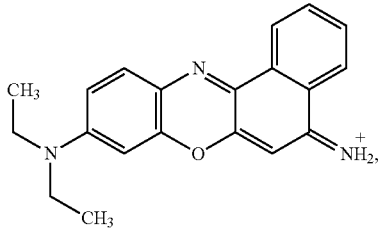 |
| ZK195 | 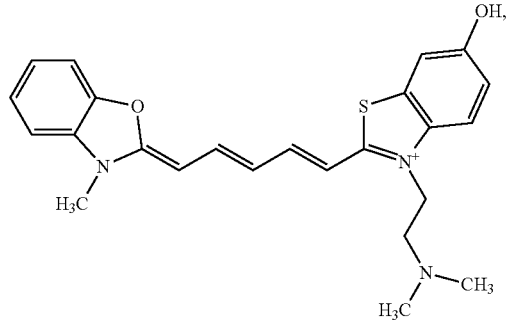 [SMILES: CN(C)CC[n+]1c(/C=C/C=C/C=C2\Oc3ccccc3N2C)sc2cc(O)ccc21] |
| A71 | 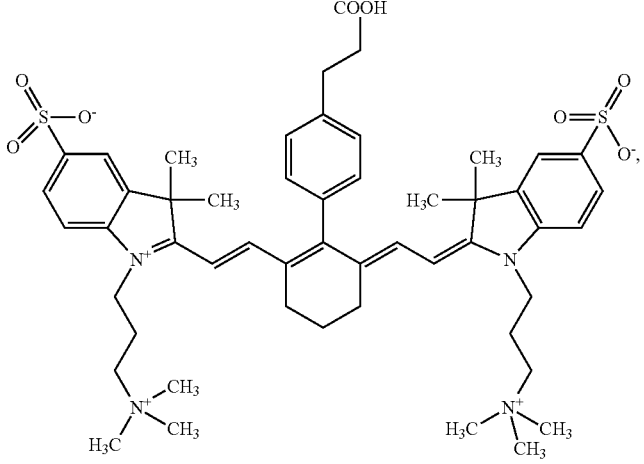 |
| YY187 | 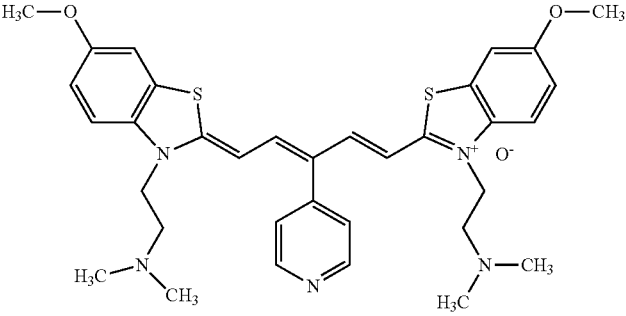 |

-continued

| Name | Structure |
|---|---|
| CNN6 | 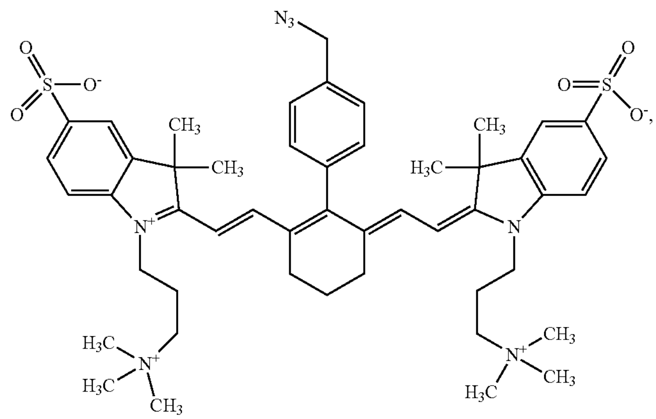 |
| TG42 | 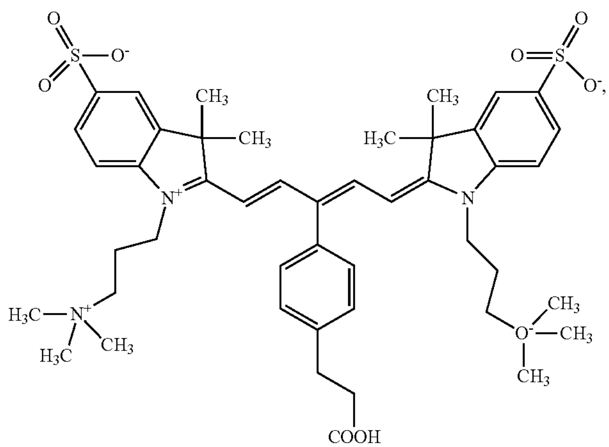 |
| TG53 | 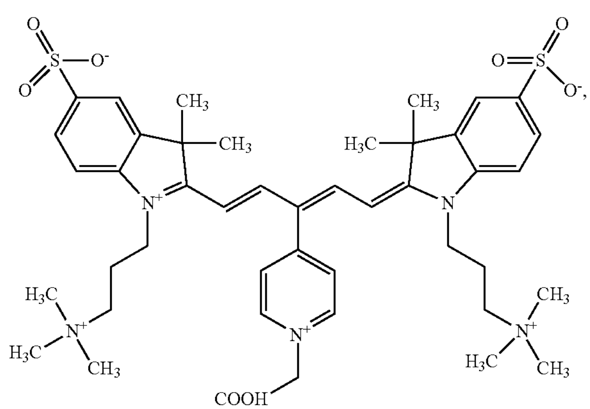 |

| Name | Structure |
|------|-----------|
| CNN4 | 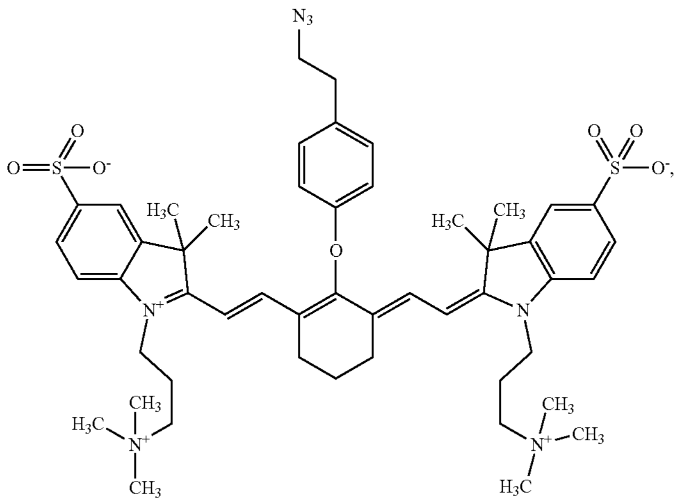 |
| CNN5 | 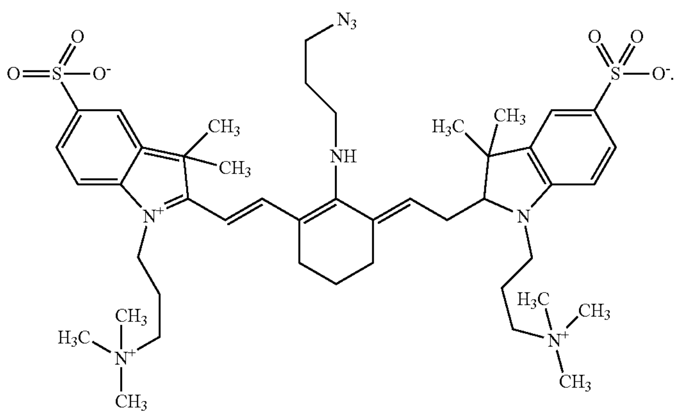 |
| LN24 | 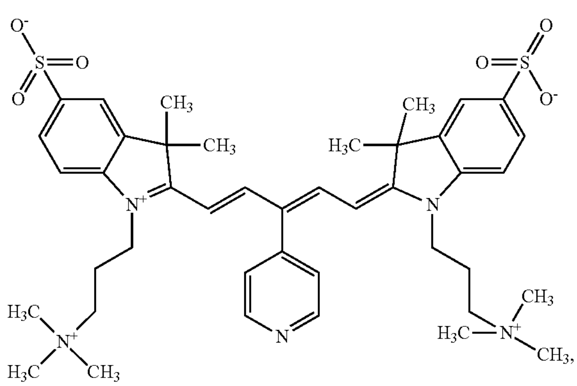 [SMILES: CC1(C)C(/C=C/C(=C/C=C2/N(CCC[N+](C)(C)C)c3ccc(S(=O)(=O)[O-])cc3C2(C)C)c2ccncc2)=[N+](CCC[N+](C)(C)C)c2ccc(S(=O)(=O)[O-])cc21] |

-continued

| Name | Structure |
|------|-----------|
| LN63 | 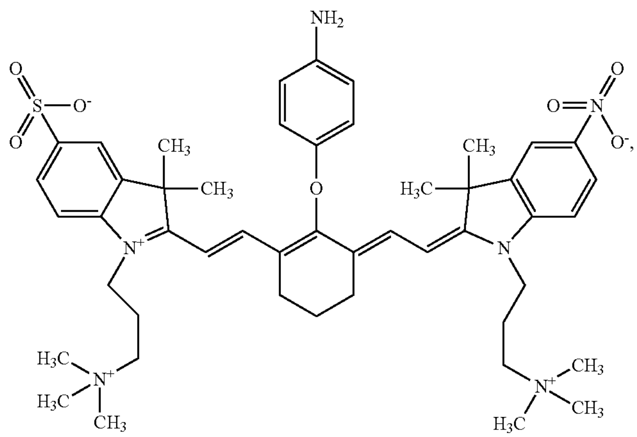 |
| LN66 | 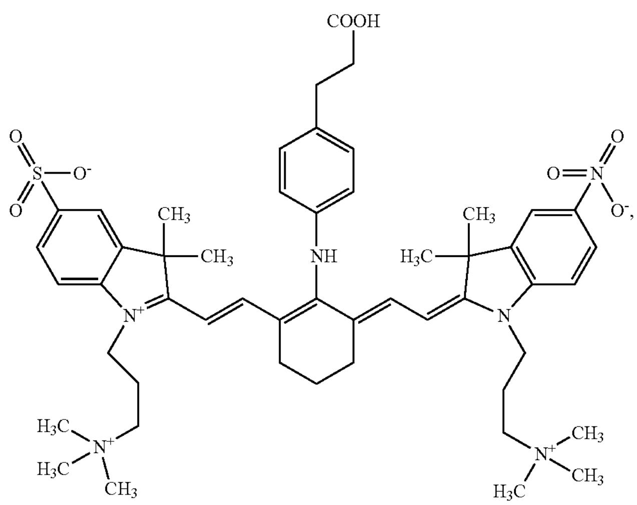 |
| LN15 | 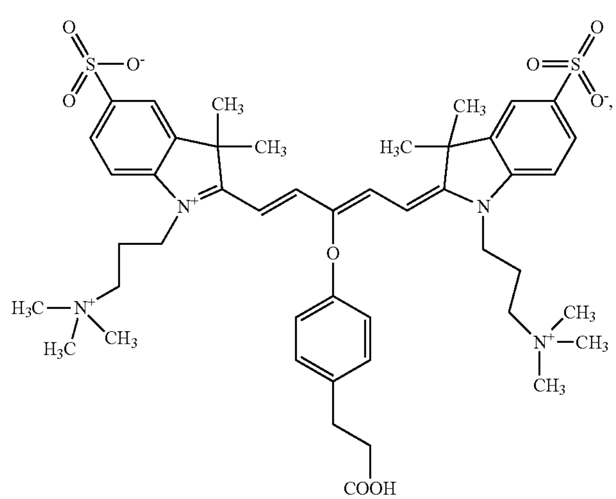 |

-continued

| Name | Structure |
|---|---|
| YY180 | 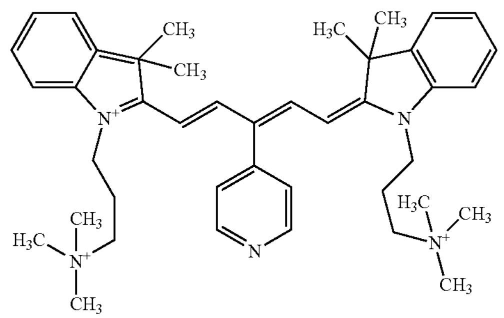 |
| NRB1 | 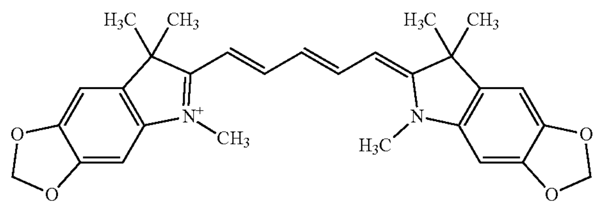 |
| NRB2 | 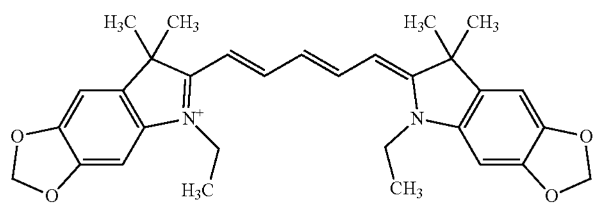 |
| NRB3 | 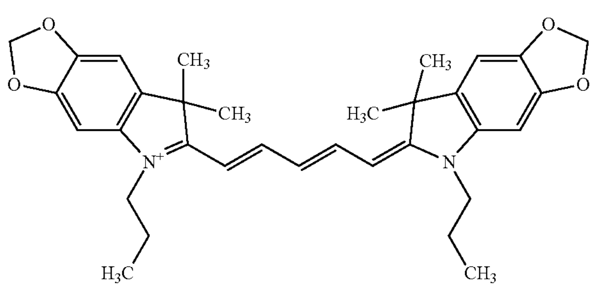 |
| ZK190 | 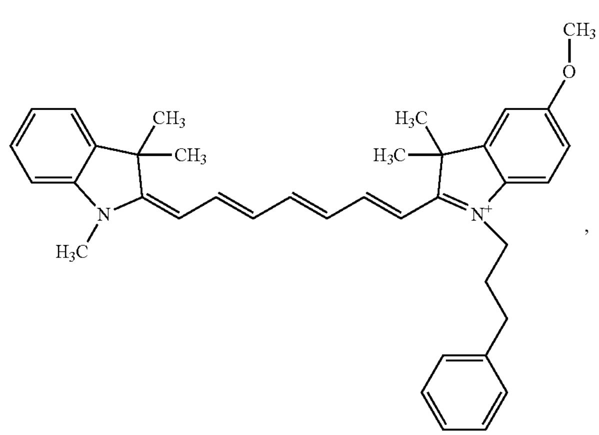 [SMILES: COc1ccc2c(c1)C(C)(C)C(/C=C/C=C/C=C/C=C1/N(C)c3ccccc3C1(C)C)=[N+]2CCCc1ccccc1] |

-continued

| Name | Structure |
|---|---|
| ZK189 | 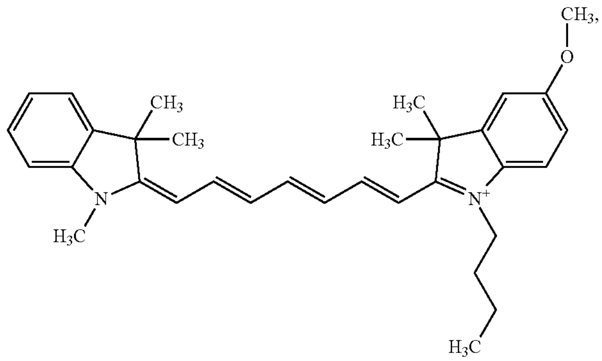 [SMILES: CCCC[N+]1=C(/C=C/C=C/C=C/C=C2/N(C)c3ccccc3C2(C)C)C(C)(C)c2cc(OC)ccc21] |
| ZK50 | 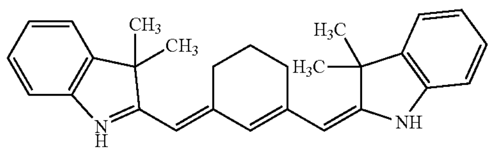 |
| SP59 | 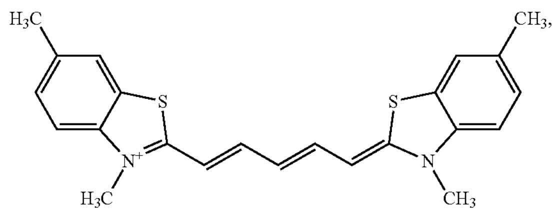 [SMILES: Cc1ccc2c(c1)S\C(=C/C=C/C=C/c1sc3cc(C)ccc3[n+]1C)N2C] |
| JM1 | 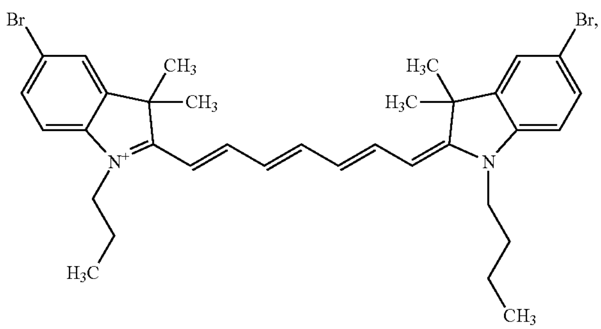 [SMILES: CCCCN1/C(=C/C=C/C=C/C=C/C2=[N+](CCC)c3ccc(Br)cc3C2(C)C)C(C)(C)c2cc(Br)ccc21] |
| SP67 | 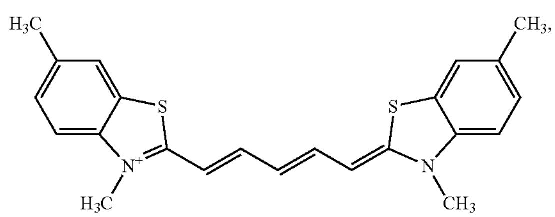 [SMILES: Cc1ccc2c(c1)S\C(=C/C=C/C=C/c1sc3cc(C)ccc3[n+]1C)N2C] |
| MM21 | 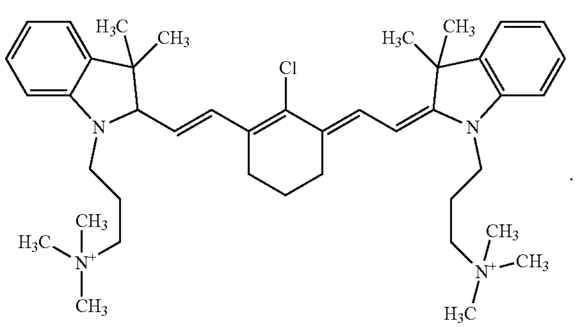 [SMILES: CC1(C)/C(=C\C=C2/CCCC(/C=C/C3N(CCC[N+](C)(C)C)c4ccccc4C3(C)C)=C2Cl)N(CCC[N+](C)(C)C)c2ccccc21] |

-continued

| Name | Structure |
|---|---|
| ZK38 | (structure) |
| E60 | (structure) |
| E58 | (structure) |
| E59 | (structure) |

-continued
| Name | Structure |
|---|---|
| LN36 | 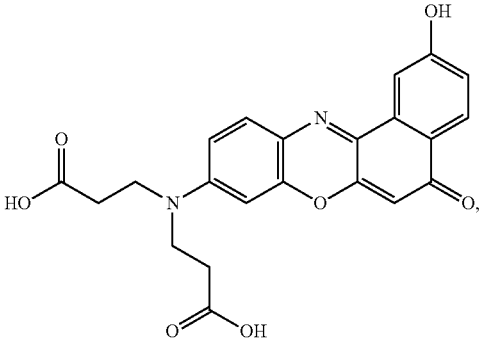 [SMILES: O=C(O)CCN(CCC(=O)O)c1ccc2nc3c4cc(O)ccc4c(=O)cc-3oc2c1] |
| AL27 | 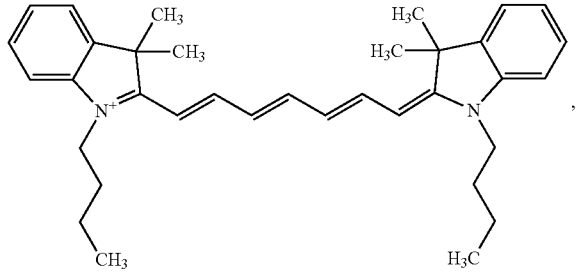 [SMILES: CCCCN1/C(=C/C=C/C=C/C=C/C2=[N+](CCCC)c3ccccc3C2(C)C)C(C)(C)c2ccccc21] |
| AL18 | 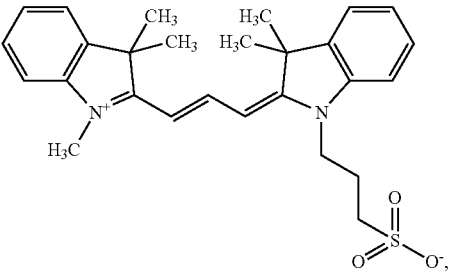 |
| AL16 | 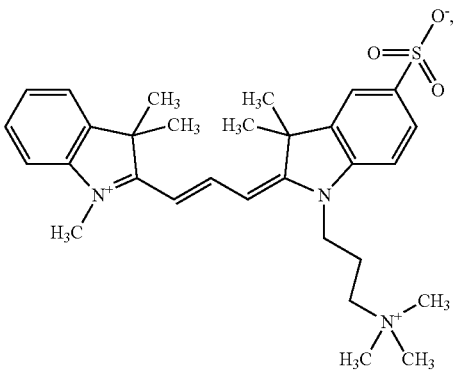 |
| AL25 | 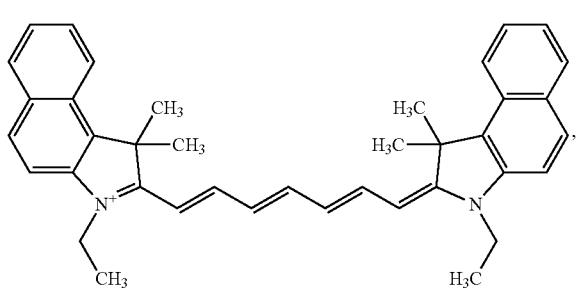 [SMILES: CCN1/C(=C/C=C/C=C/C=C/C2=[N+](CC)c3ccc4ccccc4c3C2(C)C)C(C)(C)c2c1ccc1ccccc21] |

| Name | Structure |
|---|---|
| AL29 | 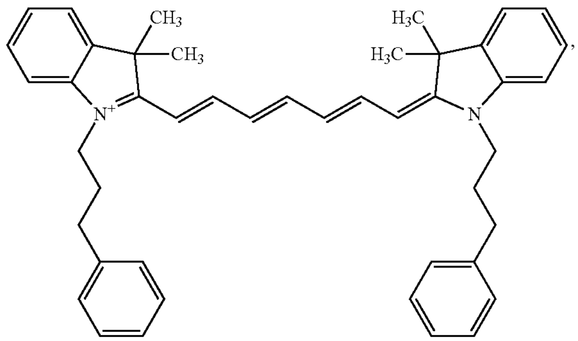 [SMILES: CC1(C)C(/C=C/C=C/C=C/C=C2/N(CCCc3ccccc3)c3ccccc3C2(C)C)=[N+](CCCc2ccccc2)c2ccccc21] |
| AL30 | 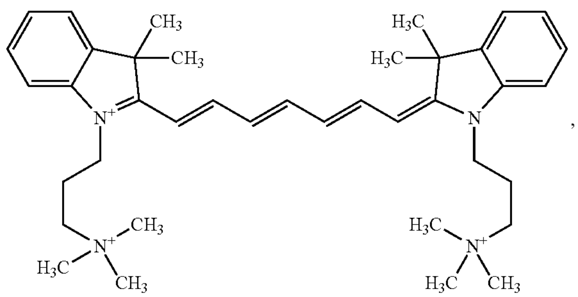 [SMILES: CC1(C)C(/C=C/C=C/C=C/C=C2/N(CCC[N+](C)(C)C)c3ccccc3C2(C)C)=[N+](CCC[N+](C)(C)C)c2ccccc21] |
| AL33 | 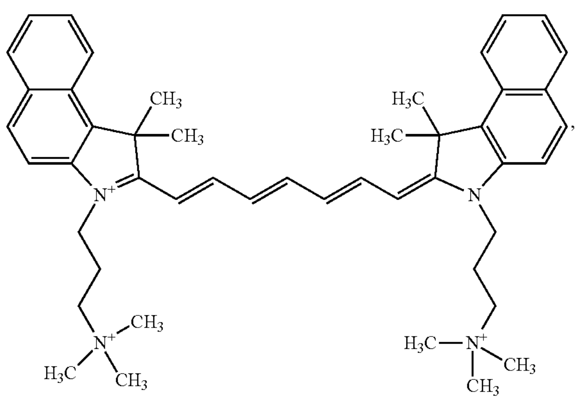 [SMILES: CC1(C)C(/C=C/C=C/C=C/C=C2/N(CCC[N+](C)(C)C)c3ccc4ccccc4c3C2(C)C)=[N+](CCC[N+](C)(C)C)c2ccc3ccccc3c21] |
| AL34 | 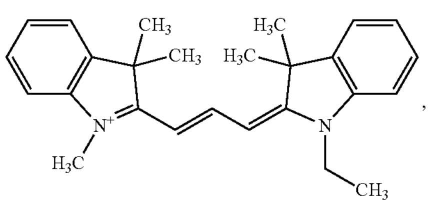 [SMILES: CCN1/C(=C/C=C/C2=[N+](C)c3ccccc3C2(C)C)C(C)(C)c2ccccc21] |
| AL35 | 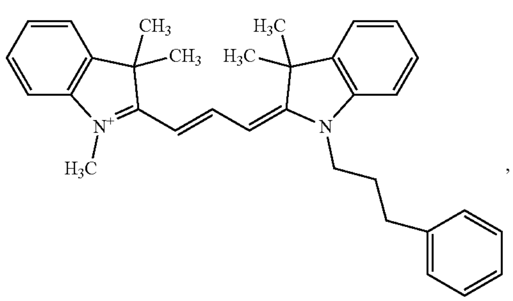 [SMILES: C[N+]1=C(/C=C/C=C2/N(CCCc3ccccc3)c3ccccc3C2(C)C)C(C)(C)c2ccccc21] |

-continued

| Name | Structure |
|---|---|
| AL36 | 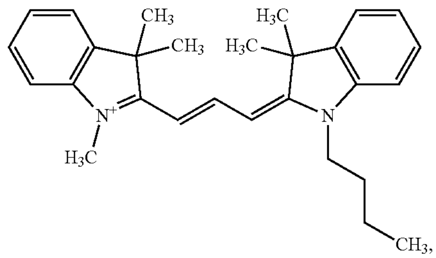 [SMILES: CCCCN1/C(=C/C=C/C2=[N+](C)c3ccccc3C2(C)C)C(C)(C)c2ccccc21] |
| AL14 | 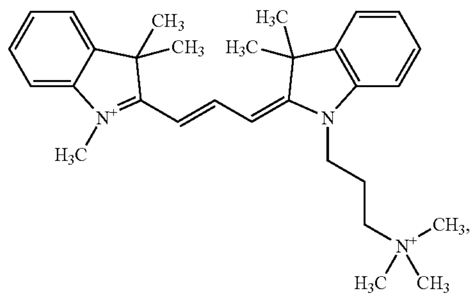 [SMILES: C[N+]1=C(/C=C/C=C2/N(CCC[N+](C)(C)C)c3ccccc3C2(C)C)C(C)(C)c2ccccc21] |
| AL79 | 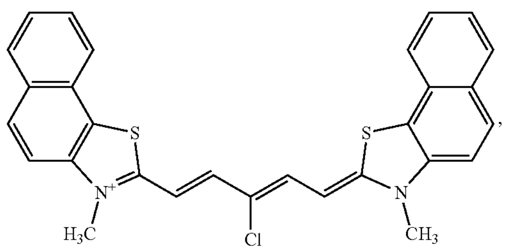 [SMILES: CN1/C(=C/C=C(Cl)/C=C/c2sc3c4ccccc4ccc3[n+]2C)Sc2c1ccc1ccccc21] |
| SP27 | 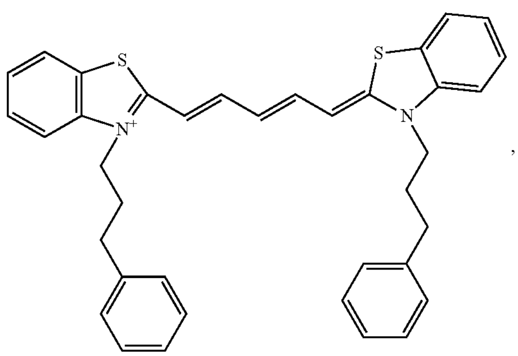 [SMILES: C(/C=C/C=C/c1sc2ccccc2[n+]1CCCc1ccccc1)=C1/Sc2ccccc2N1CCCc1ccccc1] |
| SP28 | 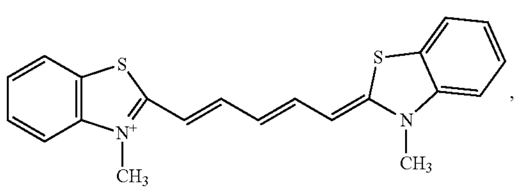 [SMILES: CN1/C(=C/C=C/C=C/c2sc3ccccc3[n+]2C)Sc2ccccc21] |
| SP29 | 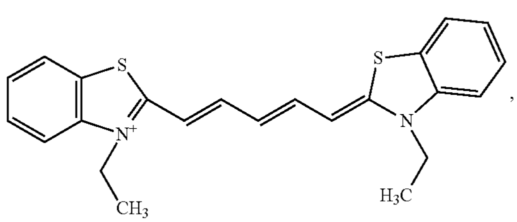 [SMILES: CCN1/C(=C/C=C/C=C/c2sc3ccccc3[n+]2CC)Sc2ccccc21] |

-continued

| Name | Structure |
|---|---|
| SP30 | 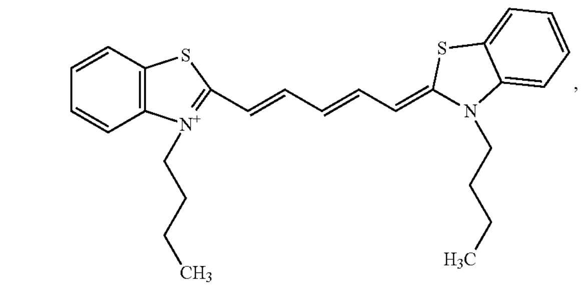 [SMILES: CCCCN1/C(=C/C=C/C=C/c2sc3ccccc3[n+]2CCCC)Sc2ccccc21] |
| SP33 | 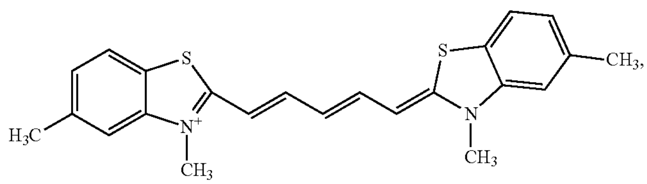 [SMILES: Cc1ccc2c(c1)N(C)/C(=C/C=C/C=C/c1sc3ccc(C)cc3[n+]1C)S2] |
| SP43 | 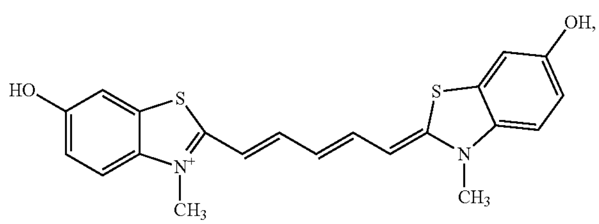 [SMILES: CN1/C(=C/C=C/C=C/c2sc3cc(O)ccc3[n+]2C)Sc2cc(O)ccc21] |
| SP49 | 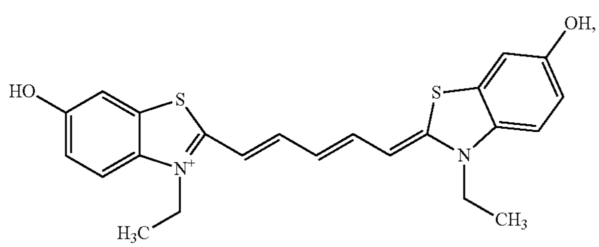 [SMILES: CCN1/C(=C/C=C/C=C/c2sc3cc(O)ccc3[n+]2CC)Sc2cc(O)ccc21] |
| SP51 | 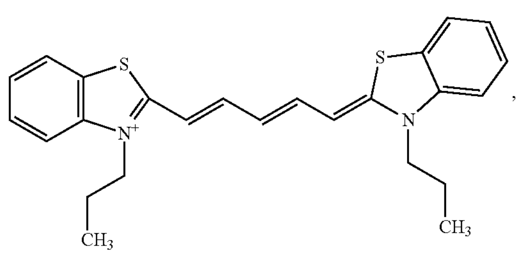 [SMILES: CCCN1/C(=C/C=C/C=C/c2sc3ccccc3[n+]2CCC)Sc2ccccc21] |
| SP53 | 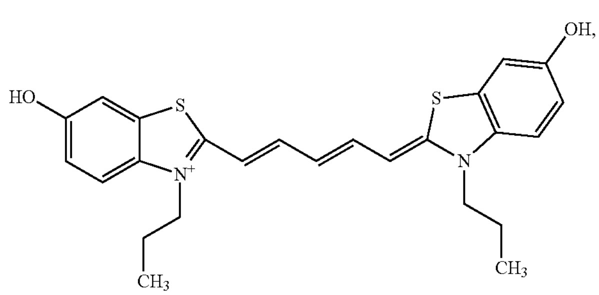 [SMILES: CCCN1/C(=C/C=C/C=C/c2sc3cc(O)ccc3[n+]2CCC)Sc2cc(O)ccc21] |

-continued

| Name | Structure |
|---|---|
| SP79 | 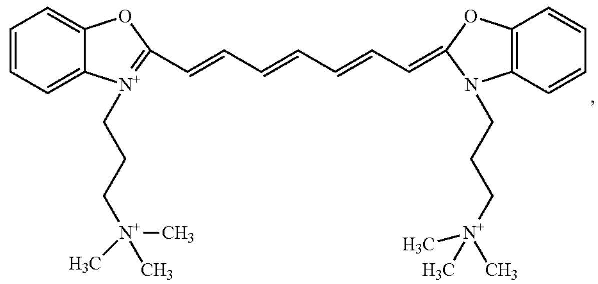 [SMILES: C[N+](C)(C)CCCN1/C(=C/C=C/C=C/C=C/c2oc3ccccc3[n+]2CCC[N+](C)(C)C)Oc2ccccc21] |
| SP99 | 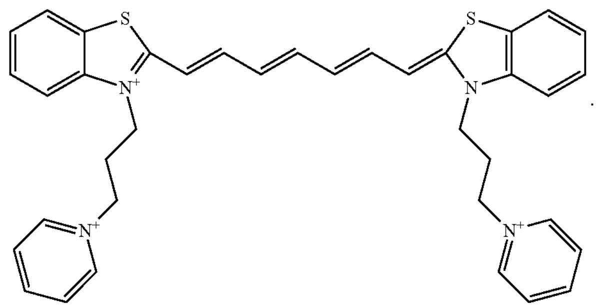 [SMILES: C(/C=C/C=C/C=C/c1sc2ccccc2[n+]1CCC[n+]1ccccc1)=C1/Sc2ccccc2N1CCC[n+]1ccccc1] |
| SP116 | 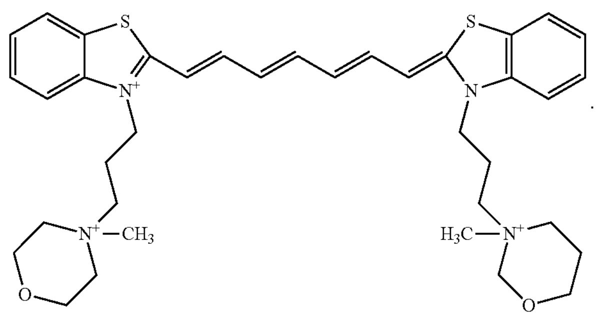 [SMILES: C[N+]1(CCC[n+]2c(/C=C/C=C/C=C/C=C3\Sc4ccccc4N3CCC[N+]3(C)CCCOC3)sc3ccccc32)CCOCC1] |
| SP117 | 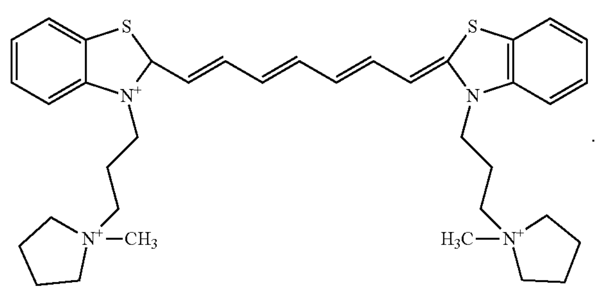 |
| ZK184 | 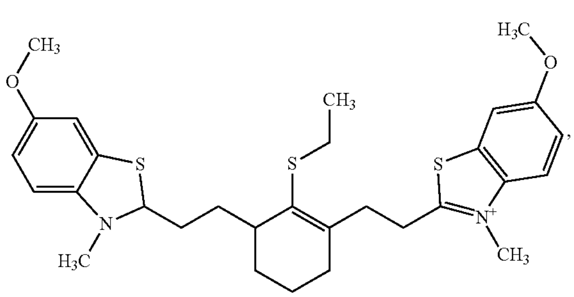 [SMILES: CCSC1=C(CCc2sc3cc(OC)ccc3[n+]2C)CCCC1CCC1Sc2cc(OC)ccc2N1C] |

-continued
| Name | Structure |
|---|---|
| ZK185 | 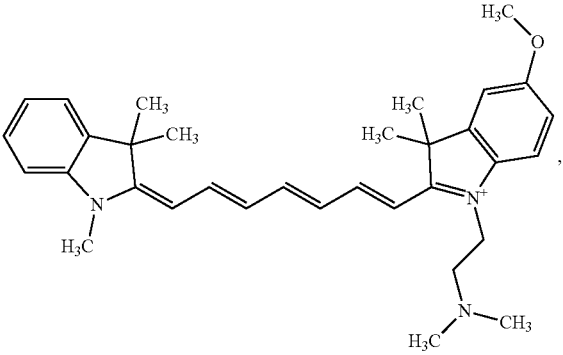 [SMILES: COc1ccc2c(c1)C(C)(C)C(/C=C/C=C/C=C/C=C1/N(C)c3ccccc3C1(C)C)=[N+]2CCN(C)C] |
| ZK197 | 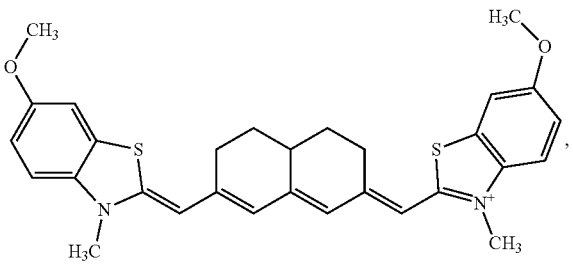 [SMILES: COc1ccc2c(c1)S/C(=C\C1=CC3=C/C(=C/c4sc5cc(OC)ccc5[n+]4C)CCC3CC1)N2C] |
| ZK198 | 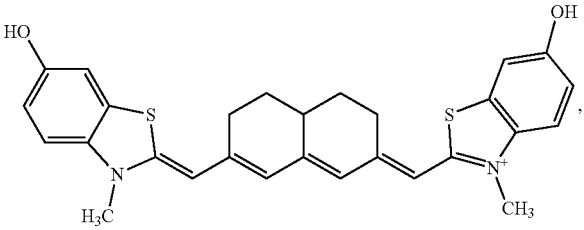 [SMILES: CN1/C(=C/C2=CC3=C/C(=C/c4sc5cc(O)ccc5[n+]4C)CCC3CC2)Sc2cc(O)ccc21] |
| ZK134 | 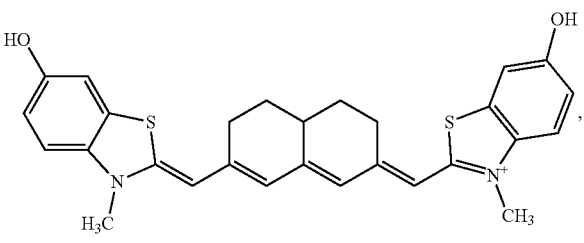 [SMILES: CN1/C(=C/C2=CC3=C/C(=C/c4sc5cc(O)ccc5[n+]4C)CCC3CC2)Sc2cc(O)ccc21] |
| ZK135 | 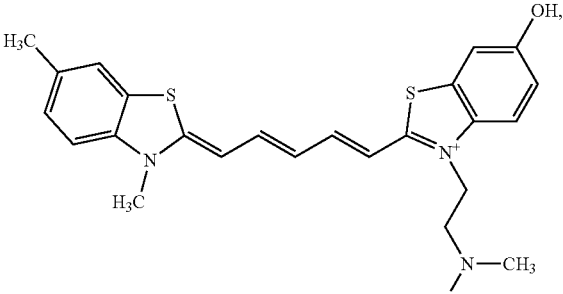 |

-continued

| Name | Structure |
|---|---|
| TG4 | (structure) |
| TG5 | (structure) |
| TG7 | (structure) |

-continued
| Name | Structure |
|---|---|
| TG8 | 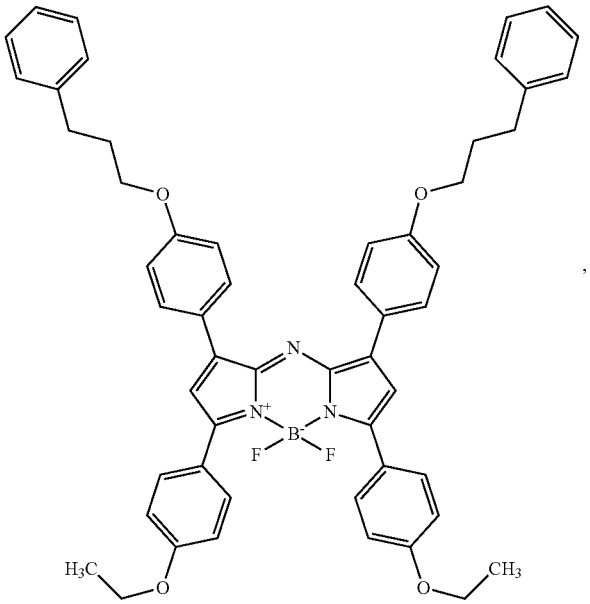 [SMILES: CCOc1ccc(C2=[N+]3C(=Nc4c(-c5ccc(OCCCc6ccccc6)cc5)cc(-c5ccc(OCC)cc5)n4[B-]3(F)F)C(c3ccc(OCCCc4ccccc4)cc3)=C2)cc1] |
| TG27 | 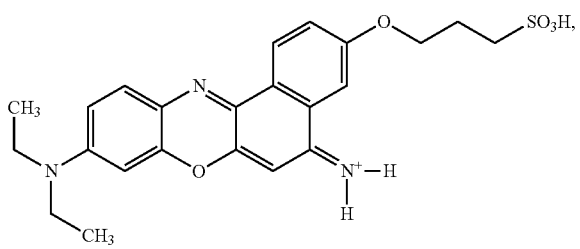 [SMILES: CCN(CC)c1ccc2nc3c4ccc(OCCCS(=O)(=O)O)cc4c(=[NH2+])cc-3oc2c1] |
| TP5 | 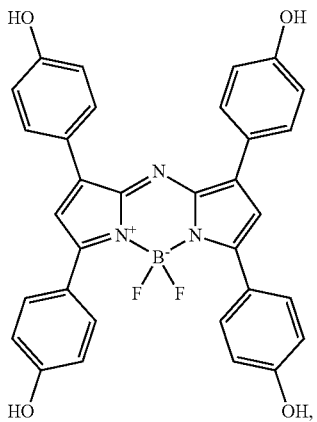 [SMILES: Oc1ccc(C2=CC(c3ccc(O)cc3)=[N+]3C2=Nc2c(-c4ccc(O)cc4)cc(-c4ccc(O)cc4)n2[B-]3(F)F)cc1] |
| QBN14 | 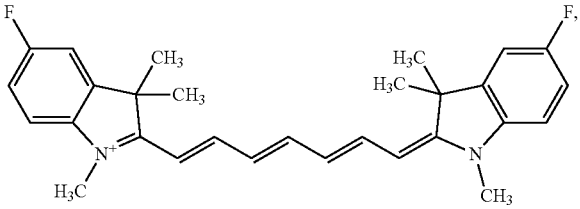 [SMILES: CN1/C(=C/C=C/C=C/C=C/C2=[N+](C)c3ccc(F)cc3C2(C)C)C(C)(C)c2cc(F)ccc21] |

-continued
| Name | Structure |
|---|---|
| CNN154 | 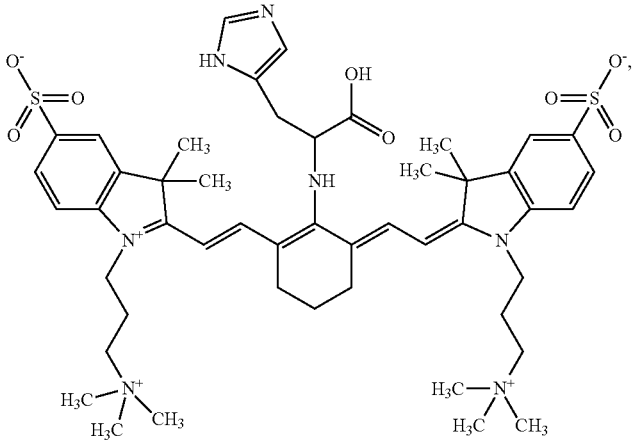 |
| EAO42 | 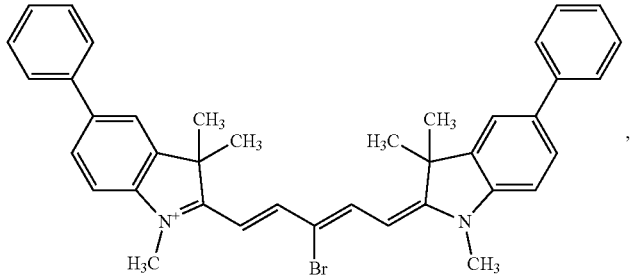 [SMILES: CN1/C(=C/C=C(Br)/C=C/C2=[N+](C)c3ccc(-c4ccccc4)cc3C2(C)C)C(C)(C)c2cc(-c3ccccc3)ccc21] |
| ZK166 | 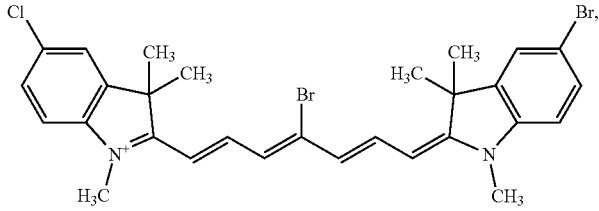 [SMILES: CN1/C(=C/C=C/C(Br)=C/C=C/C2=[N+](C)c3ccc(Cl)cc3C2(C)C)C(C)(C)c2cc(Br)ccc21] |
| PTN13 | 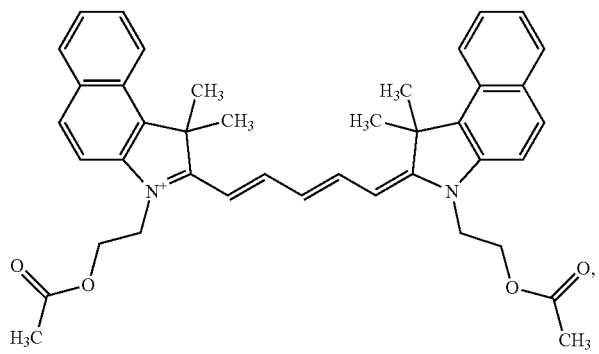 [SMILES: CC(=O)OCCN1/C(=C/C=C/C=C/C2=[N+](CCOC(C)=O)c3ccc4ccccc4c3C2(C)C)C(C)(C)c2c1ccc1ccccc21] |

-continued
| Name | Structure |
|---|---|
| PTN12 | 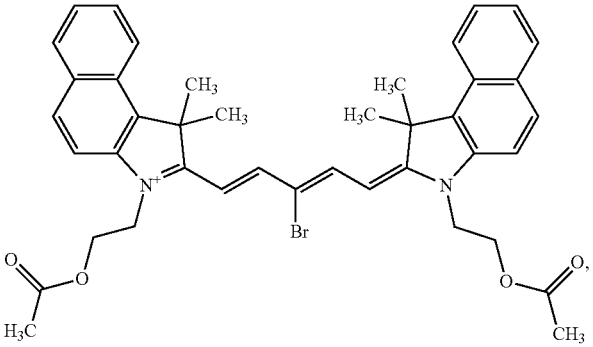 |
| ZK148 | 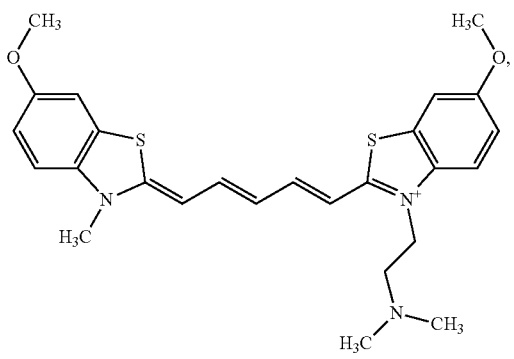 [SMILES: COc1ccc2c(c1)S\C(=C/C=C/C=C/c1sc3cc(OC)ccc3[n+]1CCN(C)C)N2C] |
| ZK154 | 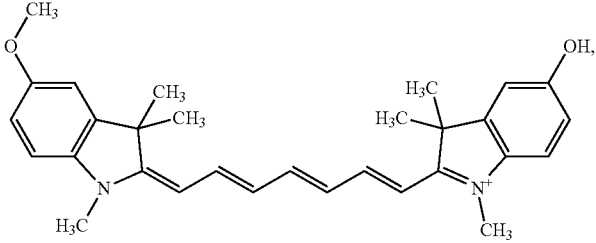 [SMILES: COc1ccc2c(c1)C(C)(C)\C(=C/C=C/C=C/C=C/C1=[N+](C)c3ccc(O)cc3C1(C)C)N2C] |
| E72 | 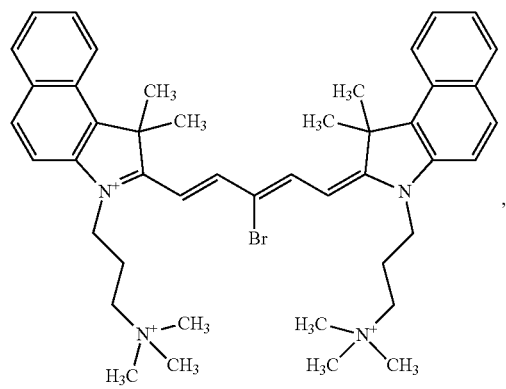 [SMILES: CC1(C)C(/C=C/C(Br)=C/C=C2/N(CCC[N+](C)(C)C)c3ccc4ccccc4c3C2(C)C)=[N+](CCC[N+](C)(C)C)c2ccc3ccccc3c21] |

-continued

| Name | Structure |
|---|---|
| ZK159 | 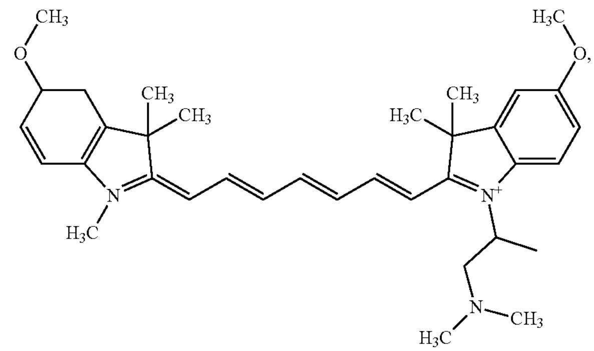 |
| E70 | 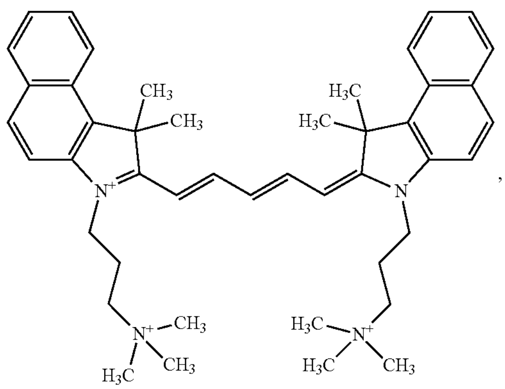 [SMILES: CC1(C)C(/C=C/C=C/C=C2/N(CCC[N+](C)(C)C)c3ccc4ccccc4c3C2(C)C)=[N+](CCC[N+](C)(C)C)c2ccc3ccccc3c21] |
| ZK153 | 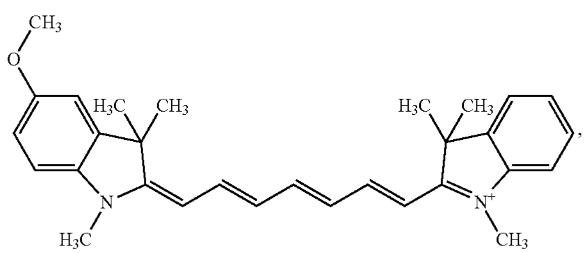 [SMILES: COc1ccc2c(c1)C(C)(C)\C(=C/C=C/C=C/C=C/C1=[N+](C)c3ccccc3C1(C)C)N2C] |
| PTN11 | 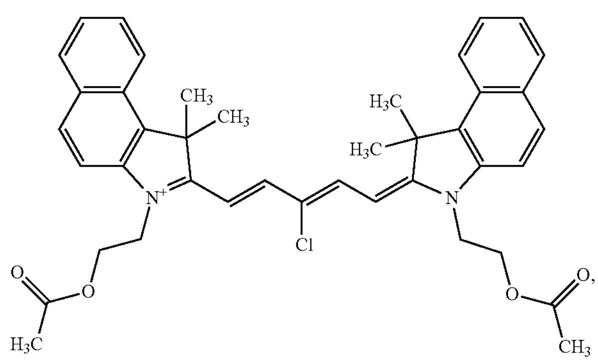 [SMILES: CC(=O)OCCN1/C(=C/C=C(Cl)/C=C/C2=[N+](CCOC(C)=O)c3ccc4ccccc4c3C2(C)C)C(C)(C)c2c1ccc1ccccc21] |
| ZK155 | 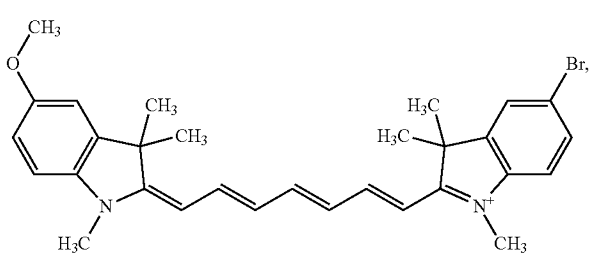 [SMILES: COc1ccc2c(c1)C(C)(C)\C(=C/C=C/C=C/C=C/C1=[N+](C)c3ccc(Br)cc3C1(C)C)N2C] |

-continued
| Name | Structure |
|---|---|
| MHI103 | 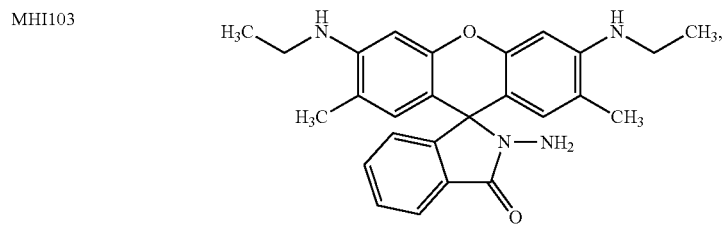 |
| CNN13 | 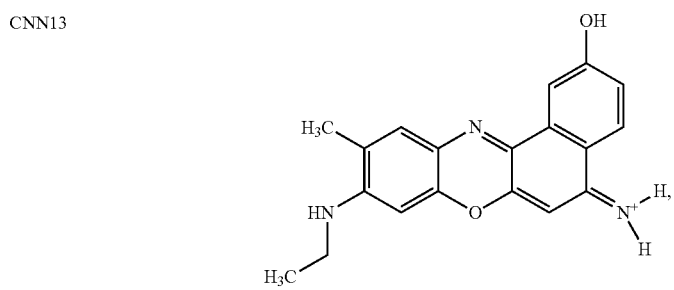 |
| WuA71 | 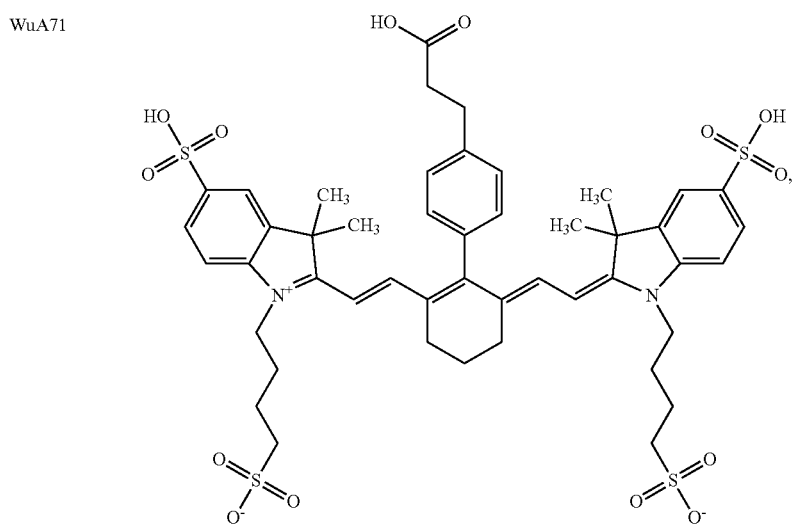 |
| ZK143 | 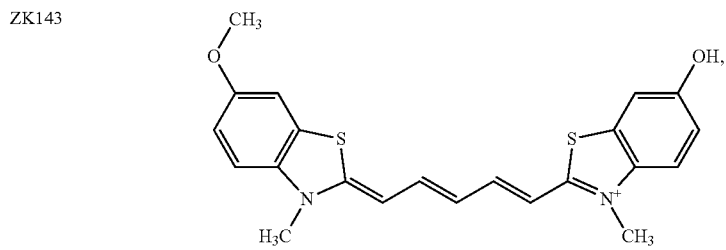 |

-continued

| Name | Structure |
|------|-----------|
| ZK140 | (chemical structure) |
| ZK29 | (chemical structure) |
| SP34 | (chemical structure) |
| ZK104 | (chemical structure) |
| TP1 | (chemical structure) |

| Name | Structure |
|---|---|
| ZK14 | 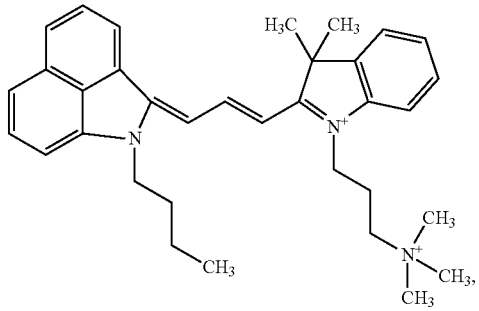 [SMILES: CCCCn1/c(=C/C=C/C2=[N+](CCC[N+](C)(C)C)c3ccccc3C2(C)C)c2cccc3cccc1c32] |
| PTN6 | 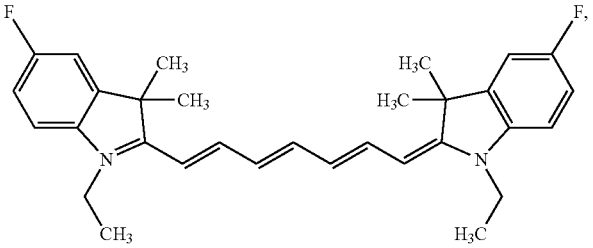 |
| LN65 | 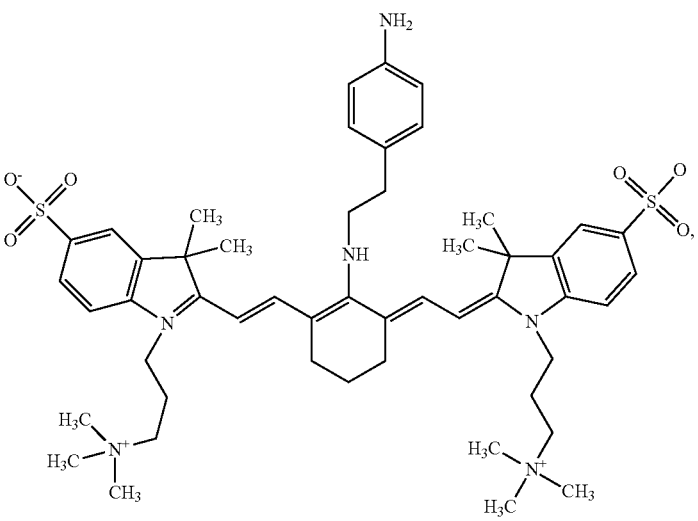 |
| LN79 | 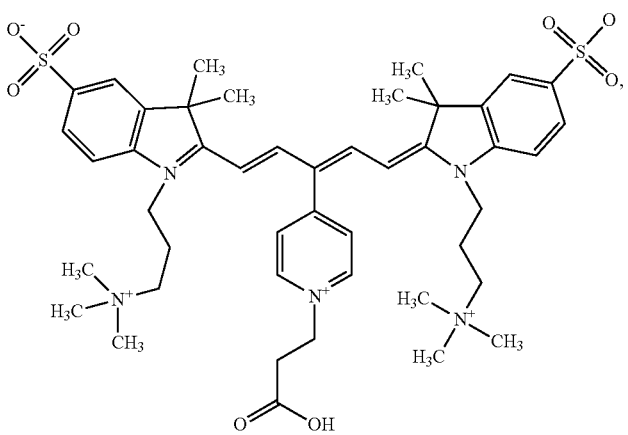 |

| Name | Structure |
|------|-----------|
| AH34 | 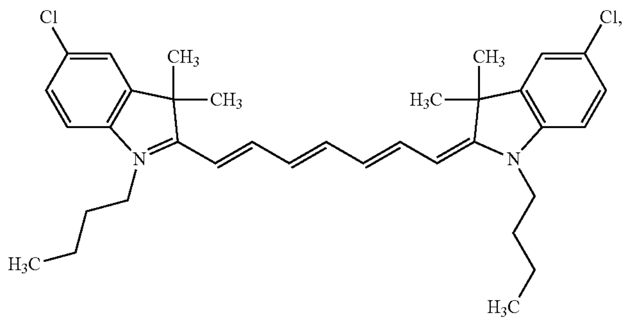 |
| TP4 | 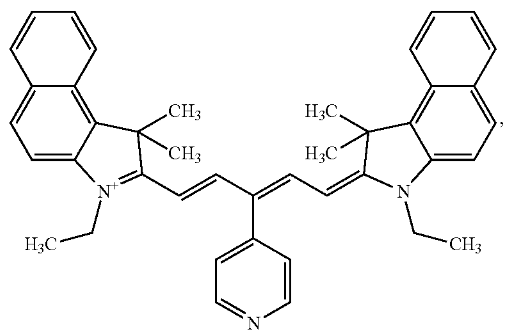 [SMILES: CCN1/C(=C/C=C(/C=C/C2=[N+](CC)c3ccc4ccccc4c3C2(C)C)c2ccncc2)C(C)(C)c2c1ccc1ccccc21] |
| LS1 | 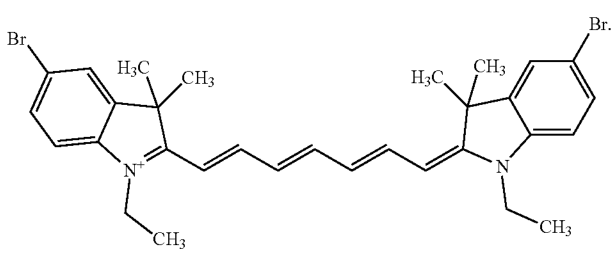 [SMILES: CCN1/C(=C/C=C/C=C/C=C/C2=[N+](CC)c3ccc(Br)cc3C2(C)C)C(C)(C)c2cc(Br)ccc21] |
| YY163 | 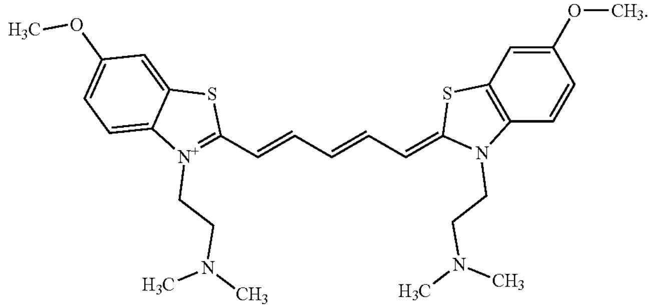 [SMILES: COc1ccc2c(c1)S\C(=C/C=C/C=C/c1sc3cc(OC)ccc3[n+]1CCN(C)C)N2CCN(C)C] |

| Name | Structure |
|---|---|
| TP6 | 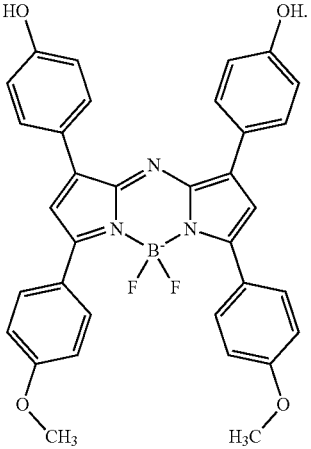 |
| ZK15 | 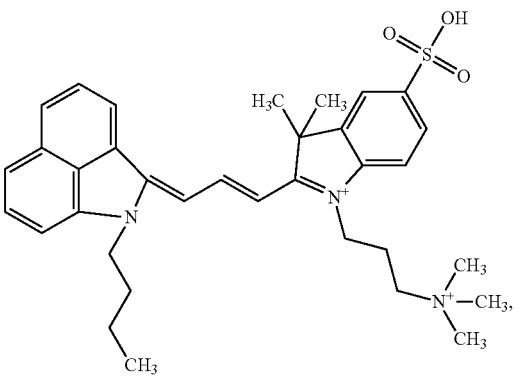 [SMILES: CCCCn1/c(=C/C=C/C2=[N+](CCC[N+](C)(C)C)c3ccc(S(=O)(=O)O)cc3C2(C)C)c2cccc3cccc1c32] |
| WuA108 | 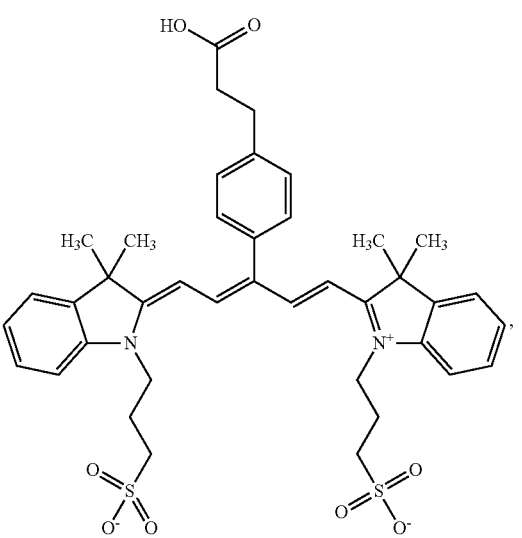 [SMILES: CC1(C)C(/C=C/C(=C/C=C2\N(CCCS(=O)(=O)[O-])c3ccccc3C2(C)C)c2ccc(CCC(=O)O)cc2)=[N+](CCCS(=O)(=O)[O-])c2ccccc21] |

| Name | Structure |
|---|---|
| ZK150 | 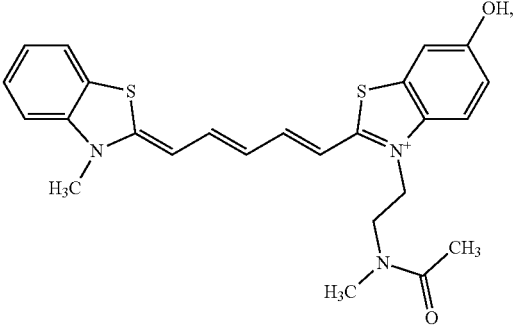 [SMILES: CC(=O)N(C)CC[n+]1c(/C=C/C=C/C=C2\Sc3ccccc3N2C)sc2cc(O)ccc21] |
| ZK156 | 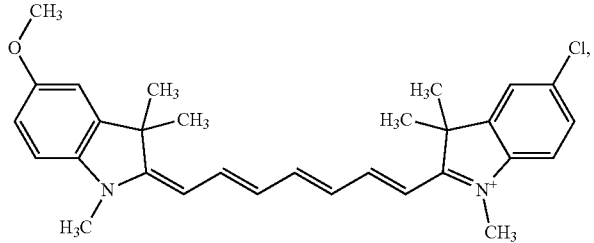 [SMILES: COc1ccc2c(c1)C(C)(C)\C(=C/C=C/C=C/C=C/C1=[N+](C)c3ccc(Cl)cc3C1(C)C)N2C] |
| ESS23 | 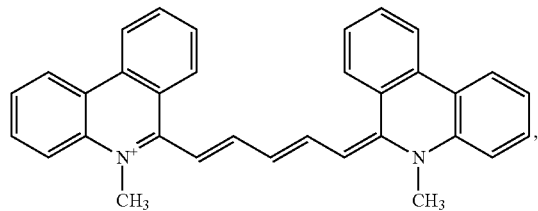 [SMILES: CN1/C(=C/C=C/C=C/c2c3ccccc3c3ccccc3[n+]2C)c2ccccc2-c2ccccc21] |
| CNN17 | 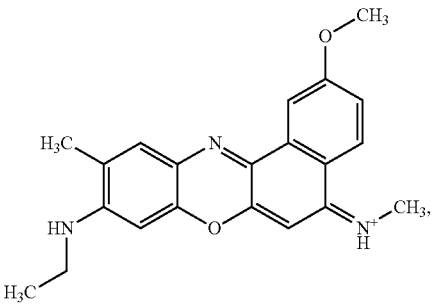 |
| TG56 | 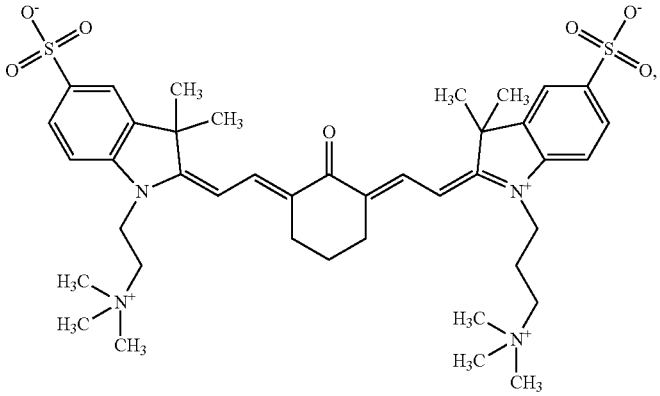 |

-continued
| Name | Structure |
|---|---|
| AL31 | 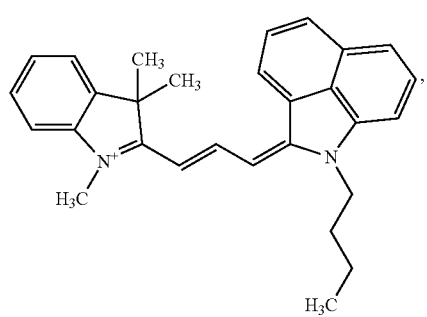 [SMILES: CCCCn1/c(=C/C=C/C2=[N+](C)c3ccccc3C2(C)C)c2cccc3cccc1c32] |
| AL43 | 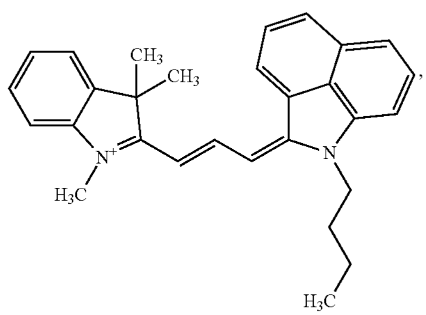 |
| TG31 | 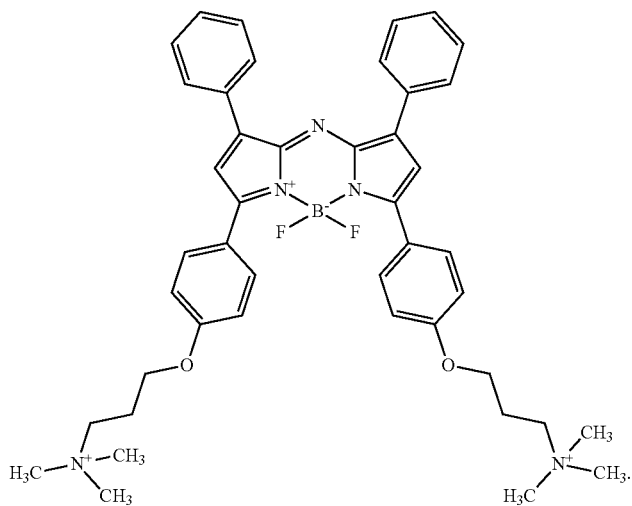 [SMILES: C[N+](C)(C)CCCOc1ccc(C2=[N+]3C(=Nc4c(-c5ccccc5)cc(-c5ccc(OCCC[N+](C)(C)C)cc5)n4[B-]3(F)F)C(c3ccccc3)=C2)cc1] |

| Name | Structure |
|---|---|
| CNN3 | 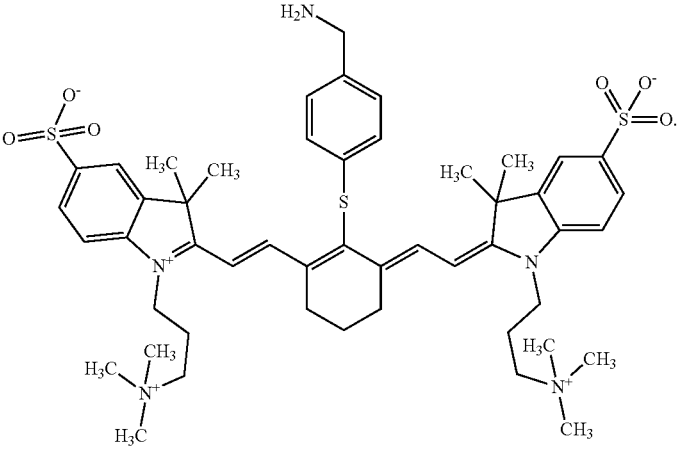 [SMILES: CC1(C)C(/C=C/C2=C(Sc3ccc(CN)cc3)C(=C/C=C3/N(CCC[N+](C)(C)C)c4ccc(S(=O)(=O)[O-])cc4C3(C)C)/CCC2)=[N+](CCC[N+](C)(C)C)c2ccc(S(=O)(=O)[O-])cc21] |
| AL20 | 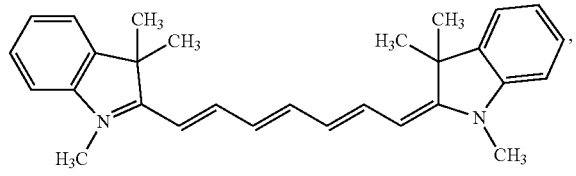 |
| TG115 | 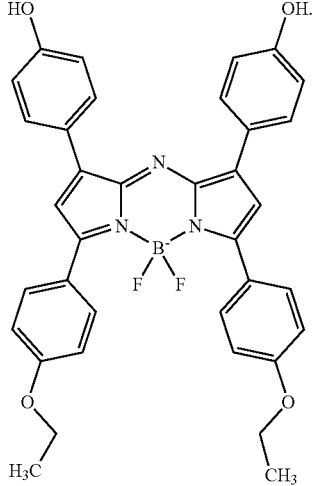 |

-continued

| Name | Structure |
|---|---|
| CNN2 | (structure) |
| TP04 | (structure) |
| ZK26 | (structure) |
| ZK48 | (structure) |

-continued

| Name | Structure |
|---|---|
| TG44 | 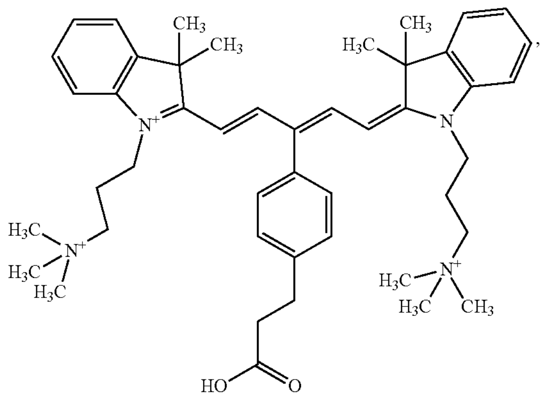 [SMILES: CC1(C)C(/C=C/C(=C/C=C2/N(CCC[N+](C)(C)C)c3ccccc3C2(C)C)c2ccc(CCC(=O)O)cc2)=[N+](CCC[N+](C)(C)C)c2ccccc21] |
| ZK27 | 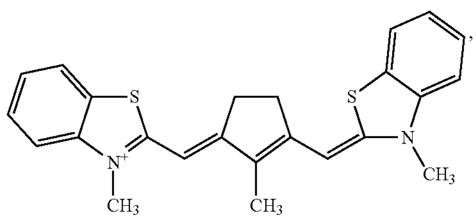 |
| ZK46 | 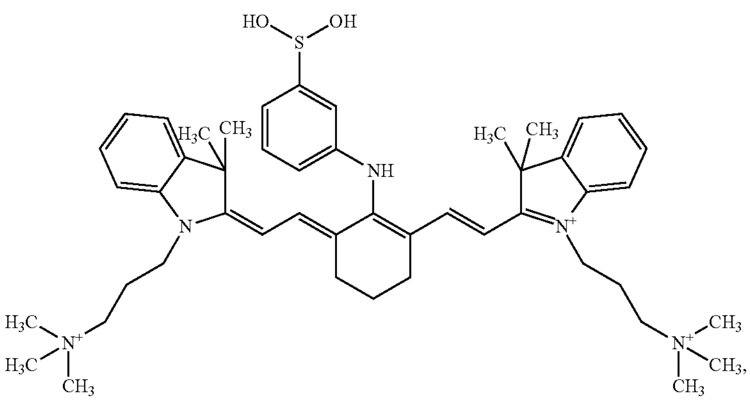 |
| CNN1 | 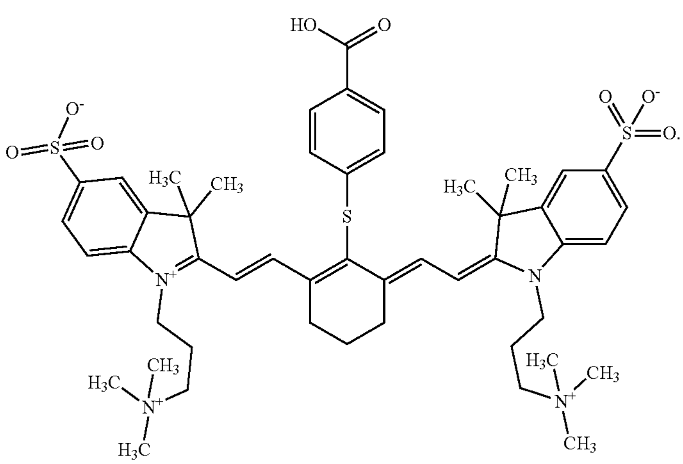 [SMILES: CC1(C)C(/C=C/C2=C(Sc3ccc(C(=O)O)cc3)C(=C/C=C3/N(CCC[N+](C)(C)C)c4ccc(S(=O)(=O)[O-])cc4C3(C)C)/CCC2)=[N+](CCC[N+](C)(C)C)c2ccc(S(=O)(=O)[O-])cc21] |

| Name | Structure |
|------|-----------|
| ZK79 | 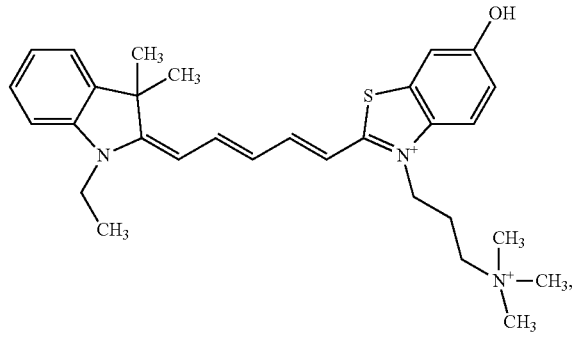 |
| WuA38 | 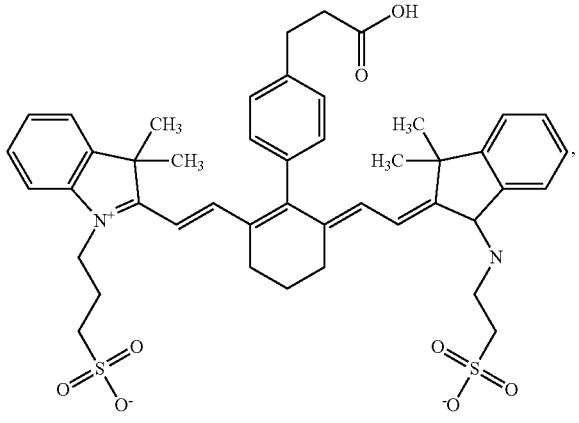 |
| LN68 | 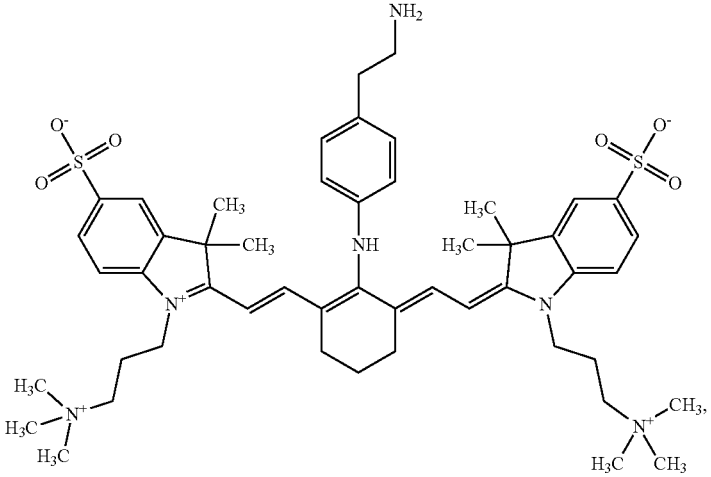 [SMILES: CC1(C)C(/C=C/C2=C(Nc3ccc(CCN)cc3)C(=C/C=C3/N(CCC[N+](C)(C)C)c4ccc(S(=O)(=O)[O-])cc4C3(C)C)/CCC2)=[N+](CCC[N+](C)(C)C)c2ccc(S(=O)(=O)[O-])cc21] |
| ESS13 | 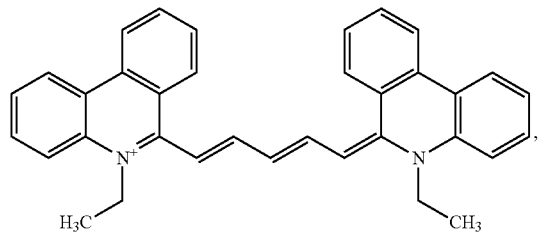 [SMILES: CCN1/C(=C/C=C/C=C/c2c3ccccc3c3ccccc3[n+]2CC)c2ccccc2-c2ccccc21] |

| Name | Structure |
|---|---|
| WuA110 | 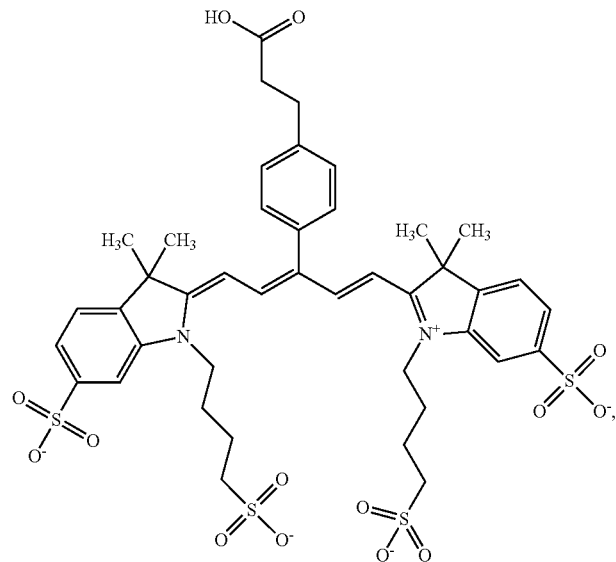 |
| YY161 | 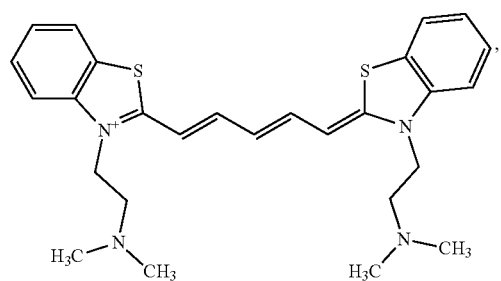 [SMILES: CN(C)CCN1/C(=C/C=C/C=C/c2sc3ccccc3[n+]2CCN(C)C)Sc2ccccc21] |
| E71 | 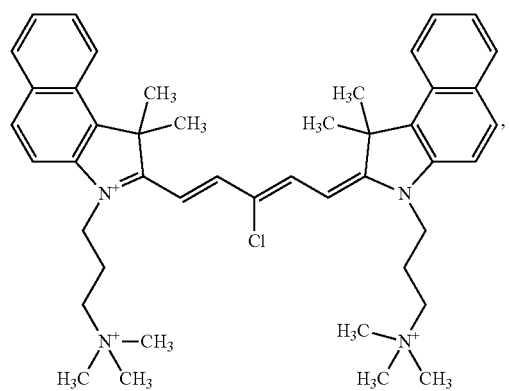 [SMILES: CC1(C)C(/C=C/C(Cl)=C/C=C2/N(CCC[N+](C)(C)C)c3ccc4ccccc4c3C2(C)C)=[N+](CCC[N+](C)(C)C)c2ccc3ccccc3c21] |

-continued
| Name | Structure |
|------|-----------|
| CNN8 | 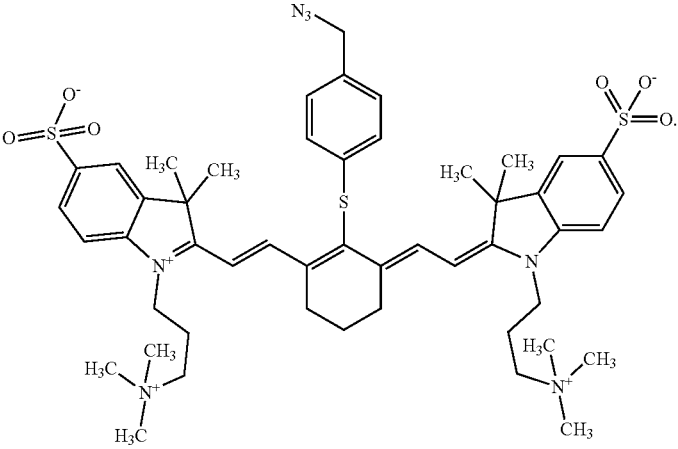 [SMILES: CC1(C)C(/C=C/C2=C(Sc3ccc(CN=[N+]=[N-])cc3)C(=C/C=C3/N(CCC[N+](C)(C)C)c4ccc(S(=O)(=O)[O-])cc4C3(C)C)/CCC2)=[N+](CCC[N+](C)(C)C)c2ccc(S(=O)(=O)[O-])cc21] |
| CNN10 | 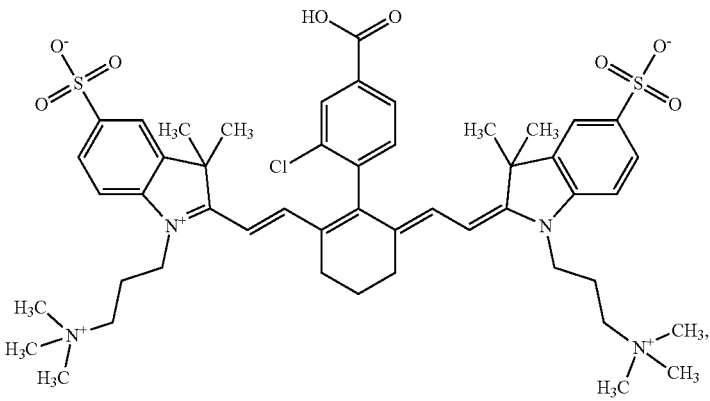 [SMILES: CC1(C)C(/C=C/C2=C(c3ccc(C(=O)O)cc3Cl)C(=C/C=C3/N(CCC[N+](C)(C)C)c4ccc(S(=O)(=O)[O-])cc4C3(C)C)/CCC2)=[N+](CCC[N+](C)(C)C)c2ccc(S(=O)(=O)[O-])cc21] |
| LN68Boc | 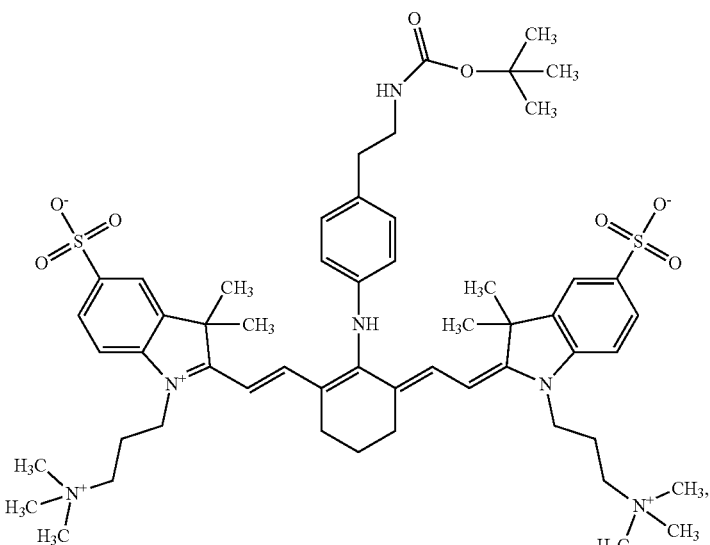 |

-continued
| Name | Structure |
|---|---|
| TG60 | 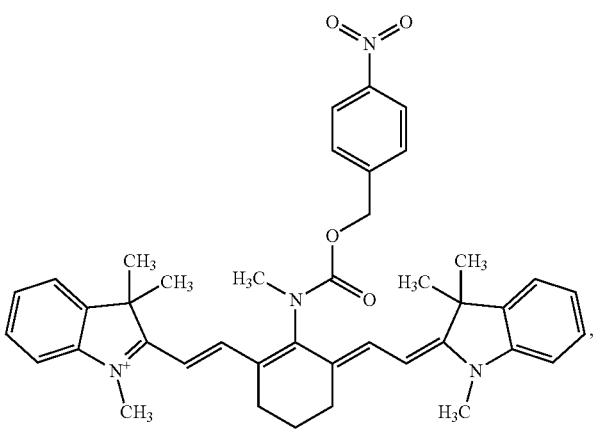 [SMILES: CN(C(=O)OCc1ccc([N+](=O)[O-])cc1)C1=C(/C=C/C2=[N+](C)c3ccccc3C2(C)C)CCC/C1=C\C=C1\N(C)c2ccccc2C1(C)C] |
| ZK78 | 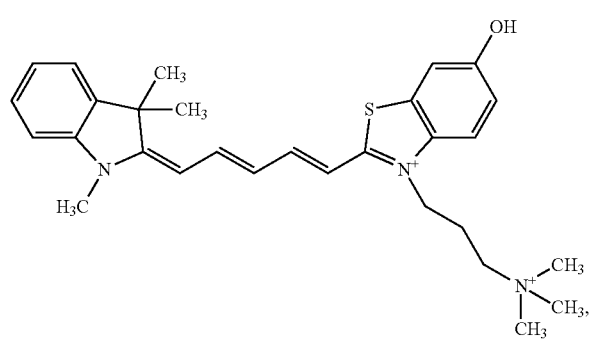 [SMILES: CN1/C(=C/C=C/C=C/c2sc3cc(O)ccc3[n+]2CCC[N+](C)(C)C)C(C)(C)c2ccccc21] |
| ZK133 | 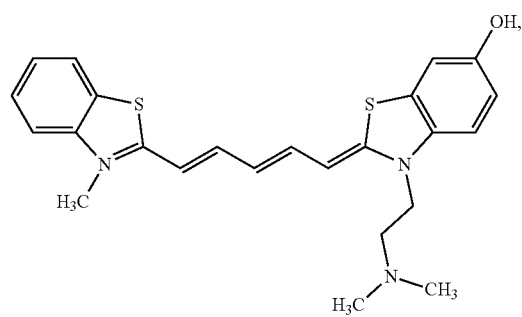 |
| CNN7 | 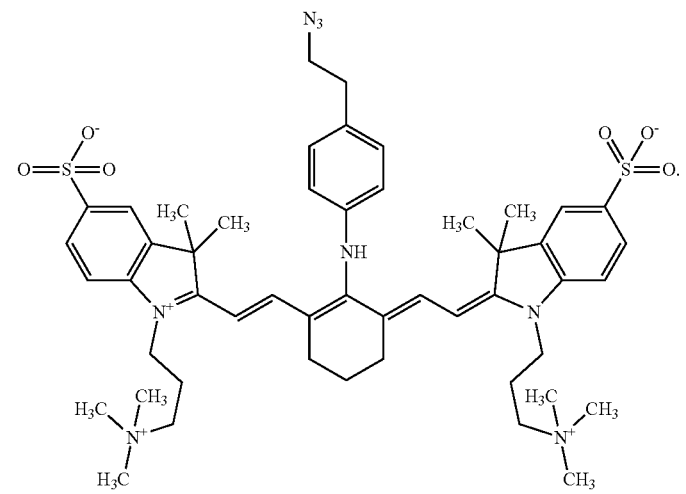 [SMILES: CC1(C)C(/C=C/C2=C(Nc3ccc(CCN=[N+]=[N-])cc3)C(=C/C=C3/N(CCC[N+](C)(C)C)c4ccc(S(=O)(=O)[O-])cc4C3(C)C)/CCC2)=[N+](CCC[N+](C)(C)C)c2ccc(S(=O)(=O)[O-])cc21] |

-continued
| Name | Structure |
|---|---|
| ZK23 | 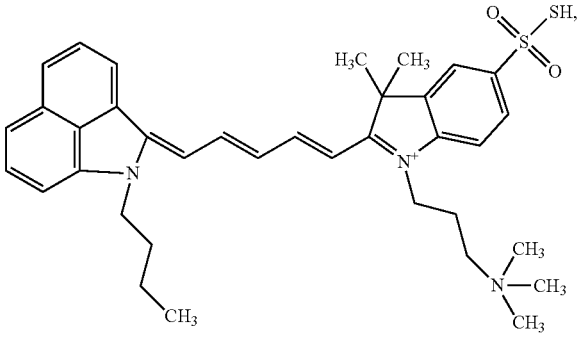 |
| MDL17 | 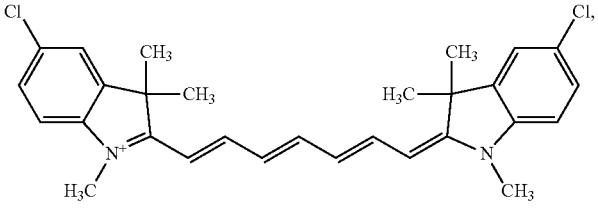 [SMILES: CN1/C(=C/C=C/C=C/C=C/C2=[N+](C)c3ccc(Cl)cc3C2(C)C)C(C)(C)c2cc(Cl)ccc21] |
| TG11A | 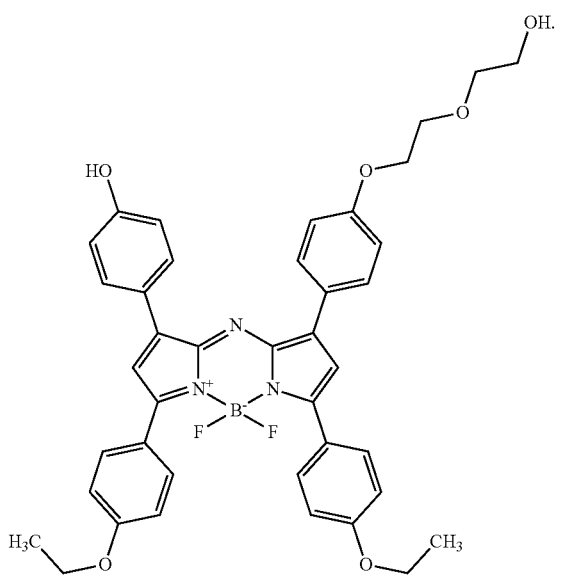 [SMILES: CCOc1ccc(C2=[N+]3C(=Nc4c(-c5ccc(OCCOCCO)cc5)cc(-c5ccc(OCC)cc5)n4[B-]3(F)F)C(c3ccc(O)cc3)=C2)cc1] |

-continued
| Name | Structure |
|---|---|
| TG11B | 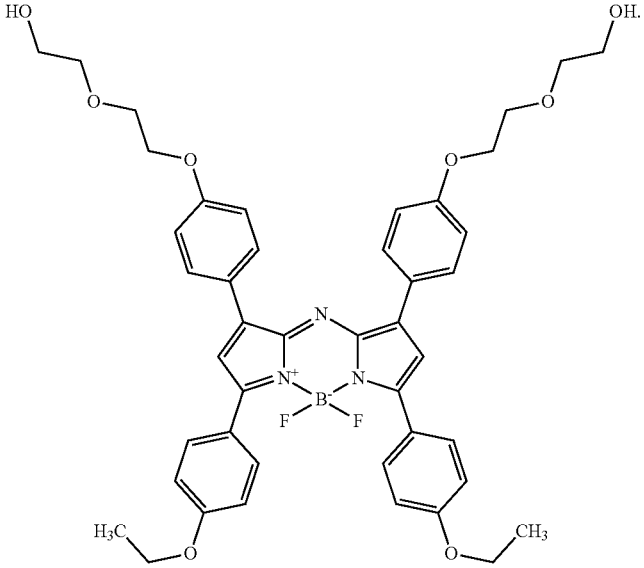 [SMILES: CCOc1ccc(C2=[N+]3C(=Nc4c(-c5ccc(OCCOCCO)cc5)cc(-c5ccc(OCC)cc5)n4[B-]3(F)F)C(c3ccc(OCCOCCO)cc3)=C2)cc1] |
| TP2 | 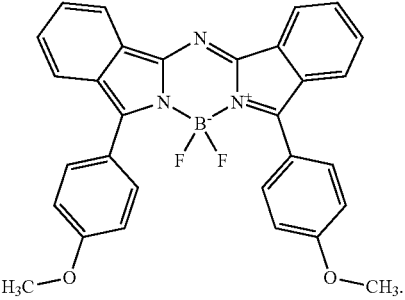 [SMILES: COc1ccc(C2=[N+]3C(=Nc4c5ccccc5c(-c5ccc(OC)cc5)n4[B-]3(F)F)c3ccccc32)cc1] |
| LN50 | 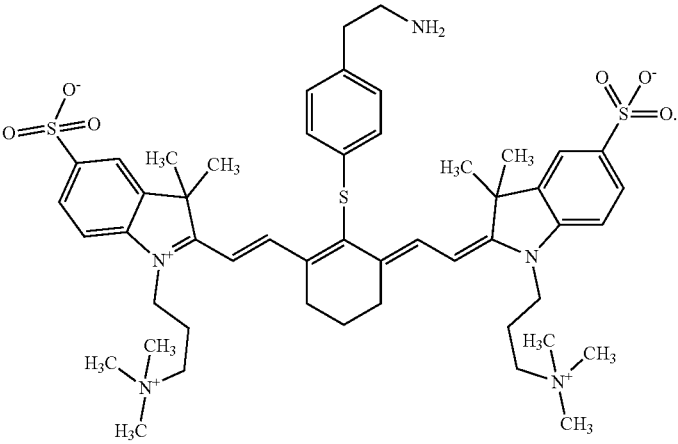 [SMILES: CC1(C)C(/C=C/C2=C(Sc3ccc(CCN)cc3)C(=C/C=C3/N(CCC[N+](C)(C)C)c4ccc(S(=O)(=O)[O-])cc4C3(C)C)/CCC2)=[N+](CCC[N+](C)(C)C)c2ccc(S(=O)(=O)[O-])cc21] |
| TG17 | 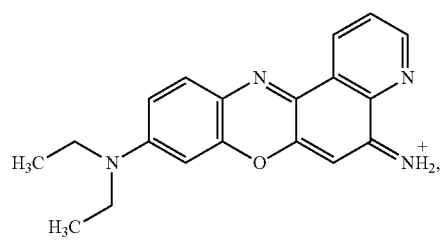 |

-continued

| Name | Structure |
|---|---|
| TG22 | 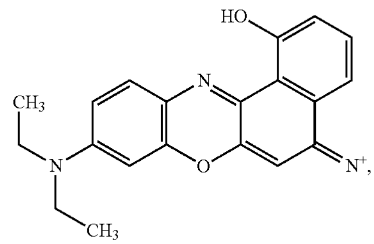 |
| LN34 | 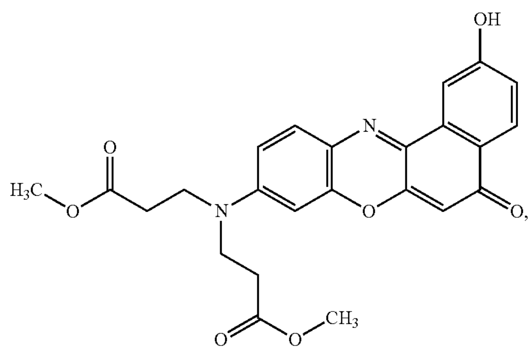 [SMILES: COC(=O)CCN(CCC(=O)OC)c1ccc2nc3c4cc(O)ccc4c(=O)cc-3oc2c1] |
| CNN16 | 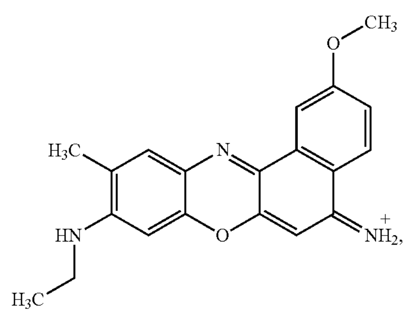 |
| CNN12 | 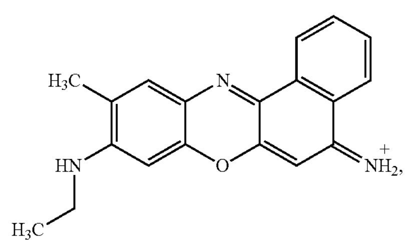 |
| CNN145 | 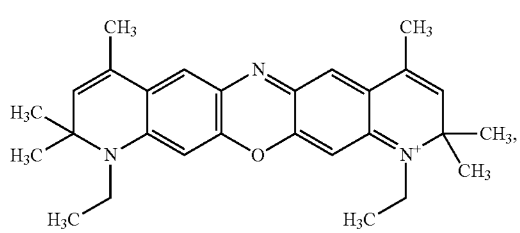 [SMILES: CCN1c2cc3c(cc2C(C)=CC1(C)C)N=c1cc2c(cc1O3)=[N+](CC)C(C)(C)C=C2C] |

-continued
| Name | Structure |
|---|---|
| ZK203 | 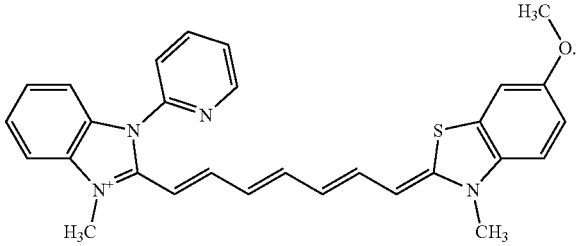 [SMILES: COc1ccc2c(c1)S\C(=C/C=C/C=C/C=C/c1n(-c3ccccn3)c3ccccc3[n+]1C)N2C] |
| ZK204 | 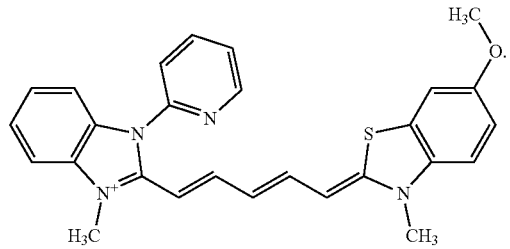 [SMILES: COc1ccc2c(c1)S\C(=C/C=C/C=C/c1n(-c3ccccn3)c3ccccc3[n+]1C)N2C] |
| ZK208 | 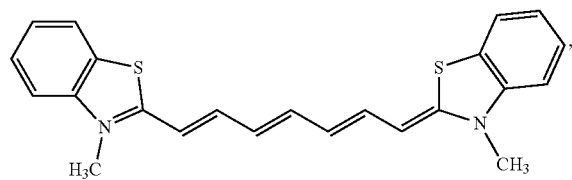 |
| ZK196 | 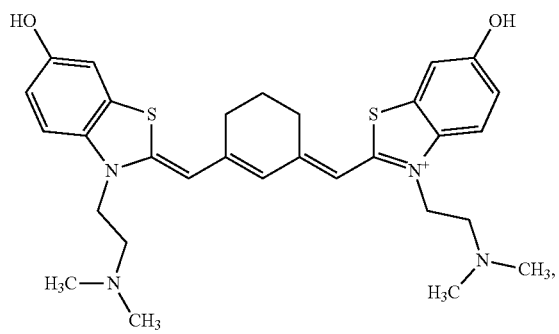 [SMILES: CN(C)CCN1/C(=C/C2=CC(=C/c3sc4cc(O)ccc4[n+]3CCN(C)C)/CCC2)Sc2cc(O)ccc21] |
| WuA67 | 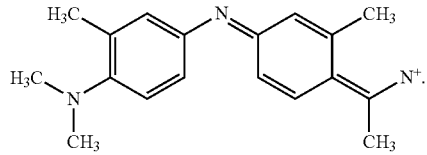 |
| WuA76 | 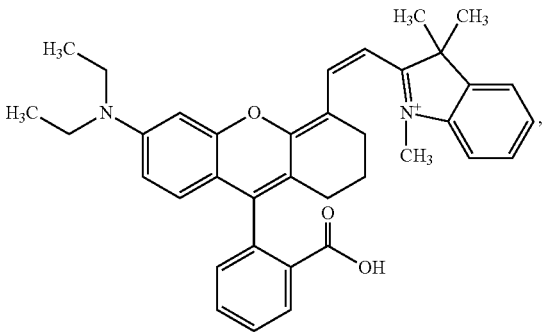 [SMILES: CCN(CC)c1ccc2c(c1)OC1=C(/C=C\C3=[N+](C)c4ccccc4C3(C)C)CCCC1=C2c1ccccc1C(=O)O] |

-continued

| Name | Structure |
|---|---|
| EAO40 | 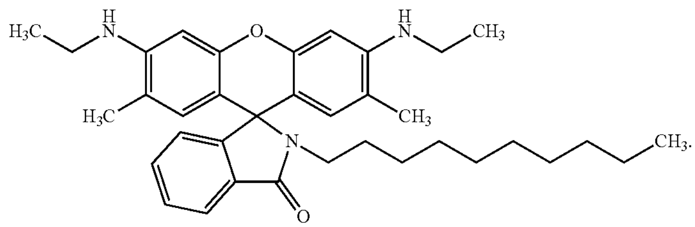 [SMILES: CCCCCCCCCCN1C(=O)c2ccccc2C12c1cc(C)c(NCC)cc1Oc1cc(NCC)c(C)cc12] |
| ZK106 | 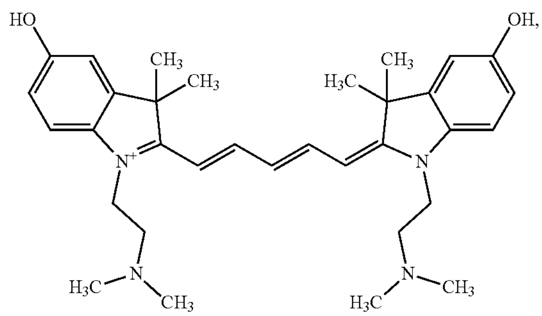 [SMILES: CN(C)CCN1/C(=C/C=C/C=C/C2=[N+](CCN(C)C)c3ccc(O)cc3C2(C)C)C(C)(C)c2cc(O)ccc21] |
| ZK124 | 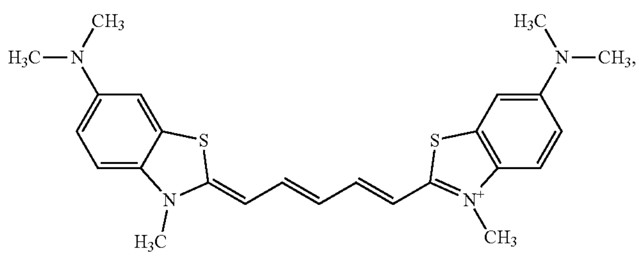 [SMILES: CN(C)c1ccc2c(c1)S\C(=C/C=C/C=C/c1sc3cc(N(C)C)ccc3[n+]1C)N2C] |
| ZK126 | 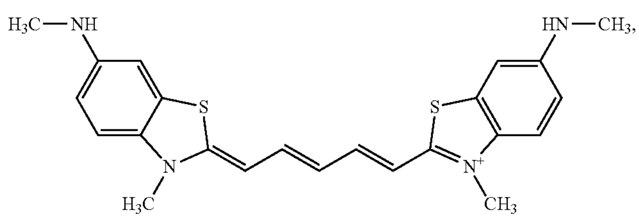 [SMILES: CNc1ccc2c(c1)S\C(=C/C=C/C=C/c1sc3cc(NC)ccc3[n+]1C)N2C] |
| ZK101 | 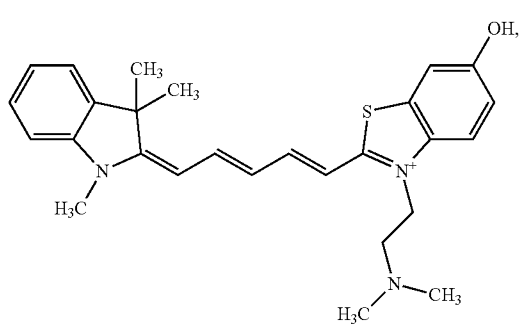 [SMILES: CN(C)CC[n+]1c(/C=C/C=C/C=C2/N(C)c3ccccc3C2(C)C)sc2cc(O)ccc21] |

-continued
| Name | Structure |
|------|-----------|
| ZK172 | 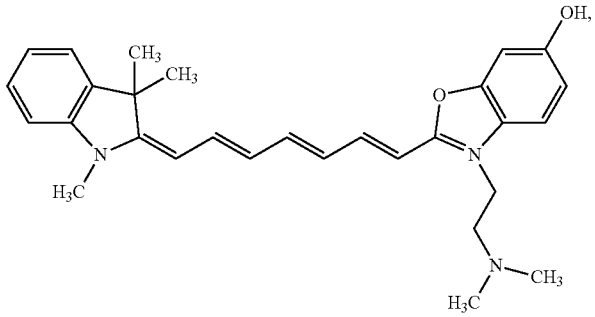 |
| TG16 | 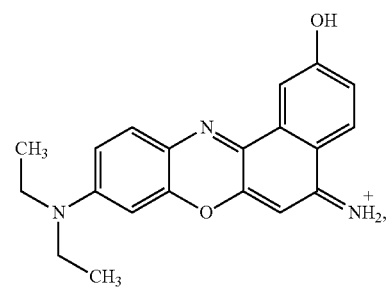 |
| MDL16 | 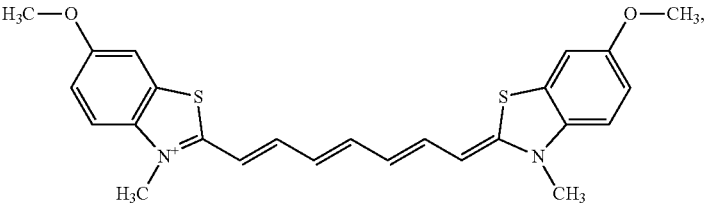 |
| CNN14 | 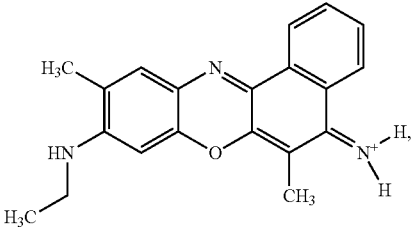 |
| LN37 | 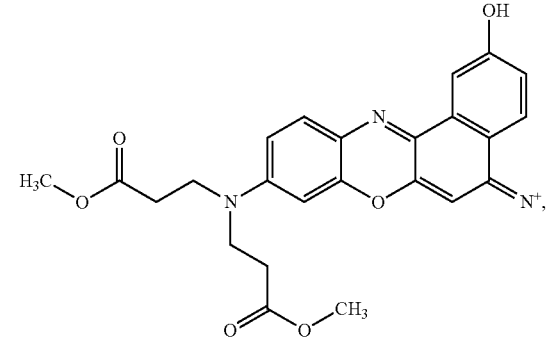 |

-continued
| Name | Structure |
|---|---|
| TG20 | 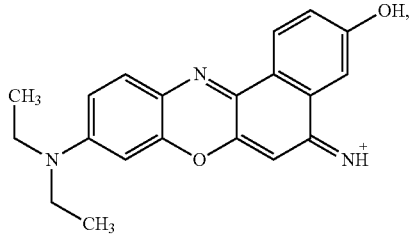 [SMILES: CCN(CC)c1ccc2nc3c4ccc(O)cc4c(=N)cc-3oc2c1] |
| LO4 | 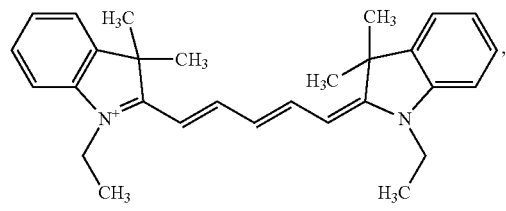 [SMILES: CCN1/C(=C/C=C/C=C/C2=[N+](CC)c3ccccc3C2(C)C)C(C)(C)c2ccccc21] |
| ZK211 | 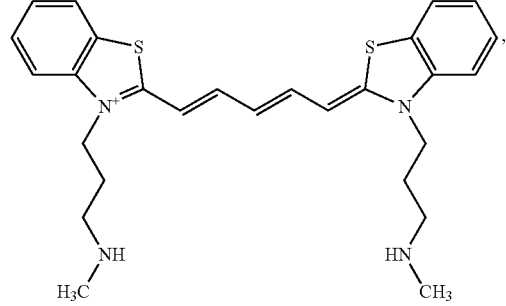 [SMILES: CNCCCN1/C(=C/C=C/C=C/c2sc3ccccc3[n+]2CCCNC)Sc2ccccc21] |
| ZK214 | 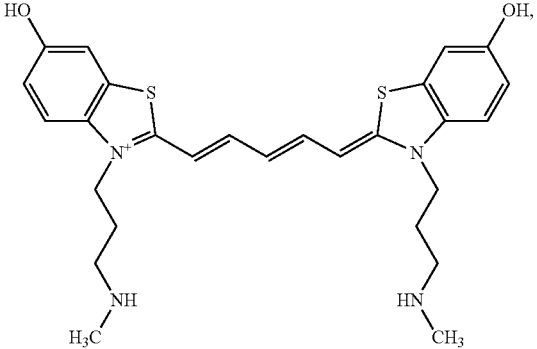 [SMILES: CNCCCN1/C(=C/C=C/C=C/c2sc3cc(O)ccc3[n+]2CCCNC)Sc2cc(O)ccc21] |
| ZK215 | 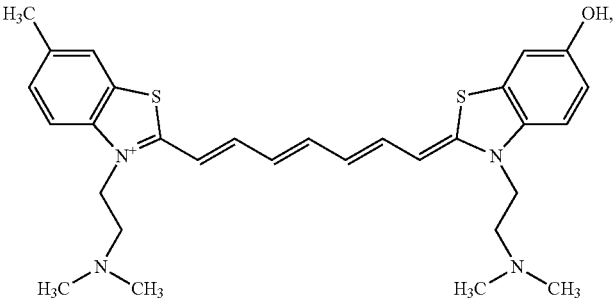 [SMILES: Cc1ccc2c(c1)sc(/C=C/C=C/C=C/C=C1\Sc3cc(O)ccc3N1CCN(C)C)[n+]2CCN(C)C] |

-continued
| Name | Structure |
|---|---|
| ZK217 | 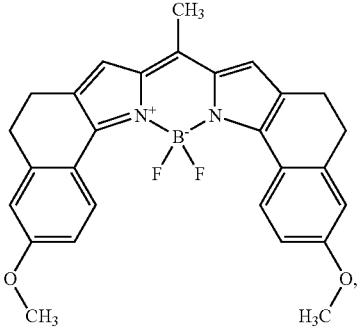 [SMILES: COc1ccc2c(c1)CCC1=CC3=C(C)c4cc5c(n4[B-](F)(F)[N+]3=C12)-c1ccc(OC)cc1CC5] |
| SRA89 | 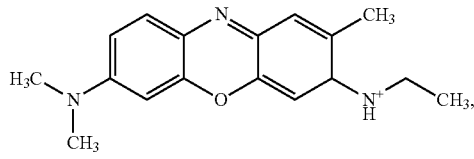 |
| YY190 | 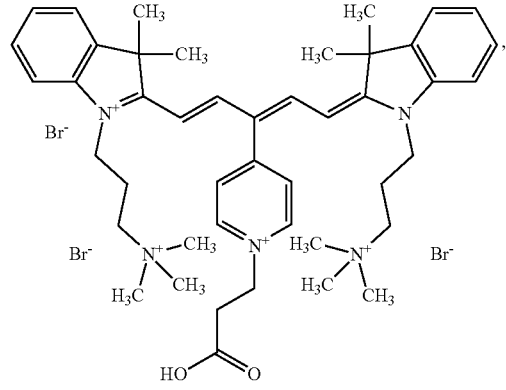 [SMILES: CC1(C)C(/C=C/C(=C/C=C2/N(CCC[N+](C)(C)C)c3ccccc3C2(C)C)c2cc[n+](CCC(=O)O)cc2)=[N+](CCC[N+](C)(C)C)c2ccccc21 ; [Br-] ; [Br-] ; [Br-]] |
| YY220 | 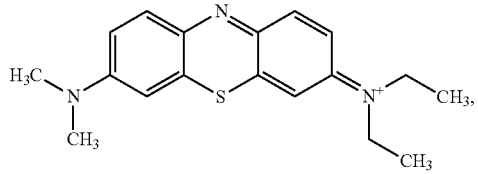 |
| YY229 | 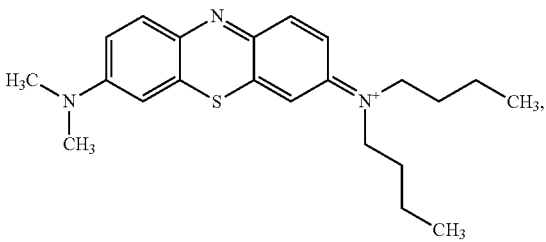 [SMILES: CCCC[N+](CCCC)=c1ccc2nc3ccc(N(C)C)cc3sc-2c1] |
| YY231 | 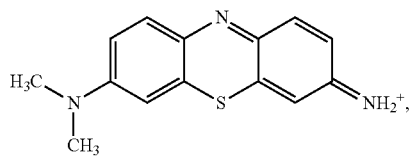 |

| Name | Structure |
|---|---|
| YY233 | 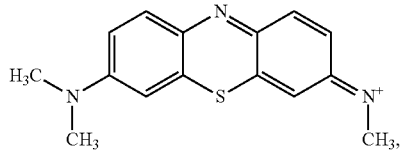 [SMILES: C/[NH+]=c1/ccc2nc3ccc(N(C)C)cc3sc-2c1] |
| YY238 | 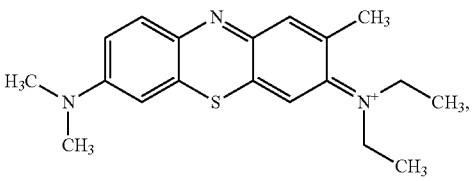 [SMILES: CC[N+](CC)=c1cc2sc3cc(N(C)C)ccc3nc-2cc1C] |
| SRA94 | 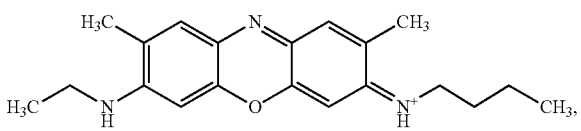 |
| PS31 | 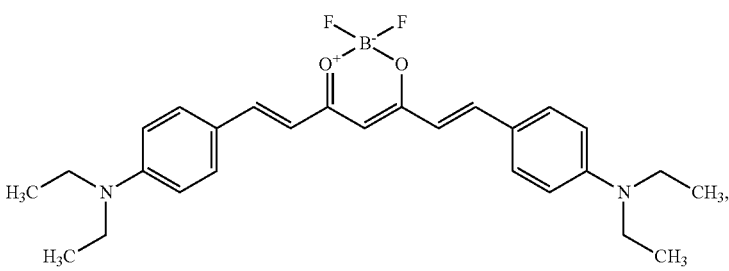 [SMILES: CCN(CC)c1ccc(/C=C/C2=CC(/C=C/c3ccc(N(CC)CC)cc3)=[O+][B-](F)(F)O2)cc1] |
| ZK239 | 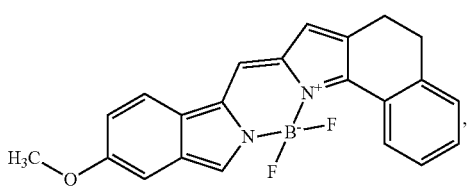 [SMILES: COc1ccc2c3n(cc2c1)[B-](F)(F)[N+]1=C2C(=CC1=C3)CCc1ccccc12] |
| AL11 | 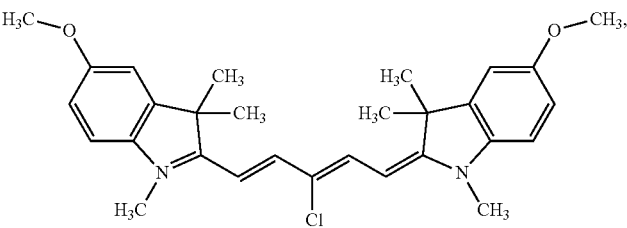 |
| AL12 | 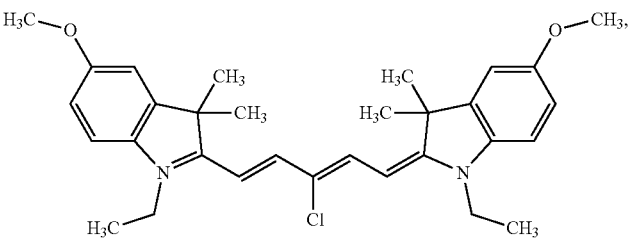 |

| Name | Structure |
|---|---|
| CMI24 | *(structure)* |
| CMI26 | *(structure)* |
| E16 | *(structure)* |
| E17 | *(structure)* |

-continued
| Name | Structure |
|---|---|
| E24 | 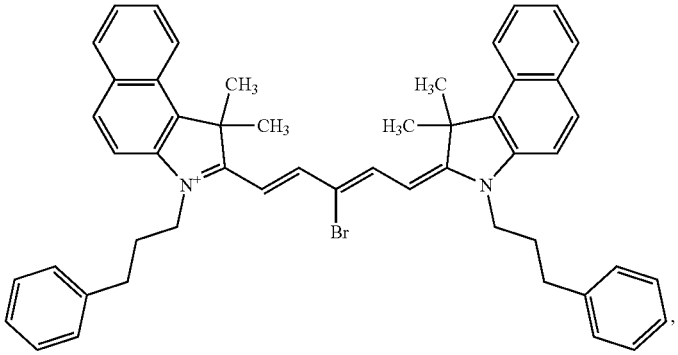 [SMILES: CC1(C)C(/C=C/C(Br)=C/C=C2/N(CCCc3ccccc3)c3ccc4ccccc4c3C2(C)C)=[N+](CCCc2ccccc2)c2ccc3ccccc3c21] |
| E27 | 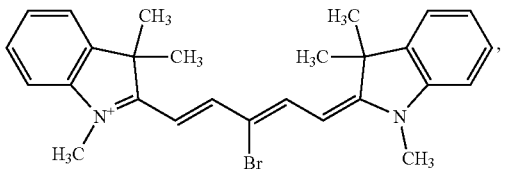 [SMILES: CN1/C(=C/C=C(Br)/C=C/C2=[N+](C)c3ccccc3C2(C)C)C(C)(C)c2ccccc21] |
| E36 | 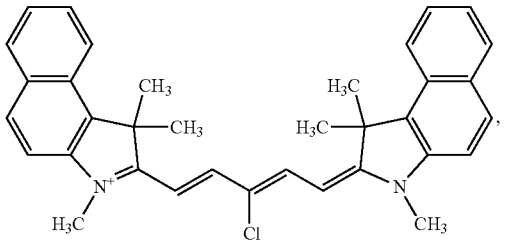 [SMILES: CN1/C(=C/C=C(Cl)/C=C/C2=[N+](C)c3ccc4ccccc4c3C2(C)C)C(C)(C)c2c1ccc1ccccc21] |
| E37 | 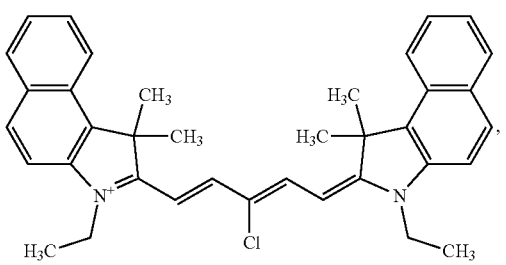 [SMILES: CCN1/C(=C/C=C(Cl)/C=C/C2=[N+](CC)c3ccc4ccccc4c3C2(C)C)C(C)(C)c2c1ccc1ccccc21] |
| E38 | 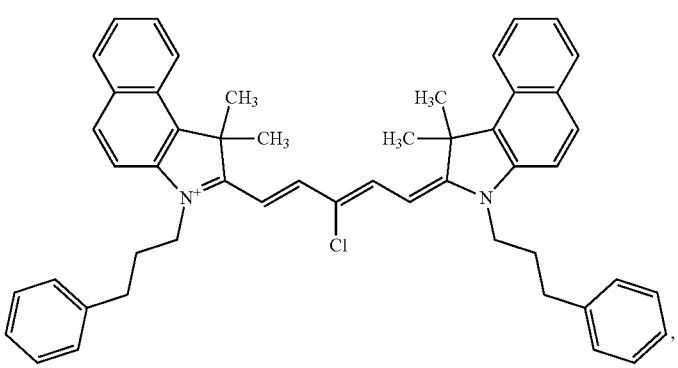 [SMILES: CC1(C)C(/C=C/C(Cl)=C/C=C2/N(CCCc3ccccc3)c3ccc4ccccc4c3C2(C)C)=[N+](CCCc2ccccc2)c2ccc3ccccc3c21] |

| Name | Structure |
|---|---|
| E39 | 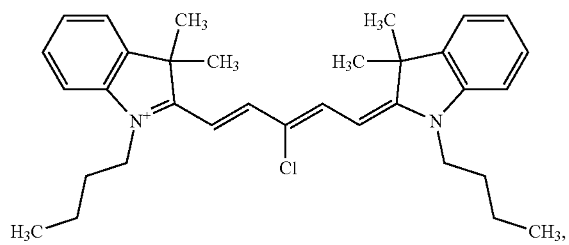 [SMILES: CCCCN1/C(=C/C=C(Cl)/C=C/C2=[N+](CCCC)c3ccccc3C2(C)C)C(C)(C)c2ccccc21] |
| E43 | 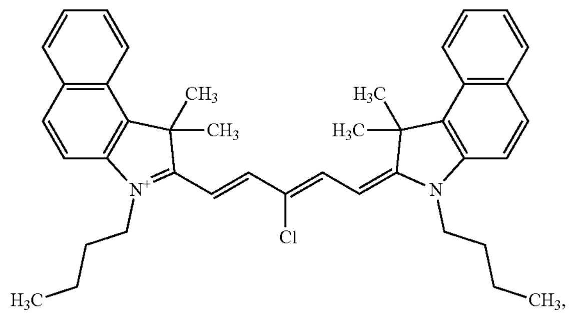 [SMILES: CCCCN1/C(=C/C=C(Cl)/C=C/C2=[N+](CCCC)c3ccc4ccccc4c3C2(C)C)C(C)(C)c2c1ccc1ccccc21] |
| E44 | 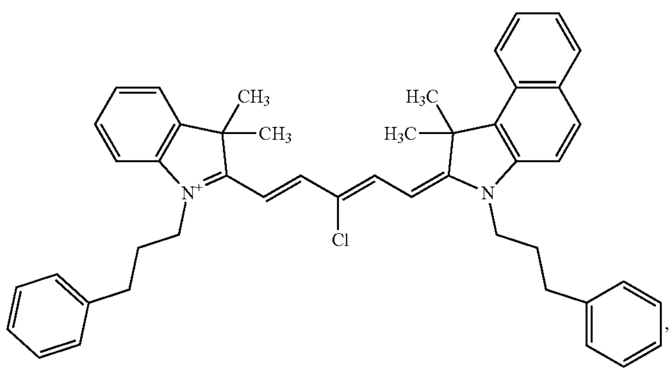 [SMILES: CC1(C)C(/C=C/C(Cl)=C/C=C2/N(CCCc3ccccc3)c3ccc4ccccc4c3C2(C)C)=[N+](CCCc2ccccc2)c2ccccc21] |
| E45 | 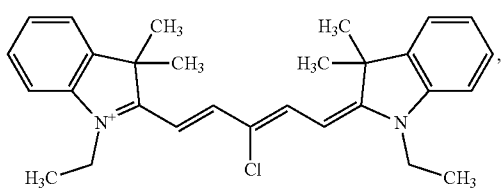 |
| E50 | 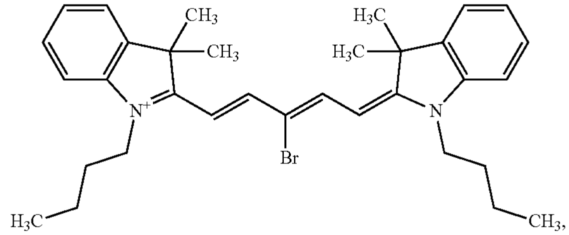 [SMILES: CCCCN1/C(=C/C=C(Br)/C=C/C2=[N+](CCCC)c3ccccc3C2(C)C)C(C)(C)c2ccccc21] |

| Name | Structure |
|---|---|
| E51 | 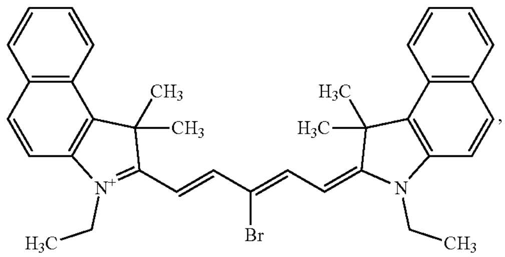 [SMILES: CCN1/C(=C/C=C(Br)/C=C/C2=[N+](CC)c3ccc4ccccc4c3C2(C)C)C(C)(C)c2c1ccc1ccccc21] |
| E77 | 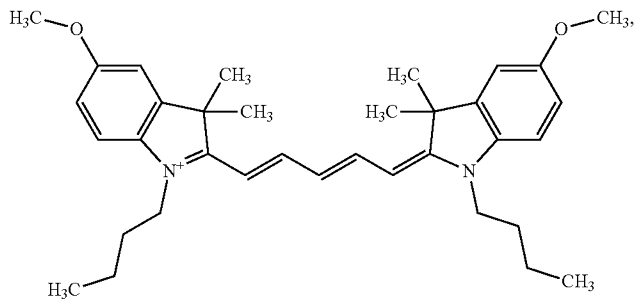 [SMILES: CCCCN1/C(=C/C=C/C=C/C2=[N+](CCCC)c3ccc(OC)cc3C2(C)C)C(C)(C)c2cc(OC)ccc21] |
| E78 | 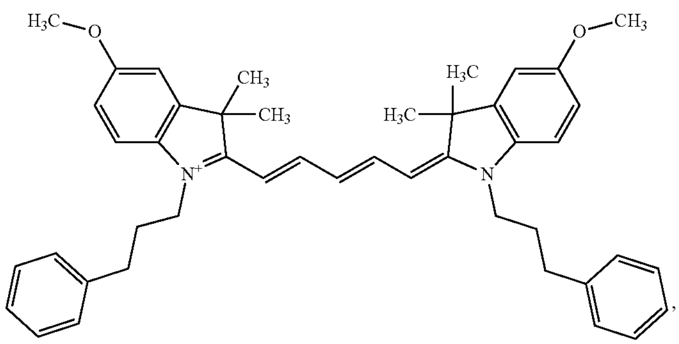 [SMILES: COc1ccc2c(c1)C(C)(C)C(/C=C/C=C/C=C1/N(CCCc3ccccc3)c3ccc(OC)cc3C1(C)C)=[N+]2CCCc1ccccc1] |
| E79 | 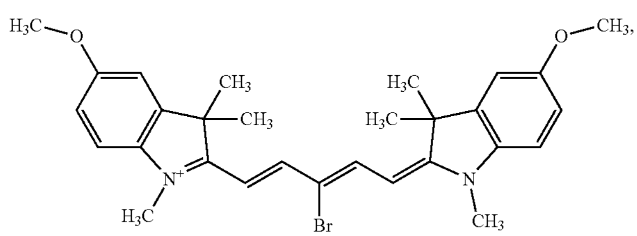 [SMILES: COc1ccc2c(c1)C(C)(C)C(/C=C/C(Br)=C/C=C1/N(C)c3ccc(OC)cc3C1(C)C)=[N+]2C] |
| E80 | 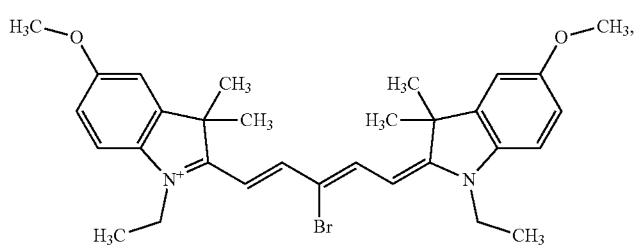 [SMILES: CCN1/C(=C/C=C(Br)/C=C/C2=[N+](CC)c3ccc(OC)cc3C2(C)C)C(C)(C)c2cc(OC)ccc21] |

-continued
| Name | Structure |
|---|---|
| E81 | 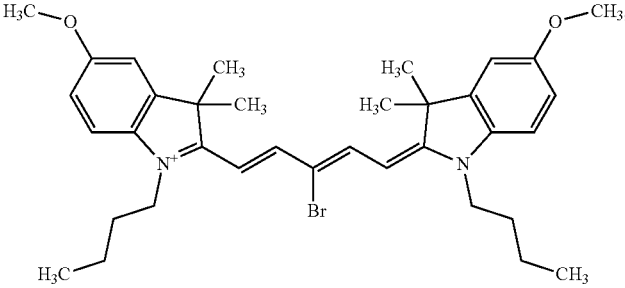 |
| ES17 | 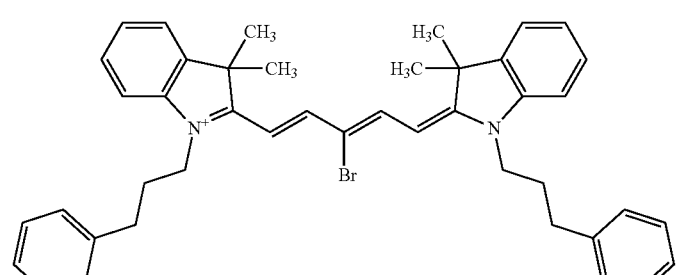 |
| ES21 | 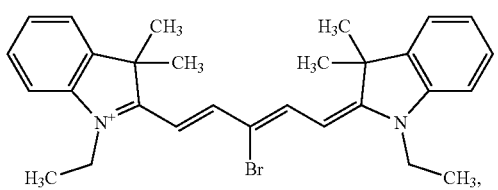 [SMILES: CCN1/C(=C/C=C(Br)/C=C/C2=[N+](CC)c3ccccc3C2(C)C)C(C)(C)c2ccccc21] |
| ESS61 | 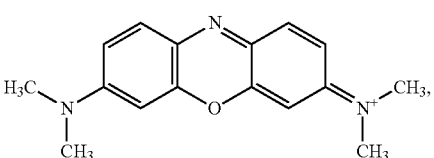 |
| LO1 | 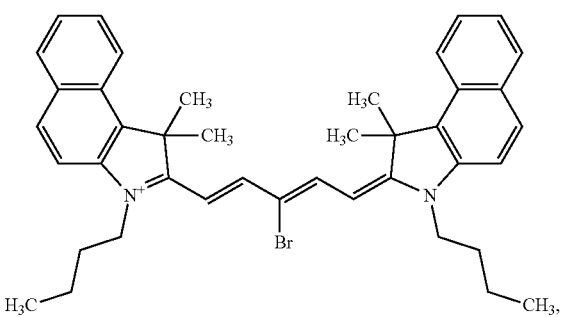 [SMILES: CCCCN1/C(=C/C=C(Br)/C=C/C2=[N+](CCCC)c3ccc4ccccc4c3C2(C)C)C(C)(C)c2c1ccc1ccccc21] |
| LO2 | 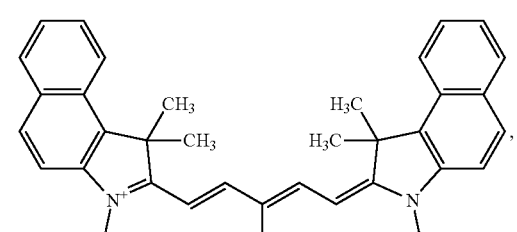 |

| Name | Structure |
|---|---|
| LO3 | 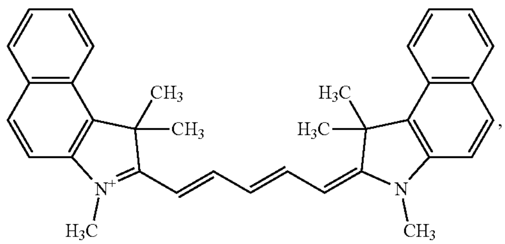 [SMILES: CN1/C(=C/C=C/C=C/C2=[N+](C)c3ccc4ccccc4c3C2(C)C)C(C)(C)c2c1ccc1ccccc21] |
| MHI106 | 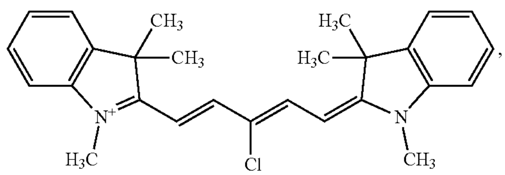 [SMILES: CN1/C(=C/C=C(Cl)/C=C/C2=[N+](C)c3ccccc3C2(C)C)C(C)(C)c2ccccc21] |
| MHI128 | 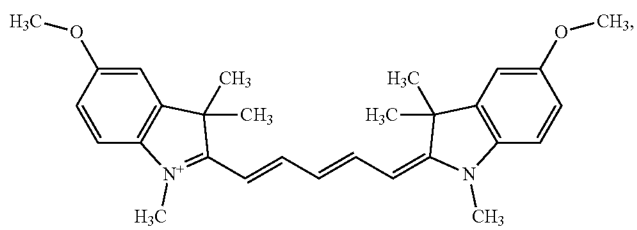 [SMILES: COc1ccc2c(c1)C(C)(C)C(/C=C/C=C/C=C1/N(C)c3ccc(OC)cc3C1(C)C)=[N+]2C] |
| MHI84 | 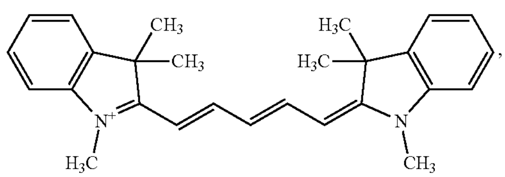 [SMILES: CN1/C(=C/C=C/C=C/C2=[N+](C)c3ccccc3C2(C)C)C(C)(C)c2ccccc21] |
| MHI86 | 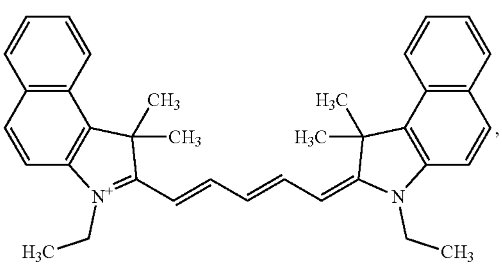 [SMILES: CCN1/C(=C/C=C/C=C/C2=[N+](CC)c3ccc4ccccc4c3C2(C)C)C(C)(C)c2c1ccc1ccccc21] |
| MHI96 | 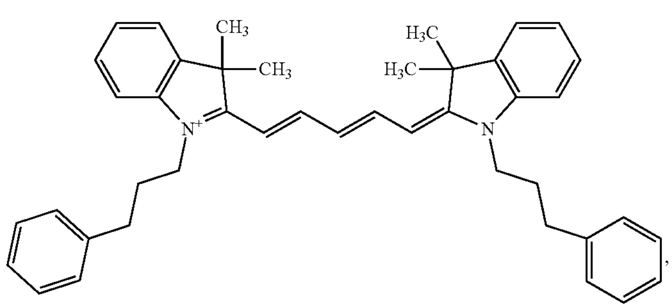 [SMILES: CC1(C)C(/C=C/C=C/C=C2/N(CCCc3ccccc3)c3ccccc3C2(C)C)=[N+](CCCc2ccccc2)c2ccccc21] |

-continued

| Name | Structure |
|------|-----------|
| MHI97 | 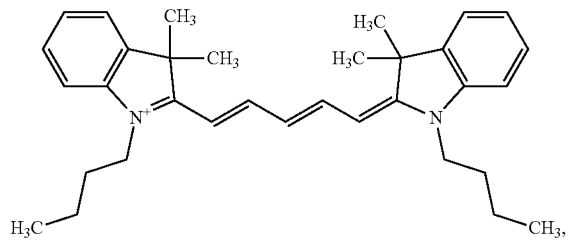 [SMILES: CCCCN1/C(=C/C=C/C=C/C2=[N+](CCCC)c3ccccc3C2(C)C)C(C)(C)c2ccccc21] |
| P700H | 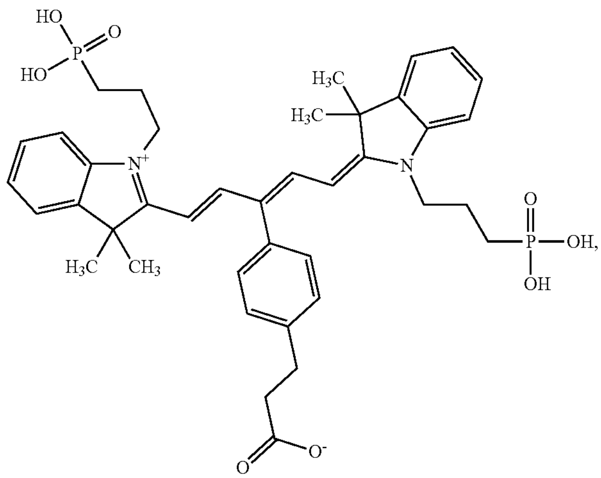 [SMILES: CC1(C)C(/C=C/C(=C/C=C2/N(CCCP(=O)(O)O)c3ccccc3C2(C)C)c2ccc(CCC(=O)[O-])cc2)=[N+](CCCP(=O)(O)O)c2ccccc21] |
| P700SO3 | 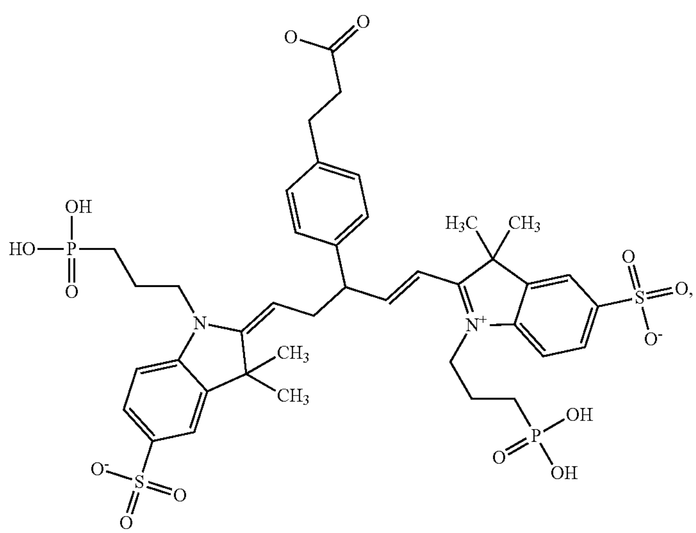 [SMILES: CC1(C)C(/C=C/C(C/C=C2/N(CCCP(=O)(O)O)c3ccc(S(=O)(=O)[O-])cc3C2(C)C)c2ccc(CCC(=O)O)cc2)=[N+](CCCP(=O)(O)O)c2ccc(S(=O)(=O)[O-])cc21] |
| P800H | 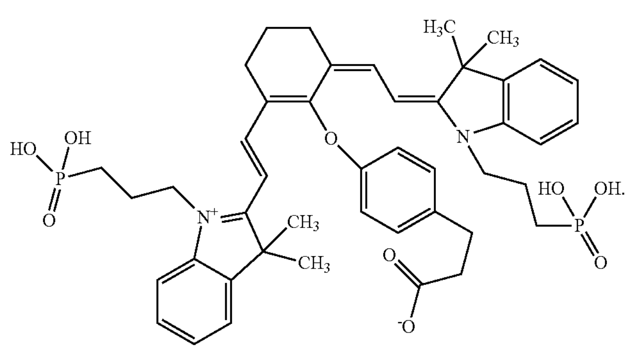 |

-continued
| Name | Structure |
|---|---|
| P800SO3 | 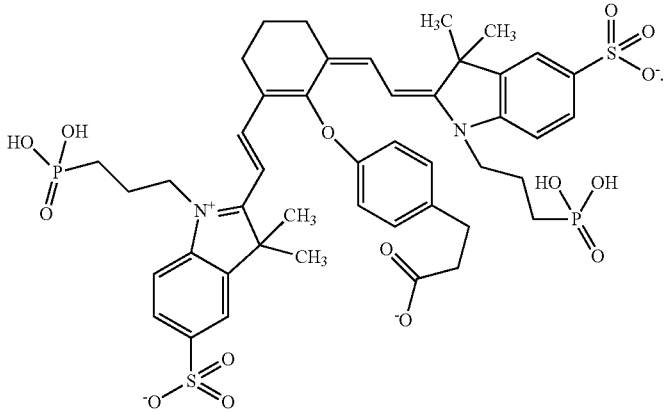 |
| T14 | 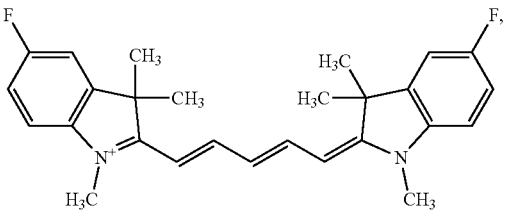 |
| T17 | 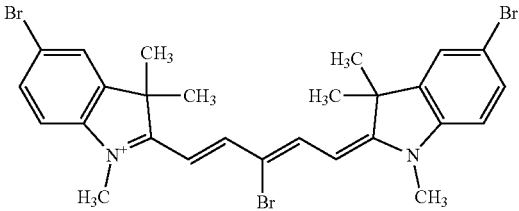 |
| T18 | 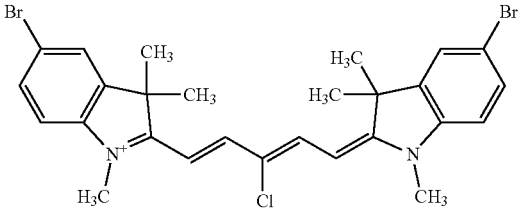 [SMILES: CN1/C(=C/C=C(Cl)/C=C/C2=[N+](C)c3ccc(Cl)cc3C2(C)C)C(C)(C)c2cc(Cl)ccc21] |
| T20 | 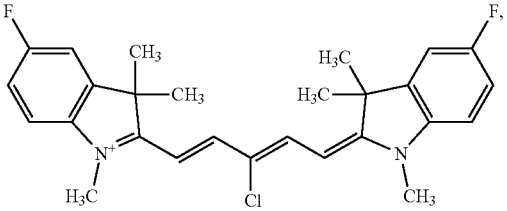 |
| T23 | 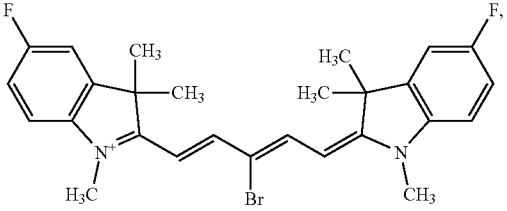 |

| Name | Structure |
|---|---|
| T24 | (chemical structure) |
| T25 | (chemical structure) |
| T27 | (chemical structure) |
| T29 | (chemical structure) |
| A20 | (chemical structure) |
| A21 | (chemical structure) |

| Name | Structure |
|---|---|
| A80 | 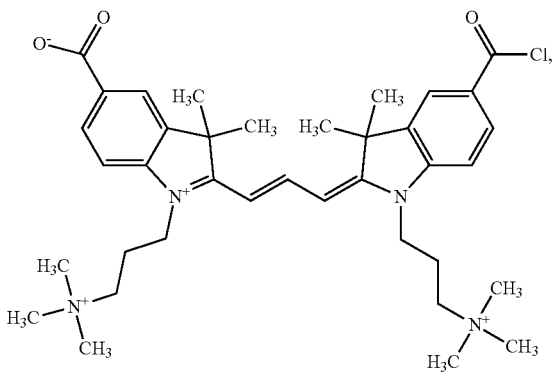 [SMILES: CC1(C)C(/C=C/C=C2/N(CCC[N+](C)(C)C)c3ccc(C(=O)Cl)cc3C2(C)C)=[N+](CCC[N+](C)(C)C)c2ccc(C(=O)[O-])cc21] |
| A100 | 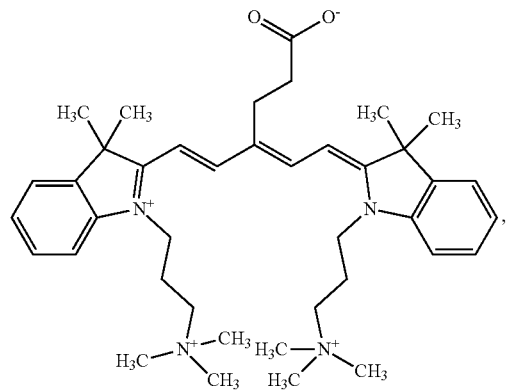 |
| A104 | 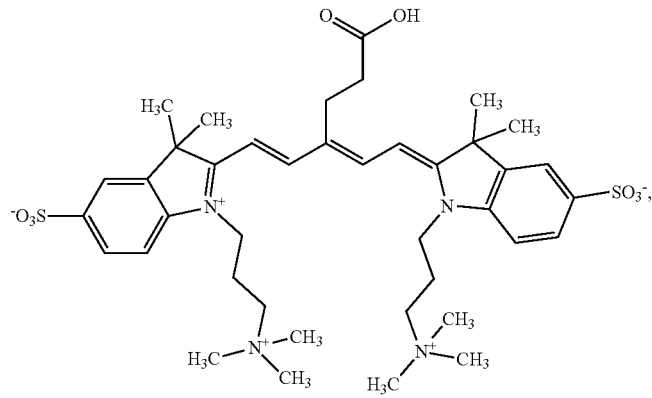 |
| A106 | 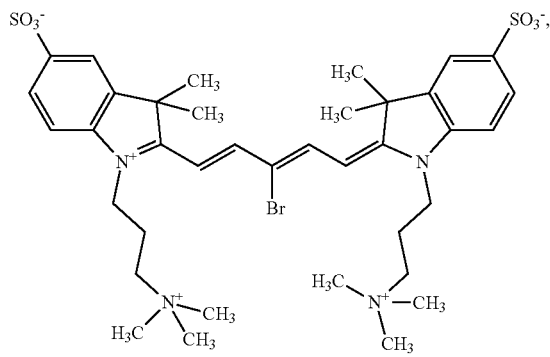 |

-continued
| Name | Structure |
|---|---|
| A134 | 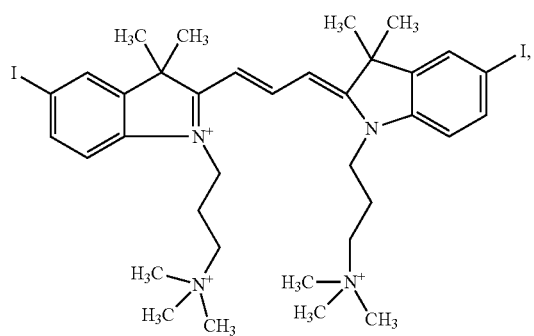 [SMILES: CC1(C)C(/C=C/C=C2\N(CCC[N+](C)(C)C)c3ccc(I)cc3C2(C)C)=[N+](CCC[N+](C)(C)C)c2ccc(I)cc21] |
| A138 | 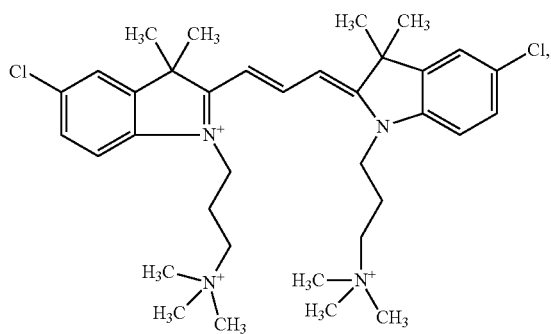 [SMILES: CC1(C)C(/C=C/C=C2\N(CCC[N+](C)(C)C)c3ccc(Cl)cc3C2(C)C)=[N+](CCC[N+](C)(C)C)c2ccc(Cl)cc21] |
| A146 | 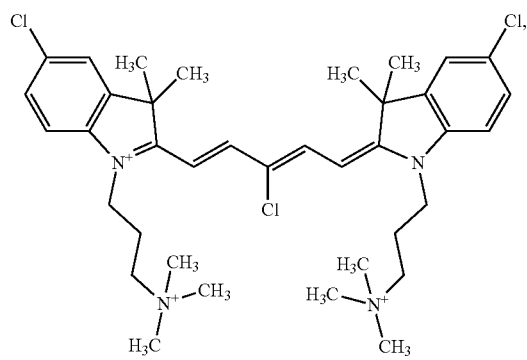 [SMILES: CC1(C)C(/C=C/C(Cl)=C/C=C2/N(CCC[N+](C)(C)C)c3ccc(Cl)cc3C2(C)C)=[N+](CCC[N+](C)(C)C)c2ccc(Cl)cc21] |
| A148 | 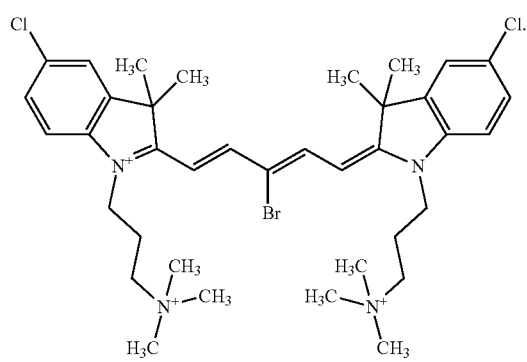 [SMILES: CC1(C)C(/C=C/C(Br)=C/C=C2/N(CCC[N+](C)(C)C)c3ccc(Cl)cc3C2(C)C)=[N+](CCC[N+](C)(C)C)c2ccc(Cl)cc21] |

-continued

| Name | Structure |
|---|---|
| A149 | 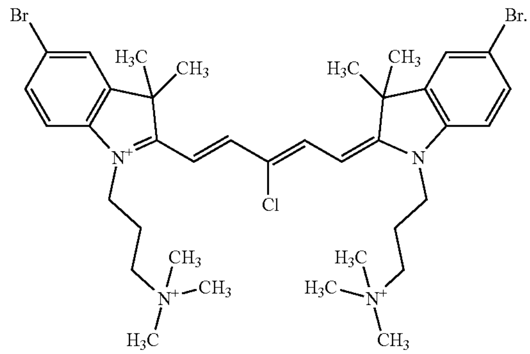 |
| A150 | 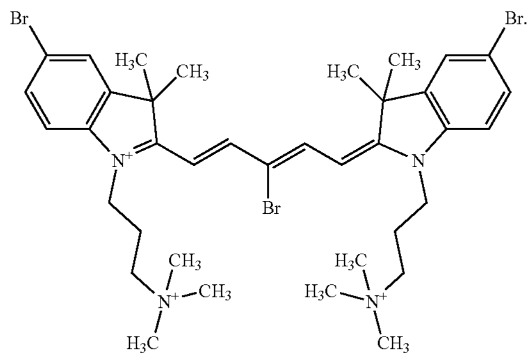 [SMILES: CC1(C)C(/C=C/C(Br)=C/C=C2/N(CCC[N+](C)(C)C)c3ccc(Br)cc3C2(C)C)=[N+](CCC[N+](C)(C)C)c2ccc(Br)cc21] |
| A160 | 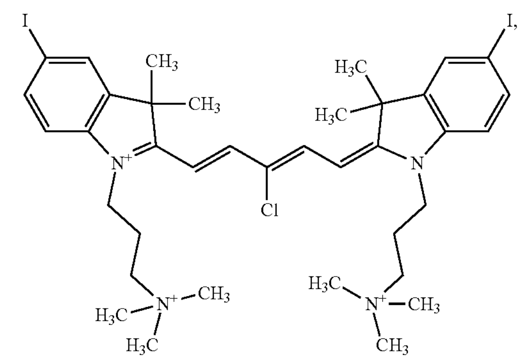 [SMILES: CC1(C)C(/C=C/C(Cl)=C/C=C2/N(CCC[N+](C)(C)C)c3ccc(I)cc3C2(C)C)=[N+](CCC[N+](C)(C)C)c2ccc(I)cc21] |
| A161 | 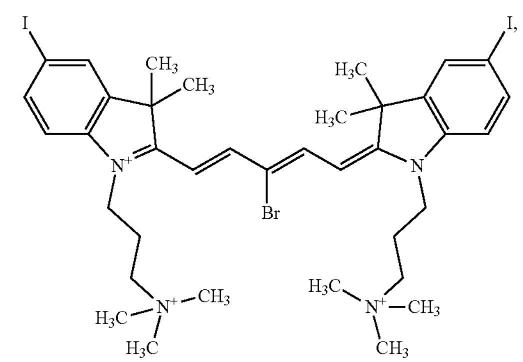 [SMILES: CC1(C)C(/C=C/C(Br)=C/C=C2/N(CCC[N+](C)(C)C)c3ccc(I)cc3C2(C)C)=[N+](CCC[N+](C)(C)C)c2ccc(I)cc21] |

-continued
| Name | Structure |
|---|---|
| A24 | 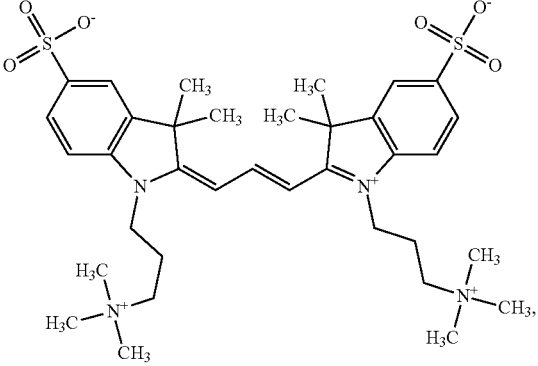 [SMILES: CC1(C)C(/C=C/C=C2/N(CCC[N+](C)(C)C)c3ccc(S(=O)(=O)[O-])cc3C2(C)C)=[N+](CCC[N+](C)(C)C)c2ccc(S(=O)(=O)[O-])cc21] |
| AC2 | 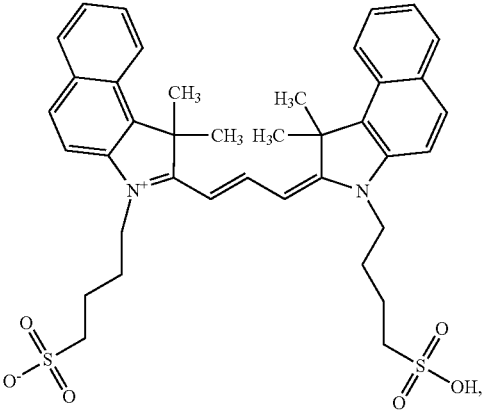 [SMILES: CC1(C)C(/C=C/C=C2/N(CCCCS(=O)(=O)O)c3ccc4ccccc4c3C2(C)C)=[N+](CCCCS(=O)(=O)[O-])c2ccc3ccccc3c21] |
| AC3 | 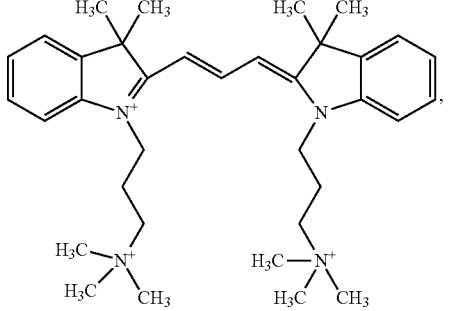 [SMILES: CC1(C)C(/C=C/C=C2\N(CCC[N+](C)(C)C)c3ccccc3C2(C)C)=[N+](CCC[N+](C)(C)C)c2ccccc21] |
| AC8 | 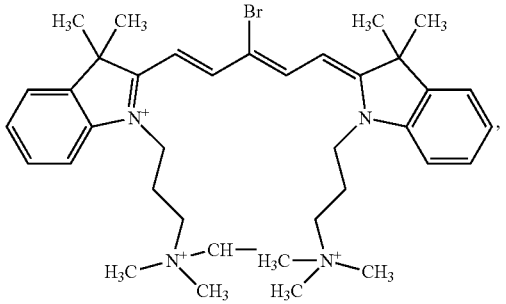 [SMILES: CC[N+](C)(C)CCC[N+]1=C(/C=C/C(Br)=C/C=C2\N(CCC[N+](C)(C)C)c3ccccc3C2(C)C)C(C)(C)c2ccccc21] |

-continued

| Name | Structure |
|------|-----------|
| AN3 | 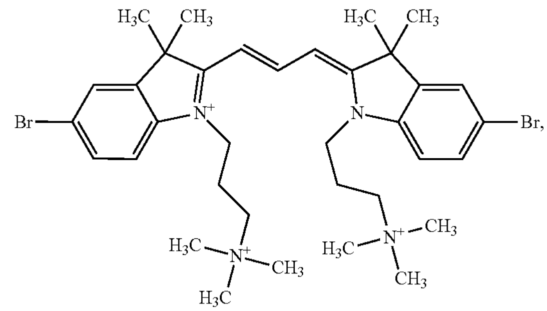 [SMILES: CC1(C)C(/C=C/C=C2\N(CCC[N+](C)(C)C)c3ccc(Br)cc3C2(C)C)=[N+](CCC[N+](C)(C)C)c2ccc(Br)cc21] |
| WuA96 | 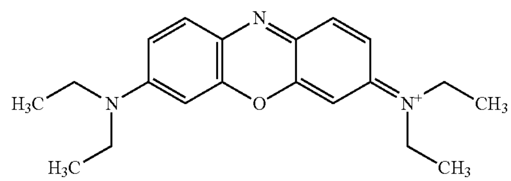 [SMILES: CCN(CC)c1ccc2nc3ccc(=[N+](CC)CC)cc-3oc2c1] |
| Ox4 | 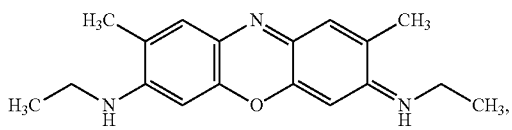 [SMILES: CC/N=c1/cc2oc3cc(NCC)c(C)cc3nc-2cc1C] |
| Ox170 | 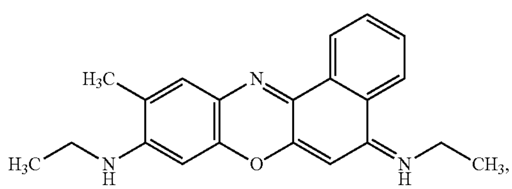 [SMILES: CC/N=c1/cc2oc3cc(NCC)c(C)cc3nc-2c2ccccc12] |
| Ox750 | 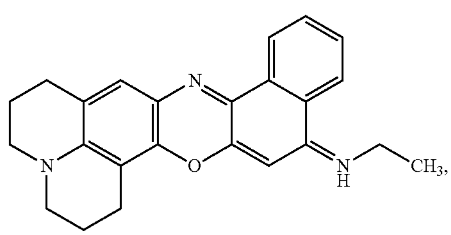 [SMILES: CC/N=c1/cc2oc3c4c5c(cc3nc-2c2ccccc12)CCCN5CCC4] |
| Rh800 | 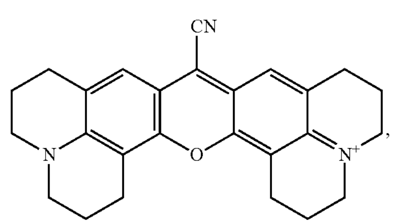 |

| Name | Structure |
|---|---|
| TG66 | 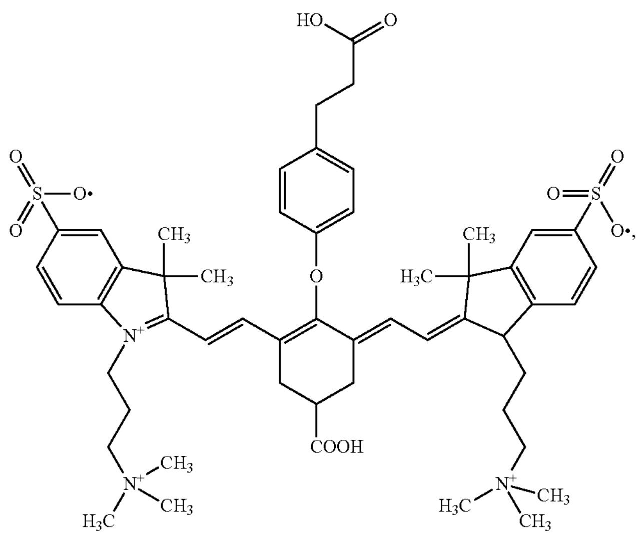 |
| MM25 | 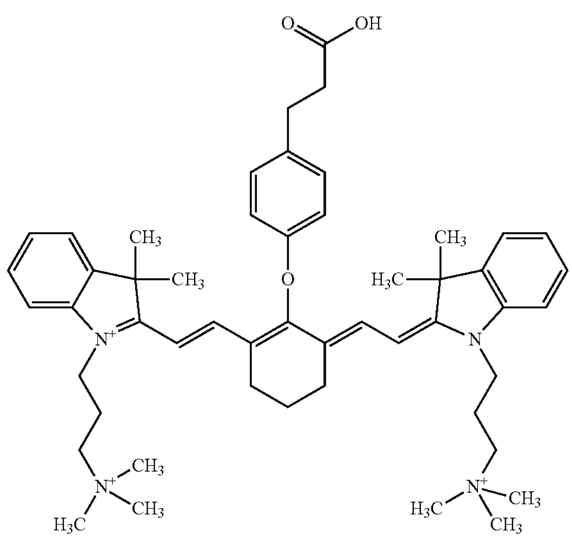 [SMILES: CC1(C)C(/C=C/C2=C(Oc3ccc(CCC(=O)O)cc3)C(=C/C=C3/N(CCC[N+](C)(C)C)c4ccccc4C3(C)C)/CCC2)=[N+](CCC[N+](C)(C)C)c2ccccc21] |
| SP72 | 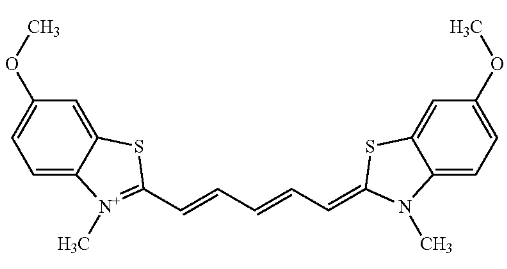 [SMILES: COc1ccc2c(c1)S\C(=C/C=C/C=C/c1sc3cc(OC)ccc3[n+]1C)N2C] |

-continued
| Name | Structure |
|---|---|
| ZK138-2 | 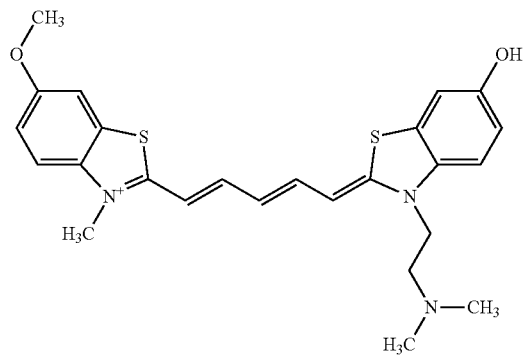 [SMILES: COc1ccc2c(c1)sc(/C=C/C=C/C=C1\Sc3cc(O)ccc3N1CCN(C)C)[n+]2C] |
| ZK169 | 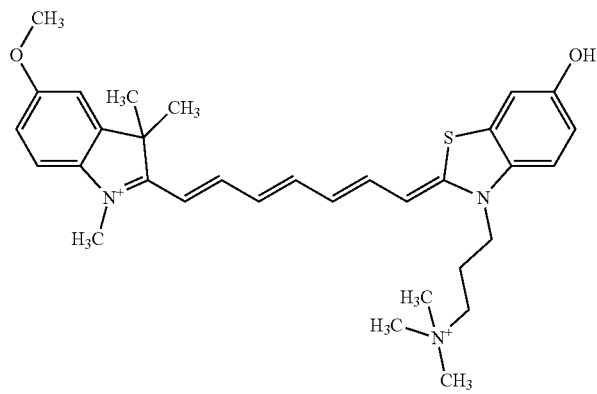 [SMILES: COc1ccc2c(c1)C(C)(C)C(/C=C/C=C/C=C/C=C1\Sc3cc(O)ccc3N1CCC[N+](C)(C)C)=[N+]2C] |
| ZW800-1 | 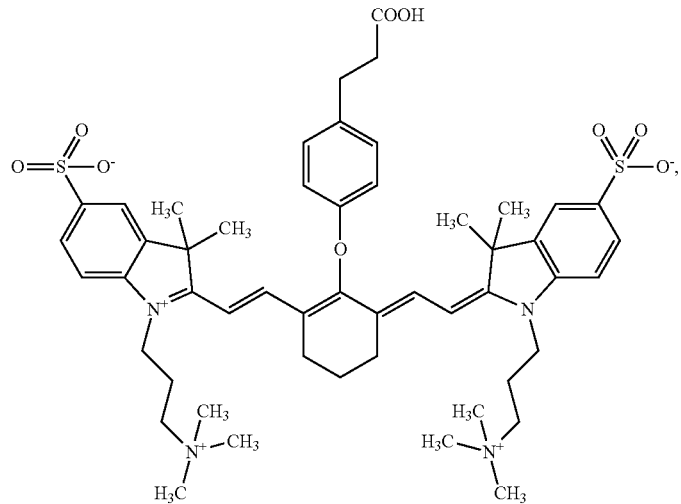 |

-continued

| Name | Structure |
|---|---|
| A64 | 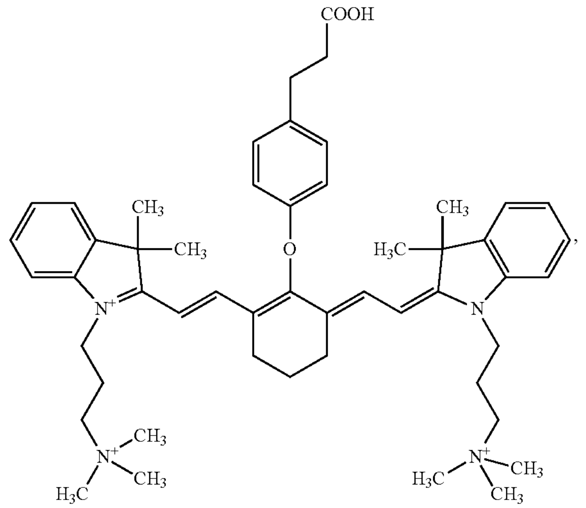 [SMILES: CC1(C)C(/C=C/C2=C(Oc3ccc(CCC(=O)O)cc3)C(=C/C=C3/N(CCC[N+](C)(C)C)c4ccccc4C3(C)C)/CCC2)=[N+](CCC[N+](C)(C)C)c2ccccc21] |
| MHI85 | 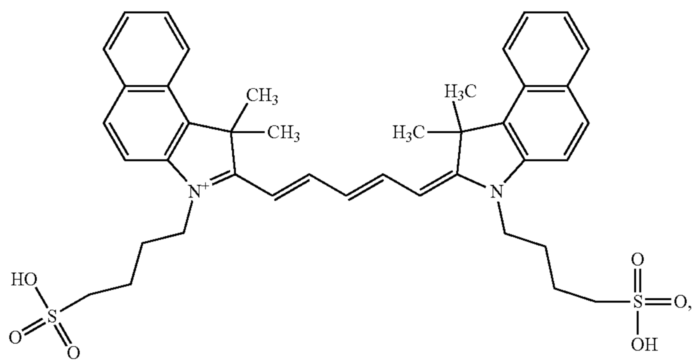 [SMILES: CC1(C)C(/C=C/C=C/C=C2/N(CCCCS(=O)(=O)O)c3ccc4ccccc4c3C2(C)C)=[N+](CCCCS(=O)(=O)O)c2ccc3ccccc3c21] |
| SP66 | 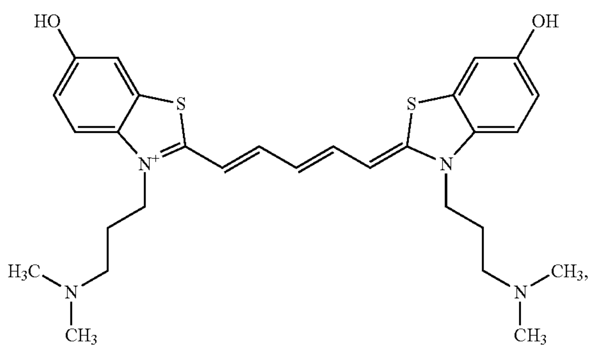 [SMILES: CN(C)CCCN1/C(=C/C=C/C=C/c2sc3cc(O)ccc3[n+]2CCCN(C)C)Sc2cc(O)ccc21] |
| YY113 | 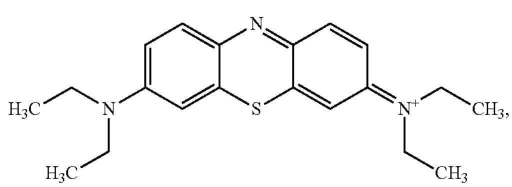 [SMILES: CCN(CC)c1ccc2nc3ccc(=[N+](CC)CC)cc-3sc2c1] |
| YY142 | 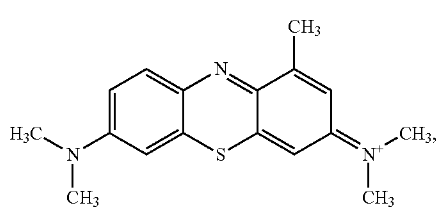 [SMILES: Cc1cc(=[N+](C)C)cc2sc3cc(N(C)C)ccc3nc1-2] |

-continued
| Name | Structure |
|---|---|
| PS37 | 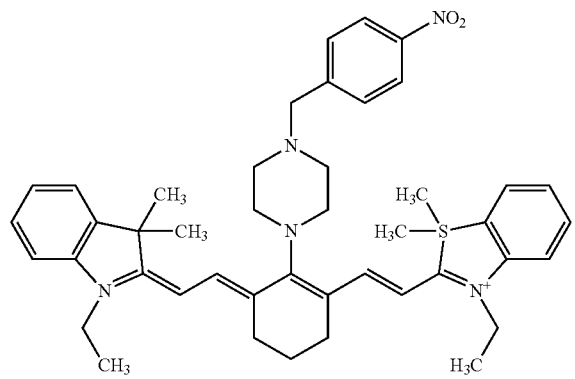 |
| PS53 | 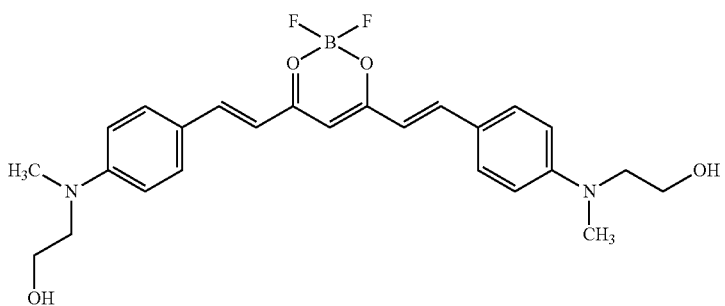 |
| ZK240 | 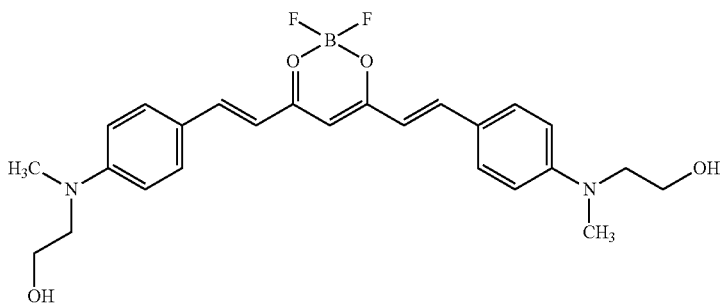 |
| ZK244 | 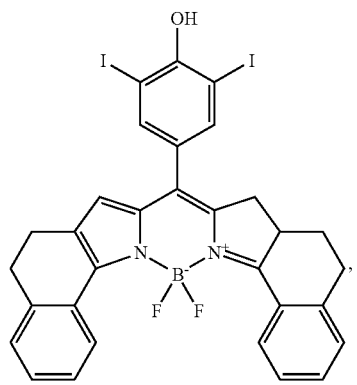 [SMILES: Oc1c(I)cc(C2=C3CC4CCc5ccccc5C4=[N+]3[B-](F)(F)n3c2cc2c3-c3ccccc3CC2)cc1I] |

-continued

| Name | Structure |
|---|---|
| EAO72 | 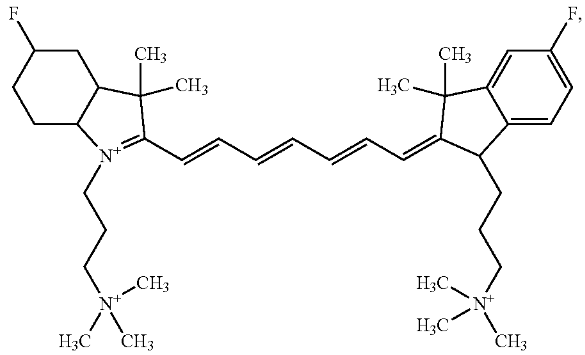 [SMILES: CC1(C)\C(=C/C=C/C=C/C=C/C2=[N+](CCC[N+](C)(C)C)C3CCC(F)CC3C2(C)C)C(CCC[N+](C)(C)C)c2ccc(F)cc21] |
| EAO76 | 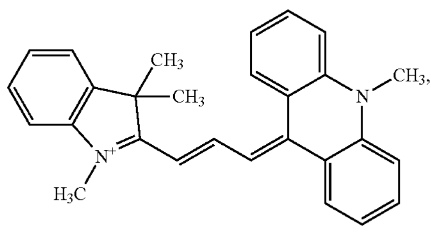 [SMILES: CN1c2ccccc2C(=C/C=C/C2=[N+](C)c3ccccc3C2(C)C)c2ccccc21] |
| PS101A | 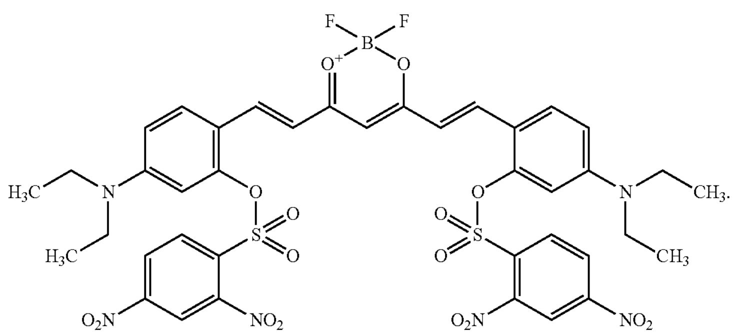 |
| PS35 | 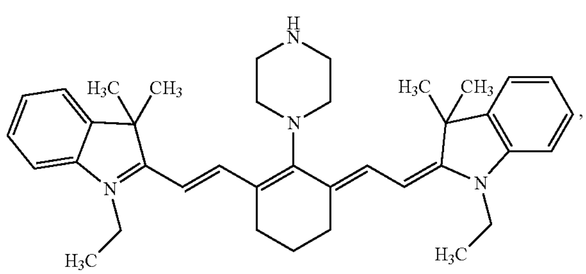 |
| PS36 | 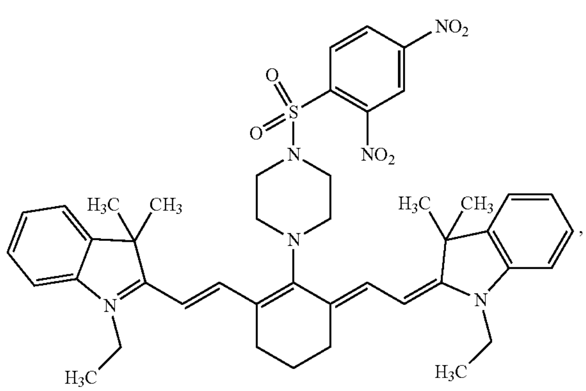 |

-continued
| Name | Structure |
|---|---|
| PS39 | 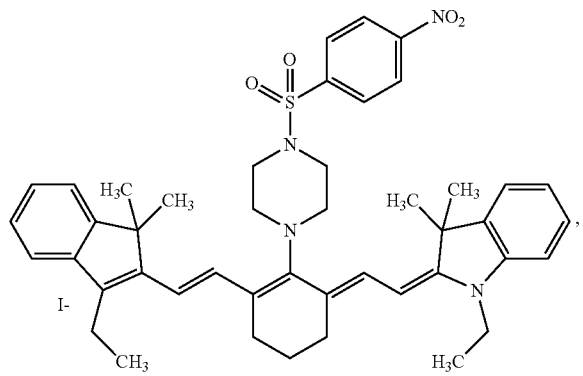 [SMILES: CCC1=C(/C=C/C2=C(N3CCN(S(=O)(=O)c4ccc([N+](=O)[O-])cc4)CC3)C(=C/C=C3/N(CC)c4ccccc4C3(C)C)/CCC2)C(C)(C)c2ccccc21 ; [I-]] |
| PS51 | 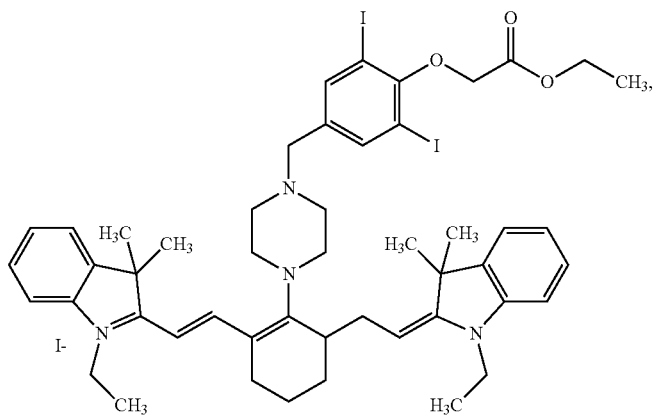 |
| PS52 | 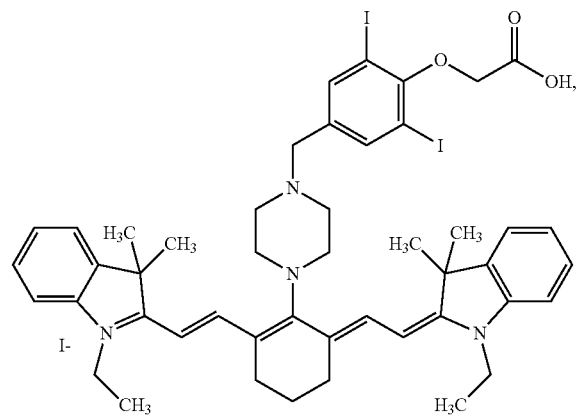 |
| PS62 | 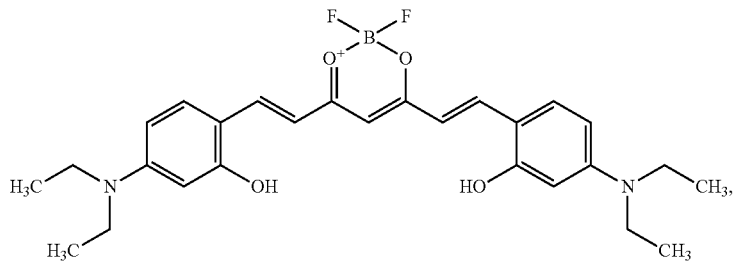 |

| Name | Structure |
|---|---|
| PS73 | 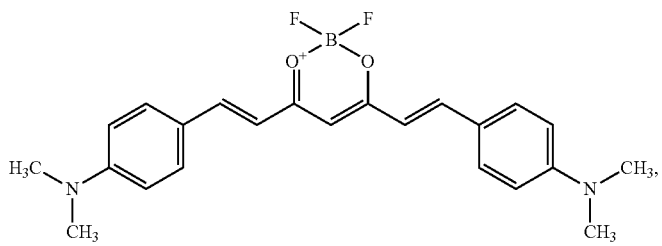 |
| PS76 | 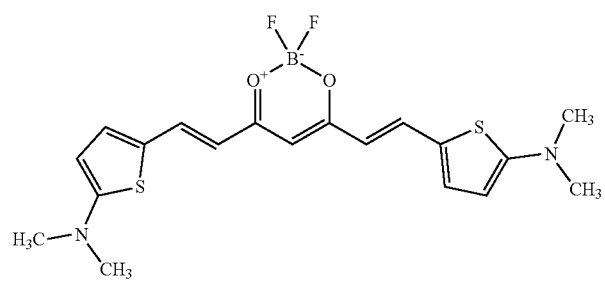 |
| YY255 | 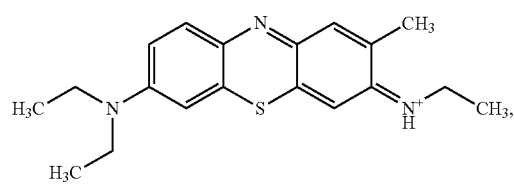 |
| YY260 | 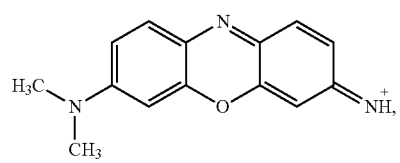 [SMILES: CN(C)c1ccc2nc3ccc(=N)cc-3oc2c1] |
| YY261 | 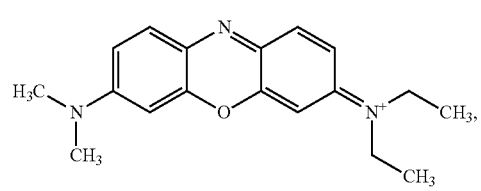 |
| YY269 | 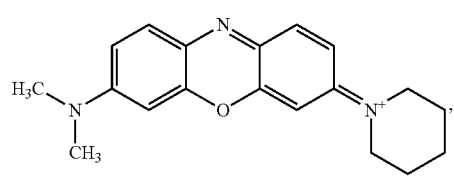 [SMILES: CN(C)c1ccc2nc3ccc(=[N+]4CCCCC4)cc-3oc2c1] |

-continued
| Name | Structure |
|---|---|
| ZK243 | 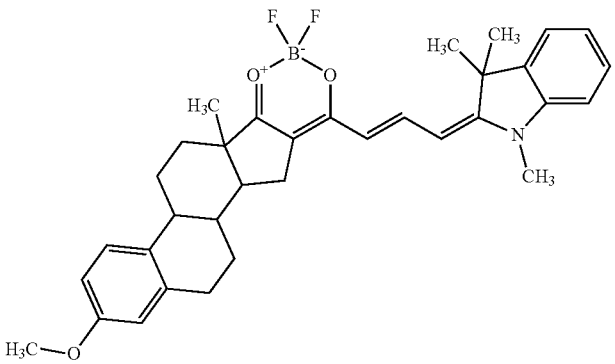 [SMILES: COc1ccc2c(c1)CCC1C2CCC2(C)C3=[O+][B-](F)(F)OC(/C=C/C=C4/N(C)c5ccccc5C4(C)C)=C3CC12] |
| ZK2515 | 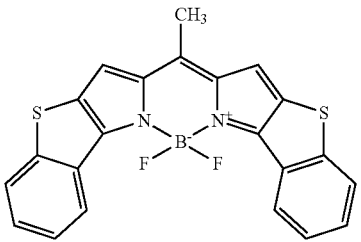 [SMILES: CC1=C2C=c3sc4ccccc4c3=[N+]2[B-](F)(F)n2c1cc1sc3ccccc3c12] |
| ZK2525 | 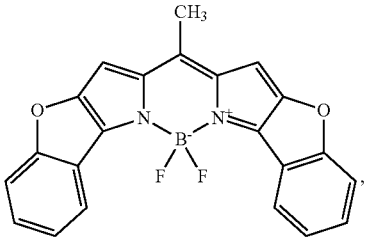 [SMILES: CC1=C2C=c3oc4ccccc4c3=[N+]2[B-](F)(F)n2c1cc1oc3ccccc3c12] |
| ZK2565 | 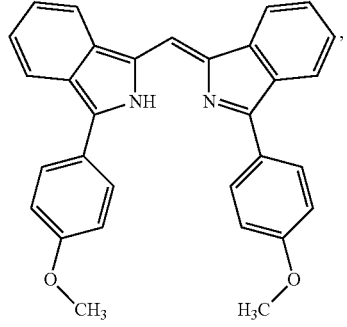 [SMILES: COc1ccc(C2=N/C(=C\c3[nH]c(-c4ccc(OC)cc4)c4ccccc34)c3ccccc32)cc1] |
| ZK2566 | 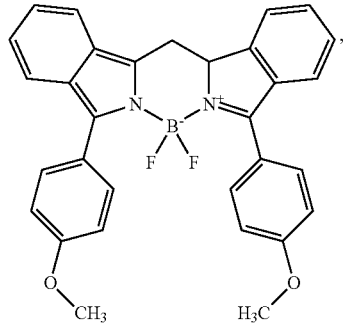 [SMILES: COc1ccc(C2=[N+]3C(Cc4c5ccccc5c(-c5ccc(OC)cc5)n4[B-]3(F)F)c3ccccc32)cc1] |

-continued
| Name | Structure |
|---|---|
| ZK258 | 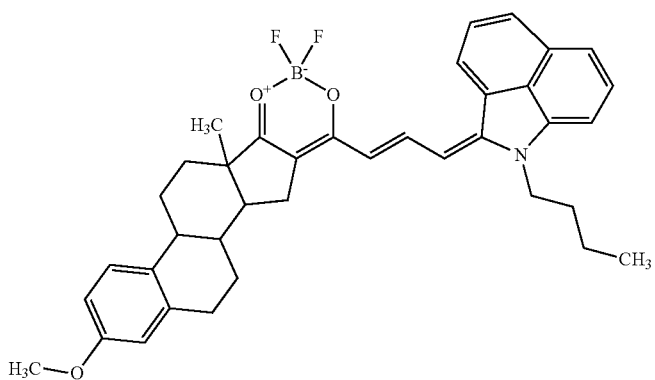 [SMILES: CCCCn1/c(=C/C=C/C2=C3CC4C5CCc6cc(OC)ccc6C5CCC4(C)C3=[O+][B-](F)(F)O2)c2cccc3cccc1c32] |
| ZK2615 | 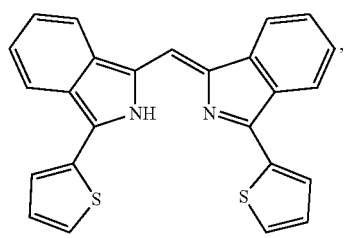 [SMILES: C(=C1/N=C(c2cccs2)c2ccccc21)/c1[nH]c(-c2cccs2)c2ccccc12] |
| A71-NHS | 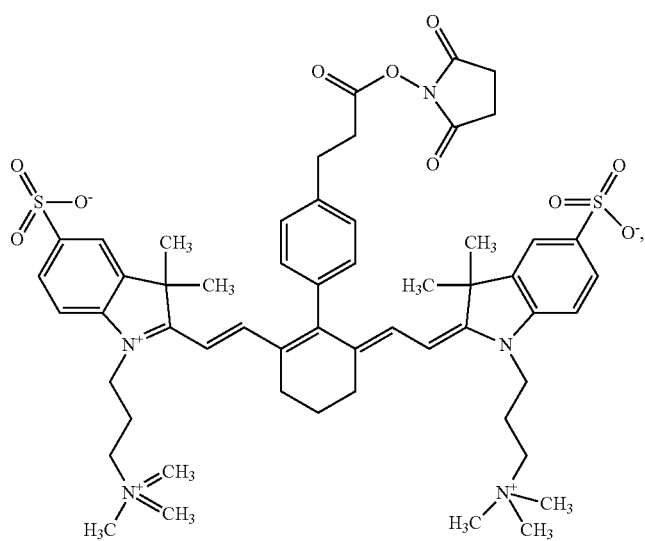 |

-continued
| Name | Structure |
|---|---|
| LN15-NHS | 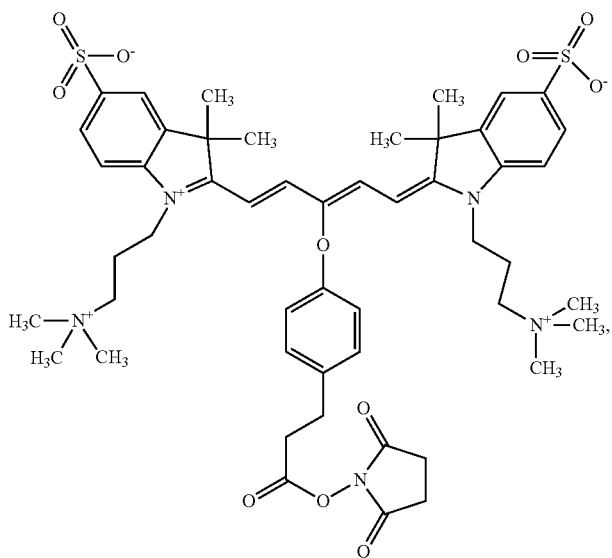 [SMILES: CC1(C)C(/C=C/C(=C/C=C2/N(CCC[N+](C)(C)C)c3ccc(S(=O)(=O)[O-])cc3C2(C)C)Oc2ccc(CCC(=O)ON3C(=O)CCC3=O)cc2)=[N+](CCC[N+](C)(C)C)c2ccc(S(=O)(=O)[O-])cc21] |
| PS126 | 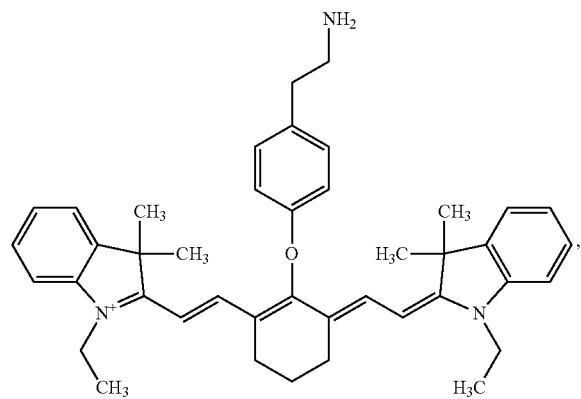 [SMILES: CCN1/C(=C/C=C2\CCCC(/C=C/C3=[N+](CC)c4ccccc4C3(C)C)=C2Oc2ccc(CCN)cc2)C(C)(C)c2ccccc21] |
| PS127 | 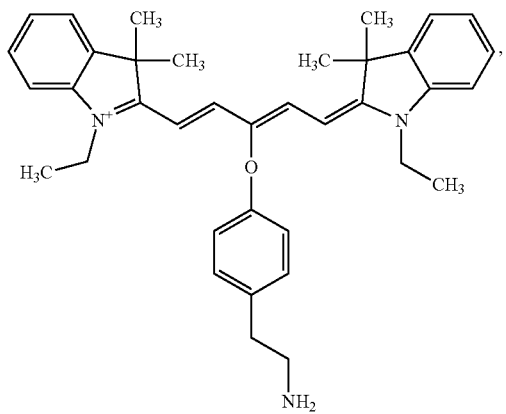 [SMILES: CCN1/C(=C/C=C(/C=C/C2=[N+](CC)c3ccccc3C2(C)C)Oc2ccc(CCN)cc2)C(C)(C)c2ccccc21] |

| Name | Structure |
|------|-----------|
| PS128 | 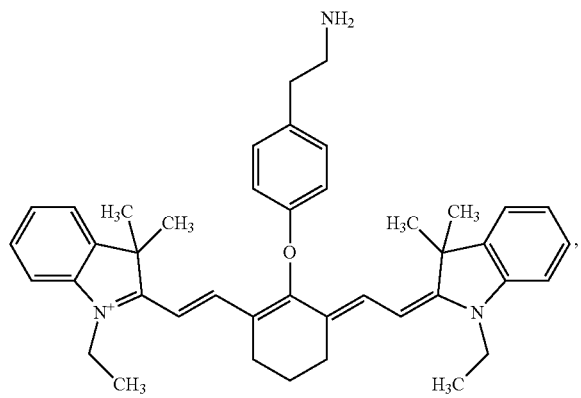 [SMILES: CCN1/C(=C/C=C2\CCCC(/C=C/C3=[N+](CC)c4ccccc4C3(C)C)=C2Oc2ccc(CCN)cc2)C(C)(C)c2ccccc21] |
| PS129 | 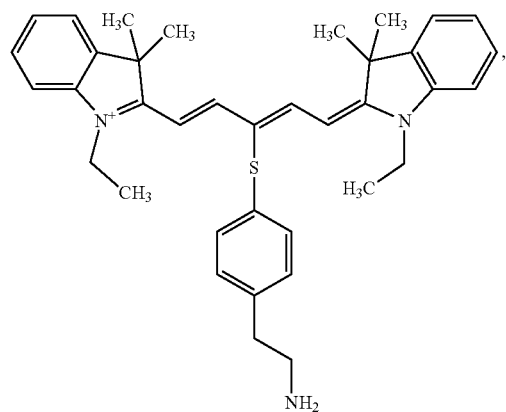 [SMILES: CCN1/C(=C/C=C(/C=C/C2=[N+](CC)c3ccccc3C2(C)C)Sc2ccc(CCN)cc2)C(C)(C)c2ccccc21] |
| PS130 | 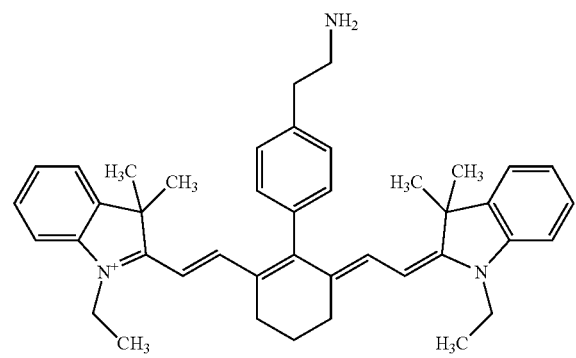 [SMILES: CCN1/C(=C/C=C2\CCCC(/C=C/C3=[N+](CC)c4ccccc4C3(C)C)=C2c2ccc(CCN)cc2)C(C)(C)c2ccccc21] |
| PS131 | 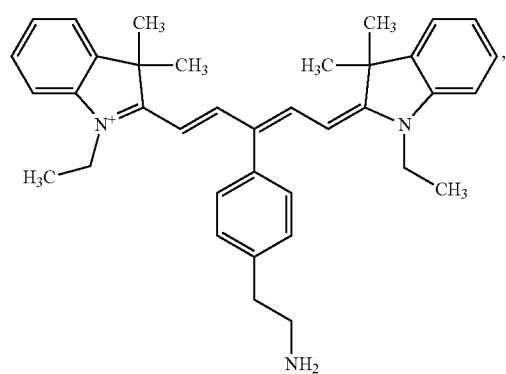 [SMILES: CCN1/C(=C/C=C(/C=C/C2=[N+](CC)c3ccccc3C2(C)C)c2ccc(CCN)cc2)C(C)(C)c2ccccc21] |

| Name | Structure |
|---|---|
| PS132 | 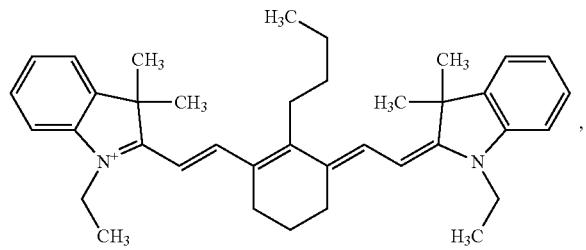 [SMILES: CCCCC1=C(/C=C/C2=[N+](CC)c3ccccc3C2(C)C)CCC/C1=C\C=C1\N(CC)c2ccccc2C1(C)C] |
| PS133 | 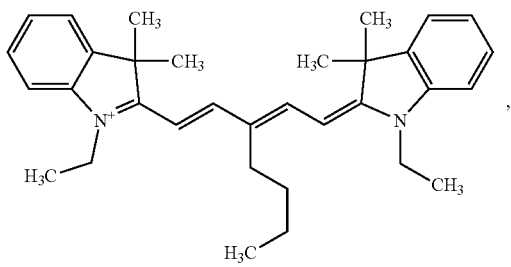 [SMILES: CCCCC(/C=C/C1=[N+](CC)c2ccccc2C1(C)C)=C\C=C1\N(CC)c2ccccc2C1(C)C] |
| YY283 | 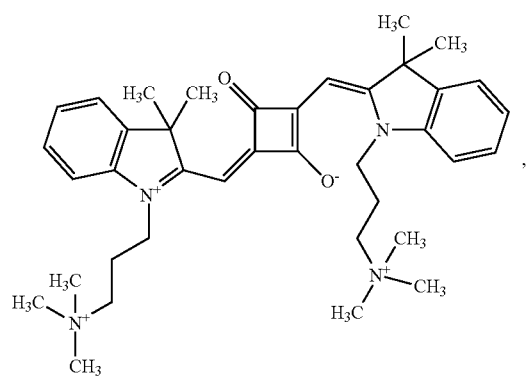 [SMILES: CC1(C)C(/C=C2\C(=O)C(/C=C3\N(CCC[N+](C)(C)C)c4ccccc4C3(C)C)=C2[O-])=[N+](CCC[N+](C)(C)C)c2ccccc21] |
| YY284 | 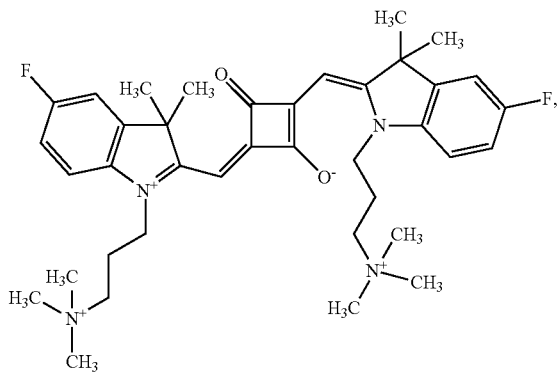 [SMILES: CC1(C)C(/C=C2\C(=O)C(/C=C3\N(CCC[N+](C)(C)C)c4ccc(F)cc4C3(C)C)=C2[O-])=[N+](CCC[N+](C)(C)C)c2ccc(F)cc21] |

-continued
| Name | Structure |
|---|---|
| YY285 | 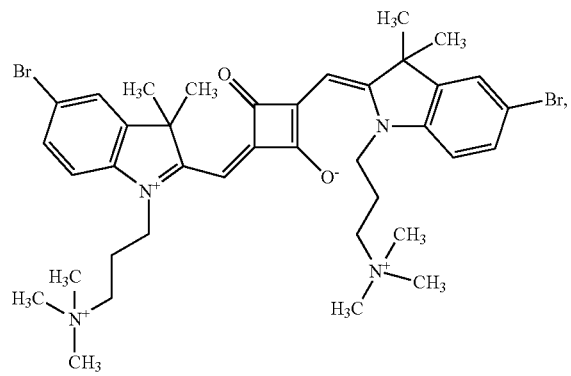 [SMILES: CC1(C)C(/C=C2\C(=O)C(/C=C3\N(CCC[N+](C)(C)C)c4ccc(Br)cc4C3(C)C)=C2[O-])=[N+](CCC[N+](C)(C)C)c2ccc(Br)cc21] |
| YY294 | 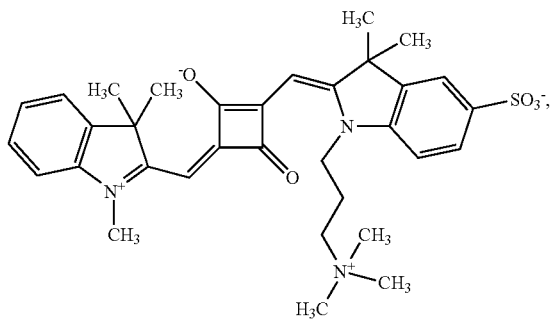 |
| YY295 | 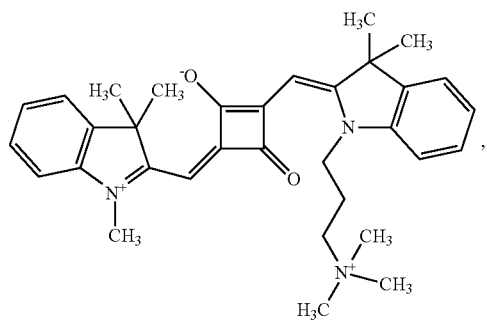 |
| YY2102 | 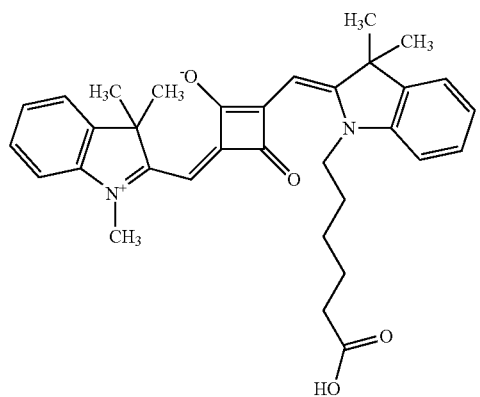 |

| Name | Structure |
|---|---|
| YY2103 | 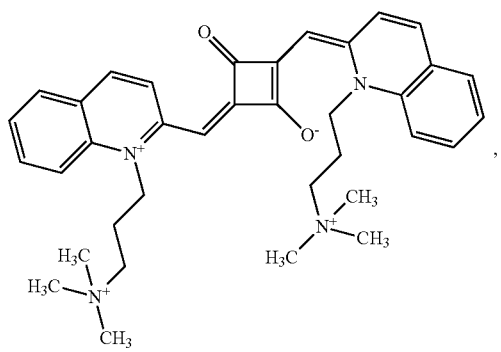 [SMILES: C[N+](C)(C)CCCN1/C(=C\C2=C([O-])C(=C/c3ccc4ccccc4[n+]3CCC[N+](C)(C)C)/C2=O)C=Cc2ccccc21] |
| YY2106 | 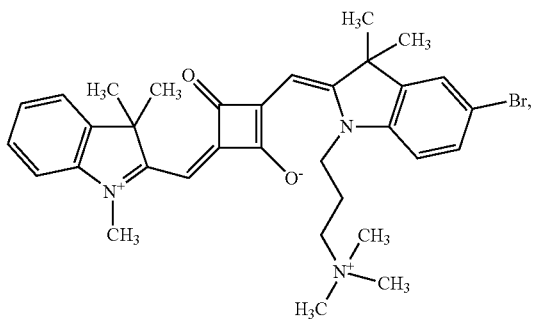 [SMILES: C[N+]1=C(/C=C2\C(=O)C(/C=C3\N(CCC[N+](C)(C)C)c4ccc(Br)cc4C3(C)C)=C2[O-])C(C)(C)c2ccccc21] |
| YY2107 | 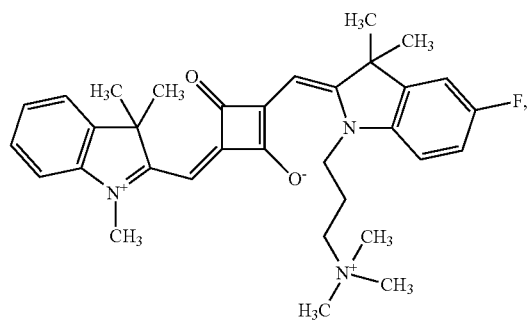 [SMILES: C[N+]1=C(/C=C2\C(=O)C(/C=C3\N(CCC[N+](C)(C)C)c4ccc(F)cc4C3(C)C)=C2[O-])C(C)(C)c2ccccc21] |
| L700-1A | 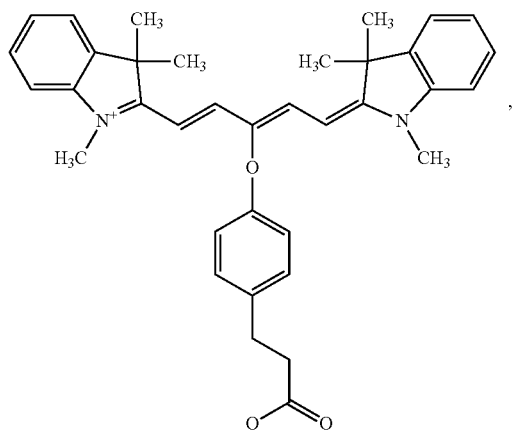 [SMILES: CN1/C(=C/C=C(/C=C/C2=[N+](C)c3ccccc3C2(C)C)Oc2ccc(CCC(=O)O)cc2)C(C)(C)c2ccccc21] |

| Name | Structure |
|---|---|
| L700-1C | 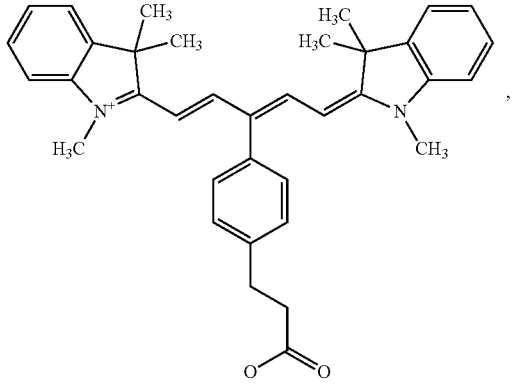 [SMILES: CN1/C(=C/C=C(/C=C/C2=[N+](C)c3ccccc3C2(C)C)c2ccc(CCC(=O)O)cc2)C(C)(C)c2ccccc21] |
| L800-1A | 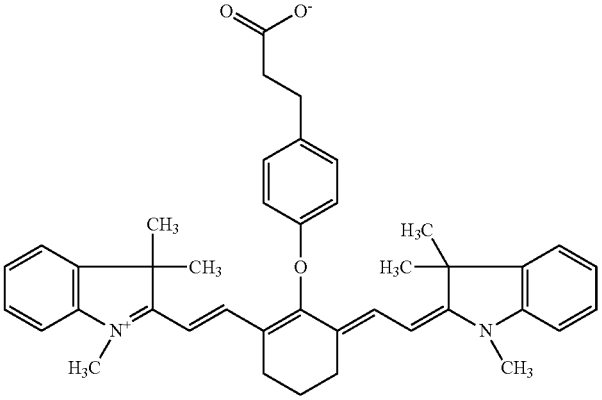 |
| L800-1C | 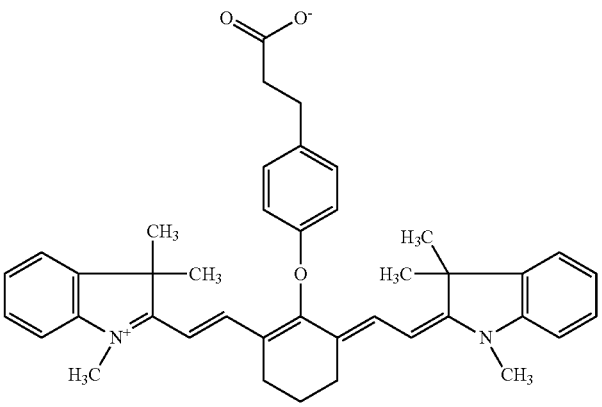 |

In certain embodiments, the imaging agent has peak absorbance at about 600 nm to 900 nm.

In certain embodiments, the tissue or cells is imaged ex vivo, e.g. for in vitro diagnostic applications.

In another aspect, the invention provides a method of imaging biological cells, the method comprising: (a) contacting the biological cells with a compound of the invention; (b) irradiating the cells at a wavelength absorbed by the compound; (c) and detecting a signal from the compound, thereby imaging the biological cells. The biological cells could be a normal cell type in the body or its malignant counterpart, i.e., a tumor formed from a normal cell type.

In certain embodiments, the biological targets are found in biological tissues or organs. In specific embodiments, the biological targets are blood vessel lumens, endothelial cells lining blood vessels, cartilage cells and/or their products, bone cells and/or their products, thyroid cells, thyroid glands, parathyroids cells, parathyroid glands, adrenal gland cells, adrenal glands, salivary gland cells, salivary glands, white adipose tissue, brown adipose tissue, ovarian cells, testicular cells, seminal vesicles, prostate cells, pancreas cells, spleen cells, gallbladder lumens, gallbladder cells, bile duct lumens, bile duct cells, Peyer's patches, brain grey matter, brain white matter, brain vasculature cells, choroid plexus tissue and fluid, cerebrospinal fluid, nerves, lymph nodes, sentinel lymph nodes, vulnerable plaque, stem cells, or neuroendocrine tumors.

In certain embodiments, the compounds of the invention accumulate in a lumen or other cavity in the body, thus highlighting the lumen's anatomical location and/or quantifying flow of the compound within the lumen. For example, a NIR fluorophore excreted by the kidney will accumulate in the ureters, thus identifying their location and also permitting direct visualization of pulsatile flow within the ureters. The same is true for blood vessels after intravenous injection of a compound or the thoracic duct after injection into the lower body.

In certain embodiments, the compounds of the invention accumulate in a tissue or organ but do so extracellularly. For example, a compound injected sub-dermally may enter the lymphatic channels and flow to a lymph node where it may be trapped in the extracellular space rather than, or in addition to, entrapment within cells of the lymph node.

In certain embodiments, the compounds of the invention may be modified to include a polyethylene glycol group. Such PEGylated compounds may be branched or linear. In certain embodiments, the linear PEGylated compounds are in the range of about 20 kDa to about 60 kDa.

In certain embodiments, the NIR fluorophores are conjugated covalently or non-covalently to other molecules, either to improve targeting of the NIR fluorophore or to co-localize other functional molecules.

In some embodiments, the compounds of the invention can be conjugated to a metal chelator agent for use in single-photon emission computed tomography (SPECT) or positron emission tomography (PET) or in magnetic resonance imaging (MRI). In certain embodiments, the metal chelator agent is a DOTA, DTPA, hydrazinonicotinic acid (HYNIC), or desferoxime, or a derivative thereof. In particular embodiments, the metal atom is selected from the group including, but not exclusively, Zr-89, Ga-68 and Rb-82, and the signal is detected by positron emission tomography; the metal atom is selected from the group including, but not exclusively, of Tc-99m, Lu-177, and In-111, and the signal is detected by single-photon emission computed tomography; or the metal atom is a lanthanide selected from the group including, but not exclusively, Gd, Eu, Y, Dy and Yb, and the signal is detected by magnetic resonance imaging.

In some embodiments, the compounds of the invention can be conjugated to a therapeutic, such as a radioisotope, cytotoxin, or immune modulator, such that the targeting ability of the compound concentrates the therapeutic in the cell, tissue, organ, or lumen of interest.

BRIEF DESCRIPTION OF THE DRAWINGS

FIG. 4—depicts the imaging of Pan LN pan lymph node identification at 700 nm using A150 (Image without irradiation, NIR irradiated image, overlay of both)

FIG. 5—depicts the imaging of SLN identification at 800 nm using MM25 (Image without irradiation, NIR irradiated image, overlay of both)

FIG. 6—depicts the imaging of SLN identification at 700 nm using MHI86 (Image without irradiation, NIR irradiated image, overlay of both)

FIG. 10—depicts the imaging of neuroendocrine tumors at 700 nm using ESS61 (Image without irradiation, NIR irradiated image, overlay of both)

FIG. 11—depicts the imaging of bone mineralization at 800 nm using P800SO3 (Image without irradiation, NIR irradiated image, overlay of both)

FIG. 12—depicts the imaging of bone mineralization at 700 nm using P700SO3 (Image without irradiation, NIR irradiated image, overlay of both)

FIG. 25—depicts the imaging of ovaries at 800 nm using AL27 (Image without irradiation, NIR irradiated image, overlay of both)

FIG. 26—depicts the imaging of ovaries at 700 nm using PS62 (Image without irradiation, NIR irradiated image, overlay of both)

FIG. 27—depicts the imaging of the seminal vesicles at 800 nm using CNN2 (Image without irradiation, NIR irradiated image, overlay of both)

FIG. 37—depicts the imaging of the bile ducts at 800 nm using ZK198 (Image without irradiation, NIR irradiated image, overlay of both)

FIG. 38—depicts the imaging of the bile ducts at 700 nm using A106 (Image without irradiation, NIR irradiated image, overlay of both)

FIG. 39—depicts the imaging of Peyer's Patches at 800 nm using AL30 (Image without irradiation, NIR irradiated image, overlay of both)

FIG. 49—depicts the imaging of PEGylated agents at 800 nm using PEG60k-ZW800-1 (Image without irradiation, NIR irradiated image, overlay of both)

FIG. 50—depicts the imaging of PEGylated agents at 700 nm using PEG60k-LN15 (Image without irradiation, NW irradiated image, overlay of both)

FIG. 51—depicts the imaging of the pituitary gland at 800 nm using AL22 (Image without irradiation, NW irradiated image, overlay of both)

FIG. 57—depicts the imaging of intravital microscopy at 800 nm using Dex70k-ZW800-1 (Image without irradiation, NIR irradiated image, overlay of both)

FIG. 58—depicts the imaging of intravital microscopy at 700 nm using Dex70k-LN15 (Image without irradiation, NIR irradiated image, overlay of both)

ABBREVIATIONS USED

Figures 1, 2, 3:
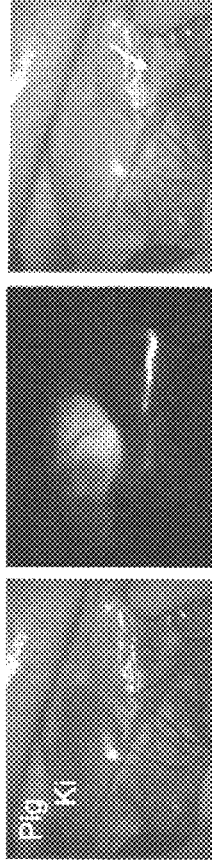
FIG. 1—depicts the imaging of Ureters at 800 nm using A71 (Image without irradiation, NIR irradiated image, overlay of both)
FIG. 2—depicts the imaging of Ureters at 700 nm using LN15 (Image without irradiation, NIR irradiated image, overlay of both)
FIG. 3—depicts the imaging of pan lymph node identification at 800 nm using MM25 (Image without irradiation, NIR irradiated image, overlay of both)

Ad: white adipose
AG: adrenal gland
BG: brain grey matter (cells)
Bl: bladder
Bo: bone
BD: bile duct
BF: brown fat
BV: brain vasculature
BW: brain white matter (nerve axons and glia)
Ca: cartilage
CF: cerebrospinal fluid
CP: choroid plexus
Du: duodenum
GB: gall bladder
He: heart
HB: hepatobiliary clearance
In: intestine:
Ki: kidney
Li: liver
Lu: lung
LN: lymph node
Mu: muscle
Ne: nerve
NT: neuroendocrine tumor
Ov: ovary
Pa: pancreas
Pp: Peyer's patches
Pr: prostate
PG: pituitary gland
PT: parathyroid gland
RE: renal clearance
Sp: spleen
SG: salivary gland
SL: sentinel lymph node
SV: seminal vesicle
TG: thyroid gland
Ur: ureter

DETAILED DESCRIPTION

It has now been found that compounds with absorption and/or emission in the near infrared (NIR) have desirable properties with respect to in vivo biodistribution and clearance, uptake and retention by cells, tissues, and/or organs of interest, and the imaging thereof. Such agents are compatible with Channel 1 ($\approx$660 nm excitation; $\approx$700 nm emission) or Channel 2 ($\approx$760 nm excitation; $\approx$800 nm emission) of the FLARE™ Imaging System, which permits color video and NIR fluorescence to be acquired simultaneously, thus providing real-time image-guidance to surgeons and others about target location.

Definitions

The following definitions will be useful in understanding the instant invention.

As used herein, the term "comprising" is intended to mean that the compositions and methods include the recited elements, but do not exclude other elements. "Consisting essentially of", when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used in the specification and claims, the singular form "a", "an" and "the" include plural references unless the context clearly dictates otherwise.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless specifically stated or obvious from context, as used herein, the term "or" is understood to be inclusive.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

As used herein, the term "subject" or "patient" encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like. Examples of non-mammals include, but are not limited to, birds, fish, parasites, microbes, and the like.

As used herein, the term "administration" or "administering" of the subject compound refers to providing a compound of the invention and/or prodrugs thereof to a subject in need of diagnosis or treatment.

As used herein, the term "carrier" refers to chemical compounds or agents that facilitate the incorporation of a compound described herein into cells or tissues.

As used herein, the term "acceptable" with respect to a formulation, composition or ingredient, as used herein, means having no persistent detrimental effect on the general health of the subject being treated.

As used herein, the term "diluent" refers to chemical compounds that are used to dilute a compound described herein prior to delivery. Diluents can also be used to stabilize compounds described herein.

The term "nerve" as used herein, includes peripheral nerve tissue and cells, including myelinated nerves. Sensory nerves and motor nerves are examples of nerve tissue. Examples of specific nerves include the laryngeal nerve, femoral nerve, brachial plexus, sciatic nerve, pudendal nerves, penile nerves, and the like. The term "nerve tissue" also includes brain grey matter and brain white matter.

The term "alkyl," refers to a straight or branched hydrocarbon radical having from 1-12 carbon atoms, from 1-8 carbon atoms, from 1-6 carbon atoms, or from 1-4 carbon atoms (unless stated otherwise) and includes, for example, methyl, ethyl, n-propyl, iso-propyl, n-butyl, sec-butyl, isobutyl, tert-butyl, n-pentyl, iso-pentyl, n-hexyl and the like. An alkyl can be unsubstituted or substituted with one or more suitable substituents.

The term "cycloalkyl" refers to a monocyclic or polycyclic hydrocarbon ring group having from 3 to 6 carbon atoms, in the hydrocarbon ring (unless stated otherwise) and includes, for example, cyclopropyl, cyclobutyl, cyclohexyl, cyclopentyl, and the like. A cycloalkyl group can be unsubstituted or substituted with one or more suitable substituents.

The term "hetero" refers to the replacement of at least one carbon atom member in a ring system with at least one heteroatom such as nitrogen, sulfur, and oxygen.

The term "heterocyclic" means a non-aromatic monocyclic ring having from 2 to 5 carbon atoms in the ring (unless stated otherwise) and at least one heteroatom, preferably, one heteroatom selected from nitrogen, sulfur (including oxidized sulfur such as sulfone or sulfoxide) and oxygen. A heterocycloalkyl group can have one or more carbon-carbon double bonds or carbon-heteroatom double bonds in the ring group as long as the ring group is not rendered aromatic by their presence.

Examples of heterocyclic groups include pyrrolidinyl, piperidinyl, tetrahydropyranyl, and the like. A heterocyclic group can be unsubstituted or substituted with one or more suitable substituents.

As used herein, the term "aryl" refers to an unsubstituted or substituted carbocyclic aromatic monocyclic group such as a phenyl group. The term "aryl" may be interchangeably used with "aryl ring".

As used herein, the term "heteroaryl: refers to an unsubstituted or substituted heterocyclic aromatic monocyclic group such as a pyridyl, furanyl, or thiophenyl group, and the like. Heteroaryl groups have 5 or 6 atoms in the heteroaromatic ring, 1 of which is independently selected from the group consisting of oxygen, sulfur and nitrogen. Typical heteroaryl groups include, for example, a pyridyl, furanyl, or thiophenyl group.

An aryl or heteroaryl can be unsubstituted or substituted with one or more suitable substituents.

A "substituent," as used herein, refers to a molecular moiety that is covalently bonded to an atom within a molecule of interest. For example, a ring substituent may be a moiety such as a halogen, alkyl group, haloalkyl group or other group that is covalently bonded to an atom (preferably a carbon or nitrogen atom) that is a ring member. Substituents of aromatic groups are generally covalently bonded to a ring carbon atom. The term "substitution" refers to replacing a hydrogen atom in a molecular structure with a substituent, such that the valence on the designated atom is not exceeded, and such that a chemically stable compound (i.e., a compound that can be isolated, characterized, and tested for biological activity) results from the substitution.

As described above, certain groups can be unsubstituted or substituted with one or more suitable substituents by other than hydrogen at one or more available positions, typically 1, 2, 3, 4 or 5 positions, by one or more suitable groups (which may be the same or different). Certain groups, when substituted, are substituted with 1, 2, 3 or 4 independently selected substituents. Suitable substituents include halo, alkyl, aryl, hydroxy, alkoxy, hydroxyalkyl, amino, and the like.

The term "halogen", as used herein, refers to F, Cl, Br, At, and I.

Other definitions appear in context throughout the disclosure.

Compounds and Compositions

It has now been found that certain compounds are useful as near-infrared absorbing and/or fluorescing biological contrast agents.

Any compositions or methods provided herein can be combined with one or more of any of the other compositions and methods provided herein.

In one aspect, the near-infrared fluorescent contrast is a compound of Formula (I):

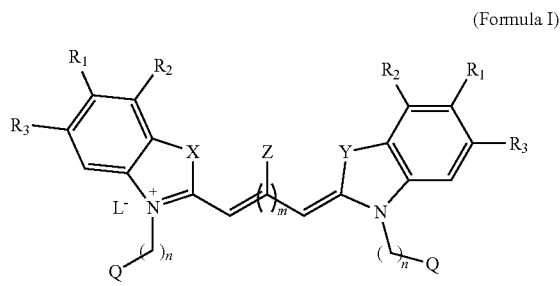

(Formula I)

Wherein for Formula (I)
Each $R_1$ is independently H, OR', halogen, sulfonato, substituted or unsubstituted amino, C(O)NH— $C_1$-$C_6$ alkyl, $C_1$-$C_6$ alkyl, $C_1$-$C_6$ alkoxy or phenyl;
Each $R_2$ is independently H, OR', halogen, sulfonato, substituted or unsubstituted amino, C(O)NH— $C_1$-$C_6$ alkyl, $C_1$-$C_6$ alkyl, $C_1$-$C_6$ alkoxy or phenyl;
Or $R^1$ and $R^2$ can be taken together with the carbon atoms to which they are attached to form a 5-6 membered aryl or heteroaryl ring, optionally substituted with halogen, alkyl, alkoxy, hydroxyl, —$SO_2OH$, or —$CO_2H$;
Each $R_3$ is independently H, OR', halogen, sulfonato, substituted or unsubstituted amino, C(O)NH— $C_1$-$C_6$ alkyl, $C_1$-$C_6$ alkyl, $C_1$-$C_6$ alkoxy or phenyl;
Q is H, alkyl optionally substituted with alkoxy, cycloalkyl, heterocycloalkyl, aryl, arylalkyl, heteroaryl, heteroarylalkyl, —$N^+(alkyl)_3$, —OCO-alkyl, —$SO_2OH$, phenyl, sulfonato, phosphates, KUE, GPI, —or —$NR_3R_4R_5$, wherein $R_3$, $R_4$ and $R_5$ are each independently for each occurrence H or $C_1$-$C_4$ alkyl, or $R_4$ and $R_5$, taken together with the nitrogen atom to which they are attached, form a heterocyclic ring;
X and Y are each independently O, S, Se, C(R")$_2$, NR'";
Z is H, halogen, CN, $R_6$, $OR_6$, $SR_6$, $NHR_6$ or $CH_2R_6$, in which $R_6$ is optionally substituted $C_1$-$C_6$ alkyl, optionally substituted aryl, or optionally substituted heteroaryl, alkyl-$N_3$, aryl-$N_3$, aryl-halogen;
Each R' is independently H, alkyl or aryl;
Each R" is independently H or alkyl;

Each R'" is independently H, akyl, akyl-$SO_3H$, or akyl-COOH;
m and n are independently an integer from 0-3; and
L is an anion;
or a salt, solvate, hydrate, polymorph, prodrug, or stereoisomer thereof.

In another aspect, the near-infrared fluorescent contrast is a compound of Formula (II):

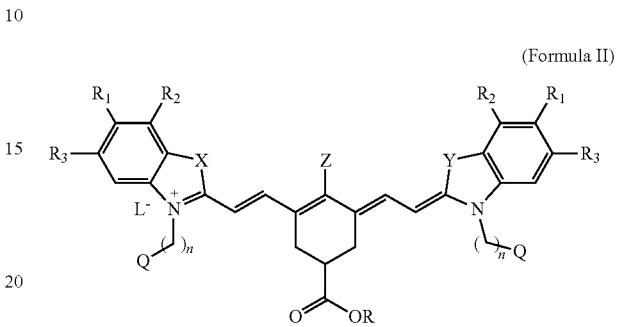

(Formula II)

Wherein for Formula (II)
Each $R_1$ is independently H, OR', halogen, sulfonato, substituted or unsubstituted amino, C(O)NH— $C_1$-$C_6$ alkyl, $C_1$-$C_6$ alkyl, $C_1$-$C_6$ alkoxy or phenyl;
Each $R_2$ is independently H, OR', halogen, sulfonato, substituted or unsubstituted amino, C(O)NH— $C_1$-$C_6$ alkyl, $C_1$-$C_6$ alkyl, $C_1$-$C_6$ alkoxy or phenyl;
Or $R^1$ and $R^2$ can be taken together with the carbon atoms to which they are attached to form a 5-6 membered aryl or heteroaryl ring, optionally substituted with halogen, alkyl, alkoxy, hydroxyl, —$SO_2OH$, or —$CO_2H$;
Each $R_3$ is independently H, OR', halogen, sulfonato, substituted or unsubstituted amino, C(O)NH— $C_1$-$C_6$ alkyl, $C_1$-$C_6$ alkyl, $C_1$-$C_6$ alkoxy or phenyl;
Q is H, alkyl optionally substituted with alkoxy, cycloalkyl, heterocycloalkyl, aryl, arylalkyl, heteroaryl, heteroarylalkyl, —$N^+(alkyl)_3$, —OCO-alkyl, —$SO_2OH$, phenyl, sulfonato, phosphates, KUE, GPI, —or —$NR_3R_4R_5$, wherein $R_3$, Ra and $R_5$ are each independently for each occurrence H or $C_1$-$C_4$ alkyl, or $R_4$ and $R_5$, taken together with the nitrogen atom to which they are attached, form a heterocyclic ring;
X and Y are each independently O, S, Se, C(R")$_2$, NR;
Z is H, halogen, CN, $R_6$, $OR_6$, $SR_6$, $NHR_6$ or $CH_2R_6$, in which $R_6$ is optionally substituted $C_1$-$C_6$ alkyl, optionally substituted aryl, or optionally substituted heteroaryl, alkyl-$N_3$, aryl-$N_3$, aryl-halogen;
R is independently H, OR"" (where R═H, akyl, or aryl, $NH_2$, NHR, alkyl $NH_2$, alkyl COOH),
L is an anion;
Each R' is independently H, alkyl or aryl;
Each R" is independently H or alkyl;
Each R'" is independently H, akyl, akyl-$SO_3H$, or akyl-COOH;
Each R"" is independently H, akyl, or aryl, $NH_2$, NHR, alkyl-$NH_2$, or alkyl-COOH;
m and n are independently an integer from 0-3; and
L is an anion;
or a salt, solvate, hydrate, polymorph, prodrug, or stereoisomer thereof.

In still another aspect, the near-infrared fluorescent contrast is a compound of Formula (III):

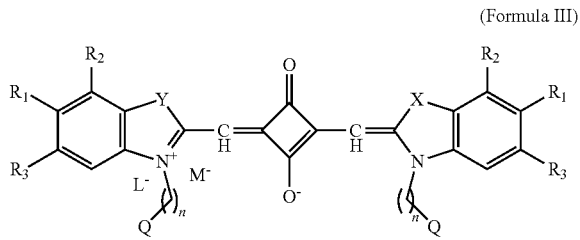

(Formula III)

wherein For Formula (III)
Each $R_1$ is independently H, OR', halogen, sulfonato, substituted or unsubstituted amino, C(O)NH— $C_1$-$C_6$ alkyl, $C_1$-$C_6$ alkyl, $C_1$-$C_6$ alkoxy or phenyl;
Each $R_2$ is independently H, OR', halogen, sulfonato, substituted or unsubstituted amino, C(O)NH— $C_1$-$C_6$ alkyl, $C_1$-$C_6$ alkyl, $C_1$-$C_6$ alkoxy or phenyl;
Or $R^1$ and $R^2$ can be taken together with the carbon atoms to which they are attached to form a 5-6 membered aryl or heteroaryl ring, optionally substituted with halogen, alkyl, alkoxy, hydroxyl, —$SO_2OH$, or —$CO_2H$;
Each $R_3$ is independently H, OR', halogen, sulfonato, substituted or unsubstituted amino, C(O)NH— $C_1$-$C_6$ alkyl, $C_1$-$C_6$ alkyl, $C_1$-$C_6$ alkoxy or phenyl;
Q is H, alkyl optionally substituted with alkoxy, cycloalkyl, heterocycloalkyl, aryl, arylalkyl, heteroaryl, heteroarylalkyl, —$N^+(alkyl)_3$, —OCO-alkyl, —$SO_2OH$, phenyl, sulfonato, phosphates, KUE, GPI, —or —$NR_3R_4R_5$, wherein $R_3$, $R_4$ and $R_5$ are each independently for each occurrence H or $C_1$-$C_4$ alkyl, or $R_4$ and $R_5$, taken together with the nitrogen atom to which they are attached, form a heterocyclic ring;
X and Y are each independently O, S, Se, C(R")$_2$, NR'''; Z is H, halogen, CN, $R_6$, O$R_6$, S$R_6$, NH$R_6$ or CH$_2R_6$, in which $R_6$ is optionally substituted $C_1$-$C_6$ alkyl, optionally substituted aryl, or optionally substituted heteroaryl, alkyl-$N_3$ (for click chemistry), aryl-$N_3$ (for click chemistry), aryl-halogen (only for palladium catalyzed reactions);
Each R' is independently H, alkyl or aryl;
Each R" is independently H or alkyl;
Each R''' is independently H, akyl, akyl-$SO_3H$, or akyl-COOH;
m and n are independently an integer from 0-3; and
L is an anion;
or a salt, solvate, hydrate, polymorph, prodrug, or stereoisomer thereof.

In another aspect, the near-infrared fluorescent contrast is a compound of Formula (IV):

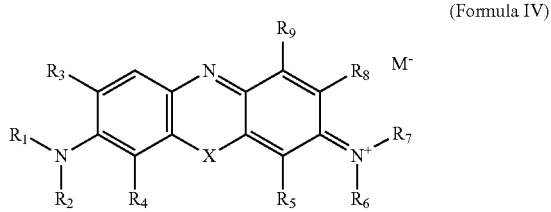

(Formula IV)

wherein
$R_1$, $R_2$, $R_3$, Ra, $R_6$ and $R_7$ are each independently H or $C_1$-$C_6$ alkyl;
$R_5$, $R_8$ and $R_9$ are each independently H, CN, OH, or $C_1$-$C_6$ alkyl;
or $R_1$ and $R_3$, taken together with the atoms to which they are connected, form a 5- to 6-membered heterocylic ring;
or $R_2$ and $R_4$, taken together with the atoms to which they are connected, form a 5- to 6-membered heterocylic ring;
or $R_5$ and $R_6$, taken together with the atoms to which they are connected, form a 5- to 6-membered heterocylic ring;
or $R_7$ and $R_8$, taken together with the atoms to which they are connected, form a 5- to 6-membered heterocylic ring;
or $R_8$ and $R_9$, taken together with the atoms to which they are connected, form an aryl or heteroaryl ring;
X is O, S, Se, N—R; where R=H or $C_1$-$C_6$ alkyl; and
$M^-$ is an anion
or a salt, solvate, hydrate, polymorph, prodrug, or stereoisomer thereof.

In still another aspect, the near-infrared fluorescent contrast is a compound of Formula (V):

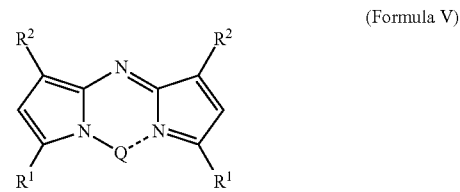

(Formula V)

Wherein:
Q is —B($R^3$)$_2$—; Si($R^3$)$_2$
Each $R^1$ is independently H, alkyl, aryl, or heteroaryl, wherein each alkyl, aryl, or heteroaryl is optionally substituted with alkoxy, alkoxy-$N^+$(alkyl)$_3$, alkoxy-OH, halogen, or COOH; and
Each $R^2$ is independently H, alkyl, aryl, or heteroaryl, wherein each alkyl, aryl, or heteroaryl is optionally substituted with alkoxy, alkoxy-$N^+$(alkyl)$_3$, alkoxy-OH, halogen, or COOH; and
Each $R^3$ is independently H, F, or alkyl; OH
or a salt, solvate, hydrate, polymorph, prodrug, or stereoisomer thereof.

In certain aspects, the near-infrared fluorescent biological contract agent is:

| Name | Structure |
|---|---|
| AL22 | 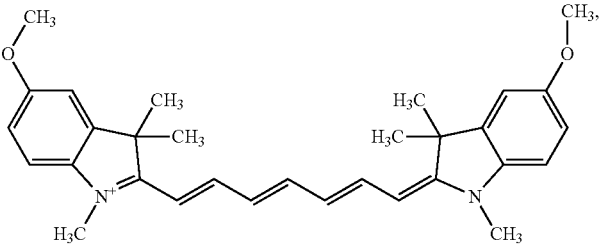 |
| SP64 | 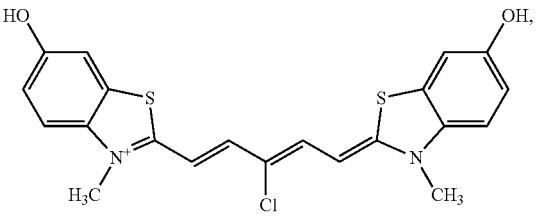 [SMILES: CN1/C(=C/C=C(Cl)/C=C/c2sc3cc(O)ccc3[n+]2C)Sc2cc(O)ccc21] |
| SP60 | 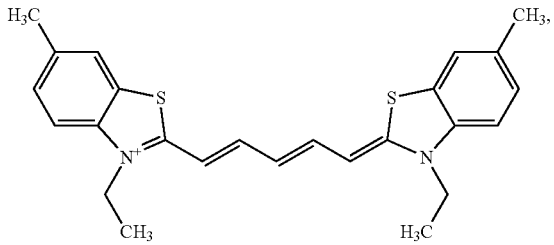 |
| PTN1 | 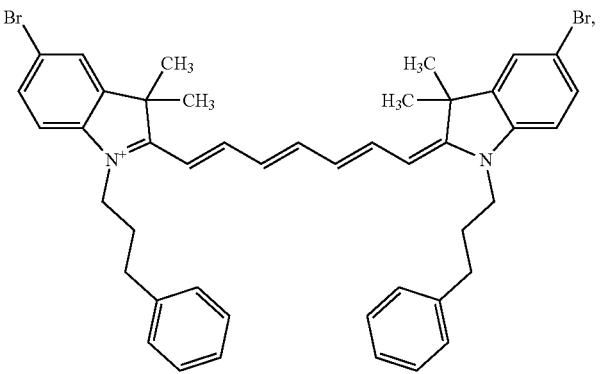 [SMILES: CC1(C)C(/C=C/C=C/C=C/C=C2/N(CCCc3ccccc3)c3ccc(Br)cc3C2(C)C)=[N+](CCCc2ccccc2)c2ccc(Br)cc21] |
| SP56 | 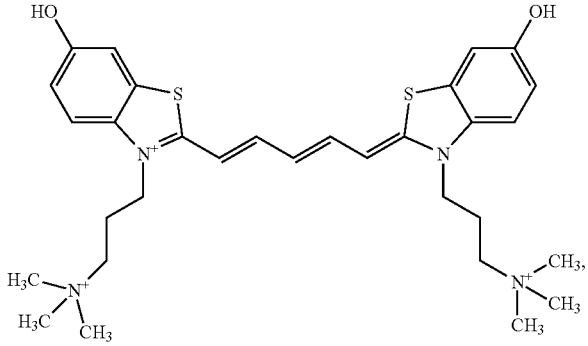 [SMILES: C[N+](C)(C)CCCN1/C(=C/C=C/C=C/c2sc3cc(O)ccc3[n+]2CCC[N+](C)(C)C)Sc2cc(O)ccc21] |

| Name | Structure |
|---|---|
| QBN1 | 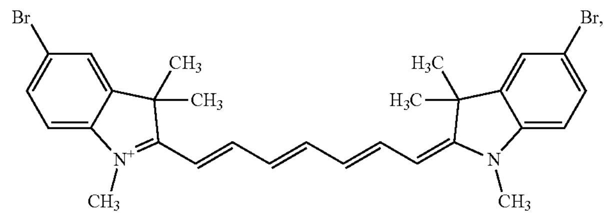 [SMILES: CN1/C(=C/C=C/C=C/C=C/C2=[N+](C)c3ccc(Br)cc3C2(C)C)C(C)(C)c2cc(Br)ccc21] |
| TG18 | 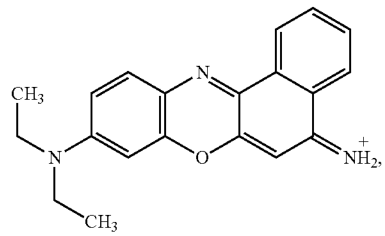 |
| ZK195 | 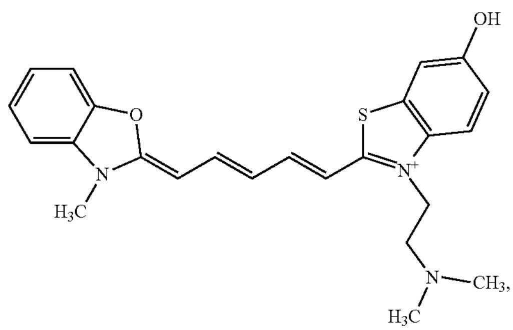 [SMILES: CN(C)CC[n+]1c(/C=C/C=C/C=C2\Oc3ccccc3N2C)sc2cc(O)ccc21] |
| A71 | 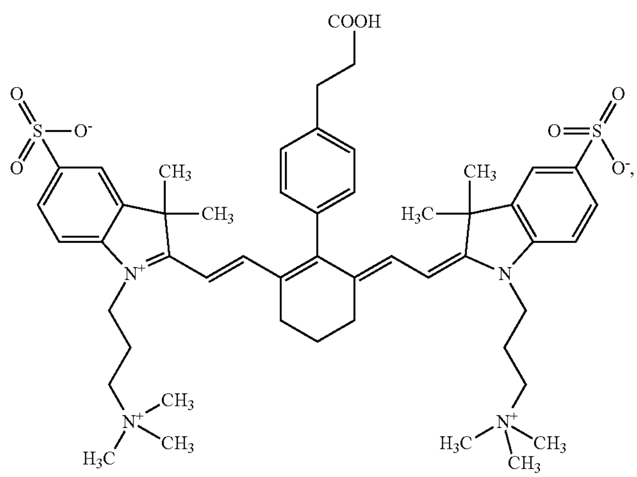 |
| YY187 | 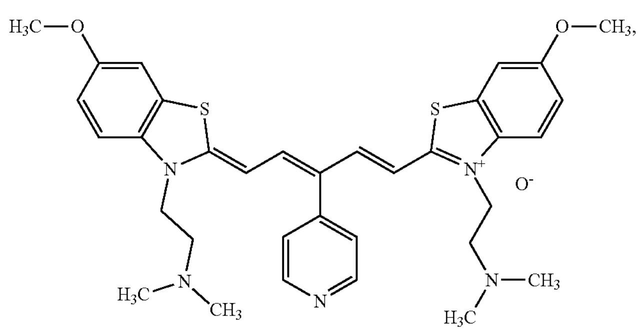 |

| Name | Structure |
|---|---|
| CNN6 | 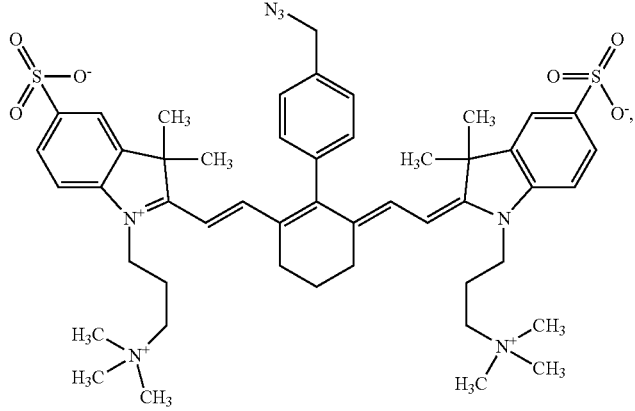 |
| TG42 | 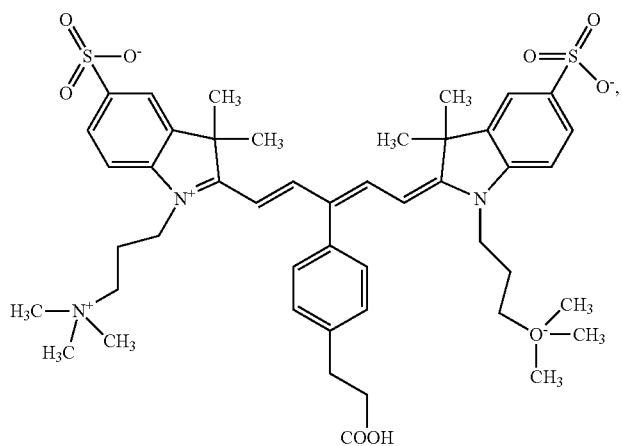 |
| TG53 | 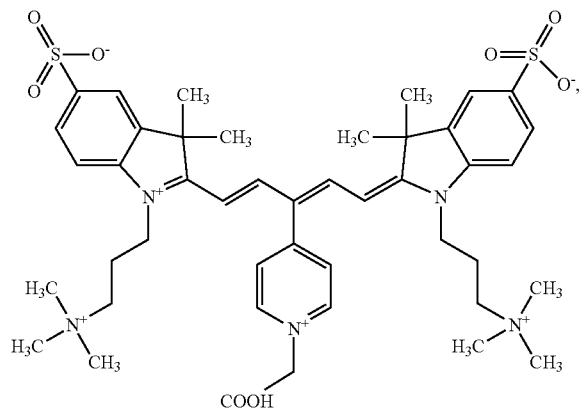 |

-continued
| Name | Structure |
|---|---|
| CNN4 | 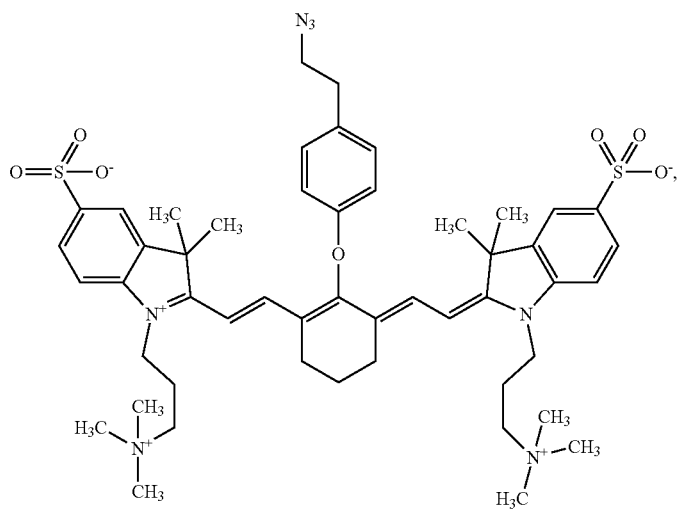 |
| CNN5 | 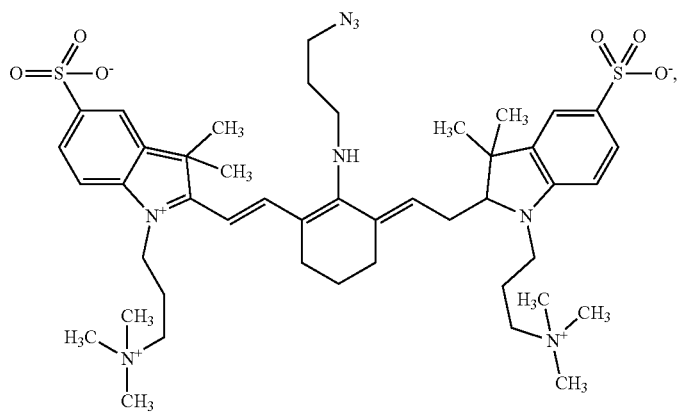 |
| LN24 | 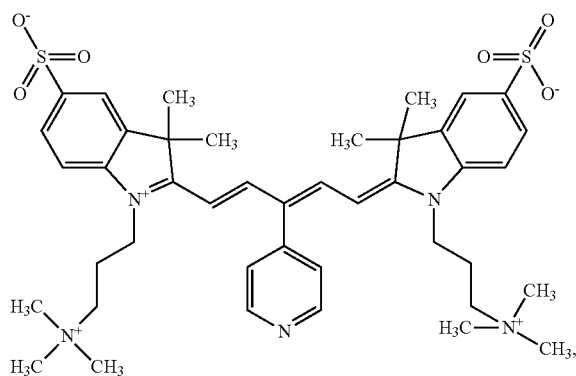 [SMILES: CC1(C)C(/C=C/C(=C/C=C2/N(CCC[N+](C)(C)C)c3ccc(S(=O)(=O)[O-])cc3C2(C)C)c2ccncc2)=[N+](CCC[N+](C)(C)C)c2ccc(S(=O)(=O)[O-])cc21] |

| Name | Structure |
|---|---|
| LN63 | 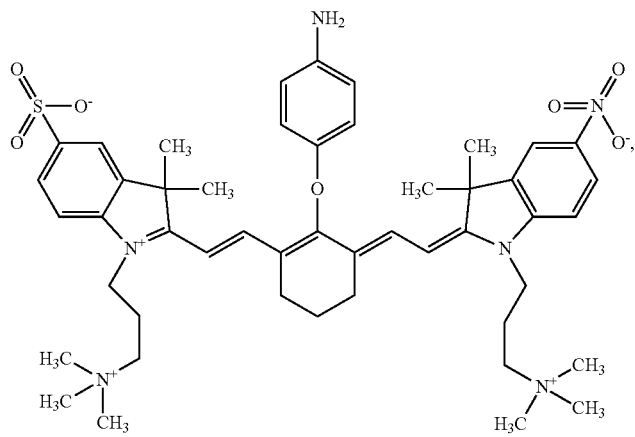 |
| LN66 | 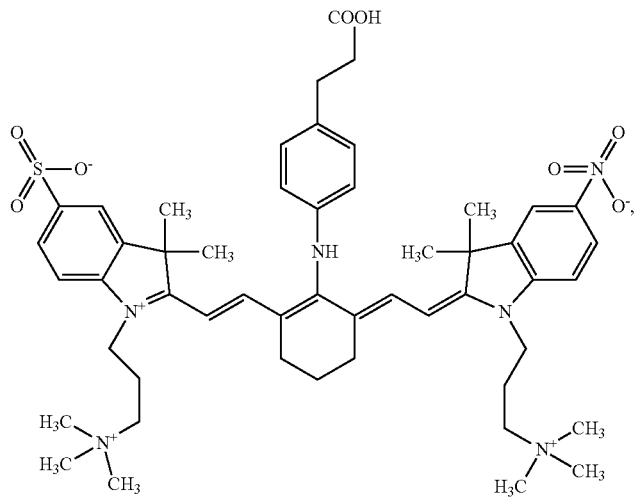 |
| LN15 | 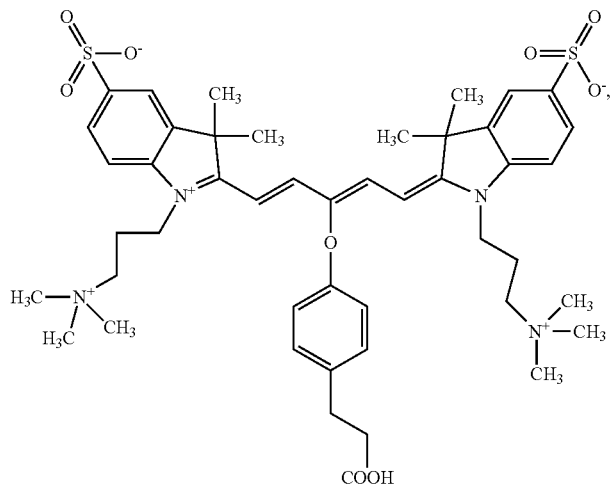 |

| Name | Structure |
|---|---|
| YY180 | 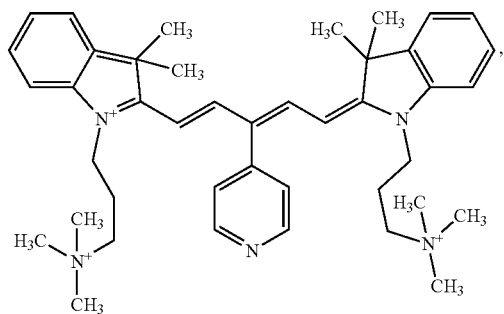 |
| NRB1 | 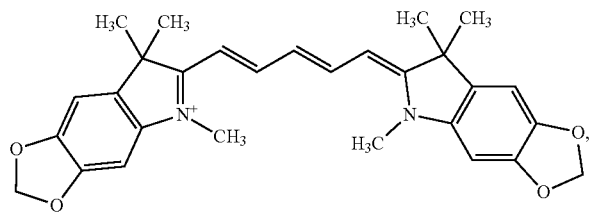 [SMILES: CN1\C(=C/C=C/C=C/C2=[N+](C)c3cc4c(cc3C2(C)C)OCO4)C(C)(C)c2cc3c(cc21)OCO3] |
| NRB2 | 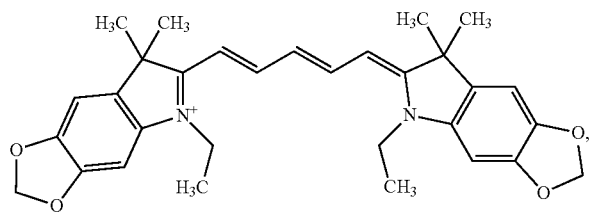 [SMILES: CCN1\C(=C/C=C/C=C/C2=[N+](CC)c3cc4c(cc3C2(C)C)OCO4)C(C)(C)c2cc3c(cc21)OCO3] |
| NRB3 | 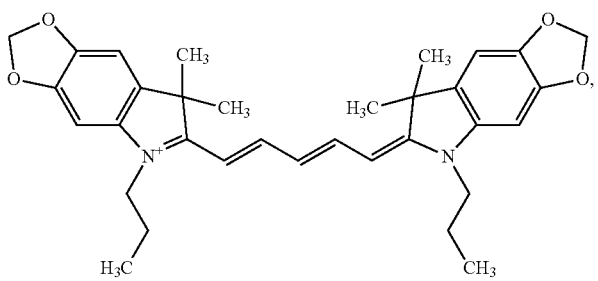 [SMILES: CCCN1/C(=C/C=C/C=C/C2=[N+](CCC)c3cc4c(cc3C2(C)C)OCO4)C(C)(C)c2cc3c(cc21)OCO3] |
| ZK190 | 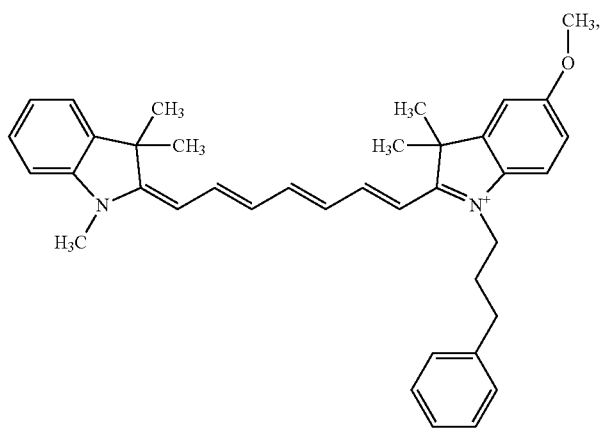 [SMILES: COc1ccc2c(c1)C(C)(C)C(/C=C/C=C/C=C/C=C1/N(C)c3ccccc3C1(C)C)=[N+]2CCCc1ccccc1] |

-continued
| Name | Structure |
|---|---|
| ZK189 | 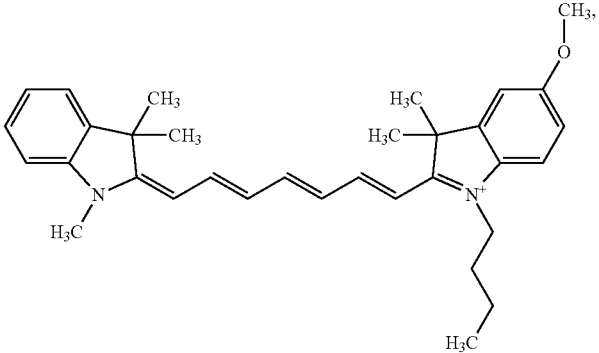 |
| ZK50 | 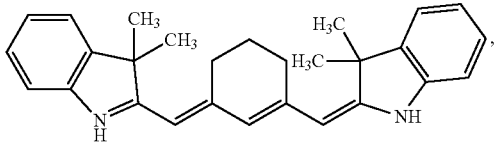 [SMILES: CC1(C)C(/C=C2C=C(/C=C3/Nc4ccccc4C3(C)C)CCC/2)=Nc2ccccc21] |
| SP59 | 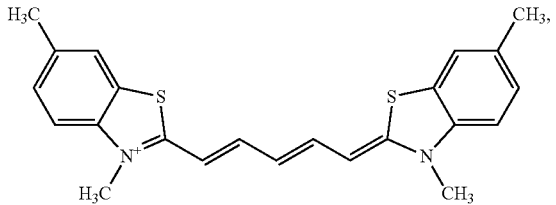 |
| JM1 | 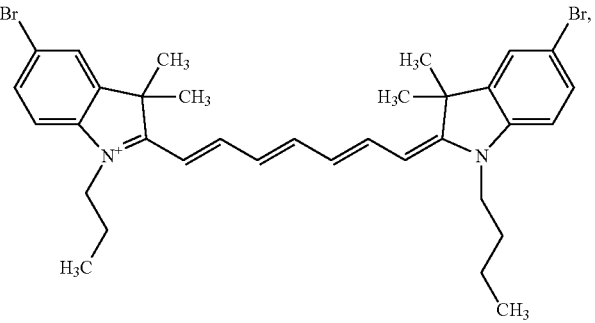 [SMILES: CCCCN1/C(=C/C=C/C=C/C=C/C2=[N+](CCC)c3ccc(Br)cc3C2(C)C)C(C)(C)c2cc(Br)ccc21] |
| SP67 | 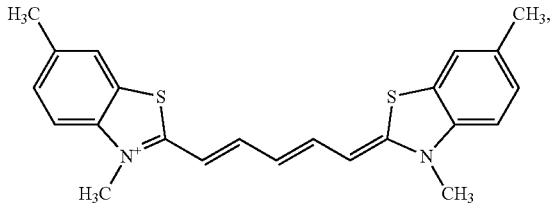 [SMILES: Cc1ccc2c(c1)S\C(=C/C=C/C=C/c1sc3cc(C)ccc3[n+]1C)N2C] |
| MM21 | 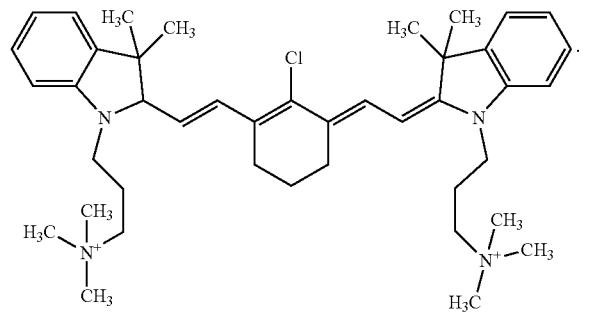 [SMILES: CC1(C)/C(=C\C=C2/CCCC(/C=C/C3N(CCC[N+](C)(C)C)c4ccccc4C3(C)C)=C2Cl)N(CCC[N+](C)(C)C)c2ccccc21] |

| Name | Structure |
|---|---|
| ZK38 | 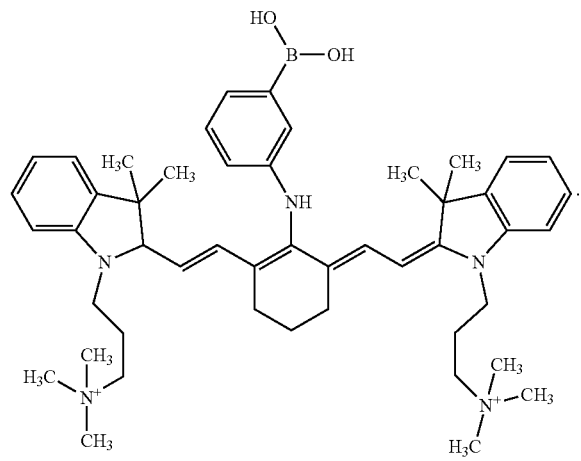 [SMILES: CC1(C)/C(=C\C=C2/CCCC(/C=C/C3N(CCC[N+](C)(C)C)c4ccccc4C3(C)C)=C2Nc2cccc(B(O)O)c2)N(CCC[N+](C)(C)C)c2ccccc21] |
| E60 | 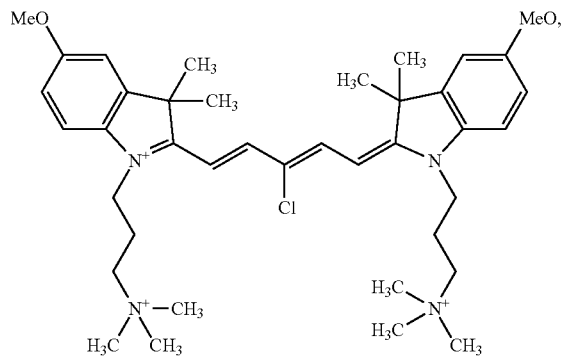 [SMILES: COc1ccc2c(c1)C(C)(C)C(/C=C/C(Cl)=C/C=C1/N(CCC[N+](C)(C)C)c3ccc(OC)cc3C1(C)C)=[N+]2CCC[N+](C)(C)C] |
| E58 | 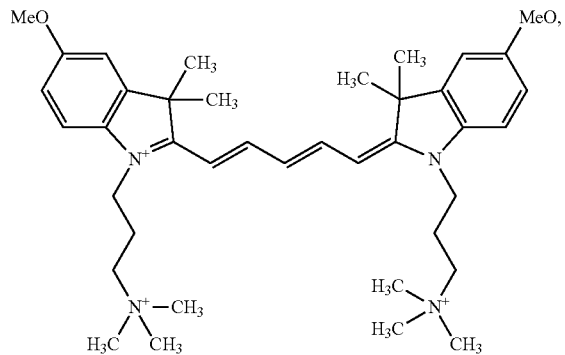 [SMILES: COc1ccc2c(c1)C(C)(C)C(/C=C/C=C/C=C1/N(CCC[N+](C)(C)C)c3ccc(OC)cc3C1(C)C)=[N+]2CCC[N+](C)(C)C] |
| E59 | 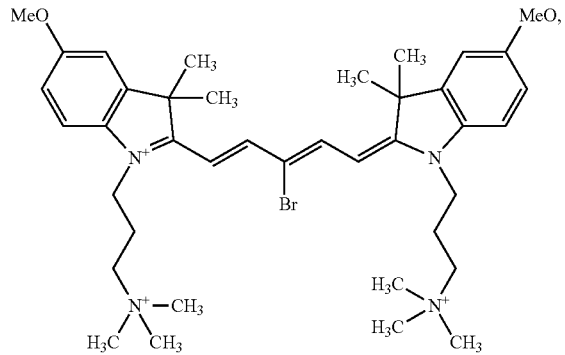 [SMILES: COc1ccc2c(c1)C(C)(C)C(/C=C/C(Br)=C/C=C1/N(CCC[N+](C)(C)C)c3ccc(OC)cc3C1(C)C)=[N+]2CCC[N+](C)(C)C] |

-continued
| Name | Structure |
|------|-----------|
| LN36 | 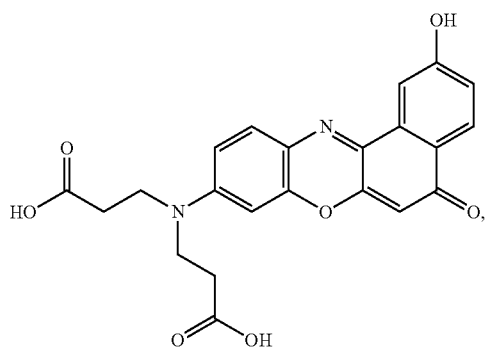 [SMILES: O=C(O)CCN(CCC(=O)O)c1ccc2nc3c4cc(O)ccc4c(=O)cc-3oc2c1] |
| AL27 | 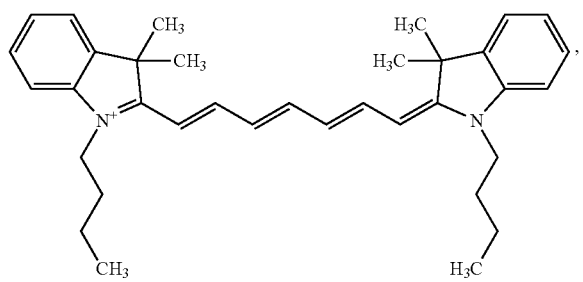 [SMILES: CCCCN1/C(=C/C=C/C=C/C=C/C2=[N+](CCCC)c3ccccc3C2(C)C)C(C)(C)c2ccccc21] |
| AL18 | 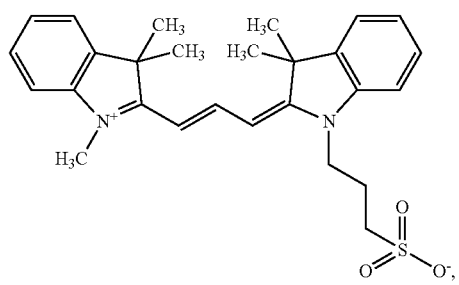 |
| AL16 | 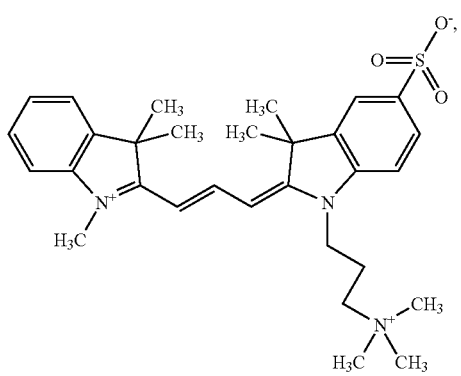 |
| AL25 | 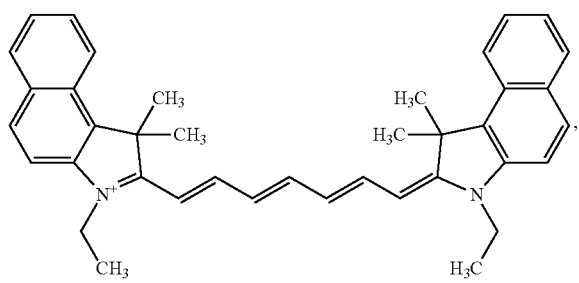 |

| Name | Structure |
|---|---|
| AL29 | 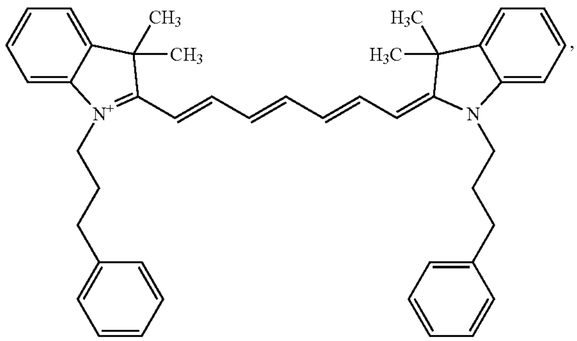 [SMILES: CC1(C)C(/C=C/C=C/C=C/C=C2/N(CCCc3ccccc3)c3ccccc3C2(C)C)=[N+](CCCc2ccccc2)c2ccccc21] |
| AL30 | 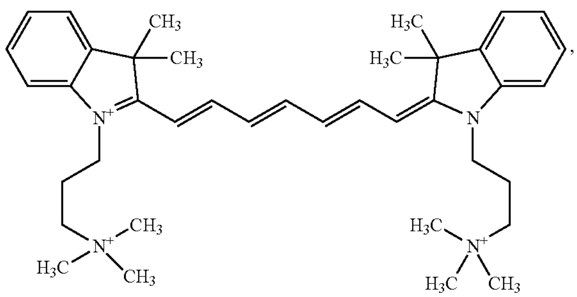 [SMILES: CC1(C)C(/C=C/C=C/C=C/C=C2/N(CCC[N+](C)(C)C)c3ccccc3C2(C)C)=[N+](CCC[N+](C)(C)C)c2ccccc21] |
| AL33 | 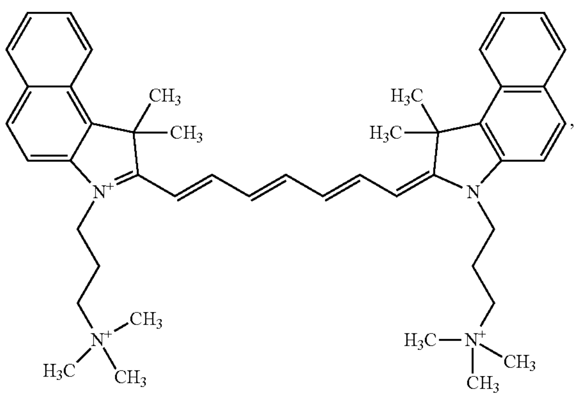 [SMILES: CC1(C)C(/C=C/C=C/C=C/C=C2/N(CCC[N+](C)(C)C)c3ccc4ccccc4c3C2(C)C)=[N+](CCC[N+](C)(C)C)c2ccc3ccccc3c21] |
| AL34 | 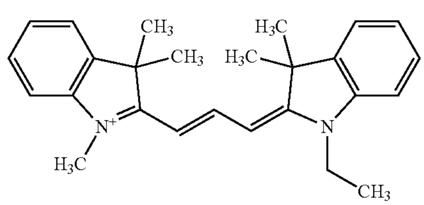 |
| AL35 | 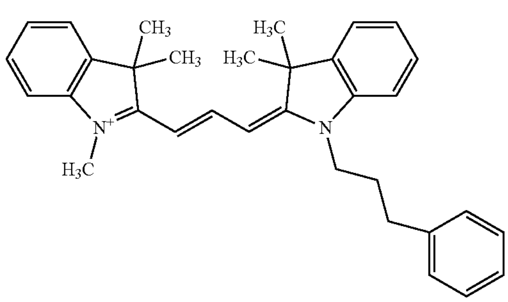 |

-continued
| Name | Structure |
|---|---|
| AL36 | 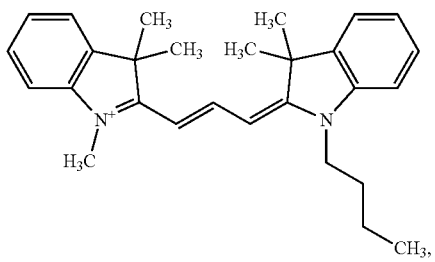 |
| AL14 | 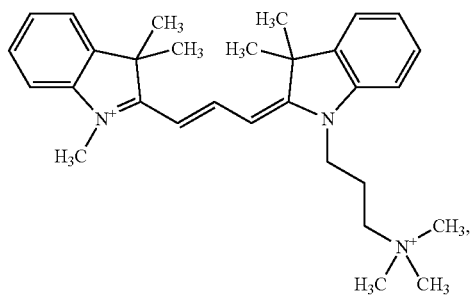 [SMILES: C[N+]1=C(/C=C/C=C2/N(CCC[N+](C)(C)C)c3ccccc3C2(C)C)C(C)(C)c2ccccc21] |
| AL79 | 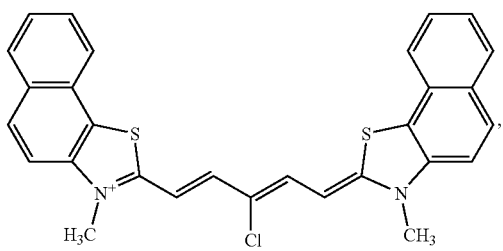 [SMILES: CN1/C(=C/C=C(Cl)/C=C/c2sc3c4ccccc4ccc3[n+]2C)Sc2c1ccc1ccccc21] |
| SP27 | 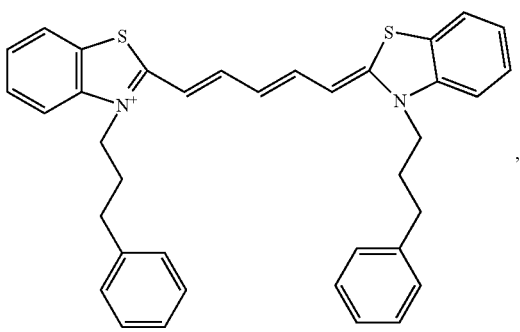 [SMILES: C(/C=C/C=C/c1sc2ccccc2[n+]1CCCc1ccccc1)=C1/Sc2ccccc2N1CCCc1ccccc1] |
| SP28 | 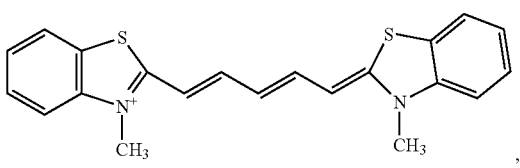 [SMILES: CN1/C(=C/C=C/C=C/c2sc3ccccc3[n+]2C)Sc2ccccc21] |
| SP29 | 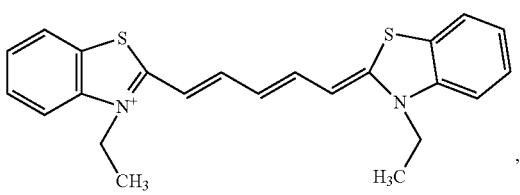 [SMILES: CCN1/C(=C/C=C/C=C/c2sc3ccccc3[n+]2CC)Sc2ccccc21] |

| Name | Structure |
|---|---|
| SP30 | 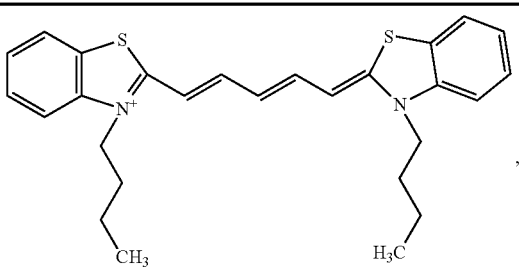 |
| SP33 | 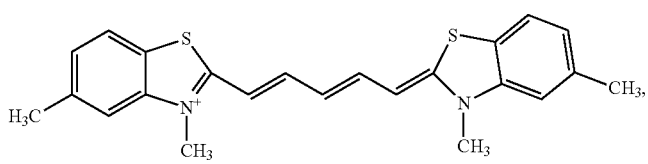 [SMILES: Cc1ccc2c(c1)N(C)/C(=C/C=C/C=C/c1sc3ccc(C)cc3[n+]1C)S2] |
| SP43 | 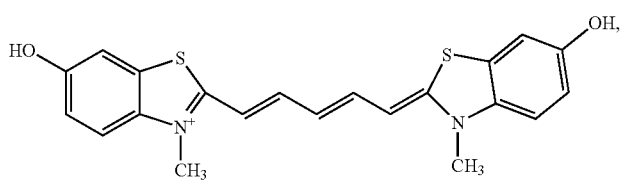 [SMILES: CN1/C(=C/C=C/C=C/c2sc3cc(O)ccc3[n+]2C)Sc2cc(O)ccc21] |
| SP49 | 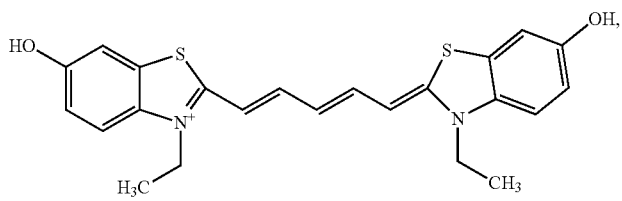 [SMILES: CCN1/C(=C/C=C/C=C/c2sc3cc(O)ccc3[n+]2CC)Sc2cc(O)ccc21] |
| SP51 | 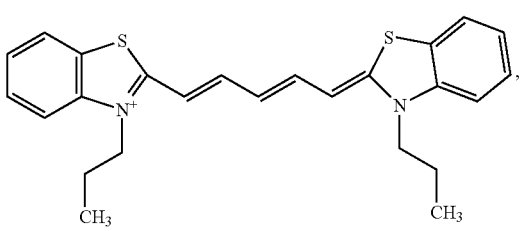 [SMILES: CCCN1/C(=C/C=C/C=C/c2sc3ccccc3[n+]2CCC)Sc2ccccc21] |
| SP53 | 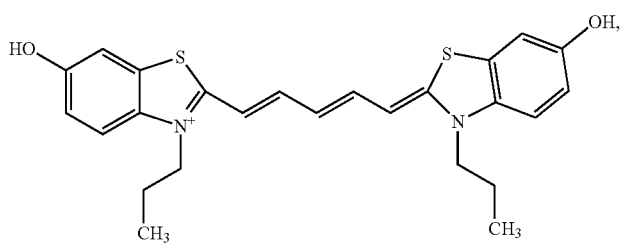 [SMILES: CCCN1/C(=C/C=C/C=C/c2sc3cc(O)ccc3[n+]2CCC)Sc2cc(O)ccc21] |
| SP79 | 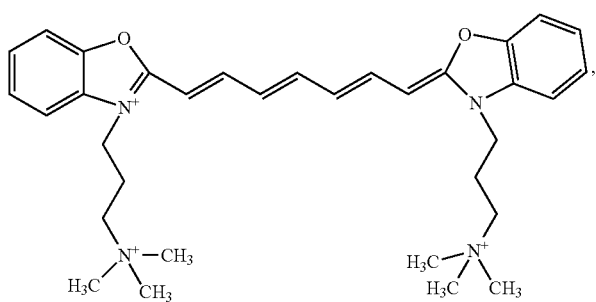 [SMILES: C[N+](C)(C)CCCN1/C(=C/C=C/C=C/C=C/c2oc3ccccc3[n+]2CCC[N+](C)(C)C)Oc2ccccc21] |

| Name | Structure |
|---|---|
| SP99 | 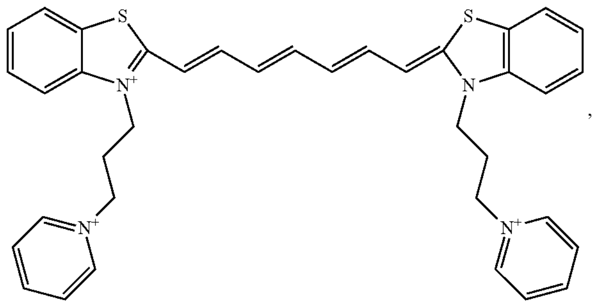 [SMILES: C(/C=C/C=C/C=C/c1sc2ccccc2[n+]1CCC[n+]1ccccc1)=C1/Sc2ccccc2N1CCC[n+]1ccccc1] |
| SP116 | 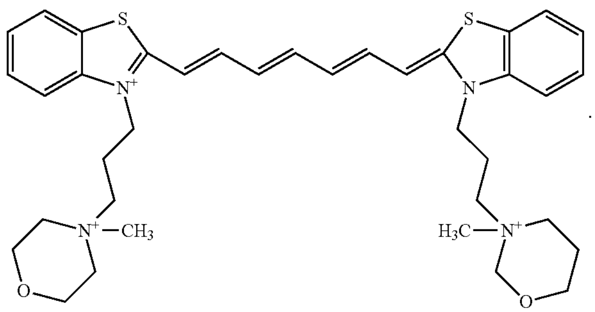 [SMILES: C[N+]1(CCC[n+]2c(/C=C/C=C/C=C/C=C3\Sc4ccccc4N3CCC[N+]3(C)CCCOC3)sc3ccccc32)CCOCC1] |
| SP117 | 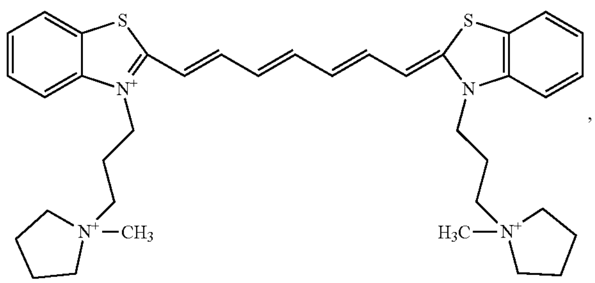 [SMILES: C[N+]1(CCCN2/C(=C/C=C/C=C/C=C/c3sc4ccccc4[n+]3CCC[N+]3(C)CCCC3)Sc3ccccc32)CCCC1] |
| ZK184 | 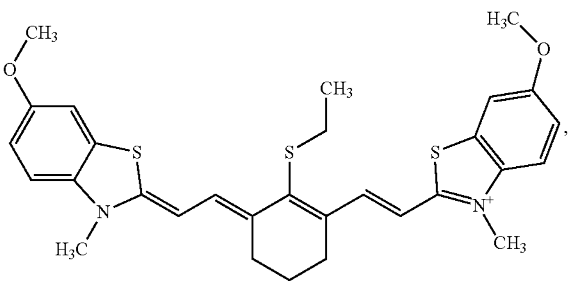 [SMILES: CCSC1=C(/C=C/c2sc3cc(OC)ccc3[n+]2C)CCC/C1=C\C=C1/Sc2cc(OC)ccc2N1C] |
| ZK185 | 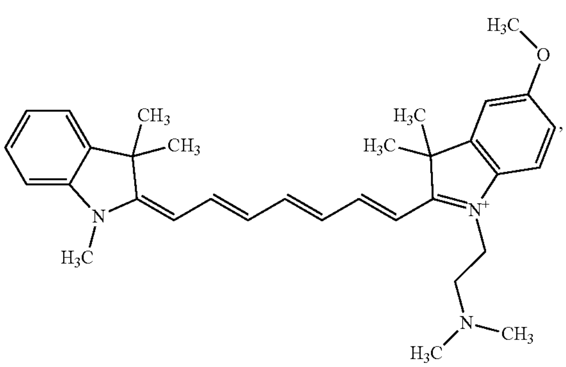 [SMILES: COc1ccc2c(c1)C(C)(C)C(/C=C/C=C/C=C/C=C1/N(C)c3ccccc3C1(C)C)=[N+]2CCN(C)C] |

-continued
| Name | Structure |
|---|---|
| ZK197 | 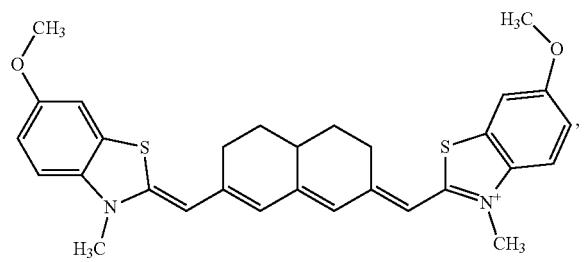 [SMILES: COc1ccc2c(c1)S/C(=C\C1=CC3=C/C(=C/c4sc5cc(OC)ccc5[n+]4C)CCC3CC1)N2C] |
| ZK198 | 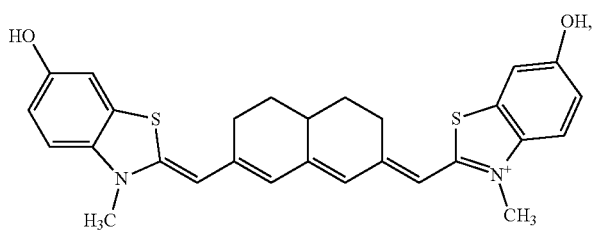 [SMILES: CN1/C(=C/C2=CC3=C/C(=C/c4sc5cc(O)ccc5[n+]4C)CCC3CC2)Sc2cc(O)ccc21] |
| ZK134 | 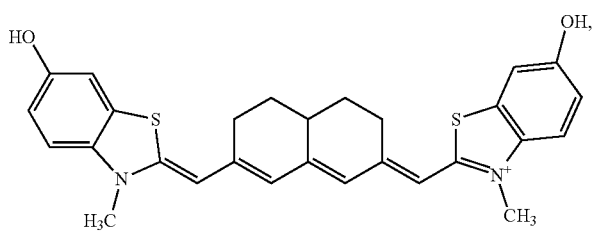 [SMILES: CN1/C(=C/C2=CC3=C/C(=C/c4sc5cc(O)ccc5[n+]4C)CCC3CC2)Sc2cc(O)ccc21] |
| ZK135 | 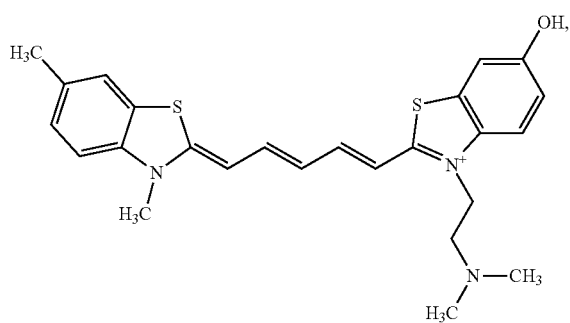 [SMILES: Cc1ccc2c(c1)S\C(=C/C=C/C=C/c1sc3cc(O)ccc3[n+]1CCN(C)C)N2C] |
| TG4 | 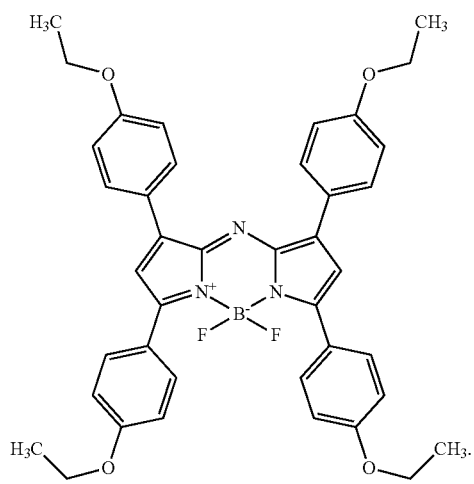 |

-continued
| Name | Structure |
|---|---|
| TG5 | 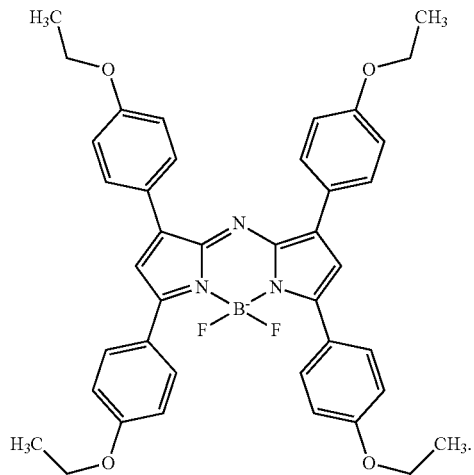 |
| TG7 | 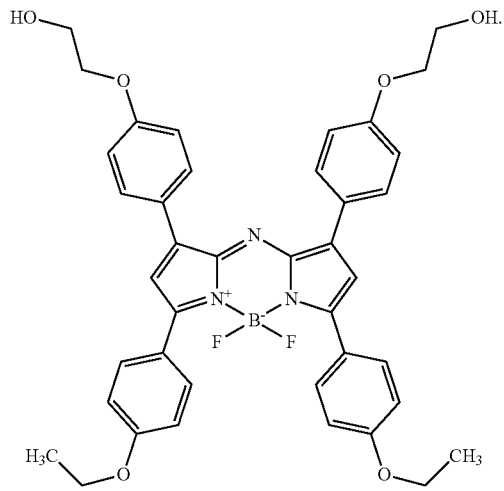 [SMILES: CCOc1ccc(C2=[N+]3C(=Nc4c(-c5ccc(OCCO)cc5)cc(-c5ccc(OCC)cc5)n4[B-]3(F)F)C(c3ccc(OCCO)cc3)=C2)cc1] |
| TG8 | 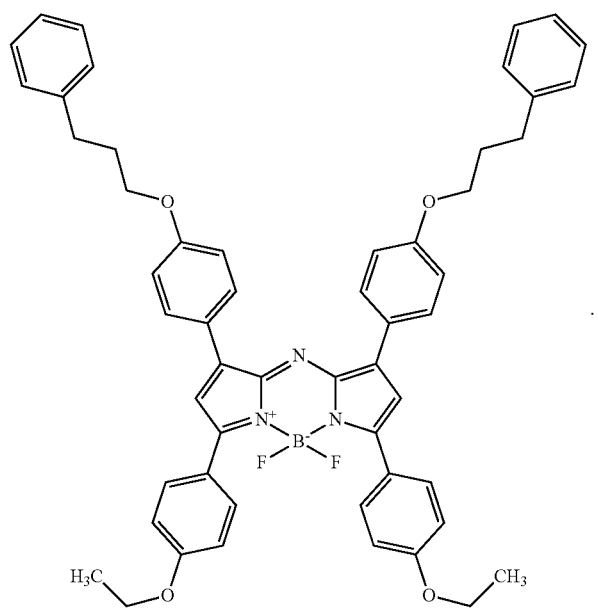 [SMILES: CCOc1ccc(C2=[N+]3C(=Nc4c(-c5ccc(OCCCc6ccccc6)cc5)cc(-c5ccc(OCC)cc5)n4[B-]3(F)F)C(c3ccc(OCCCc4ccccc4)cc3)=C2)cc1] |

-continued
| Name | Structure |
|---|---|
| TG27 | 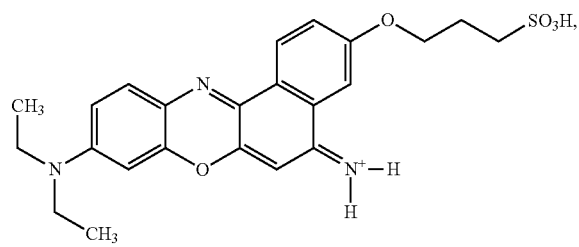 [SMILES: CCN(CC)c1ccc2nc3c4ccc(OCCCS(=O)(=O)O)cc4c(=[NH2+])cc-3oc2c1] |
| TP5 | 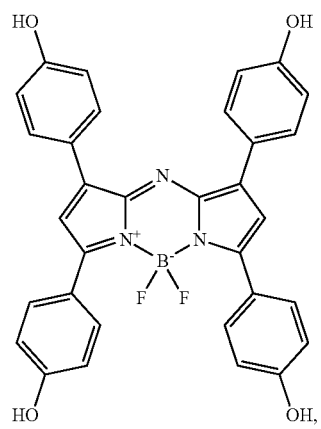 |
| QBN14 | 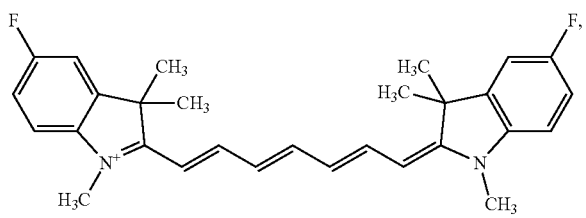 [SMILES: CN1/C(=C/C=C/C=C/C=C/C2=[N+](C)c3ccc(F)cc3C2(C)C)C(C)(C)c2cc(F)ccc21] |
| CNN154 | 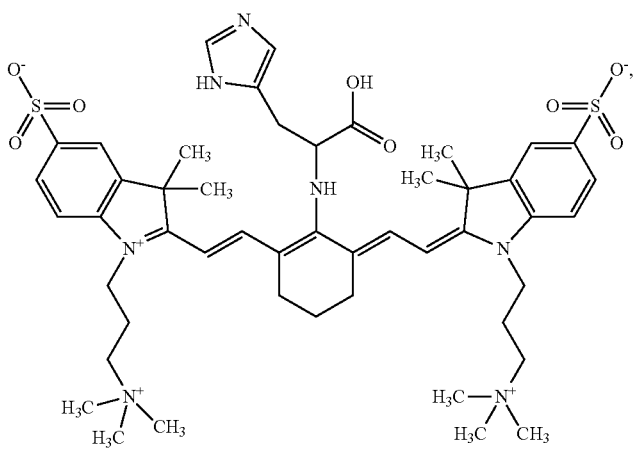 |

-continued

| Name | Structure |
|---|---|
| EAO42 | 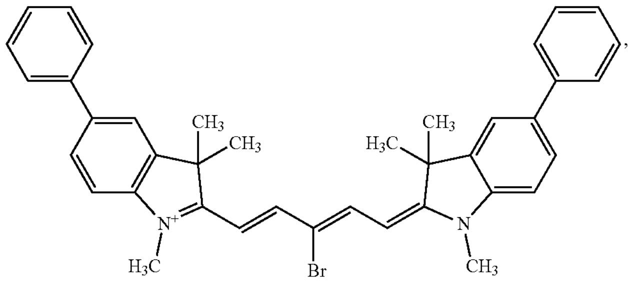 [SMILES: CN1/C(=C/C=C(Br)/C=C/C2=[N+](C)c3ccc(-c4ccccc4)cc3C2(C)C)C(C)(C)c2cc(-c3ccccc3)ccc21] |
| ZK166 | 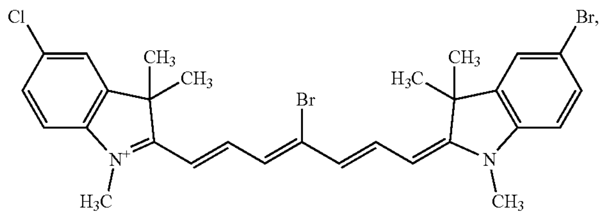 [SMILES: CN1/C(=C/C=C/C(Br)=C/C=C/C2=[N+](C)c3ccc(Cl)cc3C2(C)C)C(C)(C)c2cc(Br)ccc21] |
| PTN13 | 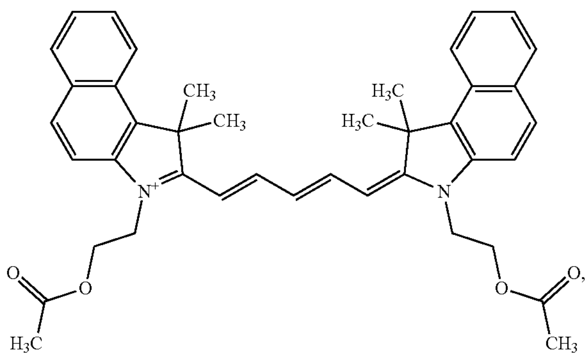 [SMILES: CC(=O)OCCN1/C(=C/C=C/C=C/C2=[N+](CCOC(C)=O)c3ccc4ccccc4c3C2(C)C)C(C)(C)c2c1ccc1ccccc21] |
| PTN12 | 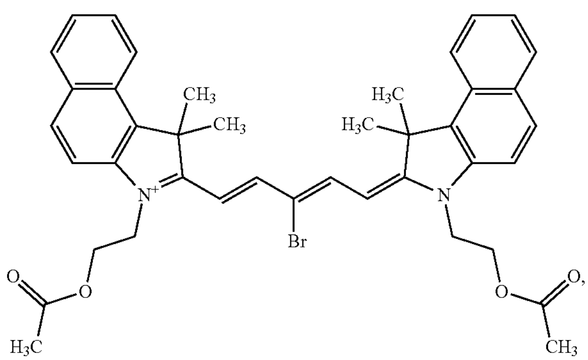 [SMILES: CC(=O)OCCN1/C(=C/C=C(Br)/C=C/C2=[N+](CCOC(C)=O)c3ccc4ccccc4c3C2(C)C)C(C)(C)c2c1ccc1ccccc21] |
| ZK148 | 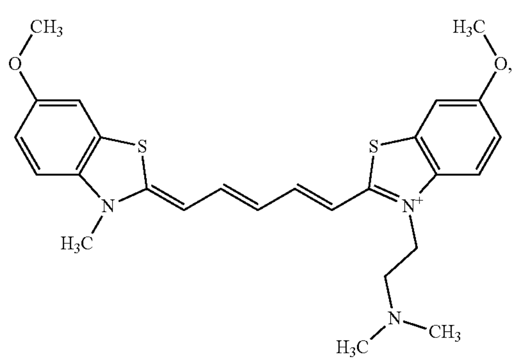 [SMILES: COc1ccc2c(c1)S\C(=C/C=C/C=C/c1sc3cc(OC)ccc3[n+]1CCN(C)C)N2C] |

-continued
| Name | Structure |
|---|---|
| ZK154 | 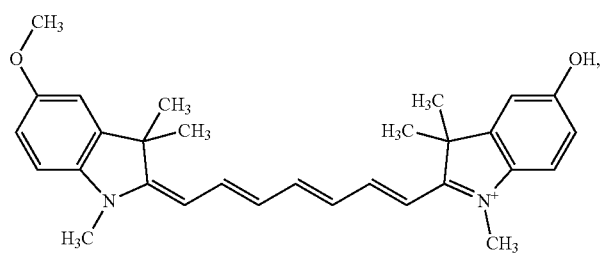 [SMILES: COc1ccc2c(c1)C(C)(C)\C(=C/C=C/C=C/C=C/C1=[N+](C)c3ccc(O)cc3C1(C)C)N2C] |
| E72 | 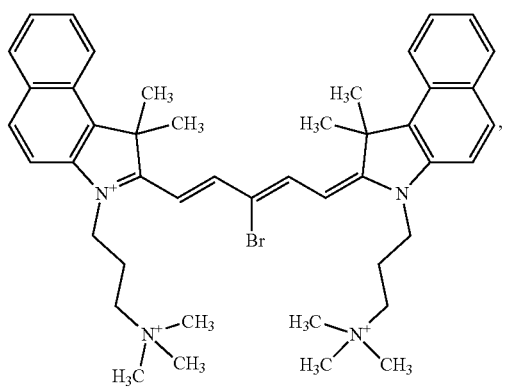 [SMILES: CC1(C)C(/C=C/C(Br)=C/C=C2/N(CCC[N+](C)(C)C)c3ccc4ccccc4c3C2(C)C)=[N+](CCC[N+](C)(C)C)c2ccc3ccccc3c21] |
| ZK159 | 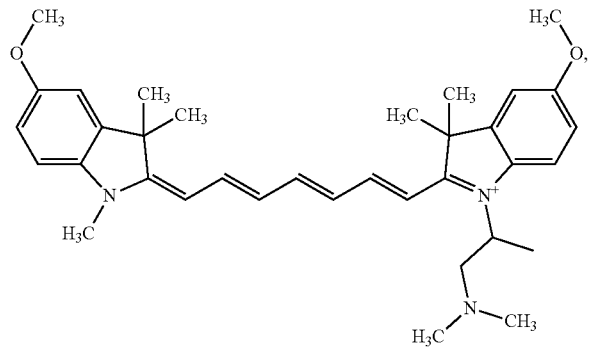 [SMILES: COc1ccc2c(c1)C(C)(C)C(/C=C/C=C/C=C/C=C1/N(C)c3ccc(OC)cc3C1(C)C)=[N+]2C(C)CN(C)C] |
| E70 | 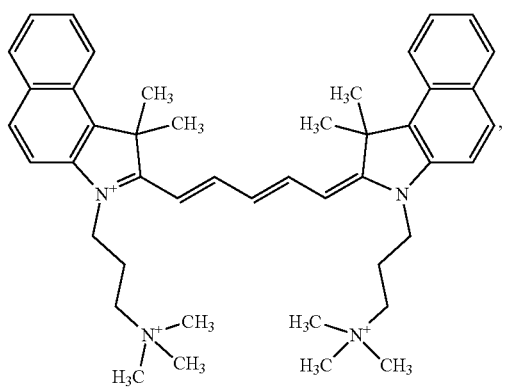 [SMILES: CC1(C)C(/C=C/C=C/C=C2/N(CCC[N+](C)(C)C)c3ccc4ccccc4c3C2(C)C)=[N+](CCC[N+](C)(C)C)c2ccc3ccccc3c21] |

-continued
| Name | Structure |
|---|---|
| ZK153 | 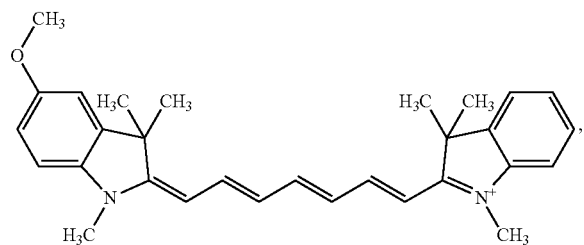 [SMILES: COc1ccc2c(c1)C(C)(C)\C(=C/C=C/C=C/C=C/C1=[N+](C)c3ccccc3C1(C)C)N2C] |
| PTN11 | 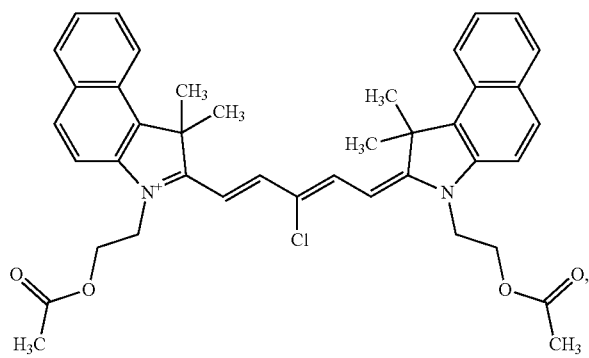 [SMILES: CC(=O)OCCN1/C(=C/C=C(Cl)/C=C/C2=[N+](CCOC(C)=O)c3ccc4ccccc4c3C2(C)C)C(C)(C)c2c1ccc1ccccc21] |
| ZK155 | 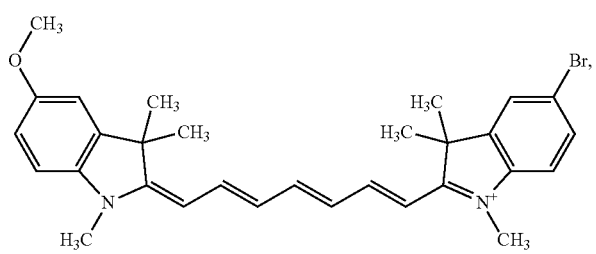 [SMILES: COc1ccc2c(c1)C(C)(C)\C(=C/C=C/C=C/C=C/C1=[N+](C)c3ccc(Br)cc3C1(C)C)N2C] |
| MHI103 | 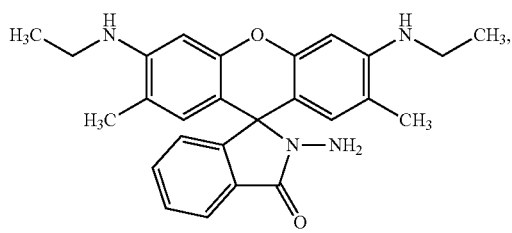 [SMILES: CCNc1cc2c(cc1C)C1(c3cc(C)c(NCC)cc3O2)c2ccccc2C(=O)N1N] |
| CNN13 | 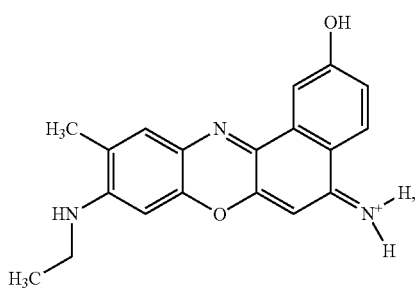 |

| Name | Structure |
|---|---|
| WuA71 | 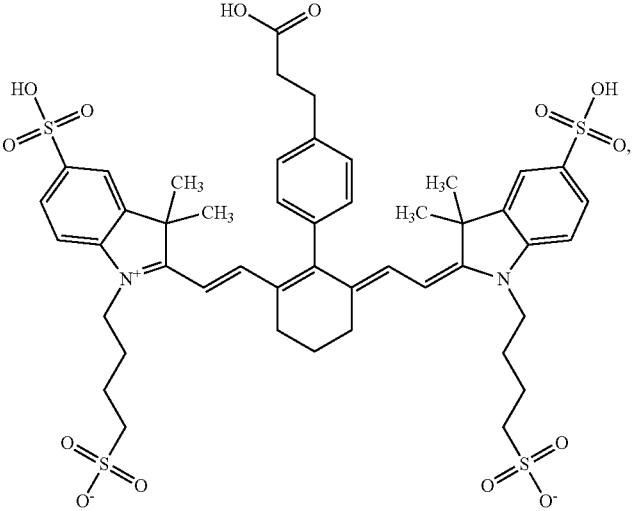 [SMILES: CC1(C)C(/C=C/C2=C(c3ccc(CCC(=O)O)cc3)C(=C/C=C3/N(CCCCS(=O)(=O)[O-])c4ccc(S(=O)(=O)O)cc4C3(C)C)/CCC2)=[N+](CCCCS(=O)(=O)[O-])c2ccc(S(=O)(=O)O)cc21] |
| ZK143 | 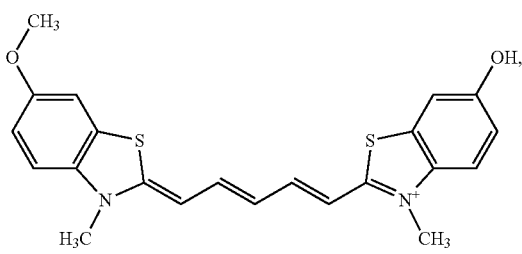 [SMILES: COc1ccc2c(c1)S\C(=C/C=C/C=C/c1sc3cc(O)ccc3[n+]1C)N2C] |
| ZK140 | 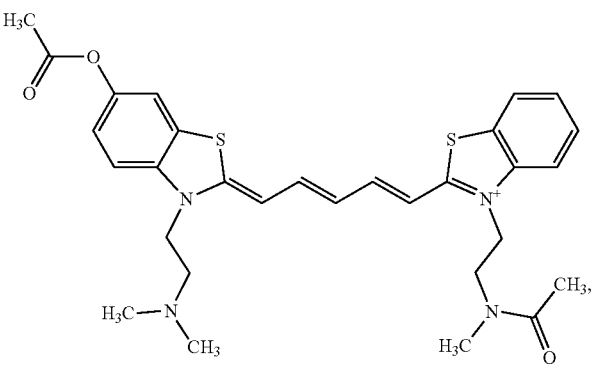 [SMILES: CC(=O)Oc1ccc2c(c1)S\C(=C/C=C/C=C/c1sc3ccccc3[n+]1CCN(C)C(C)=O)N2CCN(C)C] |
| ZK29 | 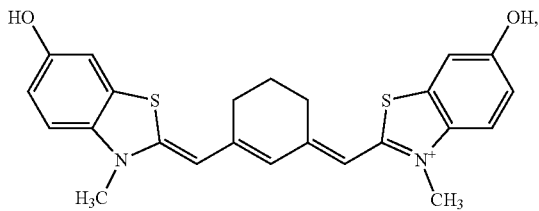 |
| SP34 | 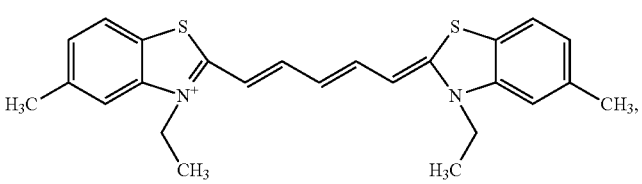 [SMILES: CCN1/C(=C/C=C/C=C/c2sc3ccc(C)cc3[n+]2CC)Sc2ccc(C)cc21] |

-continued
| Name | Structure |
|---|---|
| ZK104 | 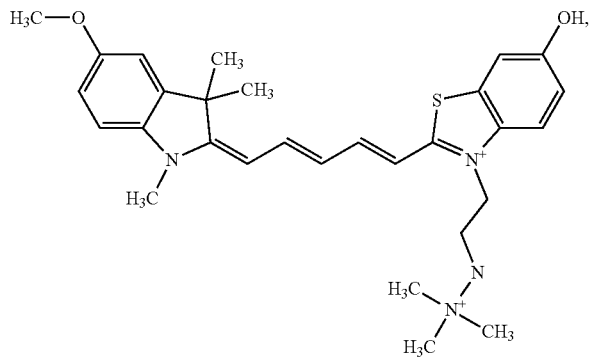 [SMILES: COc1ccc2c(c1)C(C)(C)\C(=C/C=C/C=C/c1sc3cc(O)ccc3[n+]1CCN[N+](C)(C)C)N2C] |
| TP1 | 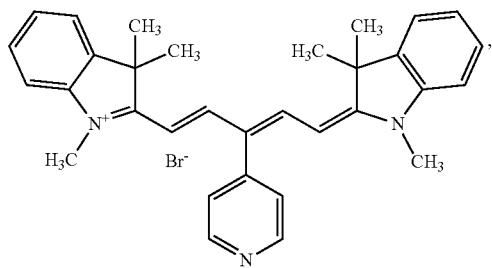 [SMILES: CN1/C(=C/C=C(/C=C/C2=[N+](C)c3ccccc3C2(C)C)c2ccncc2)C(C)(C)c2ccccc21 ; [Br-]] |
| ZK14 | 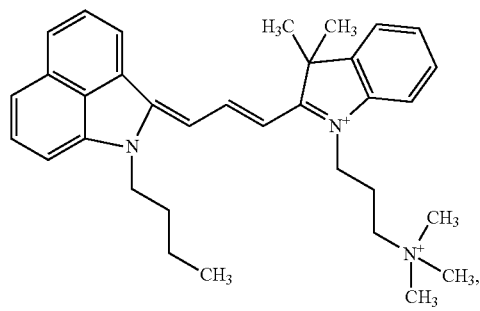 [SMILES: CCCCn1/c(=C/C=C/C2=[N+](CCC[N+](C)(C)C)c3ccccc3C2(C)C)c2cccc3cccc1c32] |
| PTN6 | 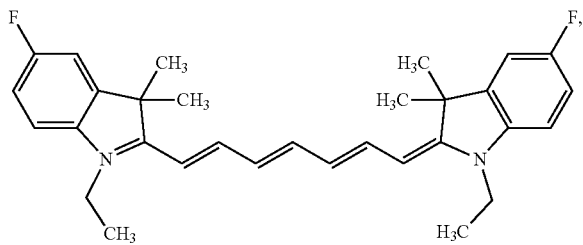 |

-continued
| Name | Structure |
|---|---|
| LN65 | 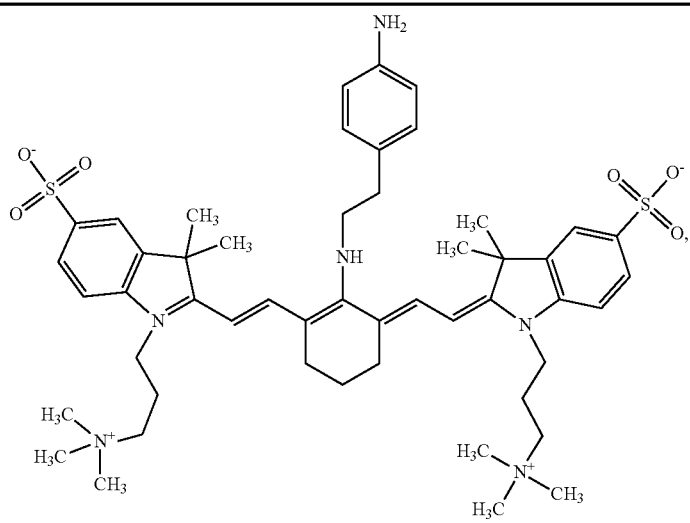 |
| LN79 | 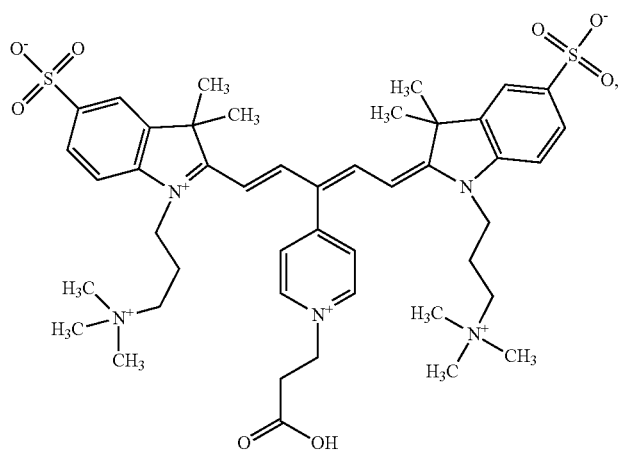 [SMILES: CC1(C)C(/C=C/C(=C/C=C2/N(CCC[N+](C)(C)C)c3ccc(S(=O)(=O)[O-])cc3C2(C)C)c2cc[n+](CCC(=O)O)cc2)=[N+](CCC[N+](C)(C)C)c2ccc(S(=O)(=O)[O-])cc21] |
| AH34 | 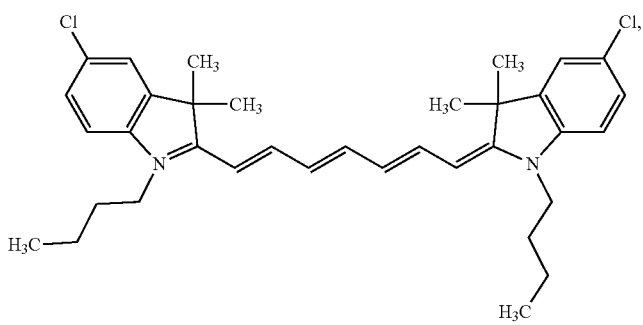 |
| TP4 | 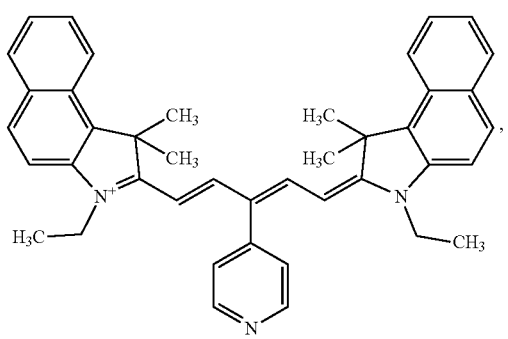 [SMILES: CCN1/C(=C/C=C(/C=C/C2=[N+](CC)c3ccc4ccccc4c3C2(C)C)c2ccncc2)C(C)(C)c2c1ccc1ccccc21] |

-continued
| Name | Structure |
|------|-----------|
| LS1 | 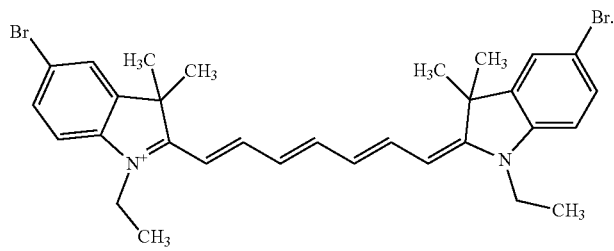 [SMILES: CCN1/C(=C/C=C/C=C/C=C/C2=[N+](CC)c3ccc(Br)cc3C2(C)C)C(C)(C)c2cc(Br)ccc21] |
| YY163 | 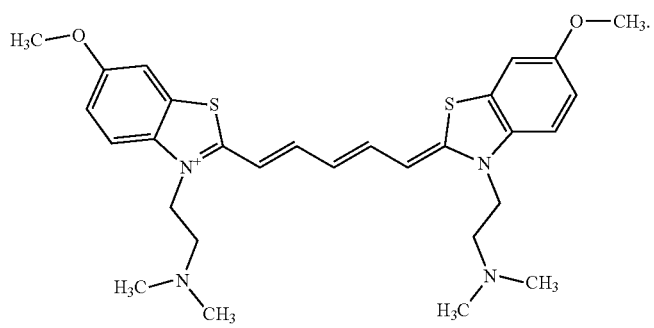 [SMILES: COc1ccc2c(c1)S\C(=C/C=C/C=C/c1sc3cc(OC)ccc3[n+]1CCN(C)C)N2CCN(C)C] |
| TP6 | 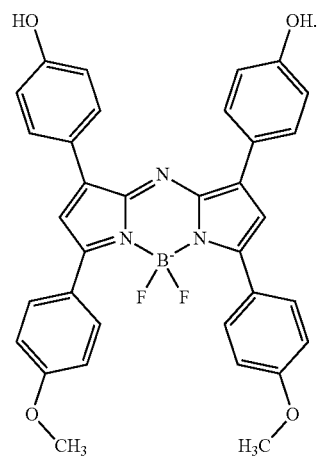 |
| ZK15 | 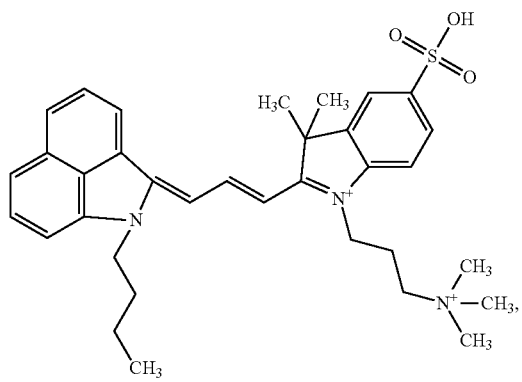 [SMILES: CCCCn1/c(=C/C=C/C2=[N+](CCC[N+](C)(C)C)c3ccc(S(=O)(=O)O)cc3C2(C)C)c2cccc3cccc1c32] |

| Name | Structure |
|---|---|
| WuA108 | 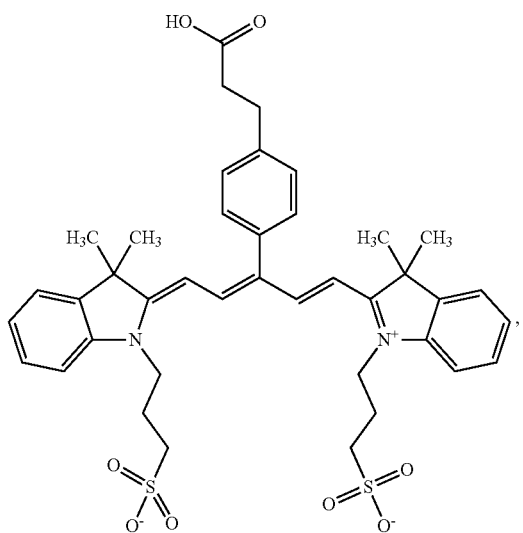 [SMILES: CC1(C)C(/C=C/C(=C/C=C2\N(CCCS(=O)(=O)[O-])c3ccccc3C2(C)C)c2ccc(CCC(=O)O)cc2)=[N+](CCCS(=O)(=O)[O-])c2ccccc21] |
| ZK150 | 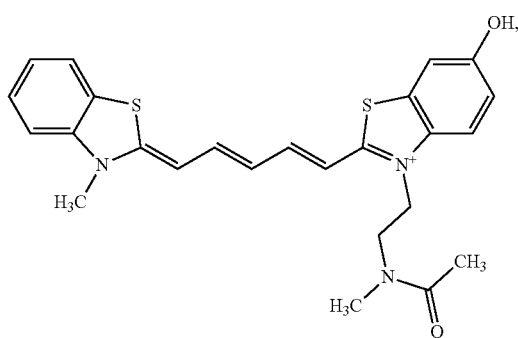 [SMILES: CC(=O)N(C)CC[n+]1c(/C=C/C=C/C=C2\Sc3ccccc3N2C)sc2cc(O)ccc21] |
| ZK156 | 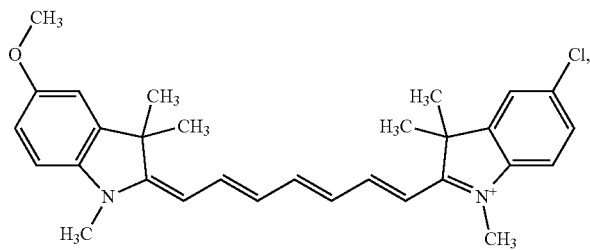 [SMILES: COc1ccc2c(c1)C(C)(C)\C(=C/C=C/C=C/C=C/C1=[N+](C)c3ccc(Cl)cc3C1(C)C)N2C] |
| ESS23 | 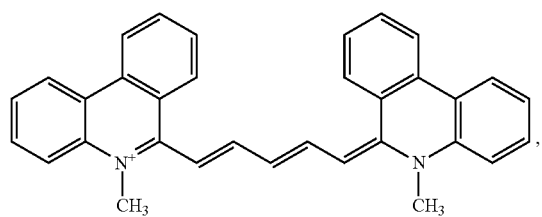 [SMILES: CN1/C(=C/C=C/C=C/c2c3ccccc3c3ccccc3[n+]2C)c2ccccc2-c2ccccc21] |

-continued
| Name | Structure |
|---|---|
| CNN17 | 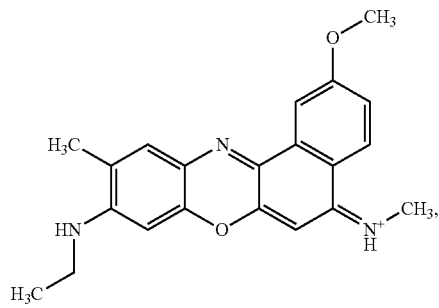 |
| TG56 | 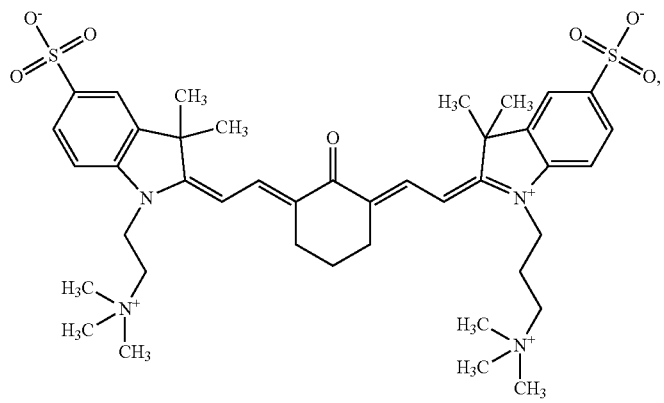 |
| AL31 | 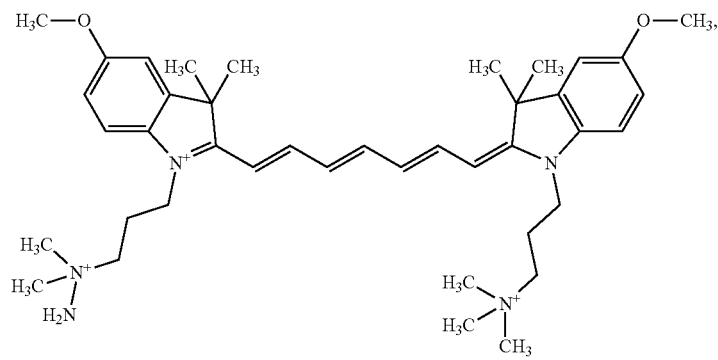 [SMILES: COc1ccc2c(c1)C(C)(C)C(/C=C/C=C/C=C/C=C1/N(CCC[N+](C)(C)C)c3ccc(OC)cc3C1(C)C)=[N+]2CCC[N+](C)(C)N] |
| AL43 | 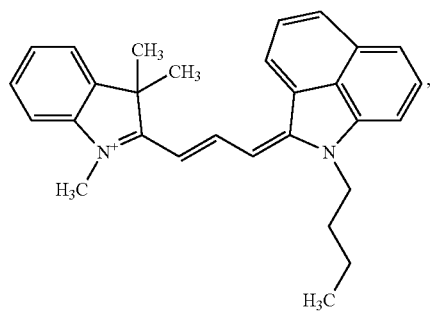 [SMILES: CCCCn1/c(=C/C=C/C2=[N+](C)c3ccccc3C2(C)C)c2cccc3cccc1c32] |

| Name | Structure |
|---|---|
| TG31 | 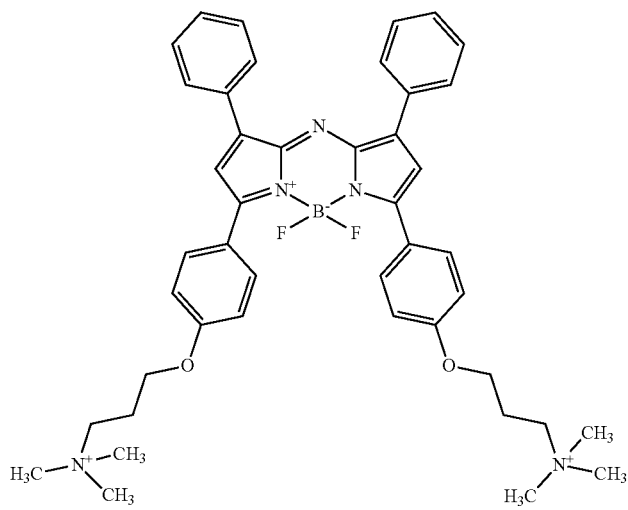 [SMILES: C[N+](C)(C)CCCOc1ccc(C2=[N+]3C(=Nc4c(-c5ccccc5)cc(-c5ccc(OCCC[N+](C)(C)C)cc5)n4[B-]3(F)F)C(c3ccccc3)=C2)cc1] |
| CNN3 | 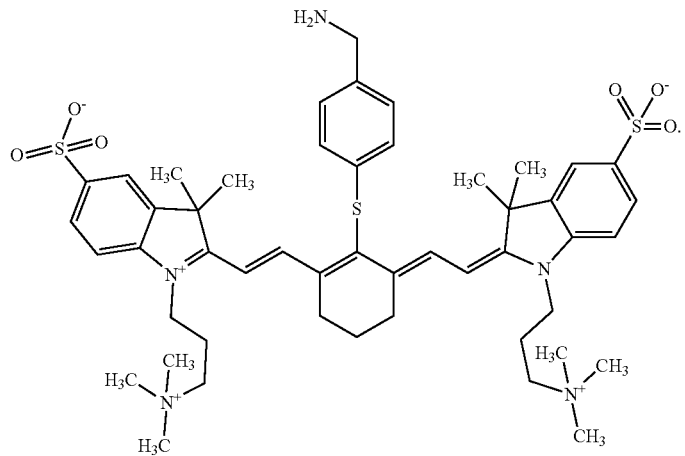 [SMILES: CC1(C)C(/C=C/C2=C(Sc3ccc(CN)cc3)C(=C/C=C3/N(CCC[N+](C)(C)C)c4ccc(S(=O)(=O)[O-])cc4C3(C)C)/CCC2)=[N+](CCC[N+](C)(C)C)c2ccc(S(=O)(=O)[O-])cc21] |
| AL20 | 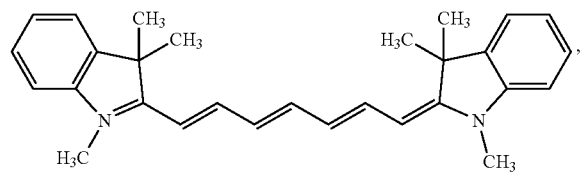 |

-continued
| Name | Structure |
|---|---|
| TG115 | 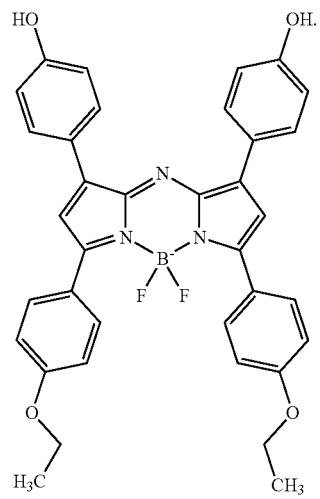 |
| CNN2 | 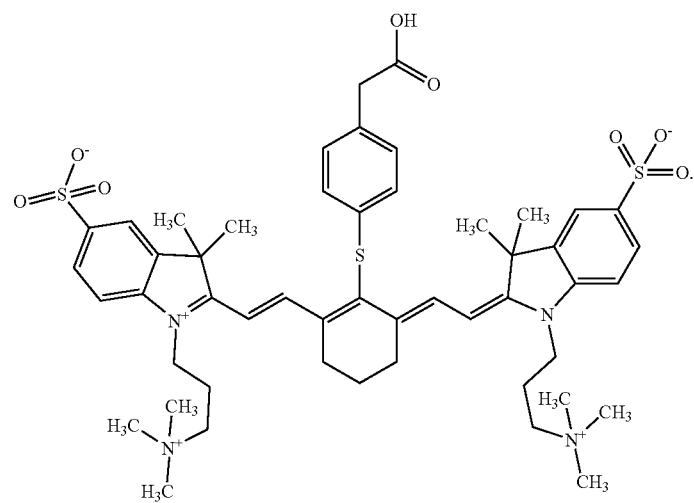 [SMILES: CC1(C)C(/C=C/C2=C(Sc3ccc(CC(=O)O)cc3)C(=C/C=C3/N(CCC[N+](C)(C)C)c4ccc(S(=O)(=O)[O-])cc4C3(C)C)/CCC2)=[N+](CCC[N+](C)(C)C)c2ccc(S(=O)(=O)[O-])cc21] |
| TP04 | 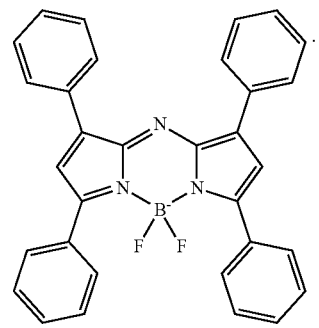 |
| ZK26 | 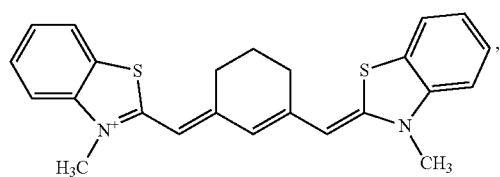 |

-continued
| Name | Structure |
|---|---|
| ZK48 | 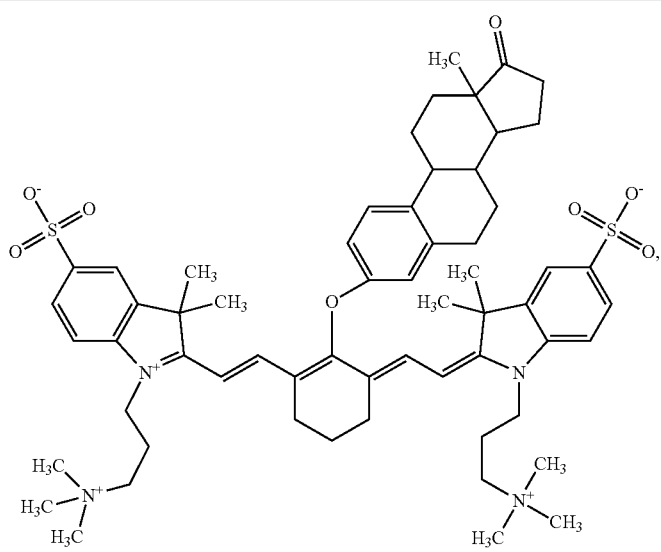 [SMILES: CC1(C)C(/C=C/C2=C(Oc3ccc4c(c3)CCC3C4CCC4(C)C(=O)CCC34)C(=C/C=C3/N(CCC[N+](C)(C)C)c4ccc(S(=O)(=O)[O-])cc4C3(C)C)/CCC2)=[N+](CCC[N+](C)(C)C)c2ccc(S(=O)(=O)[O-])cc21] |
| TG44 | 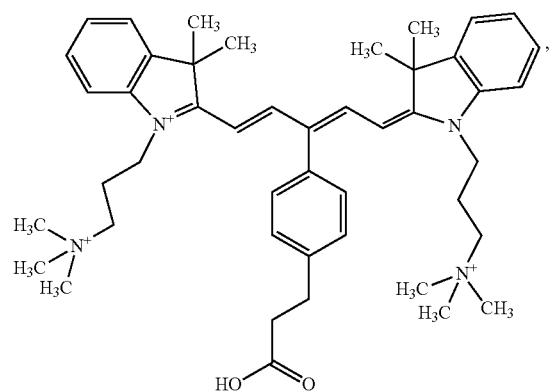 [SMILES: CC1(C)C(/C=C/C(=C/C=C2/N(CCC[N+](C)(C)C)c3ccccc3C2(C)C)c2ccc(CCC(=O)O)cc2)=[N+](CCC[N+](C)(C)C)c2ccccc21] |
| ZK27 | 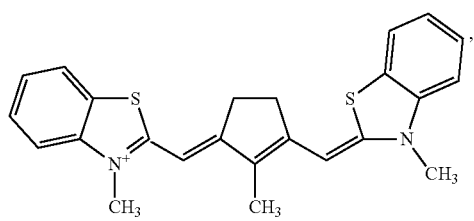 |
| ZK46 | 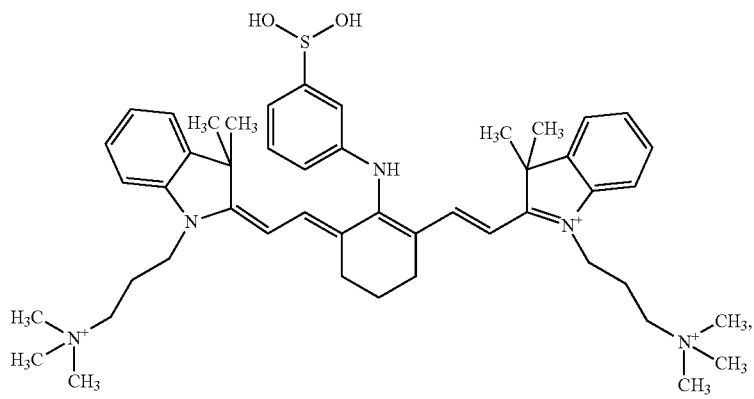 |

-continued
| Name | Structure |
|---|---|
| CNN1 | 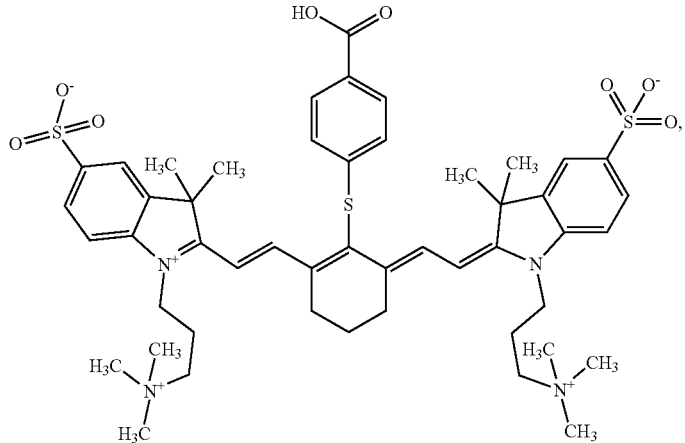 [SMILES: CC1(C)C(/C=C/C2=C(Sc3ccc(C(=O)O)cc3)C(=C/C=C3/N(CCC[N+](C)(C)C)c4ccc(S(=O)(=O)[O-])cc4C3(C)C)/CCC2)=[N+](CCC[N+](C)(C)C)c2ccc(S(=O)(=O)[O-])cc21] |
| ZK79 | 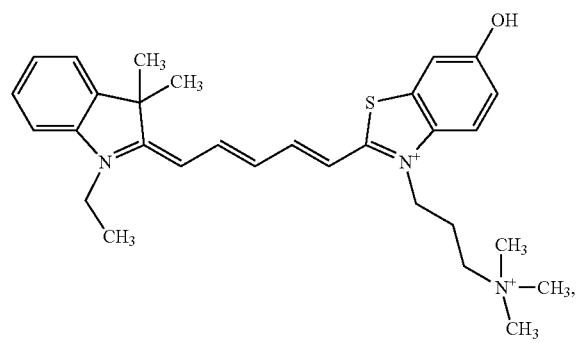 |
| WuA38 | 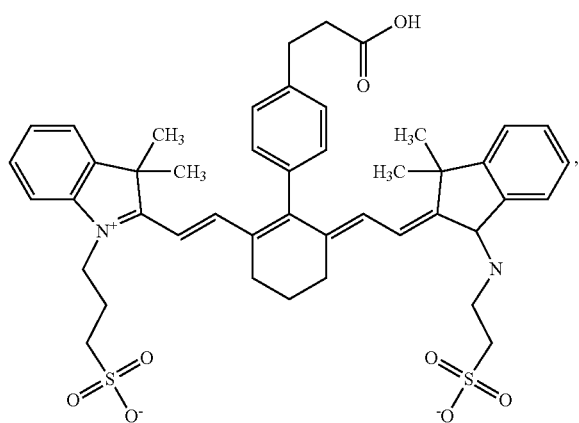 |

| Name | Structure |
|------|-----------|
| LN68 | 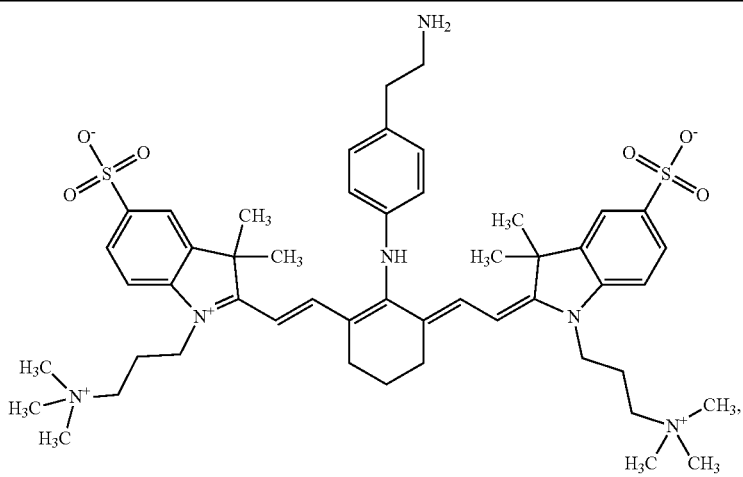 |
| ESS13 | 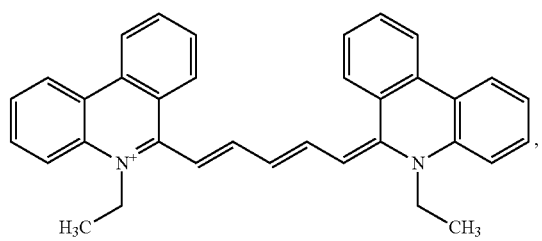 [SMILES: CCN1/C(=C/C=C/C=C/c2c3ccccc3c3ccccc3[n+]2CC)c2ccccc2-c2ccccc21] |
| WuA110 | 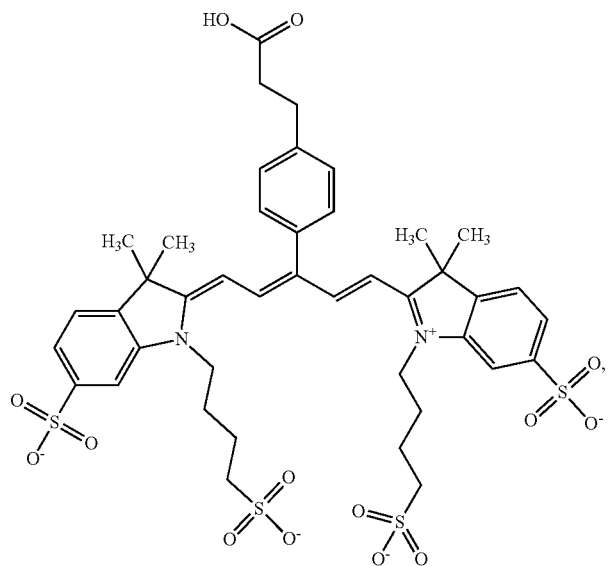 [SMILES: CC1(C)C(/C=C/C(=C/C=C2\N(CCCCS(=O)(=O)[O-])c3cc(S(=O)(=O)[O-])ccc3C2(C)C)c2ccc(CCC(=O)O)cc2)=[N+](CCCCS(=O)(=O)[O-])c2cc(S(=O)(=O)[O-])ccc21] |
| YY161 | 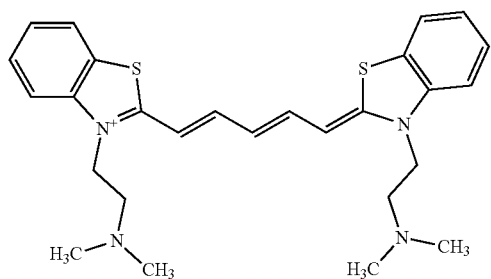 [SMILES: CN(C)CCN1/C(=C/C=C/C=C/c2sc3ccccc3[n+]2CCN(C)C)Sc2ccccc21] |

-continued
| Name | Structure |
|---|---|
| E71 | 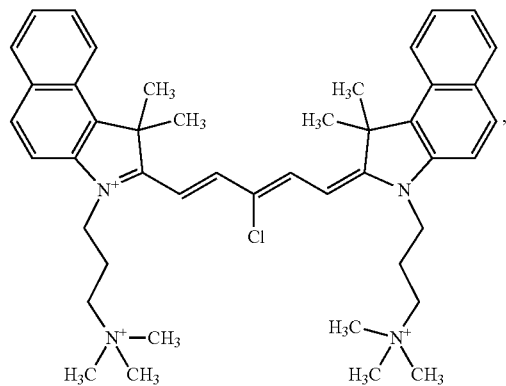 [SMILES: CC1(C)C(/C=C/C(Cl)=C/C=C2/N(CCC[N+](C)(C)C)c3ccc4ccccc4c3C2(C)C)=[N+](CCC[N+](C)(C)C)c2ccc3ccccc3c21] |
| CNN8 | 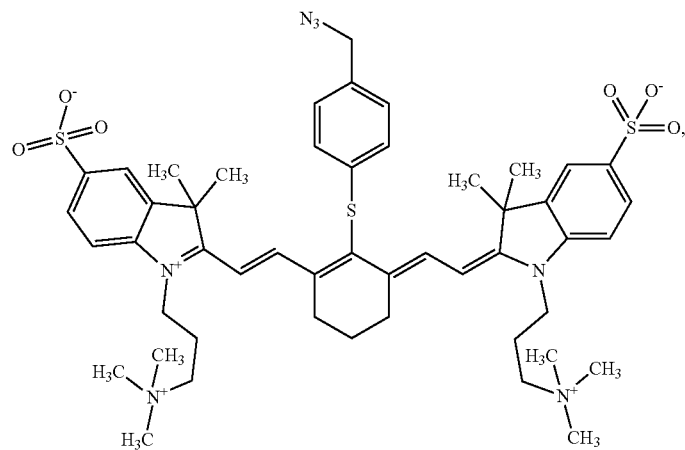 [SMILES: CC1(C)C(/C=C/C2=C(Sc3ccc(CN=[N+]=[N-])cc3)C(=C/C=C3/N(CCC[N+](C)(C)C)c4ccc(S(=O)(=O)[O-])cc4C3(C)C)/CCC2)=[N+](CCC[N+](C)(C)C)c2ccc(S(=O)(=O)[O-])cc21] |
| CNN10 | 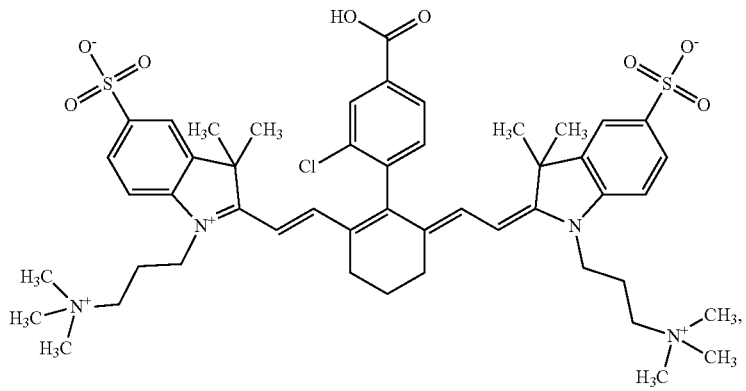 [SMILES: CC1(C)C(/C=C/C2=C(c3ccc(C(=O)O)cc3Cl)C(=C/C=C3/N(CCC[N+](C)(C)C)c4ccc(S(=O)(=O)[O-])cc4C3(C)C)/CCC2)=[N+](CCC[N+](C)(C)C)c2ccc(S(=O)(=O)[O-])cc21] |

-continued
| Name | Structure |
|---|---|
| LN68Boc | 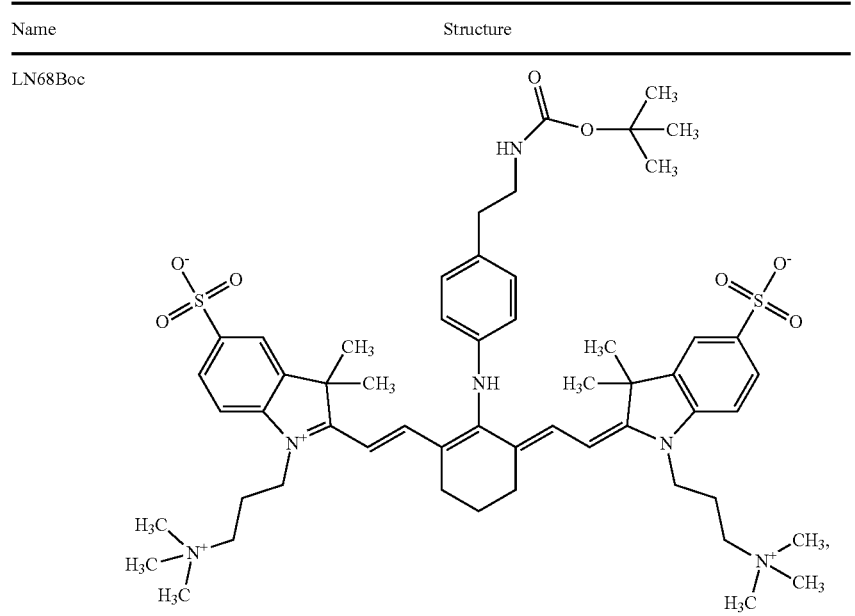 |
| TG60 | 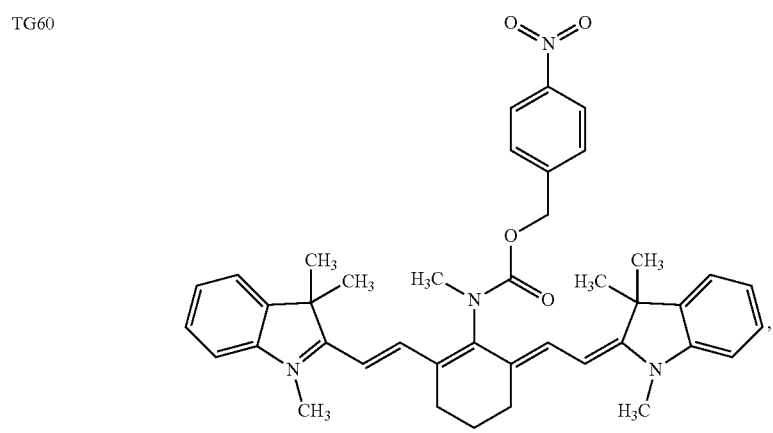 |
| ZK78 | 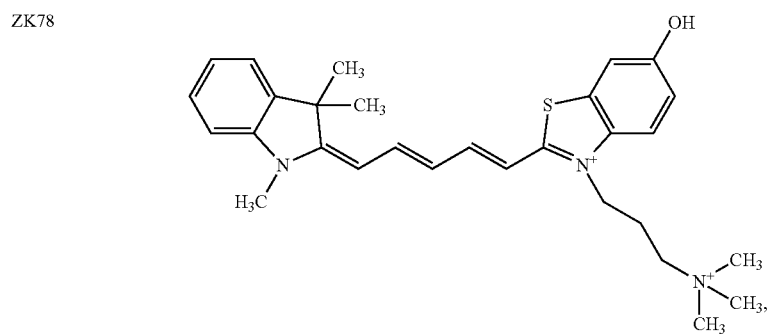 |

-continued
| Name | Structure |
|------|-----------|
| ZK133 | 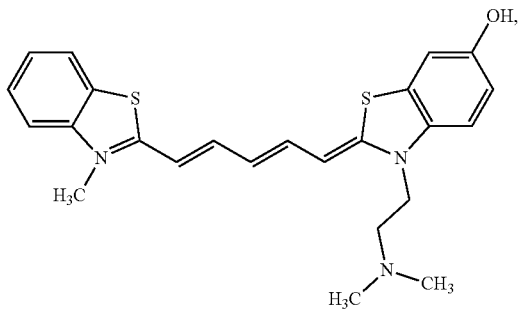 |
| CNN7 | 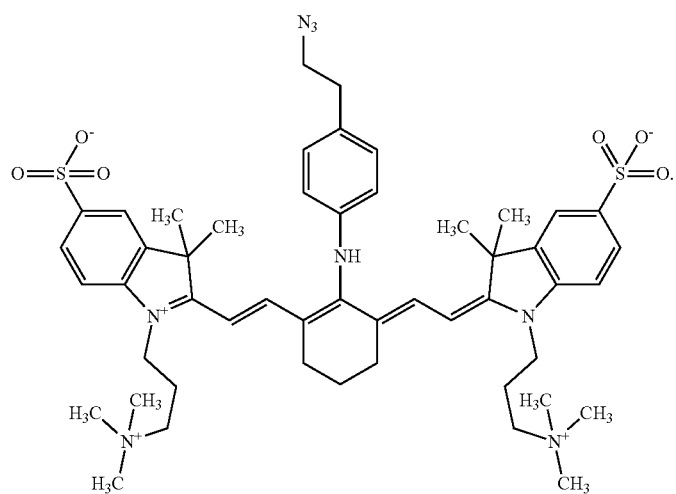 [SMILES: CC1(C)C(/C=C/C2=C(Nc3ccc(CCN=[N+]=[N-])cc3)C(=C/C=C3/N(CCC[N+](C)(C)C)c4ccc(S(=O)(=O)[O-])cc4C3(C)C)/CCC2)=[N+](CCC[N+](C)(C)C)c2ccc(S(=O)(=O)[O-])cc21] |
| ZK23 | 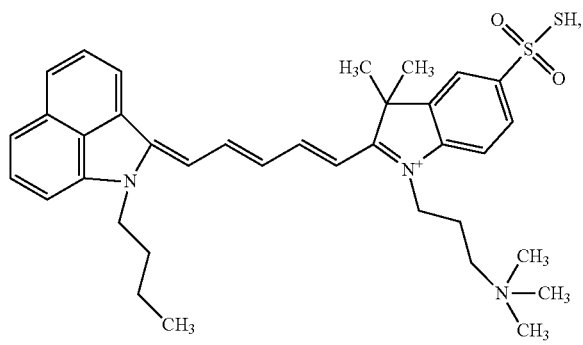 |
| MDL17 | 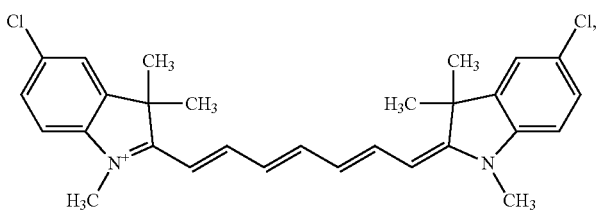 [SMILES: CN1/C(=C/C=C/C=C/C=C/C2=[N+](C)c3ccc(Cl)cc3C2(C)C)C(C)(C)c2cc(Cl)ccc21] |

-continued

| Name | Structure |
|---|---|
| TG11A | 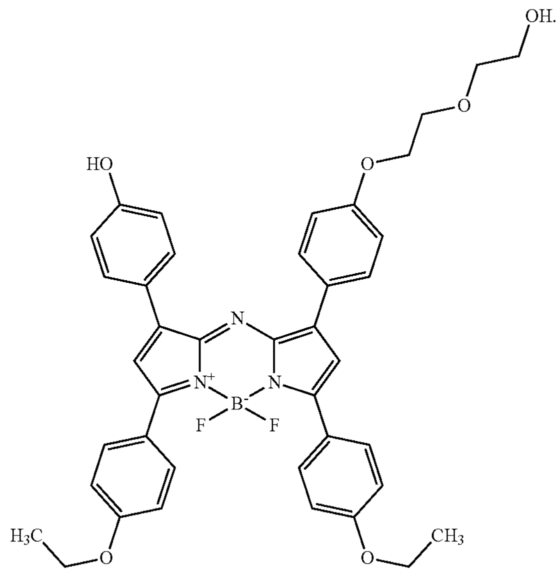 [SMILES: CCOc1ccc(C2=[N+]3C(=Nc4c(-c5ccc(OCCOCCO)cc5)cc(-c5ccc(OCC)cc5)n4[B-]3(F)F)C(c3ccc(O)cc3)=C2)cc1] |
| TG11B | 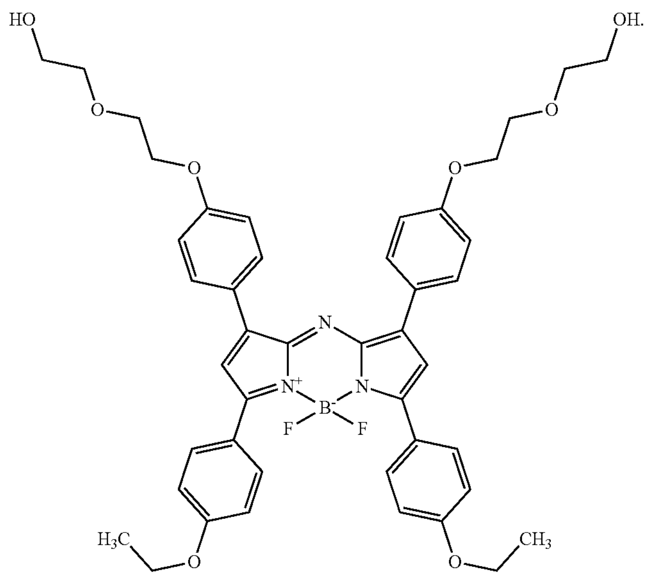 [SMILES: CCOc1ccc(C2=[N+]3C(=Nc4c(-c5ccc(OCCOCCO)cc5)cc(-c5ccc(OCC)cc5)n4[B-]3(F)F)C(c3ccc(OCCOCCO)cc3)=C2)cc1] |
| TP2 | 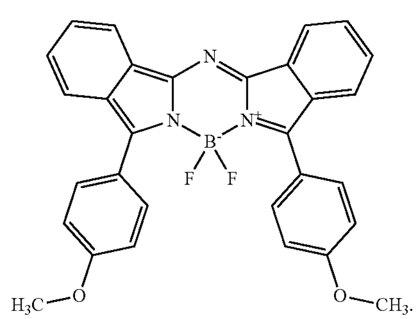 [SMILES: COc1ccc(C2=[N+]3C(=Nc4c5ccccc5c(-c5ccc(OC)cc5)n4[B-]3(F)F)c3ccccc32)cc1] |

-continued
| Name | Structure |
|---|---|
| LN50 | 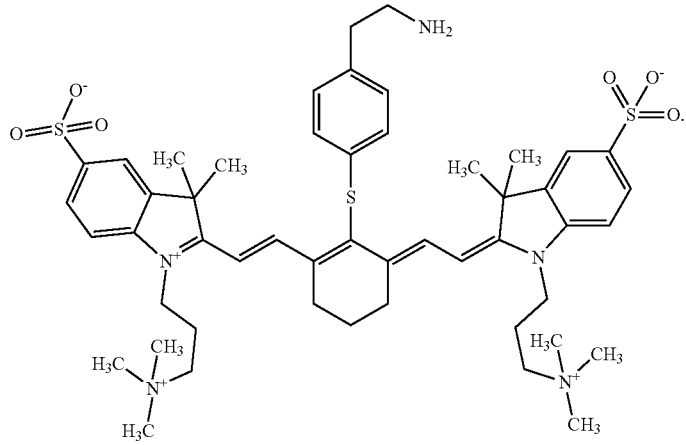 [SMILES: CC1(C)C(/C=C/C2=C(Sc3ccc(CCN)cc3)C(=C/C=C3/N(CCC[N+](C)(C)C)c4ccc(S(=O)(=O)[O-])cc4C3(C)C)/CCC2)=[N+](CCC[N+](C)(C)C)c2ccc(S(=O)(=O)[O-])cc21] |
| TG17 | 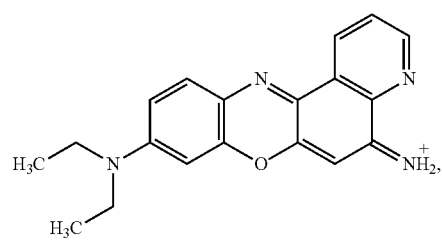 |
| TG22 | 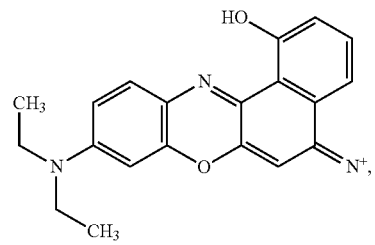 |
| LN34 | 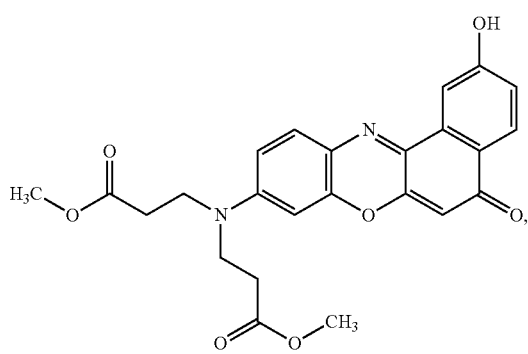 [SMILES: COC(=O)CCN(CCC(=O)OC)c1ccc2nc3c4cc(O)ccc4c(=O)cc-3oc2c1] |
| CNN16 | 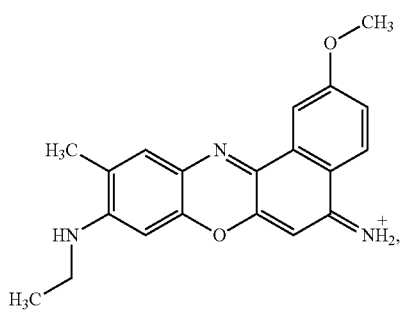 |

| Name | Structure |
|---|---|
| CNN12 | 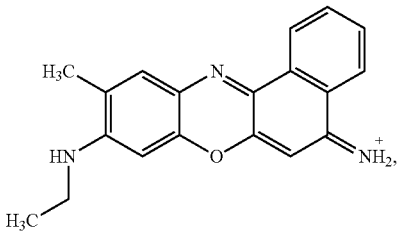 |
| CNN145 | 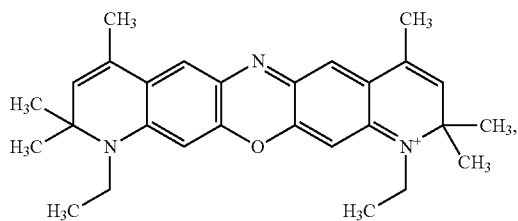 [SMILES: CCN1c2cc3c(cc2C(C)=CC1(C)C)N=c1cc2c(cc1O3)=[N+](CC)C(C)(C)C=C2C] |
| ZK203 | 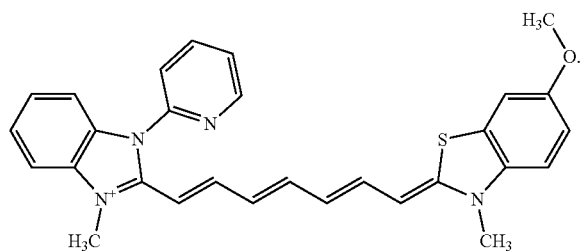 [SMILES: COc1ccc2c(c1)S\C(=C/C=C/C=C/C=C/c1n(-c3ccccn3)c3ccccc3[n+]1C)N2C] |
| ZK204 | 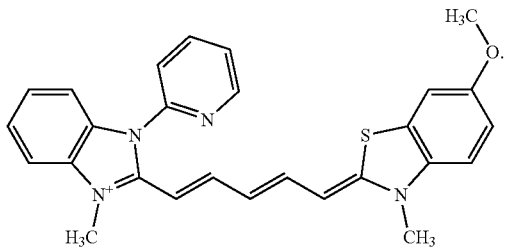 [SMILES: COc1ccc2c(c1)S\C(=C/C=C/C=C/c1n(-c3ccccn3)c3ccccc3[n+]1C)N2C] |
| ZK208 | 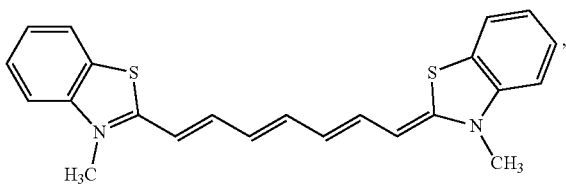 |
| ZK196 | 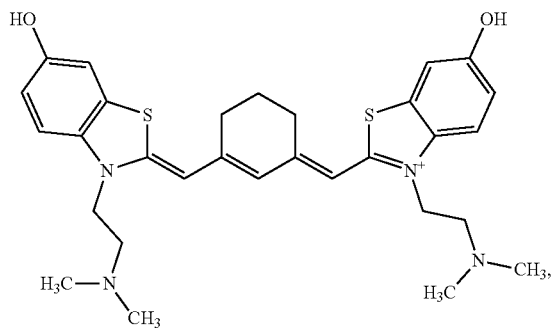 [SMILES: CN(C)CCN1/C(=C/C2=CC(=C/c3sc4cc(O)ccc4[n+]3CCN(C)C)/CCC2)Sc2cc(O)ccc21] |

-continued
| Name | Structure |
|---|---|
| WuA67 | 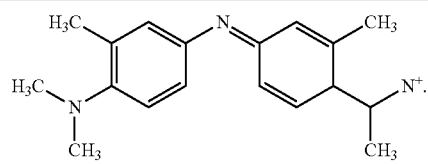 |
| WuA76 | 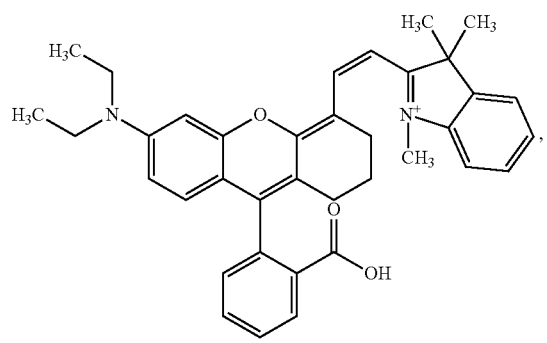 [SMILES: CCN(CC)c1ccc2c(c1)OC1=C(/C=C\C3=[N+](C)c4ccccc4C3(C)C)CCCC1=C2c1ccccc1C(=O)O] |
| EAO40 | 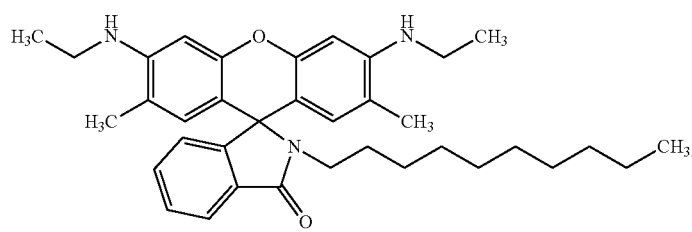 [SMILES: CCCCCCCCCCN1C(=O)c2ccccc2C12c1cc(C)c(NCC)cc1Oc1cc(NCC)c(C)cc12] |
| ZK106 | 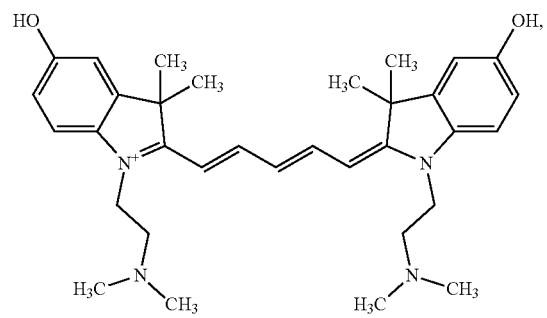 [SMILES: CN(C)CCN1/C(=C/C=C/C=C/C2=[N+](CCN(C)C)c3ccc(O)cc3C2(C)C)C(C)(C)c2cc(O)ccc21] |
| ZK124 | 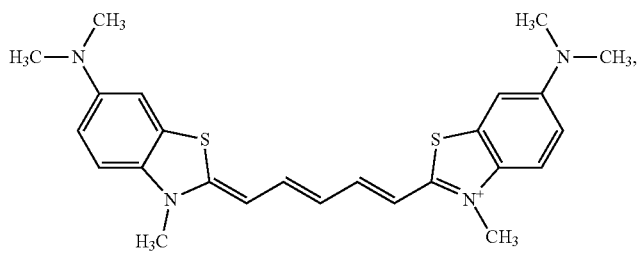 [SMILES: CN(C)c1ccc2c(c1)S\C(=C/C=C/C=C/c1sc3cc(N(C)C)ccc3[n+]1C)N2C] |
| ZK126 | 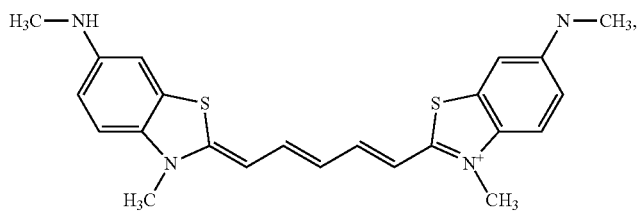 |

| Name | Structure |
|---|---|
| ZK101 | 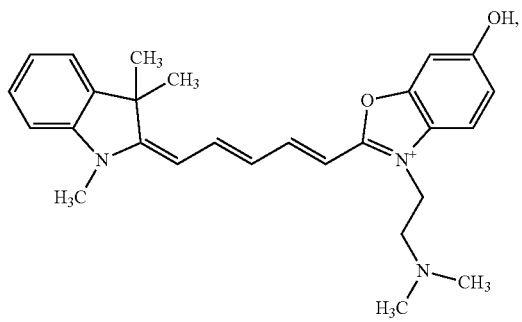 [SMILES: CN(C)CC[n+]1c(/C=C/C=C/C=C2/N(C)c3ccccc3C2(C)C)oc2cc(O)ccc21] |
| ZK172 | 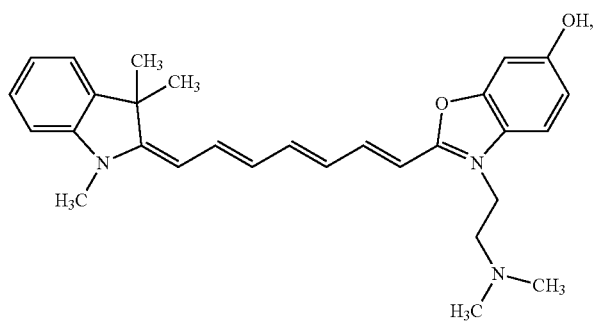 |
| TG16 | 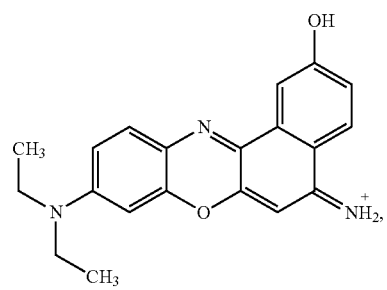 |
| MDL16 | 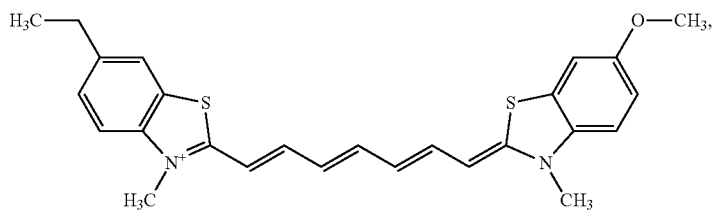 |
| CNN14 | 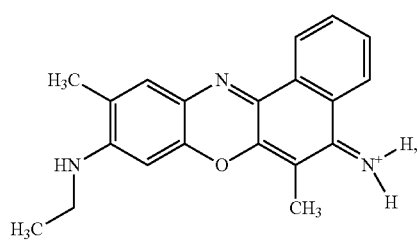 |

| Name | Structure |
|---|---|
| LN37 | 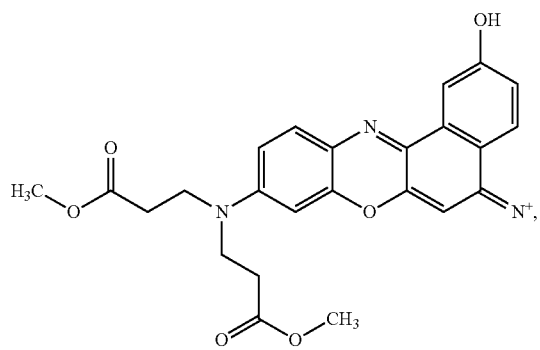 |
| TG20 | 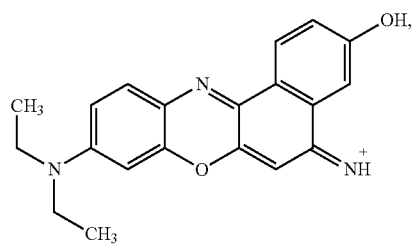 [SMILES: CCN(CC)c1ccc2nc3c4ccc(O)cc4c(=N)cc-3oc2c1] |
| LO4 | 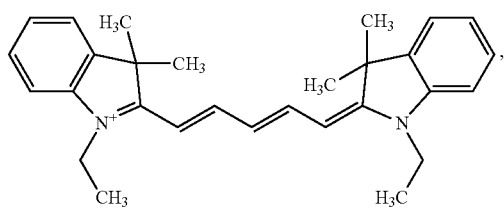 [SMILES: CCN1/C(=C/C=C/C=C/C2=[N+](CC)c3ccccc3C2(C)C)C(C)(C)c2ccccc21] |
| ZK211 | 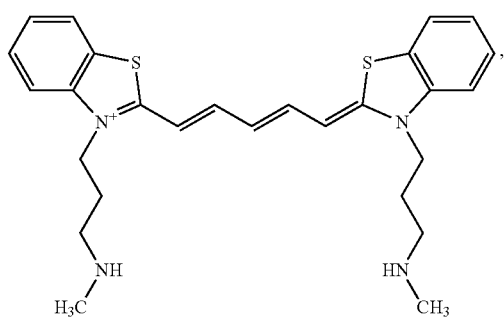 [SMILES: CNCCCN1/C(=C/C=C/C=C/c2sc3ccccc3[n+]2CCCNC)Sc2ccccc21] |
| ZK214 | 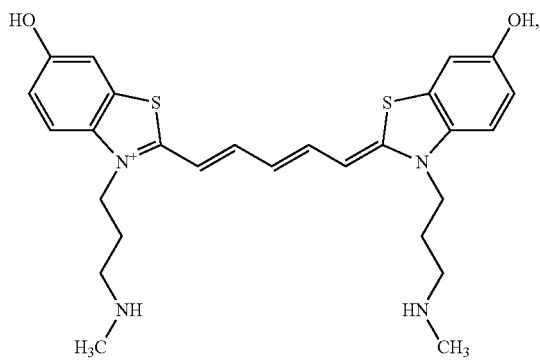 [SMILES: CNCCCN1/C(=C/C=C/C=C/c2sc3cc(O)ccc3[n+]2CCCNC)Sc2cc(O)ccc21] |

-continued
| Name | Structure |
|---|---|
| ZK215 | 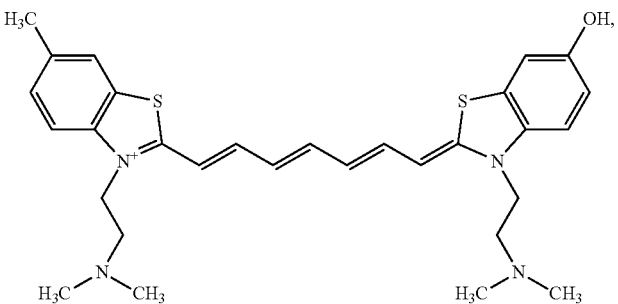 [SMILES: Cc1ccc2c(c1)sc(/C=C/C=C/C=C/C=C1\Sc3cc(O)ccc3N1CCN(C)C)[n+]2CCN(C)C] |
| ZK217 | 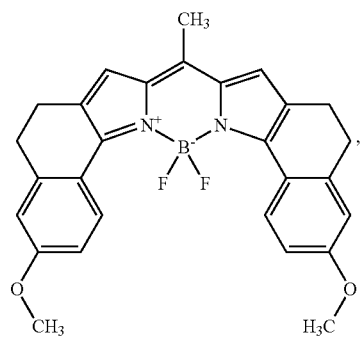 [SMILES: COc1ccc2c(c1)CCC1=CC3=C(C)c4cc5c(n4[B-](F)(F)[N+]3=C12)-c1ccc(OC)cc1CC5] |
| SRA89 | 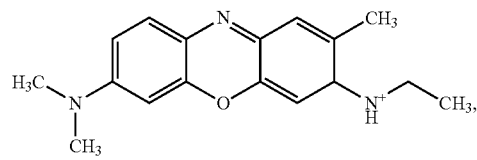 |
| YY190 | 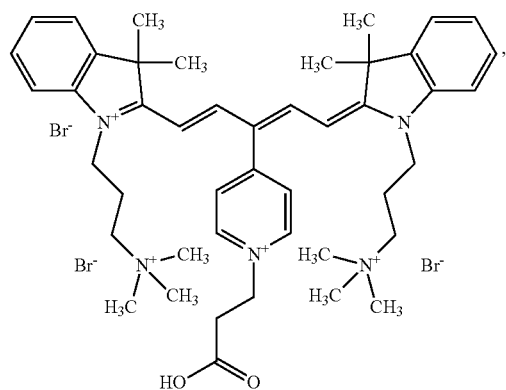 [SMILES: CC1(C)C(/C=C/C(=C/C=C2/N(CCC[N+](C)(C)C)c3ccccc3C2(C)C)c2cc[n+](CCC(=O)O)cc2)=[N+](CCC[N+](C)(C)C)c2ccccc21 ; [Br-] ; [Br-] ; [Br-]] |
| YY220 | 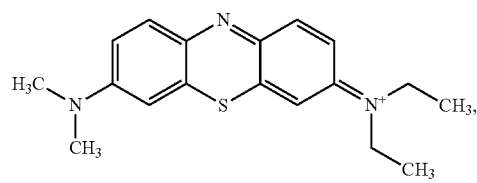 |

-continued

| Name | Structure |
|---|---|
| YY229 | (structure) |
| YY231 | (structure) |
| YY233 | (structure) |
| YY238 | (structure) |
| SRA94 | (structure) |
| PS31 | (structure) |
| ZK239 | (structure) |
| AL11 | (structure) |

-continued

| Name | Structure |
|---|---|
| AL12 | (structure) |
| CMI24 | (structure) |
| CMI26 | (structure) |
| EI6 | (structure) |
| EI7 | (structure) |

| Name | Structure |
|---|---|
| E24 | 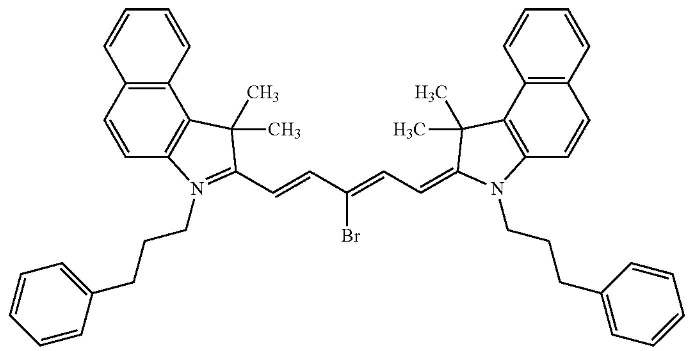 |
| E27 | 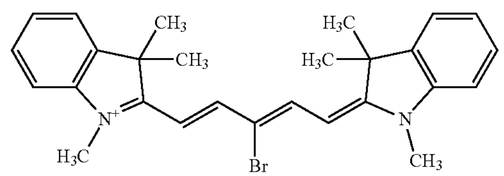 |
| E36 | 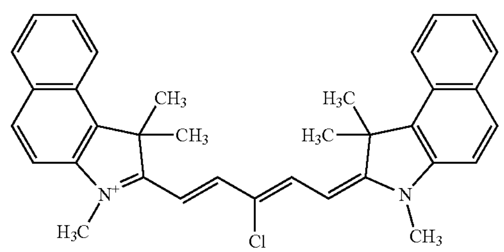 |
| E37 | 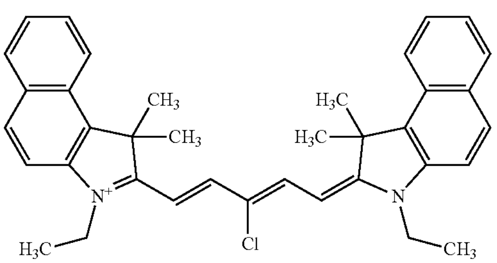 |
| E38 | 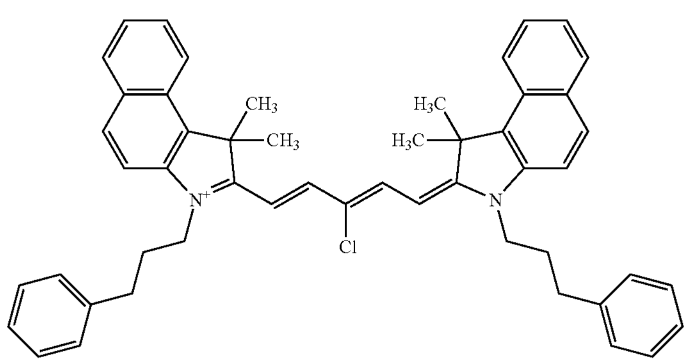 |

| Name | Structure |
|---|---|
| E39 | 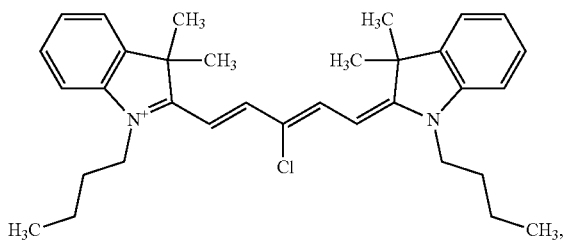 [SMILES: CCCCN1/C(=C/C=C(Cl)/C=C/C2=[N+](CCCC)c3ccccc3C2(C)C)C(C)(C)c2ccccc21] |
| E43 | 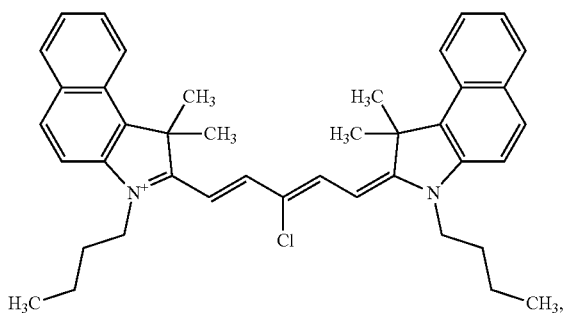 |
| E44 | 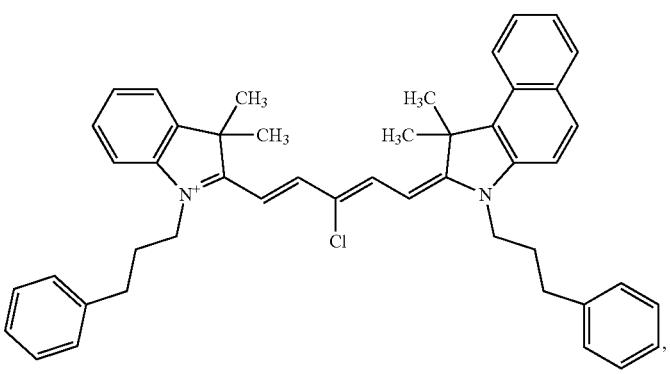 [SMILES: CC1(C)C(/C=C/C(Cl)=C/C=C2/N(CCCc3ccccc3)c3ccc4ccccc4c3C2(C)C)=[N+](CCCc2ccccc2)c2ccccc21] |
| E45 | 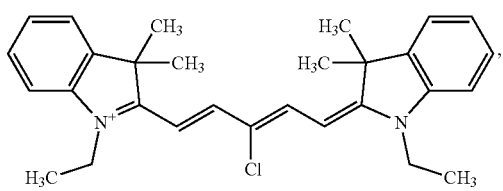 |
| E50 | 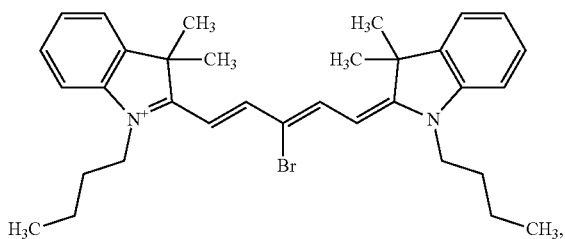 |

-continued

| Name | Structure |
|---|---|
| E51 | (structure) |
| E77 | (structure) |
| E78 | (structure) |
| E79 | (structure) |
| E80 | (structure) |

| Name | Structure |
|---|---|
| E81 | 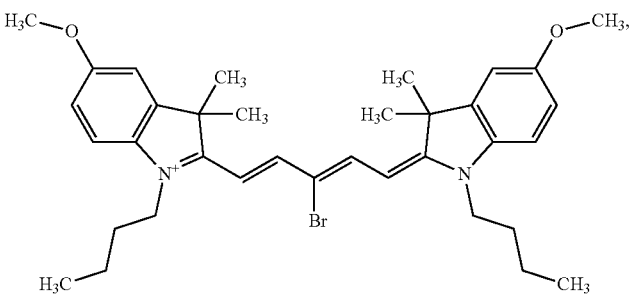 [SMILES: CCCCN1/C(=C/C=C(Br)/C=C/C2=[N+](CCCC)c3ccc(OC)cc3C2(C)C)C(C)(C)c2cc(OC)ccc21] |
| ES17 | 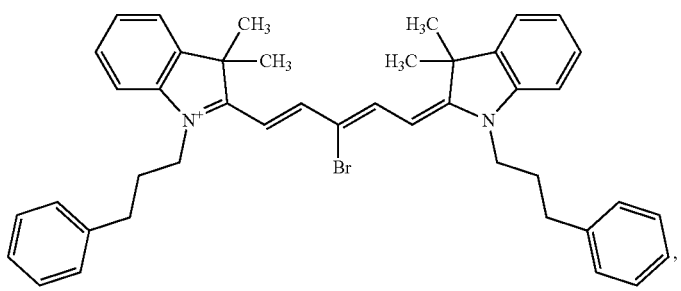 [SMILES: CC1(C)C(/C=C/C(Br)=C/C=C2/N(CCCc3ccccc3)c3ccccc3C2(C)C)=[N+](CCCc2ccccc2)c2ccccc21] |
| ES21 | 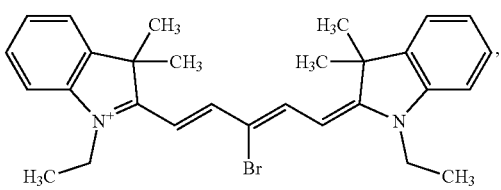 [SMILES: CCN1/C(=C/C=C(Br)/C=C/C2=[N+](CC)c3ccccc3C2(C)C)C(C)(C)c2ccccc21] |
| ESS61 | 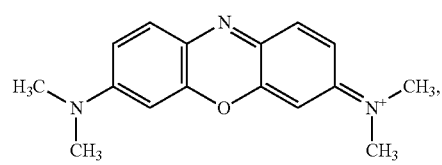 [SMILES: CN(C)c1ccc2nc3ccc(=[N+](C)C)cc-3oc2c1] |
| LO1 | 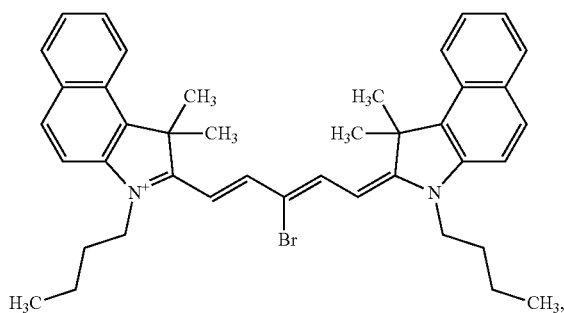 [SMILES: CCCCN1/C(=C/C=C(Br)/C=C/C2=[N+](CCCC)c3ccc4ccccc4c3C2(C)C)C(C)(C)c2c1ccc1ccccc21] |
| LO2 | 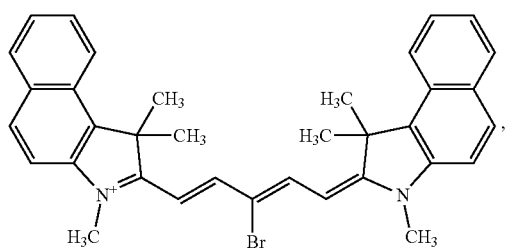 [SMILES: CN1/C(=C/C=C(Br)/C=C/C2=[N+](C)c3ccc4ccccc4c3C2(C)C)C(C)(C)c2c1ccc1ccccc21] |

| Name | Structure |
|---|---|
| LO3 | 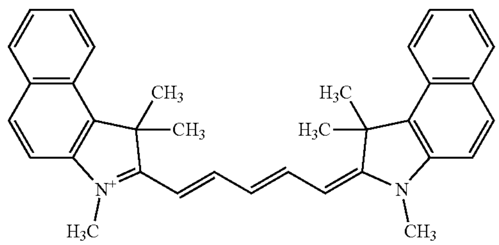 |
| MHI106 | 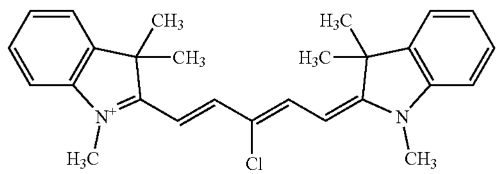 |
| MHI128 | 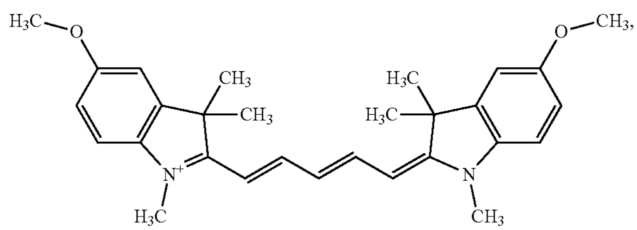 [SMILES: COc1ccc2c(c1)C(C)(C)C(/C=C/C=C/C=C1/N(C)c3ccc(OC)cc3C1(C)C)=[N+]2C] |
| MHI84 | 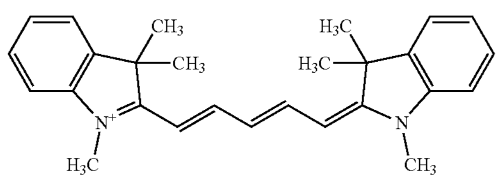 |
| MHI86 | 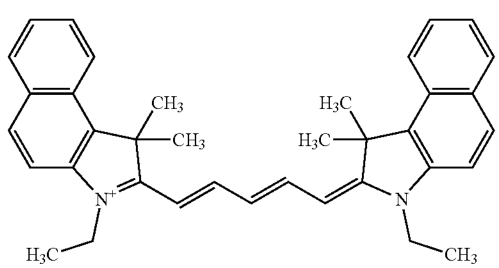 |
| MHI96 | 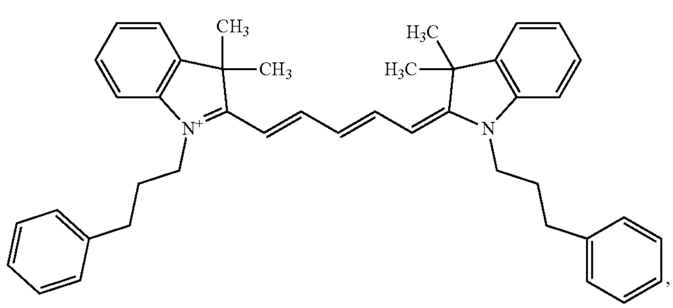 [SMILES: CC1(C)C(/C=C/C=C/C=C2/N(CCCc3ccccc3)c3ccccc3C2(C)C)=[N+](CCCc2ccccc2)c2ccccc21] |

| Name | Structure |
|---|---|
| MHI97 | 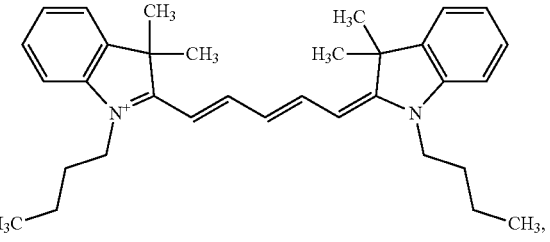 |
| P700H | 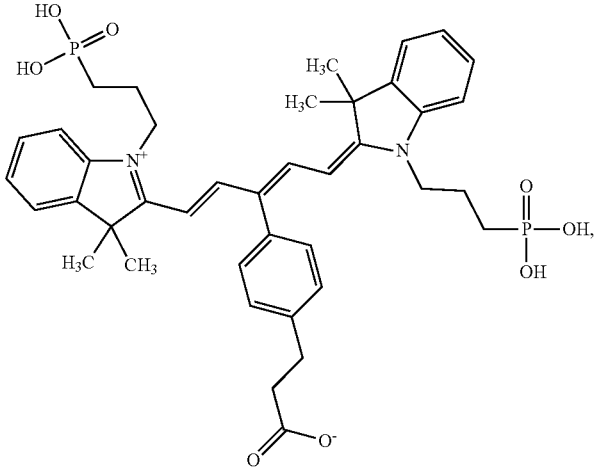 [SMILES: CC1(C)C(/C=C/C(=C/C=C2/N(CCCP(=O)(O)O)c3ccccc3C2(C)C)c2ccc(CCC(=O)[O-])cc2)=[N+](CCCP(=O)(O)O)c2ccccc21] |
| P700SO3 | 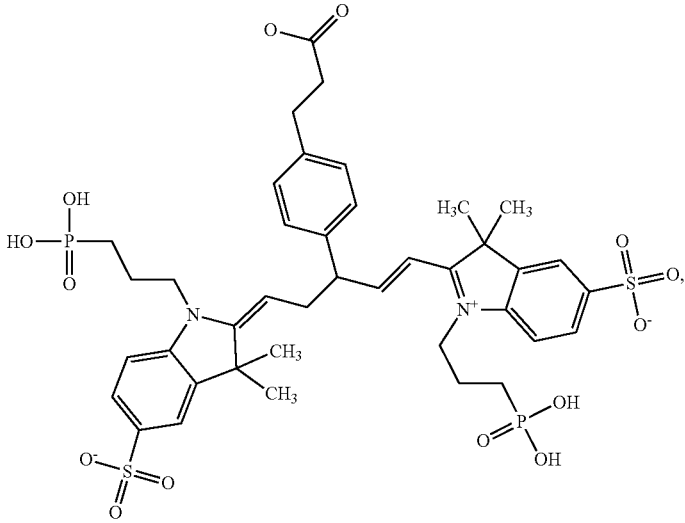 [SMILES: CC1(C)C(/C=C/C(C/C=C2/N(CCCP(=O)(O)O)c3ccc(S(=O)(=O)[O-])cc3C2(C)C)c2ccc(CCC(=O)O)cc2)=[N+](CCCP(=O)(O)O)c2ccc(S(=O)(=O)[O-])cc21] |
| P800H | 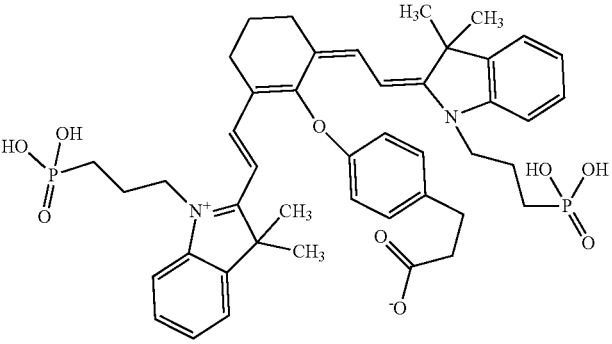 |

-continued
| Name | Structure |
|---|---|
| P800SO3 | 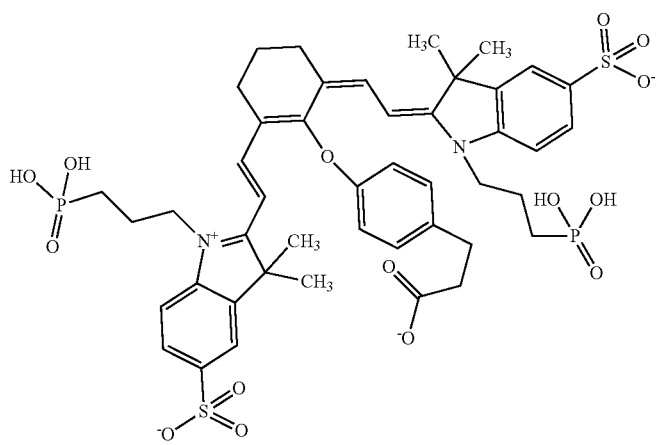 |
| T14 | 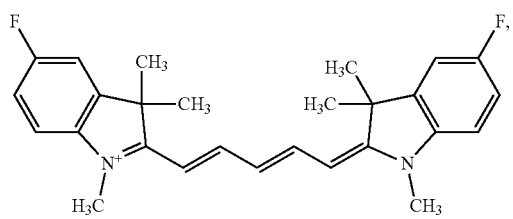 [SMILES: CN1/C(=C/C=C/C=C/C2=[N+](C)c3ccc(F)cc3C2(C)C)C(C)(C)c2cc(F)ccc21] |
| T17 | 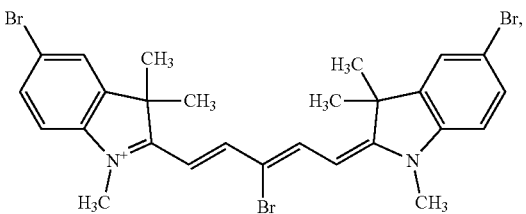 [SMILES: CN1/C(=C/C=C(Br)/C=C/C2=[N+](C)c3ccc(Br)cc3C2(C)C)C(C)(C)c2cc(Br)ccc21] |
| T18 | 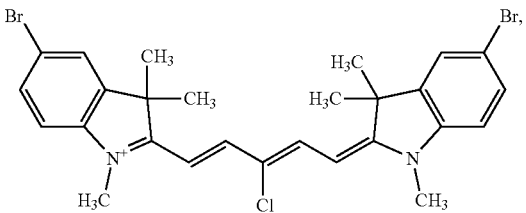 |
| T20 | 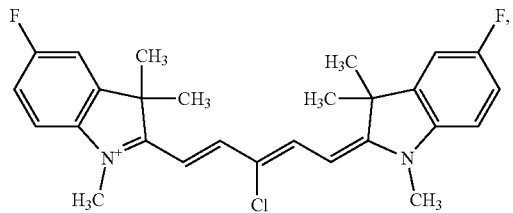 [SMILES: CN1/C(=C/C=C(Cl)/C=C/C2=[N+](C)c3ccc(F)cc3C2(C)C)C(C)(C)c2cc(F)ccc21] |
| T23 | 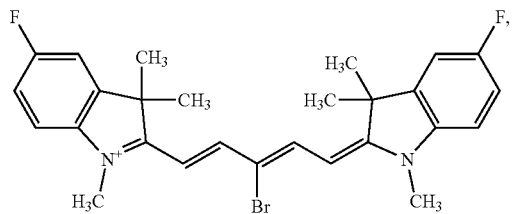 [SMILES: CN1/C(=C/C=C(Br)/C=C/C2=[N+](C)c3ccc(F)cc3C2(C)C)C(C)(C)c2cc(F)ccc21] |

-continued

| Name | Structure |
|---|---|
| T24 | (structure) |
| T25 | (structure) |
| T27 | (structure) |
| T29 | (structure) |
| A20 | (structure) |
| A21 | (structure) |

-continued
| Name | Structure |
|---|---|
| A80 | 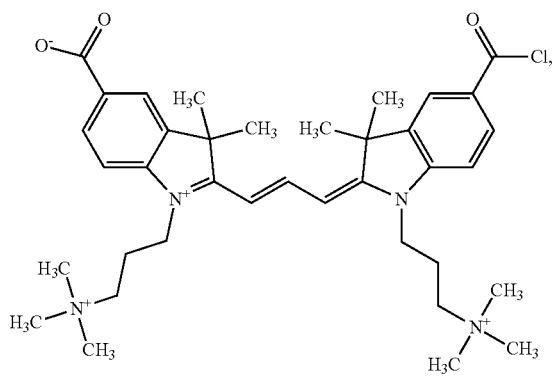 [SMILES: CC1(C)C(/C=C/C=C2/N(CCC[N+](C)(C)C)c3ccc(C(=O)Cl)cc3C2(C)C)=[N+](CCC[N+](C)(C)C)c2ccc(C(=O)[O-])cc21] |
| A100 | 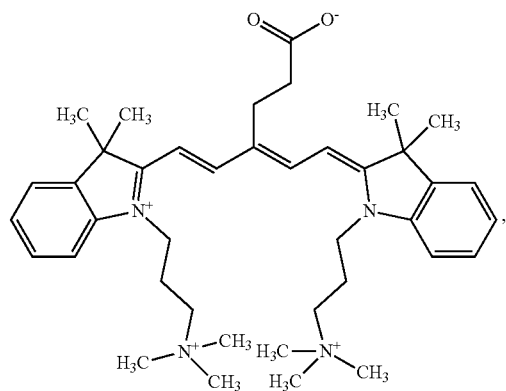 [SMILES: CC1(C)C(/C=C/C(=C/C=C2\N(CCC[N+](C)(C)C)c3ccccc3C2(C)C)CCC(=O)[O-])=[N+](CCC[N+](C)(C)C)c2ccccc21] |
| A104 | 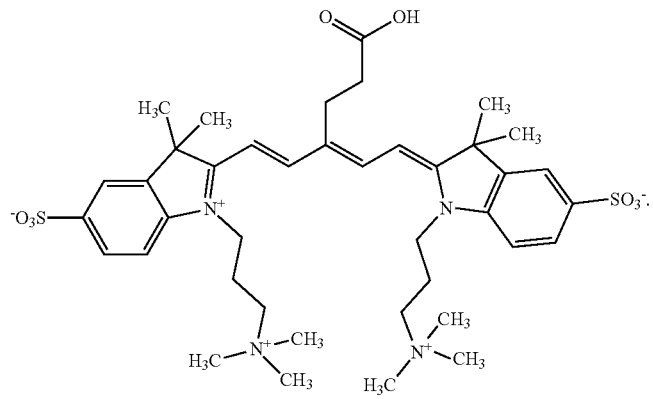 |
| A106 | 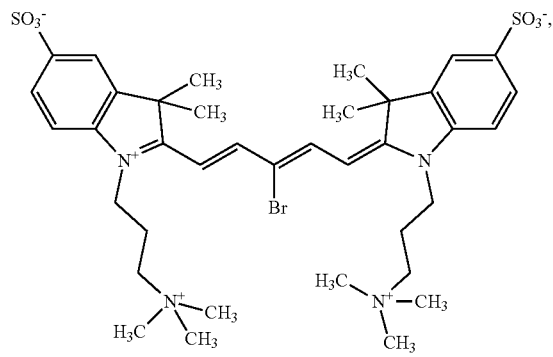 |

-continued
| Name | Structure |
|---|---|
| A134 | 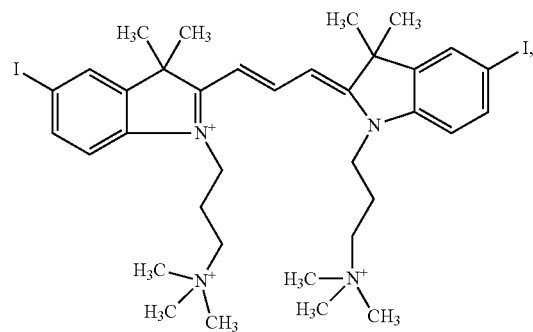 |
| A138 | 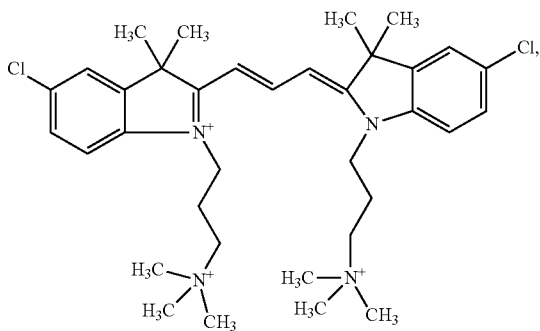 [SMILES: CC1(C)C(/C=C/C=C2\N(CCC[N+](C)(C)C)c3ccc(Cl)cc3C2(C)C)=[N+](CCC[N+](C)(C)C)c2ccc(Cl)cc21] |
| A146 | 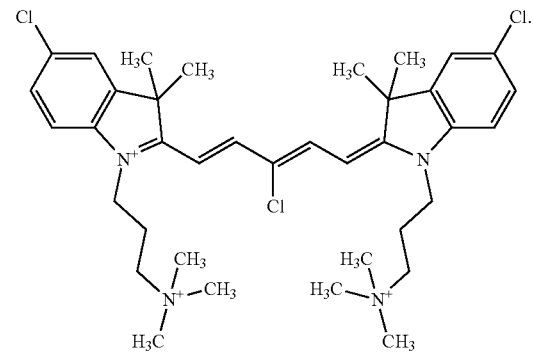 |
| A148 | 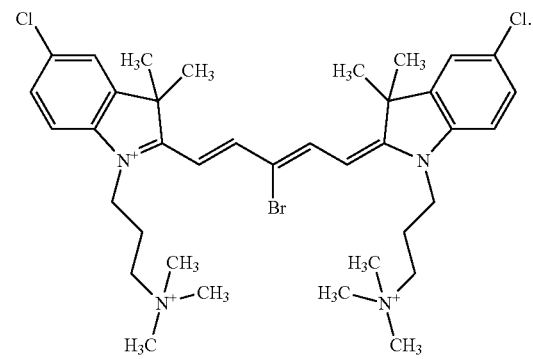 |

| Name | Structure |
|---|---|
| A149 | 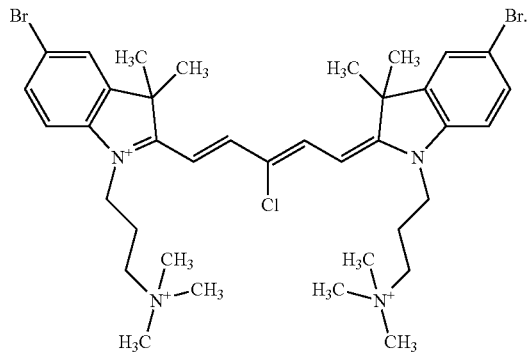 |
| A150 | 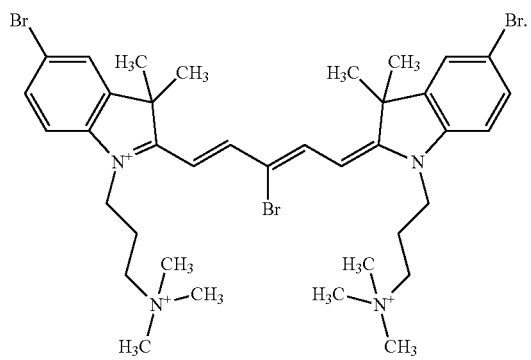 [SMILES: CC1(C)C(/C=C/C(Br)=C/C=C2/N(CCC[N+](C)(C)C)c3ccc(Cl)cc3C2(C)C)=[N+](CCC[N+](C)(C)C)c2ccc(Cl)cc21] |
| A160 | 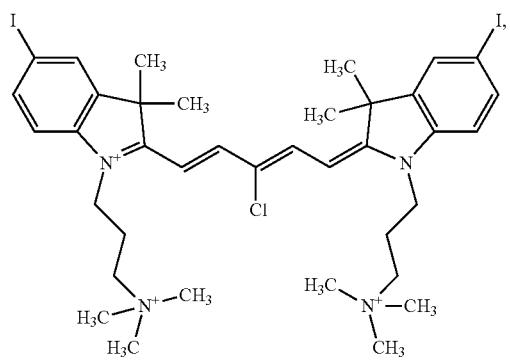 [SMILES: CC1(C)C(/C=C/C(Cl)=C/C=C2/N(CCC[N+](C)(C)C)c3ccc(I)cc3C2(C)C)=[N+](CCC[N+](C)(C)C)c2ccc(I)cc21] |
| A161 | 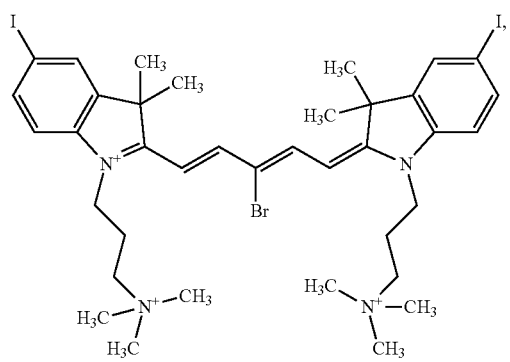 [SMILES: CC1(C)C(/C=C/C(Br)=C/C=C2/N(CCC[N+](C)(C)C)c3ccc(I)cc3C2(C)C)=[N+](CCC[N+](C)(C)C)c2ccc(I)cc21] |

| Name | Structure |
|---|---|
| A24 | 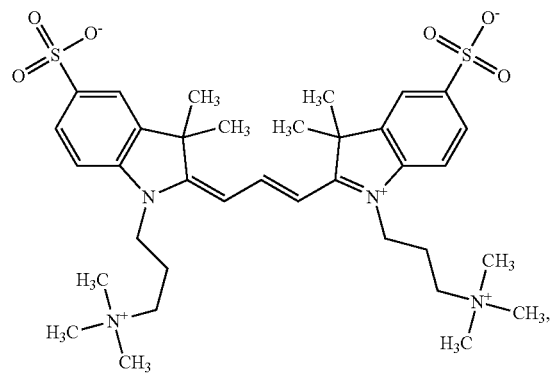 [SMILES: CC1(C)C(/C=C/C=C2/N(CCC[N+](C)(C)C)c3ccc(S(=O)(=O)[O-])cc3C2(C)C)=[N+](CCC[N+](C)(C)C)c2ccc(S(=O)(=O)[O-])cc21] |
| AC2 | 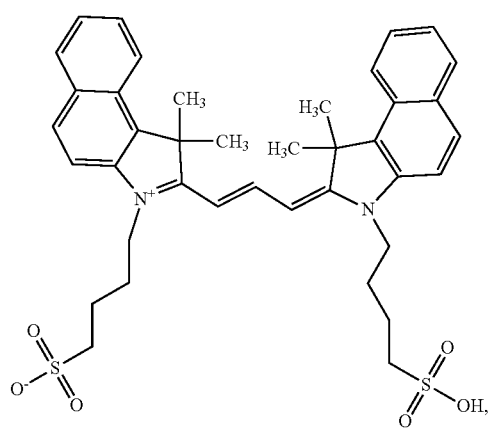 [SMILES: CC1(C)C(/C=C/C=C2/N(CCCCS(=O)(=O)O)c3ccc4ccccc4c3C2(C)C)=[N+](CCCCS(=O)(=O)[O-])c2ccc3ccccc3c21] |
| AC3 | 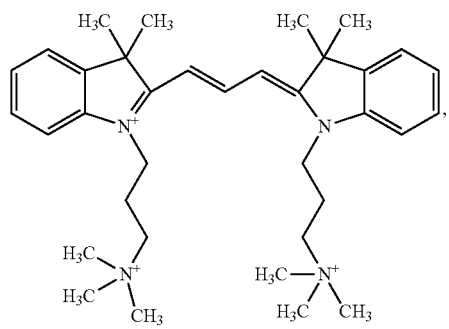 [SMILES: CC1(C)C(/C=C/C=C2\N(CCC[N+](C)(C)C)c3ccccc3C2(C)C)=[N+](CCC[N+](C)(C)C)c2ccccc21] |
| AC8 | 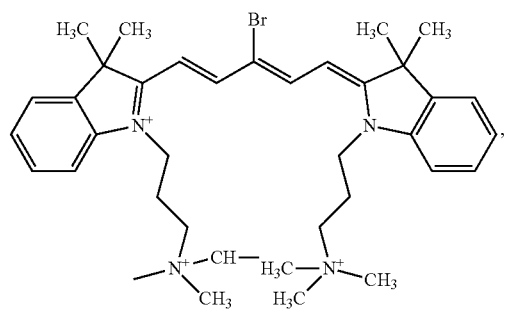 [SMILES: CC[N+](C)(C)CCC[N+]1=C(/C=C/C(Br)=C/C=C2\N(CCC[N+](C)(C)C)c3ccccc3C2(C)C)C(C)(C)c2ccccc21] |

-continued
| Name | Structure |
|---|---|
| AN3 | 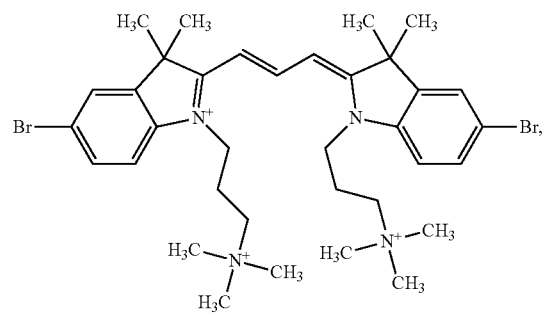 [SMILES: CC1(C)C(/C=C/C=C2\N(CCC[N+](C)(C)C)c3ccc(Br)cc3C2(C)C)=[N+](CCC[N+](C)(C)C)c2ccc(Br)cc21] |
| WuA96 | 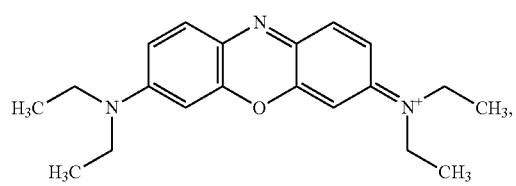 [SMILES: CCN(CC)c1ccc2nc3ccc(=[N+](CC)CC)cc-3oc2c1] |
| Ox4 | 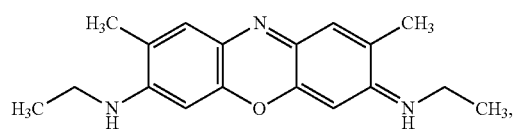 [SMILES: CC/N=c1/cc2oc3cc(NCC)c(C)cc3nc-2cc1C] |
| Ox170 | 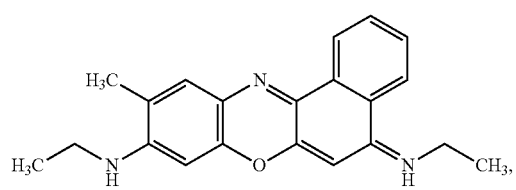 |
| Ox750 | 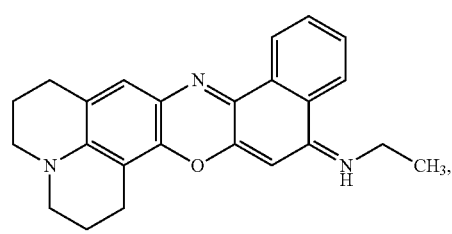 [SMILES: CC/N=c1/cc2oc3c4c5c(cc3nc-2c2ccccc12)CCCN5CCC4] |
| Rh800 | 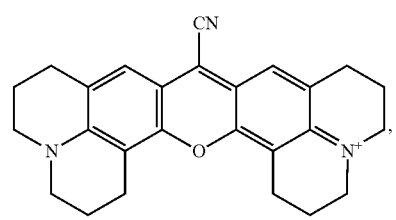 |

| Name | Structure |
|---|---|
| TG66 | 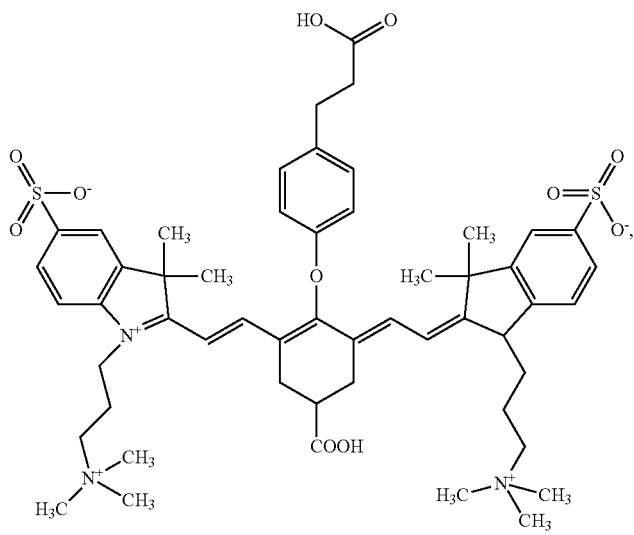 |
| MM25 | 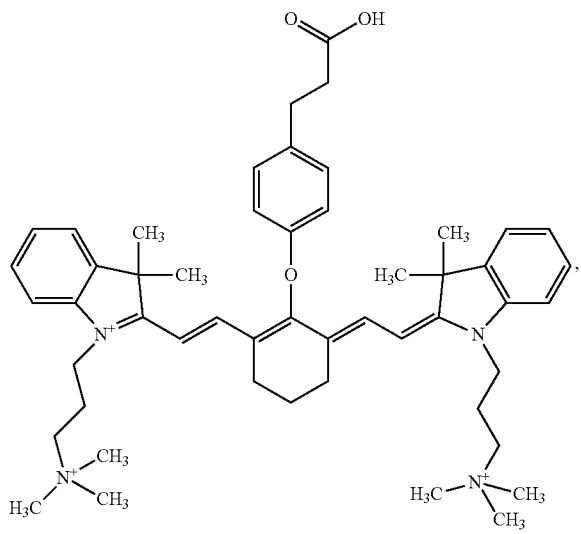 [SMILES: CC1(C)C(/C=C/C2=C(Oc3ccc(CCC(=O)O)cc3)C(=C/C=C3/N(CCC[N+](C)(C)C)c4ccccc4C3(C)C)/CCC2)=[N+](CCC[N+](C)(C)C)c2ccccc21] |
| SP72 | 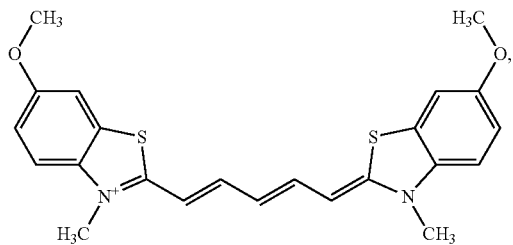 [SMILES: COc1ccc2c(c1)S\C(=C/C=C/C=C/c1sc3cc(OC)ccc3[n+]1C)N2C] |

| Name | Structure |
|---|---|
| ZK138-2 | 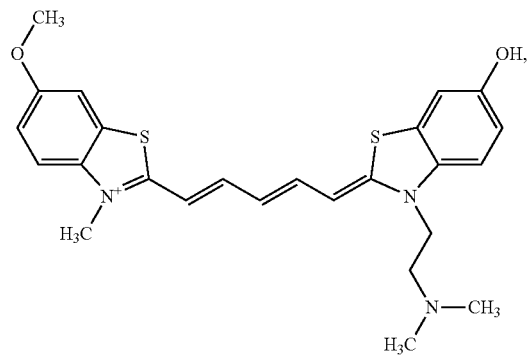 [SMILES: COc1ccc2c(c1)sc(/C=C/C=C/C=C1\Sc3cc(O)ccc3N1CCN(C)C)[n+]2C] |
| ZK169 | 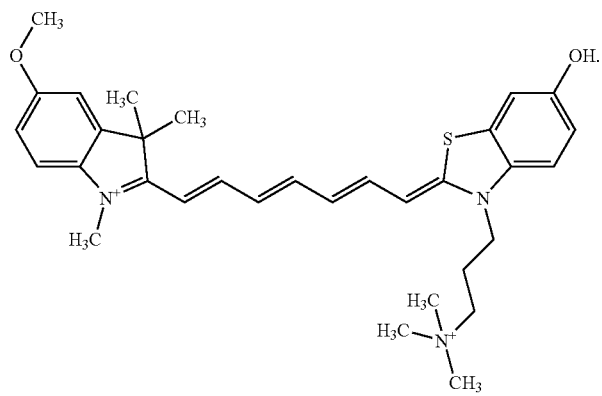 [SMILES: COc1ccc2c(c1)C(C)(C)C(/C=C/C=C/C=C/C=C1\Sc3cc(O)ccc3N1CCC[N+](C)(C)C)=[N+]2C] |
| ZW800-1 | 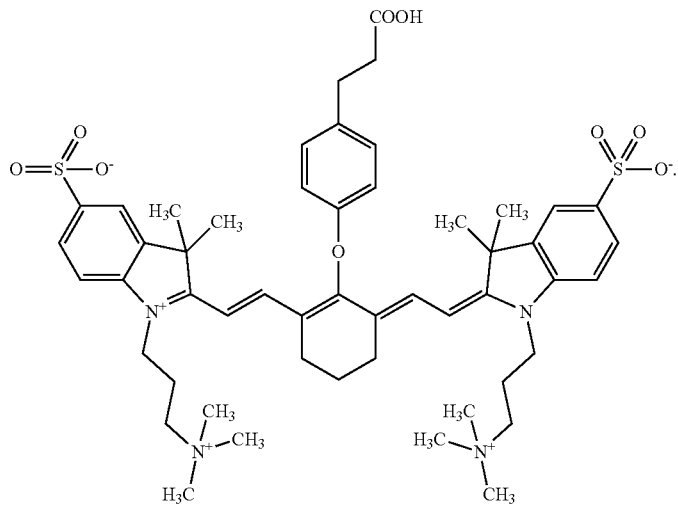 |

-continued
| Name | Structure |
|---|---|
| A64 | 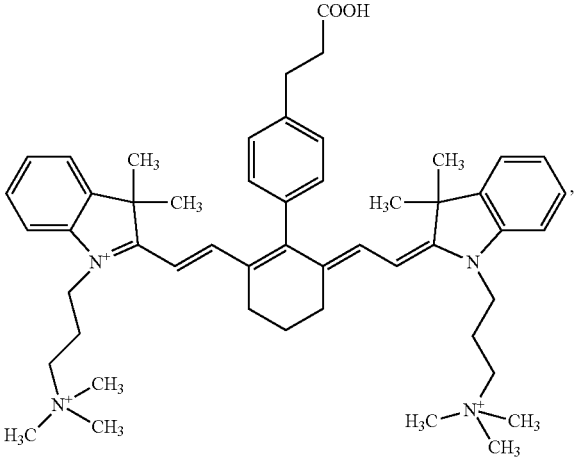 [SMILES: CC1(C)C(/C=C/C2=C(c3ccc(CCC(=O)O)cc3)C(=C/C=C3/N(CCC[N+](C)(C)C)c4ccccc4C3(C)C)/CCC2)=[N+](CCC[N+](C)(C)C)c2ccccc21] |
| MHI85 | 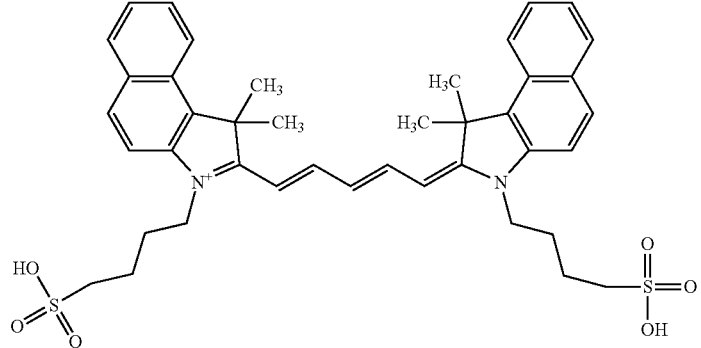 [SMILES: CC1(C)C(/C=C/C=C/C=C2/N(CCCCS(=O)(=O)O)c3ccc4ccccc4c3C2(C)C)=[N+](CCCCS(=O)(=O)O)c2ccc3ccccc3c21] |
| SP66 | 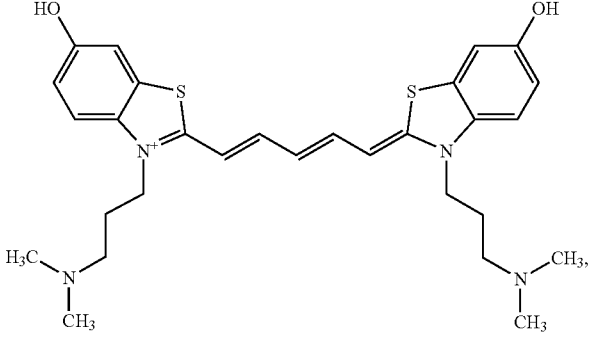 [SMILES: CN(C)CCCN1/C(=C/C=C/C=C/c2sc3cc(O)ccc3[n+]2CCCN(C)C)Sc2cc(O)ccc21] |
| YY113 | 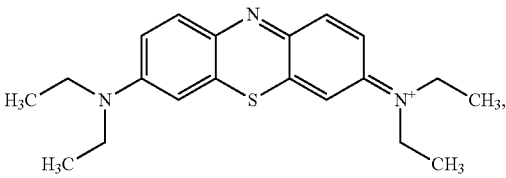 [SMILES: CCN(CC)c1ccc2nc3ccc(=[N+](CC)CC)cc-3sc2c1] |
| YY142 | 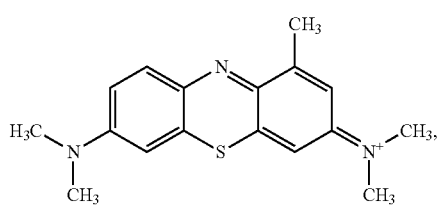 |

-continued
| Name | Structure |
|---|---|
| PS37 | 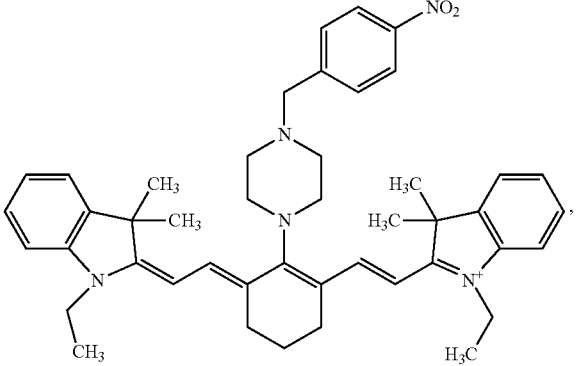 [SMILES: CCN1/C(=C/C=C2\CCCC(/C=C/C3=[N+](CC)c4ccccc4C3(C)C)=C2N2CCN(Cc3ccc([N+](=O)[O-])cc3)CC2)C(C)(C)c2ccccc21] |
| PS53 | 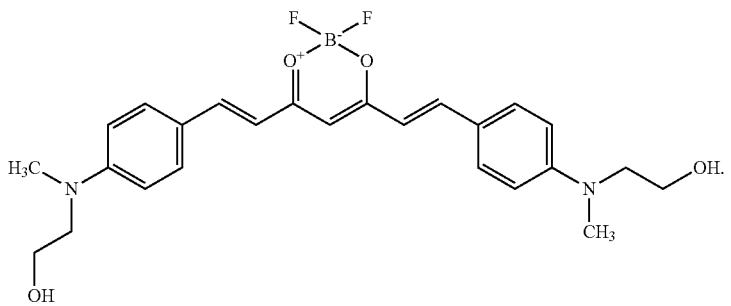 [SMILES: CN(CCO)c1ccc(/C=C/C2=CC(/C=C/c3ccc(N(C)CCO)cc3)=[O+][B-](F)(F)O2)cc1] |
| ZK240 | 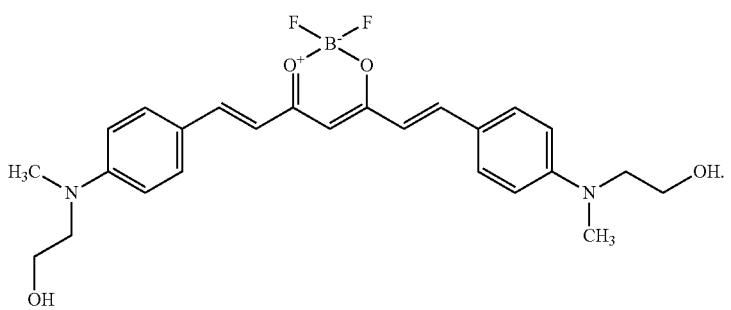 [SMILES: CN(CCO)c1ccc(/C=C/C2=CC(/C=C/c3ccc(N(C)CCO)cc3)=[O+][B-](F)(F)O2)cc1] |
| ZK244 | 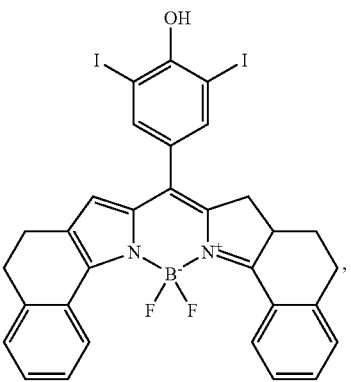 [SMILES: Oc1c(I)cc(C2=C3CC4CCc5ccccc5C4=[N+]3[B-](F)(F)n3c2cc2c3-c3ccccc3CC2)cc1I] |

| Name | Structure |
|------|-----------|
| EAO72 | 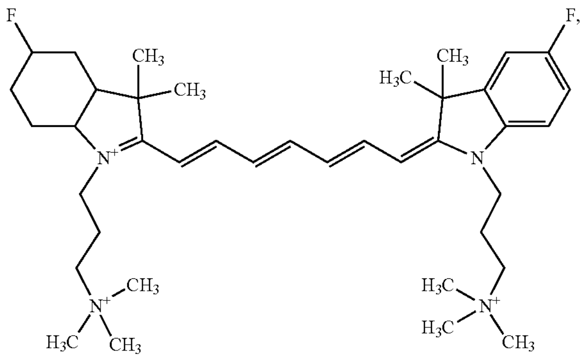 [SMILES: CC1(C)\C(=C/C=C/C=C/C=C/C2=[N+](CCC[N+](C)(C)C)C3CCC(F)CC3C2(C)C)N(CCC[N+](C)(C)C)c2ccc(F)cc21] |
| EAO76 | 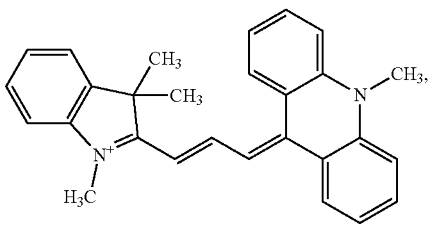 [SMILES: CN1c2ccccc2C(=C/C=C/C2=[N+](C)c3ccccc3C2(C)C)c2ccccc21] |
| PS101A | 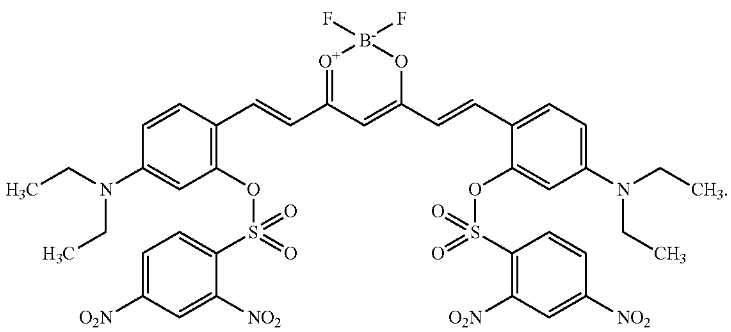 |
| PS35 | 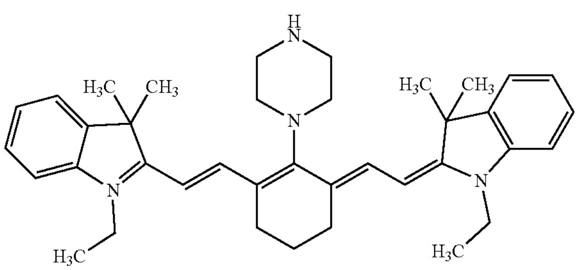 |
| PS36 | 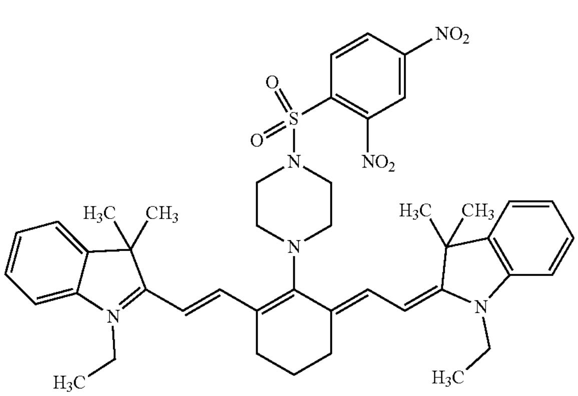 |

| Name | Structure |
|---|---|
| PS39 | 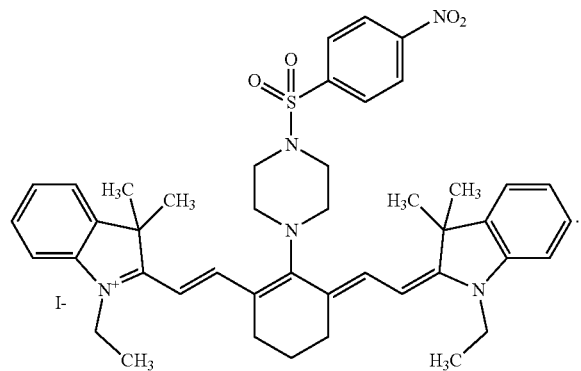 [SMILES: CCN1/C(=C/C=C2\CCCC(/C=C/C3=[N+](CC)c4ccccc4C3(C)C)=C2N2CCN(S(=O)(=O)c3ccc([N+](=O)[O-])cc3)CC2)C(C)(C)c2ccccc21 ; [I-]] |
| PS51 | 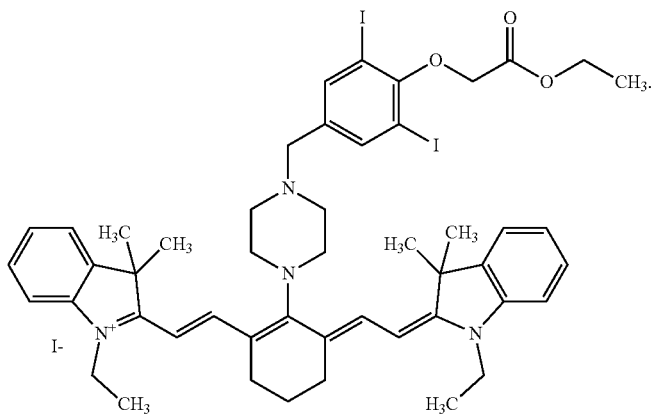 [SMILES: CCOC(=O)COc1c(I)cc(CN2CCN(C3=C(/C=C/C4=[N+](CC)c5ccccc5C4(C)C)CCC/C3=C\C=C3\N(CC)c4ccccc4C3(C)C)CC2)cc1I ; [I-]] |
| PS52 | 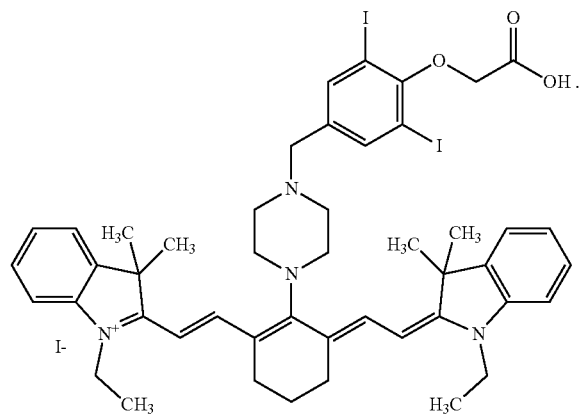 [SMILES: CCN1/C(=C/C=C2\CCCC(/C=C/C3=[N+](CC)c4ccccc4C3(C)C)=C2N2CCN(Cc3cc(I)c(OCC(=O)O)c(I)c3)CC2)C(C)(C)c2ccccc21 ; [I-]] |
| PS62 | 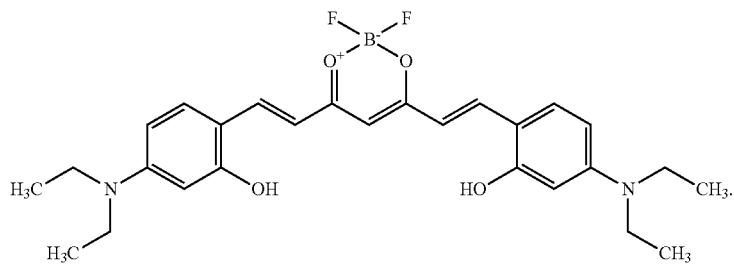 |

-continued

| Name | Structure |
|---|---|
| PS73 | 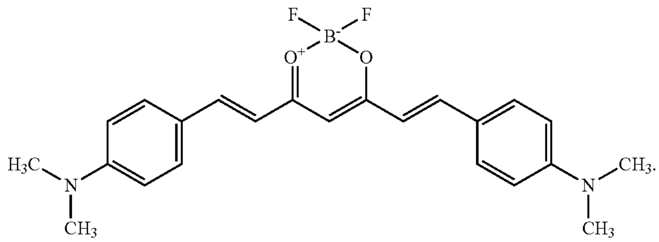 |
| PS76 | 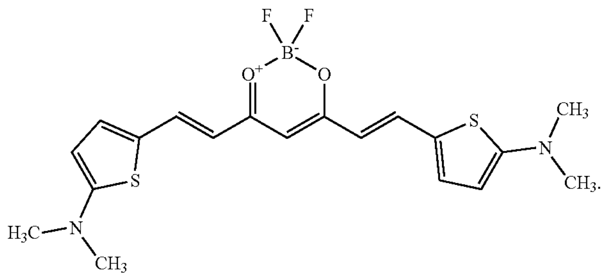 [SMILES: CN(C)c1ccc(/C=C/C2=CC(/C=C/c3ccc(N(C)C)s3)=[O+][B-](F)(F)O2)s1] |
| YY255 | 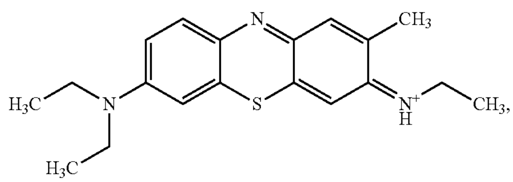 |
| YY260 | 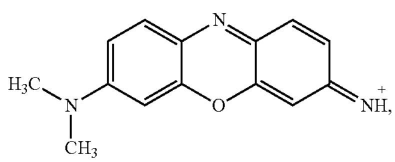 [SMILES: CN(C)c1ccc2nc3ccc(=N)cc-3oc2c1] |
| YY261 | 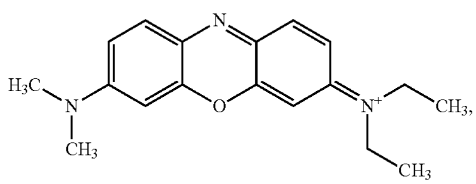 [SMILES: CC[N+](CC)=c1ccc2nc3ccc(N(C)C)cc3oc-2c1] |
| YY269 | 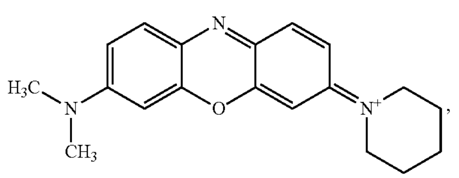 [SMILES: CN(C)c1ccc2nc3ccc(=[N+]4CCCCC4)cc-3oc2c1] |
| ZK243 | 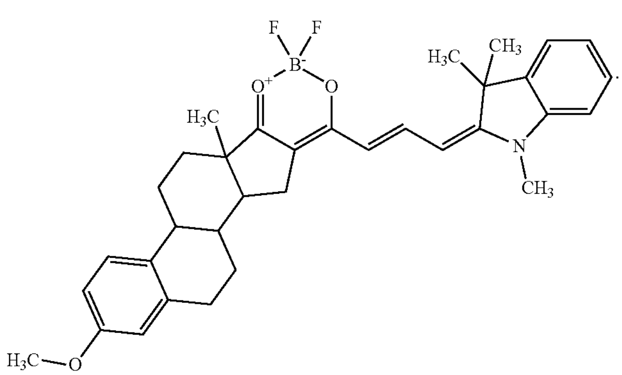 [SMILES: COc1ccc2c(c1)CCC1C2CCC2(C)C3=[O+][B-](F)(F)OC(/C=C/C=C4/N(C)c5ccccc5C4(C)C)=C3CC12] |

-continued
| Name | Structure |
|---|---|
| ZK2515 | 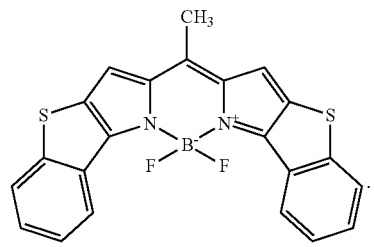 [SMILES: CC1=C2C=c3sc4ccccc4c3=[N+]2[B-](F)(F)n2c1cc1sc3ccccc3c12] |
| ZK2525 | 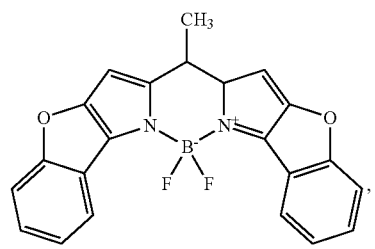 [SMILES: CC1c2cc3oc4ccccc4c3n2[B-](F)(F)[N+]2=c3c(oc4ccccc34)=CC12] |
| ZK2565 | 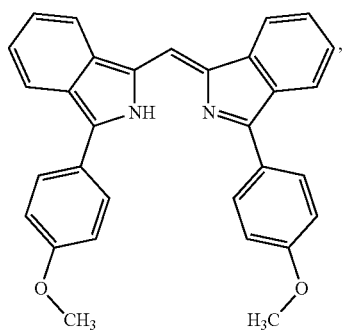 [SMILES: COc1ccc(C2=N/C(=C\c3[nH]c(-c4ccc(OC)cc4)c4ccccc34)c3ccccc32)cc1] |
| ZK2566 | 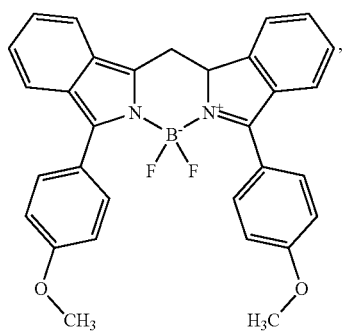 [SMILES: COc1ccc(C2=[N+]3C(Cc4c5ccccc5c(-c5ccc(OC)cc5)n4[B-]3(F)F)c3ccccc32)cc1] |
| ZK258 | 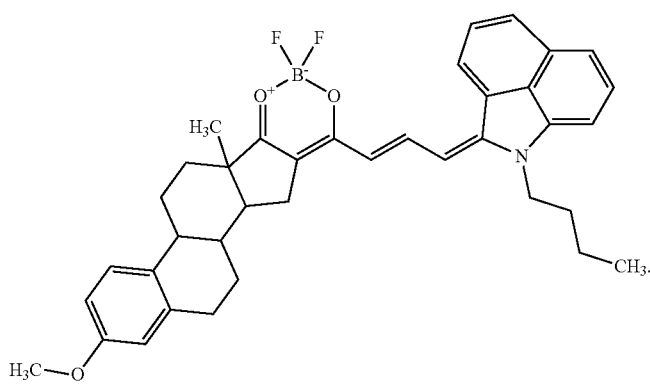 [SMILES: CCCCn1/c(=C/C=C/C2=C3CC4C5CCc6cc(OC)ccc6C5CCC4(C)C3=[O+][B-](F)(F)O2)c2cccc3cccc1c32] |

-continued
| Name | Structure |
|---|---|
| ZK2615 | 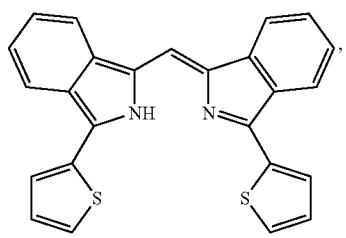 [SMILES: C(=C1/N=C(c2cccs2)c2ccccc21)/c1[nH]c(-c2cccs2)c2ccccc12] |
| A71-NHS | 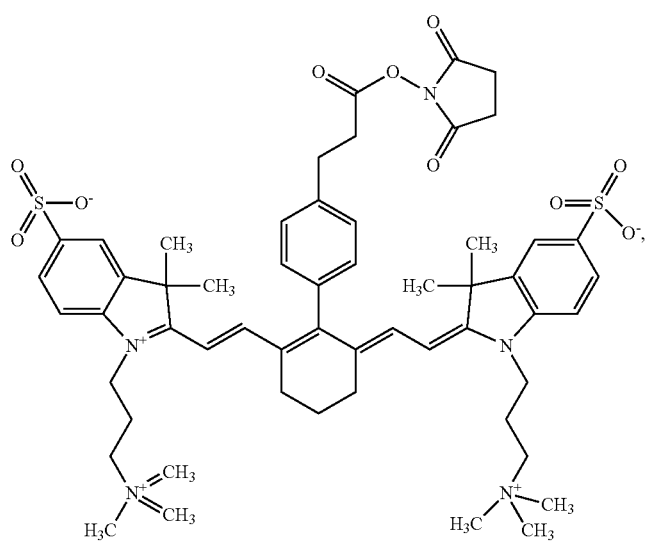 |
| LN15-NHS | 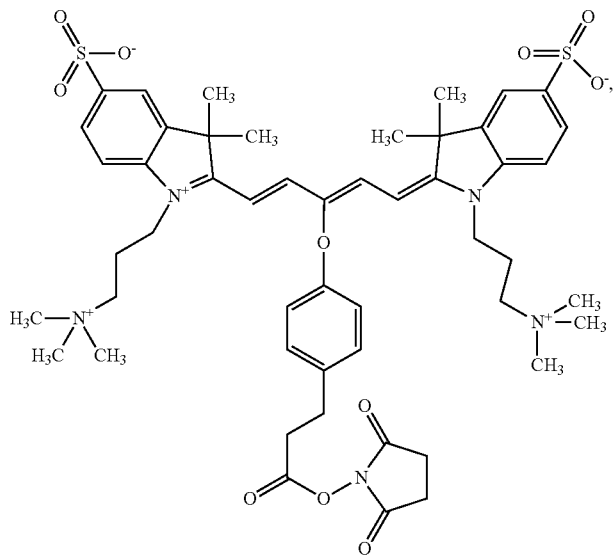 |

-continued
| Name | Structure |
|---|---|
| PS126 | 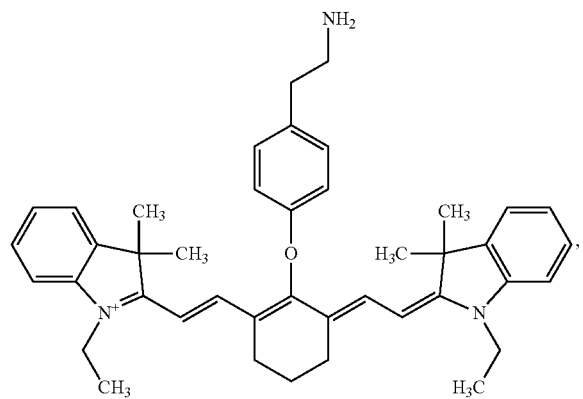 [SMILES: CCN1/C(=C/C=C2\CCCC(/C=C/C3=[N+](CC)c4ccccc4C3(C)C)=C2Oc2ccc(CCN)cc2)C(C)(C)c2ccccc21] |
| PS127 | 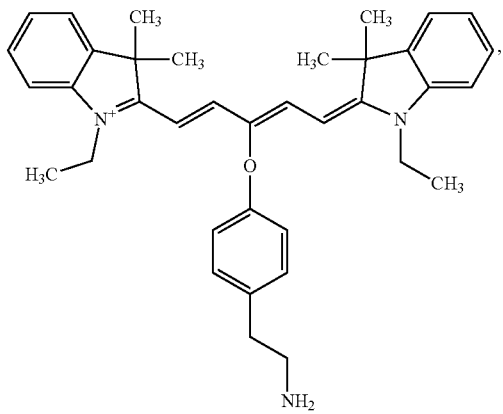 [SMILES: CCN1/C(=C/C=C(/C=C/C2=[N+](CC)c3ccccc3C2(C)C)Oc2ccc(CCN)cc2)C(C)(C)c2ccccc21] |
| PS128 | 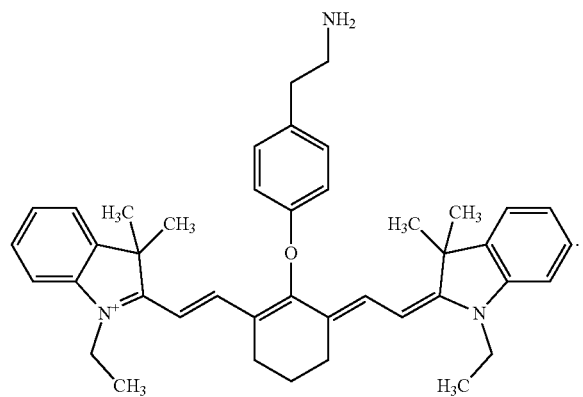 [SMILES: CCN1/C(=C/C=C2\CCCC(/C=C/C3=[N+](CC)c4ccccc4C3(C)C)=C2Oc2ccc(CCN)cc2)C(C)(C)c2ccccc21] |

-continued
| Name | Structure |
|---|---|
| PS129 | 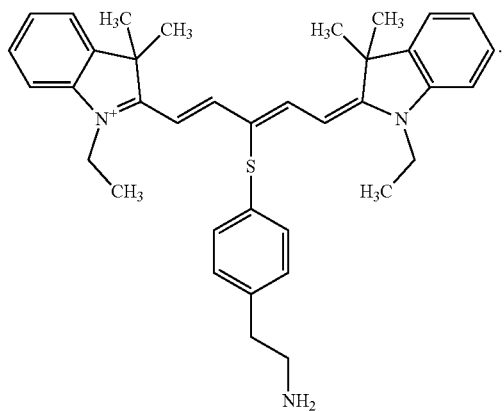 [SMILES: CCN1/C(=C/C=C(/C=C/C2=[N+](CC)c3ccccc3C2(C)C)Sc2ccc(CCN)cc2)C(C)(C)c2ccccc21] |
| PS130 | 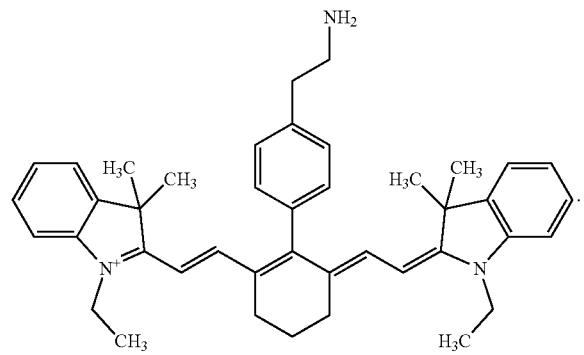 [SMILES: CCN1/C(=C/C=C2\CCCC(/C=C/C3=[N+](CC)c4ccccc4C3(C)C)=C2c2ccc(CCN)cc2)C(C)(C)c2ccccc21] |
| PS131 | 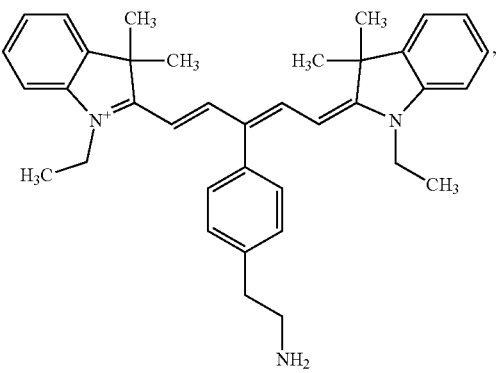 [SMILES: CCN1/C(=C/C=C(/C=C/C2=[N+](CC)c3ccccc3C2(C)C)c2ccc(CCN)cc2)C(C)(C)c2ccccc21] |
| PS132 | 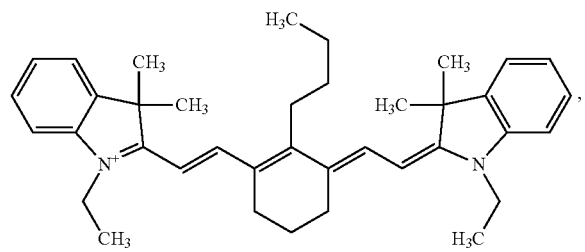 [SMILES: CCCCC1=C(/C=C/C2=[N+](CC)c3ccccc3C2(C)C)CCC/C1=C\C=C1\N(CC)c2ccccc2C1(C)C] |

-continued
| Name | Structure |
|---|---|
| PS133 | 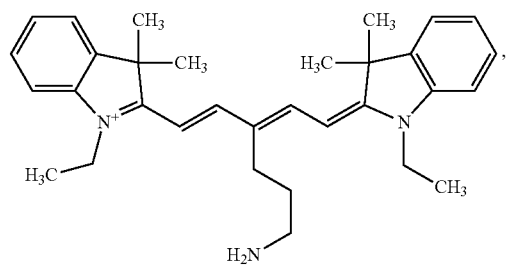 [SMILES: CCN1/C(=C/C=C(/C=C/C2=[N+](CC)c3ccccc3C2(C)C)CCCN)C(C)(C)c2ccccc21] |
| YY283 | 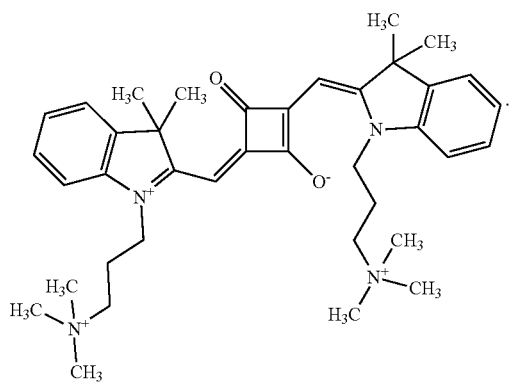 [SMILES: CC1(C)C(/C=C2\C(=O)C(/C=C3\N(CCC[N+](C)(C)C)c4ccccc4C3(C)C)=C2[O-])=[N+](CCC[N+](C)(C)C)c2ccccc21] |
| YY284 | 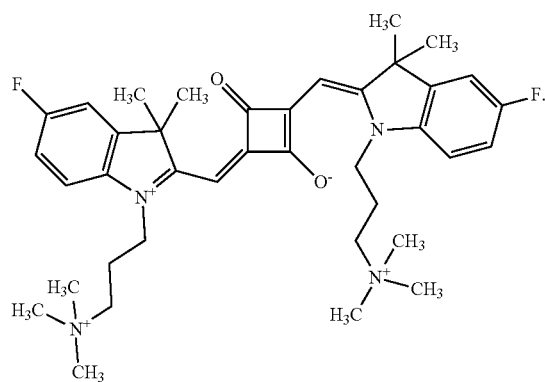 [SMILES: CC1(C)C(/C=C2\C(=O)C(/C=C3\N(CCC[N+](C)(C)C)c4ccc(F)cc4C3(C)C)=C2[O-])=[N+](CCC[N+](C)(C)C)c2ccc(F)cc21] |
| YY285 | 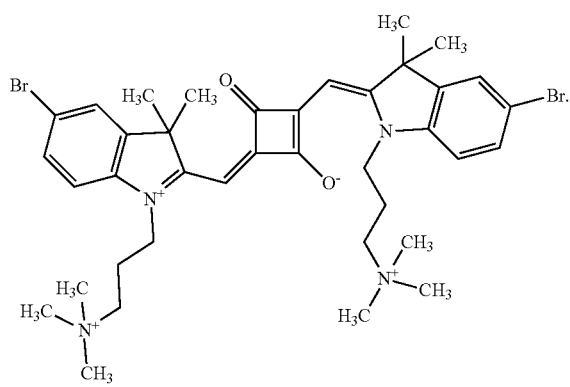 [SMILES: CC1(C)C(/C=C2\C(=O)C(/C=C3\N(CCC[N+](C)(C)C)c4ccc(Br)cc4C3(C)C)=C2[O-])=[N+](CCC[N+](C)(C)C)c2ccc(Br)cc21] |

| Name | Structure |
|------|-----------|
| YY294 | 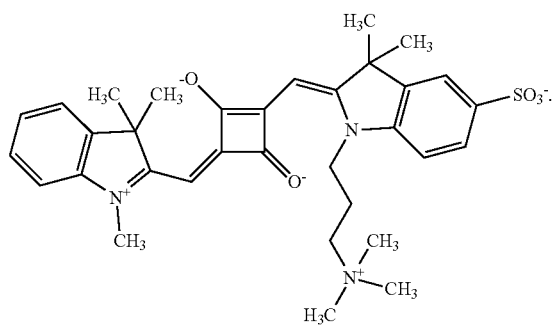 |
| YY295 | 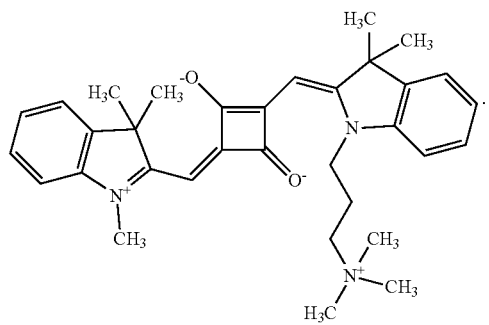 |
| YY2102 | 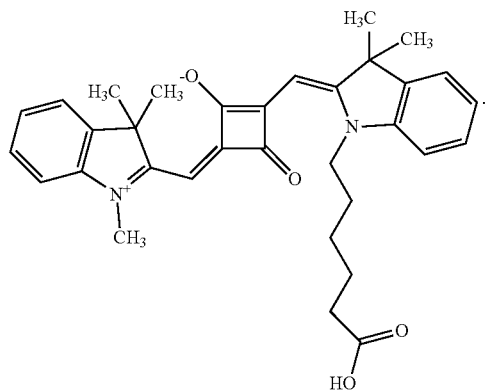 |
| YY2103 | 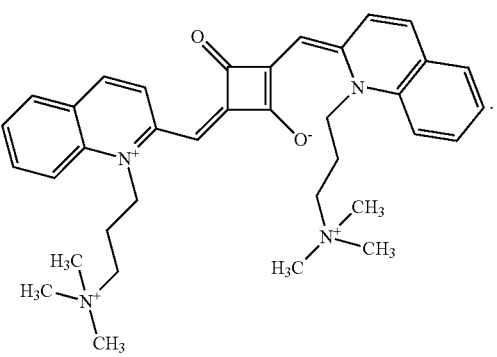 [SMILES: C[N+](C)(C)CCCN1/C(=C\C2=C([O-])C(=C/c3ccc4ccccc4[n+]3CCC[N+](C)(C)C)/C2=O)C=Cc2ccccc21] |

| Name | Structure |
|---|---|
| YY2106 | 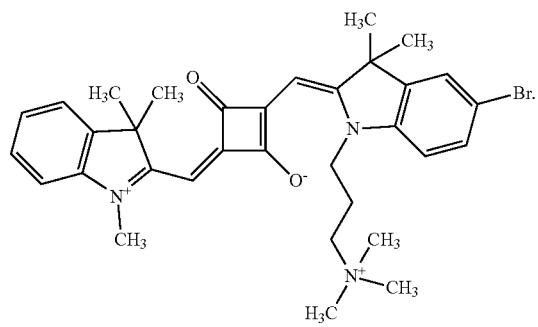 [SMILES: C[N+]1=C(/C=C2\C(=O)C(/C=C3\N(CCC[N+](C)(C)C)c4ccc(Br)cc4C3(C)C)=C2[O-])C(C)(C)c2ccccc21] |
| YY2107 | 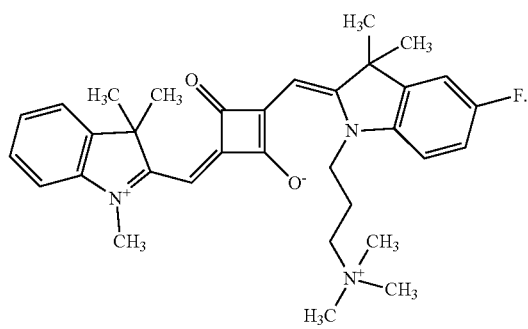 [SMILES: C[N+]1=C(/C=C2\C(=O)C(/C=C3\N(CCC[N+](C)(C)C)c4ccc(F)cc4C3(C)C)=C2[O-])C(C)(C)c2ccccc21] |
| L700-1A | 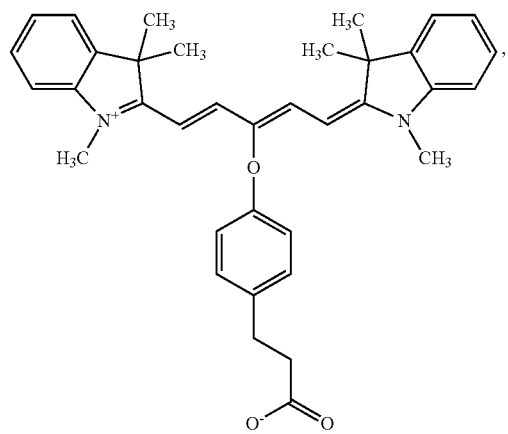 [SMILES: CN1/C(=C/C=C(/C=C/C2=[N+](C)c3ccccc3C2(C)C)Oc2ccc(CCC(=O)[O-])cc2)C(C)(C)c2ccccc21] |
| L700-1C | 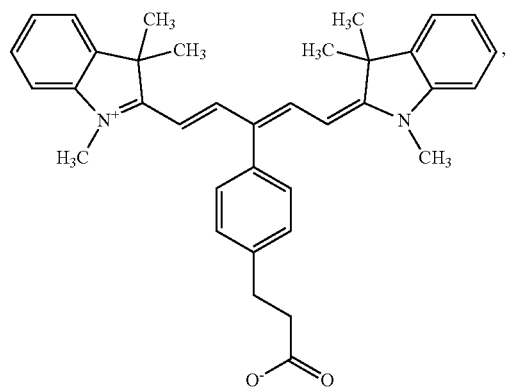 [SMILES: CN1/C(=C/C=C(/C=C/C2=[N+](C)c3ccccc3C2(C)C)c2ccc(CCC(=O)[O-])cc2)C(C)(C)c2ccccc21] |

| Name | Structure |
|------|-----------|
| L800-1A | 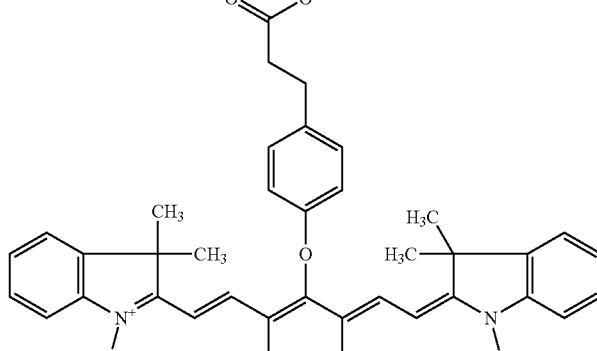 |
| L800-1C | 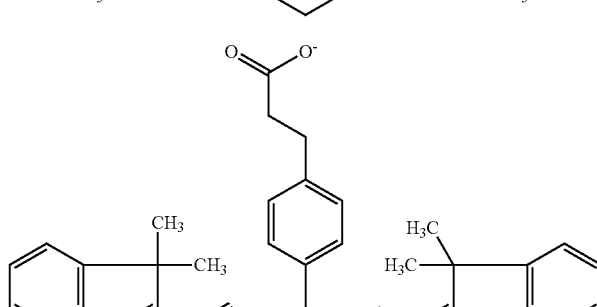 |

Some of these molecules are shown in their carboxylic acid form, but are not limited thereto. In certain embodiments, such as those that will conjugate covalently to other molecules, the compounds may be prepared using a suitable leaving group or reactive group. Examples of preferred leaving groups include, but are not limited to N-hydroxysuccinimide (NHS) ester derivatives, sulfo-N-hydroxysuccinimide ester derivatives, and tetrafluorophenyl (TFP) esters. An example of a reactive group would be an azide or an alkyne as used for click chemistry.

In certain embodiments, the near-infrared fluorescent biological contrast agent is: LN15, A104, TG42, or A71.

In certain embodiments, the compounds of the invention absorb light at different wavelengths in the near-infrared region. Specifically, in some embodiments, the compounds of the invention absorb light in the 660-720 nm range. In other embodiments, the compounds of the invention absorb light in the 760-820 nm range.

In particular embodiments, the near-infrared fluorescent biological contract agent is:

LN15, A104, or TG42; and absorbs light in the 660-720 nm range.

In another particular embodiment, the near-infrared fluorescent biological contract agent is A71 and absorbs light in the 760-820 nm range.

In preferred embodiments, the compounds of the invention are cell-permeable. In preferred embodiments, the compounds of the invention are not significantly toxic to cells (e.g., to cells in culture or in vivo).

In certain embodiments, the imaging agent of the invention comprises a radioisotope having a single-photon or positron emission decay mode and suitable for detection by single-photon emission tomography (SPECT) or positron emission tomography (PET) in addition to its detection via optical properties (i.e., absorption and/or fluorescence). Examples of suitable radioisotopes include C-11 and F-18. Such isotopes can be incorporated into a compound of the invention, e.g., by use of appropriate isotopically-enriched reagents during synthesis of the compound. Additional useful radiotracers, such as Ga-68 Zr-89, or Rb-82 (PET), or Tc-99m (SPECT), can be attached to the compound through a radiometal chelator such as 1,4,7,10-tetraazacyclododecane-1,4,7,10-tetraacetic acid (DOTA), diethylene triamine pentaacetic acid (DTPA), hydrazinonicotinic acid (HYNIC), or desferoxime, respectively (or derivatives thereof). Chelator moieties can be covalently attached to an oxazine compound, e.g., through a linking atom or group, e.g., by acylation of a hydroxyl group of a compound of Formula I-V with a carboxylate group of a chelator such as DOTA. By incorporation of an appropriate PET- or SPECT-detectable isotope, a compound according to the invention can be detected using SPECT or PET imaging (e.g., even when administered at a low dose), e.g., using a conventional SPECT or PET imaging system, while also being detectable optically (e.g., by fluorescence imaging), e.g., when administered at a higher dose. Dual-mode optical and SPECT or PET imaging is also possible using such compounds. Similarly, imaging by magnetic resonance imaging (MRI), including dual-mode optical/MRI imaging, can be performed by using a compound of the invention comprising a lanthanide (such as $Yb^{3+}$, $Dy^{3+}$ or $Gd^{3+}$), e.g., by chelating the lanthanide ion using a suitable chelating moiety.

Compounds of the invention can be prepared using a variety of methods, some of which are known in the art. For example, the compounds can be prepared using conventional methods of synthetic organic chemistry (see, e.g., Michael B. Smith, "March's Advanced Organic Chemistry: Reactions, Mechanisms, and Structure, 7th Edition", Wiley (2013)).

For example, compounds of the invention can be synthesized using the syntheses described in schemes 1-12 shown below. General references for the syntheses described in the schemes 1-6, 7a-c, 7e, 8-10, 11, 11a, and 12 is found in Henary, M. et al. Bioorg. & Med. Chem. Let. 22, 242-1246, (2012), Henary, M. et al. J. Heterocycl. Chem. 46: 84-87, (2009), Henary, M. et al. Dyes and Pigments. 99, 1107-1116 (2013), Henary, M. et al. Heterocycl. Commun. 19 (1), 1-11 (2013), Mojzych, M. et al. Topics in Heterocyclic, Springer-Verlag Berlin Heidelberg. 14, 1-9 (2008), Strekowski, L. et al. J. Org. Chem. 57, 4578-80 (1992), Halder, S. et. al. Eur. J. Med. Chem. 54, 647-59 (2012), Sakiko, A. et al. Chem.-A Eur. J., 15, 9191-9200 (2009), Chang, Y-T. et al. Chem. Commun. 47, 3514-3516 (2011), Myochin, T. J. Am. Chem. Soc. 134, 13730-13737 (2012), Briza, T. et al. Chem. Comm. 16, 1901-1903 (2008), Chang, Y-T. et al. Chem. Commum. 46, 7406-7408 (2010), Zaheer, A., et al. Molecular Imag. 1 (4), 1536-0121 (2002), Misra, P. et al. J Nucl Med. 2007 August; 48(8):1379-89, and Humblet, V. et al, J Med Chem. 2009 Jan. 22; 52(2):544-50.

Scheme 1 outlines the synthesis of a series of 700 nm NIR emitting pentamethine cyanine dye derivatives 10-15. The key step is the quaternization of the nitrogen atom in indolenine derivatives 1-3 in either refluxing acetonitrile or toluene for between 10 hours and 3 days, depending on the alkylating agent, to yield the cationic salts 4-9. Condensation of salts 4-9, in a two molar ratio, containing an activated methyl group with malonoaldehyde bisphenylamine hydrochloride under basic conditions, normally achieved through the addition of triethyl amine or sodium acetate, furnished the pentacyanines in 70 to 90% yield, as depicted in Scheme 1, in less than 6 hours.

A series of chloro derivatives of pentamethine cyanine dyes 16-20 (Scheme 1) have also been prepared. Using the same chemistry the chloro-substituted pentamethine cyanine dyes can readily undergo nucleophilic substitution at the meso position to replace the chlorine atom with versatile functionalities, although care has to be taken with charged substituents, which may complicate cross-coupling reactions. Chloro-substitution is also useful for introducing specific targeting ligands or biomolecules via covalent conjugation. These reactions require a precise choice of functionalities, as well as a feasible synthetic methodology. A majority of these dyes are constructed via a well-established $S_{NR}1$ mechanistic pathway where the meso chlorine atom of the polymethine dye is substituted with various nucleofugal functionalities. This route renders an array of fluorophores that contain highly functional aminoalkyl, hydroxyalkyl, hydroxyaryl, thioalkyl, and thioaryl substituents, which can be further conjugated to ligands or biomolecules.

Scheme 1

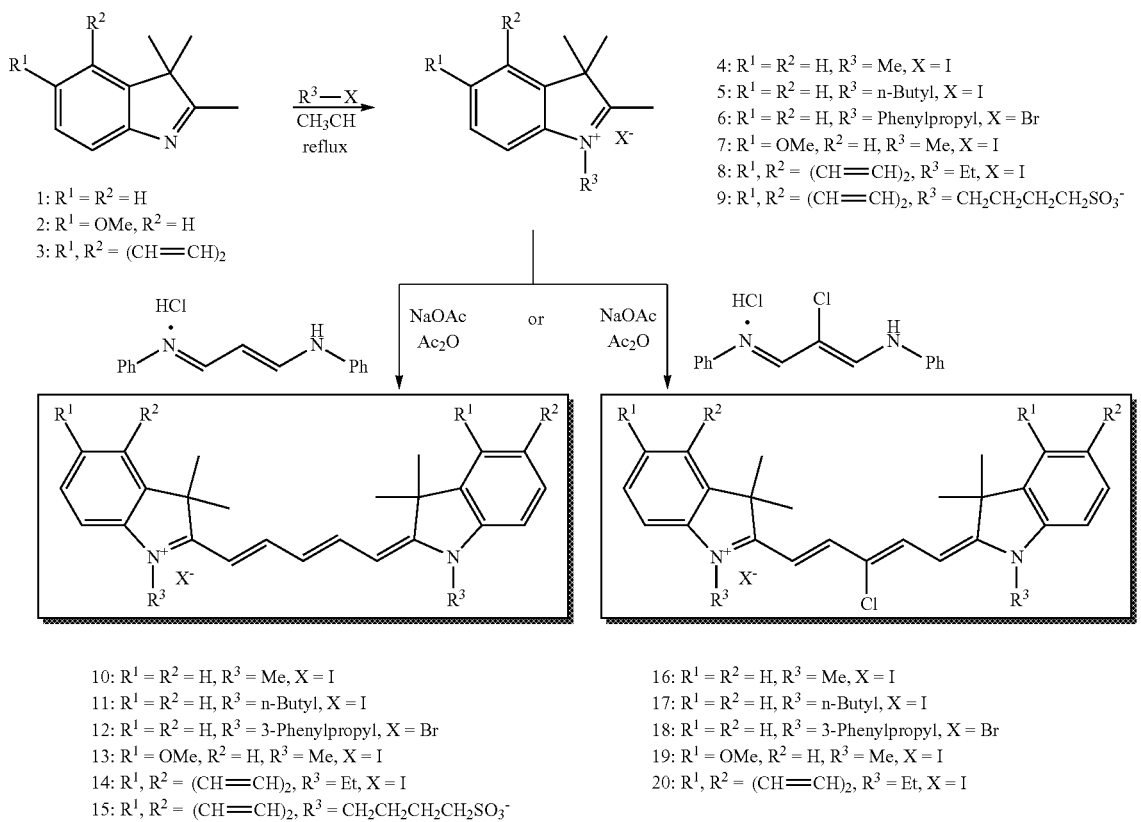

Scheme 2

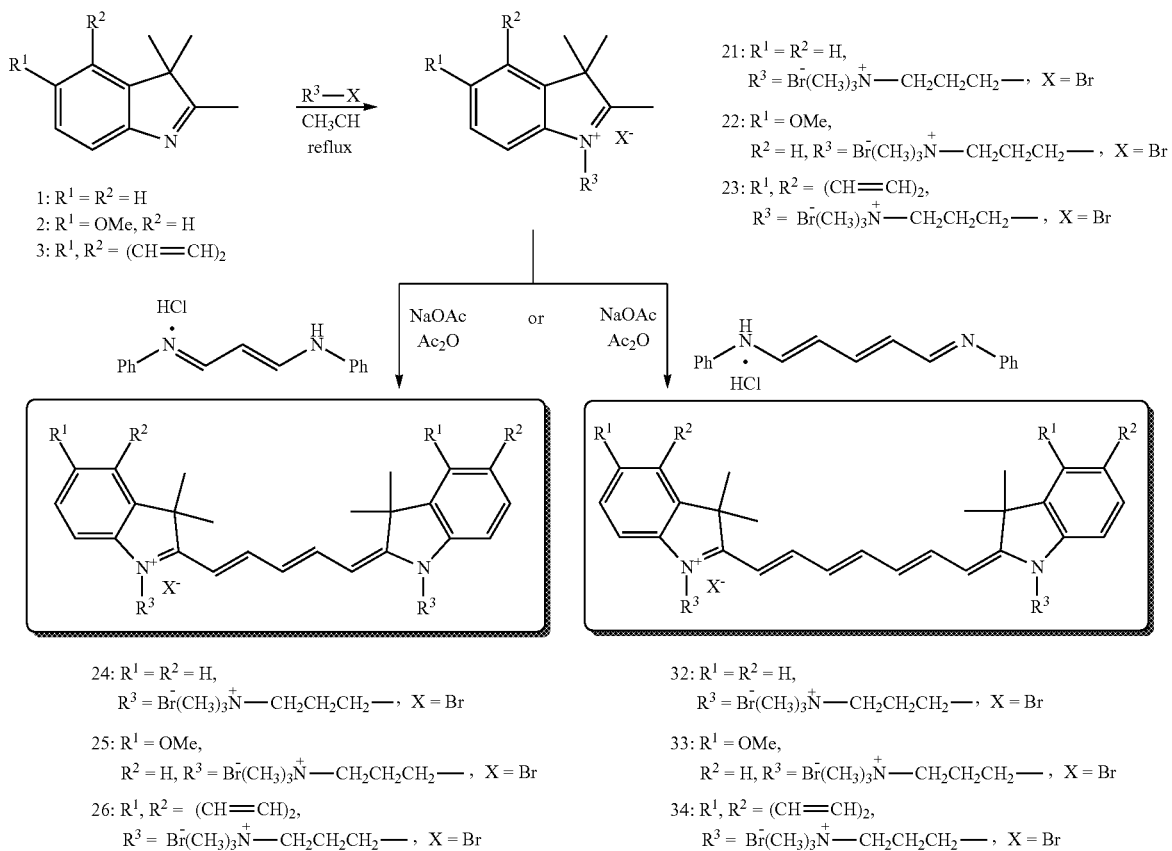

Using similar chemistry as described in Scheme 1, including reaction conditions, the compounds depicted in Scheme 2 were synthesized. The compounds prepared contain cationic quaternary ammonium substituents on the heterocyclic nitrogen. Additionally, the heterocyclic character was varied by incorporating a methoxy group at the 5-position or by using a benz[e]indolenine core. The systematic set of 700 nm cyanines (24-26) was replicated using the heptamethine cyanine structure to achieve fluorescence wavelengths around 800 nm (32-34). Compared to the compounds depicted in Scheme 1, these final products (25, 26, 33 and 34) exhibit red-shifted optical properties (wavelength of maximum absorption and wavelength of maximum emission) of approximately 20 nm. These compounds also take slightly longer to form and an additional 2 hours are required to facilitate the completion of the condensation reaction in 60 to 80% yield after purification.

Scheme 3

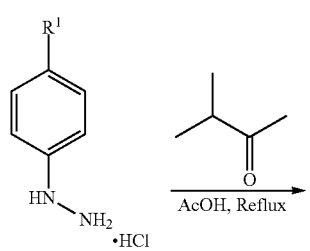

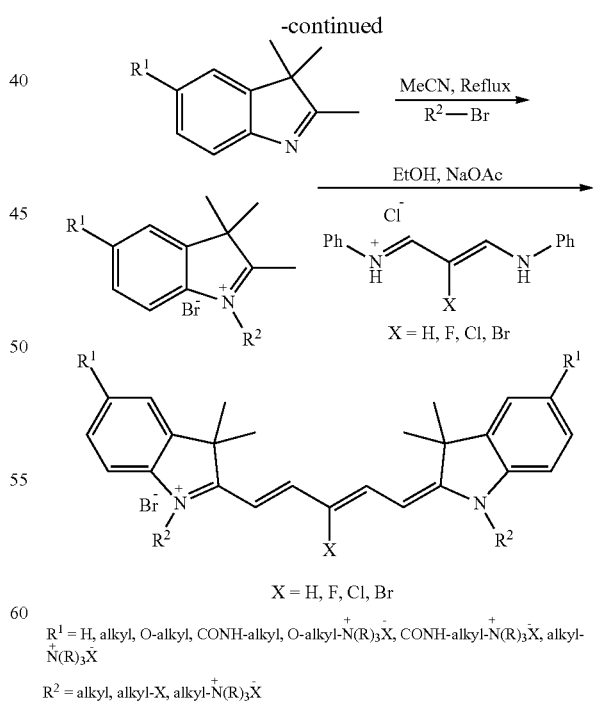

In order to form heterocyclic-substituted pentamethine cyanine dyes originating from the indolenine only provides limited chemical space for modification; however, beginning with the 4-substituted phenylhydrazine hydrochloride and upon treatment with a single molar ratio of 3-methyl-2-butanone in acidic conditions (boiling glacial acetic acid) yields the corresponding indolene derivative which is then alkylated using aforementioned synthetic protocol to afford the quaternized nitrogen salts. These salts then react with substituted dianil-malononitrile analogs to yield the highly substituted pentamethine cyanines.

This synthetic route is necessary to prepare the ether, amide and highly charged analogs shown in Scheme 3. The amide-containing compounds require synthesizing the corresponding carboxylic acid which is then coupled to an amine to form the depicted compounds which would synthetically occur after amine quaternization. The compounds with ether linkages would begin with the aryl alcohol at $R^1$ followed by treatment with sodium hydride and addition of the appropriate alkylating reagent.

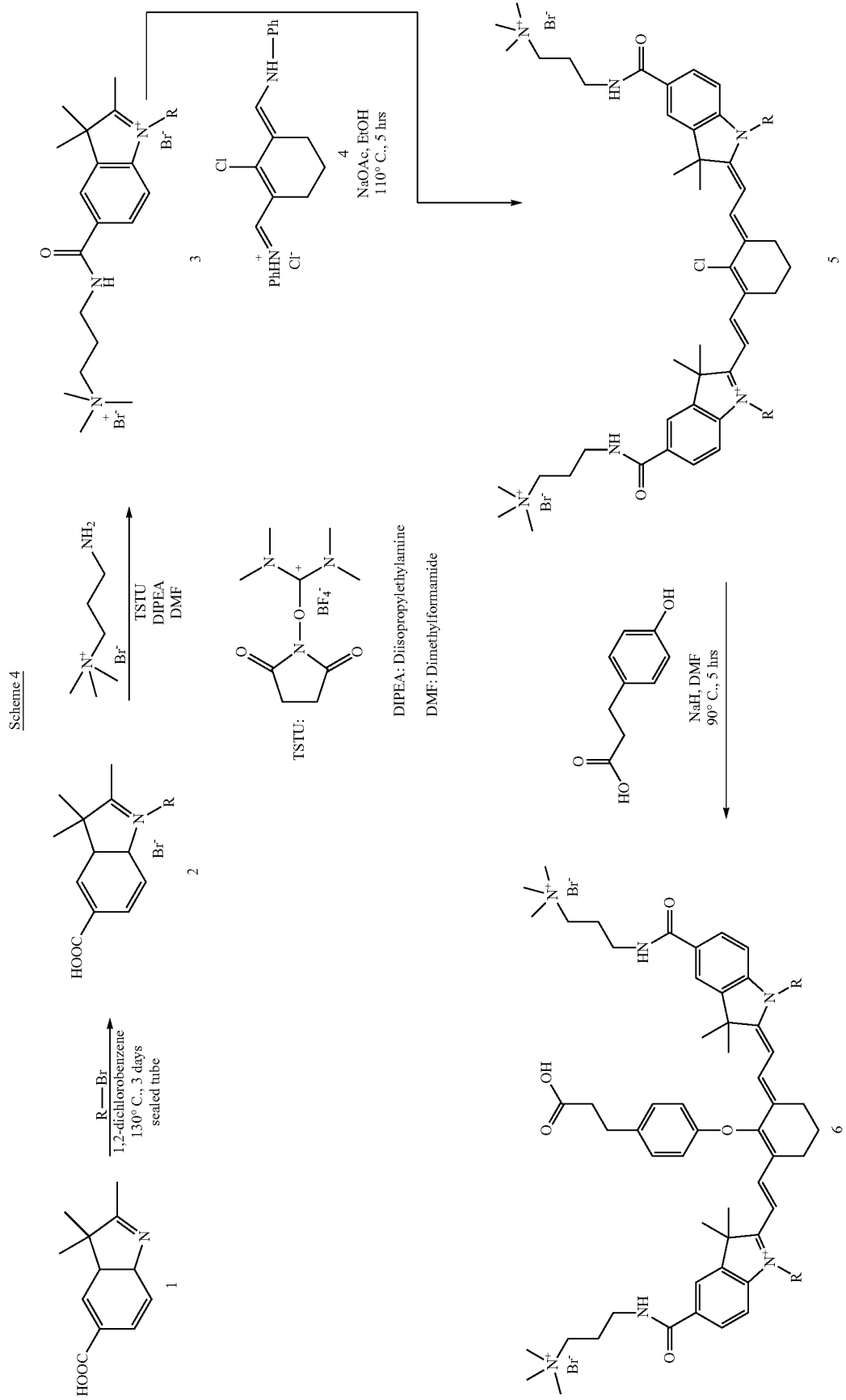

Scheme 4 outlines the synthesis of compounds with net charges between +2 to +4 (compound 6 in Scheme 4), which affords the potential for 4 quaternary ammonium cations. The heterocyclic nitrogen of 2 is quaternized with trimethyl (3-bromopropyl)ammonium bromide or other alkylating agent with reaction conditions as described above to give intermediate product 2. The carboxylic acid group of 2 is allowed to react with the free primary amine of (3-aminopropyl)trimethylammonium bromide in the presence of TSTU for 3-5 h under basic conditions to furnish amide 3. The reaction of 3 with the Vilsmeier-Haack reagent 4 provides the chloro-substituted dye 5. The treatment of 5 with a disodium derivative of 3-(4-hydroxyphenyl)propionic acid in DMF or in DW/DMSO at 65° C. for 6 hours produces a carboxylic derivative 6 (ZW-4) for effective coupling, via its single carboxylic acid, to targeting ligands with a +4 net charge. Other compounds carrying +2 can be synthesized using the same methodology as outlined in Scheme 4.

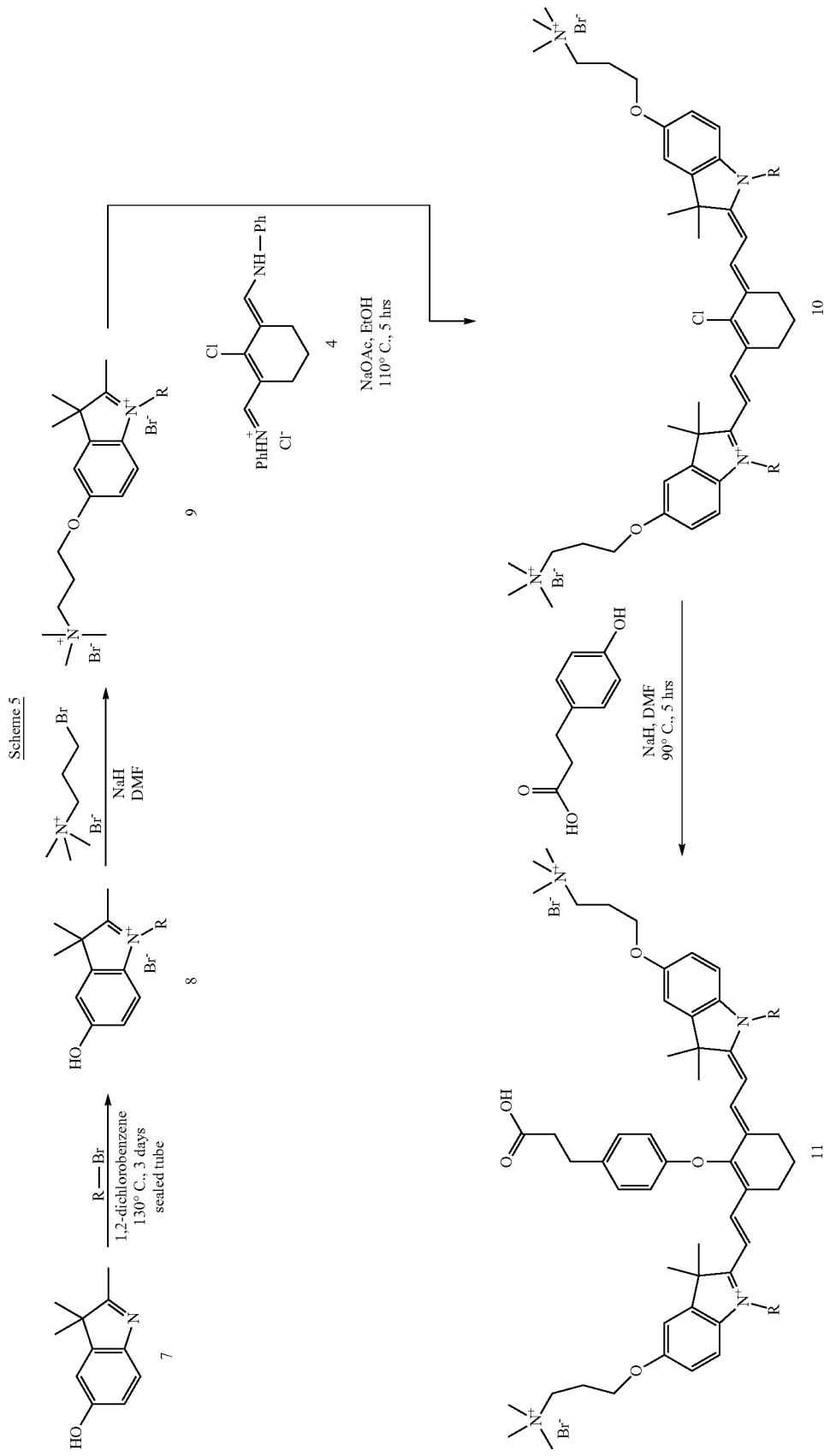

309

Scheme 5 summarizes the synthesis of analogs of NF800 (net charge+2) ether derivatives. The phenolic nature of the Fischer salt heterocycle is modified further with quaternary salts via ether linkage under basic conditions in DMF at 80° C. and the heterocyclic ring nitrogens will be altered with various alkyl groups. To synthesize analogs of NF800 with higher net charge (+4) the alkyl group of the heterocyclic nitrogens is terminated with additional quaternary ammonium salts. This is achieved by synthesizing the quaternary ammonium salt by reacting the 5-hydroxyindolenine compound with iodomethane for 3 days by heating 1,2-dichlorobenzene in a sealed tube. After obtaining the desired compound 8 the alcohol is deprotonated using 1.2 molar equivalents of sodium hydride in dry DMF followed by the addition of 3-bromopropyltrimethylammmonium bromide alkylating agent. The reactive methyl group reacts as previously discussed to afford the final target compound 11.

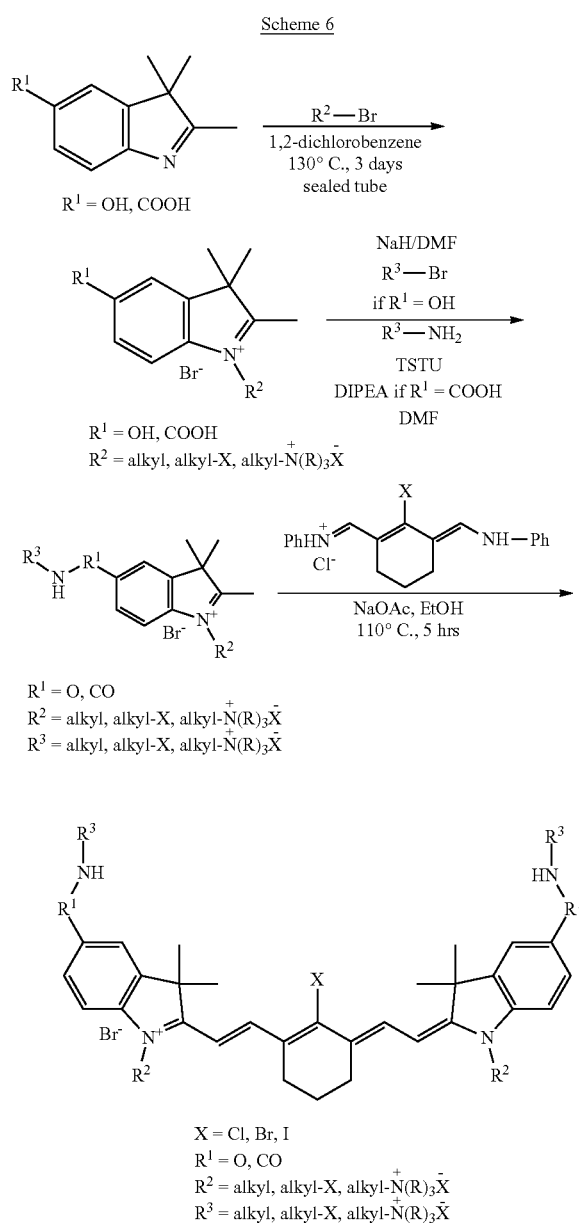

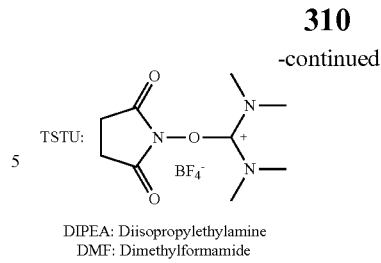

DIPEA: Diisopropylethylamine
DMF: Dimethylformamide

Using identical reaction conditions as outlined in Schemes 4 and 5 other synthetic routes are presented in Scheme 6 to synthesize various halogenated analogs of compounds type 5 (Scheme 4) and 10 (Scheme 5) at the central carbon of the heptamethine cyanine dye.

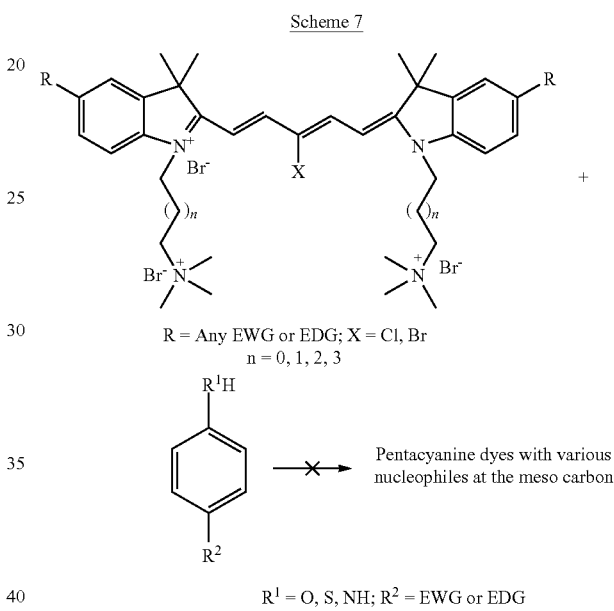

As shown in Scheme 7, the replacement of the halogen at the meso carbon of the dye with various nucleophiles does not occur under various reaction conditions (with/without base and lower/higher reaction temperature) due to the steric effect of cis-trans photoisomerization. To overcome this problem, the synthetic procedures in Schemes 7a-c and 7d are optimized to synthesize large numbers of novel pentacyanine dyes substituted various nucleophiles at the meso carbon of the dye.

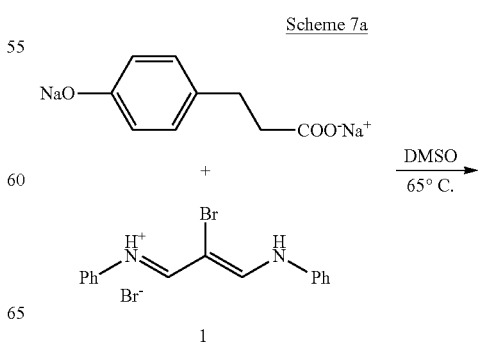

311
-continued
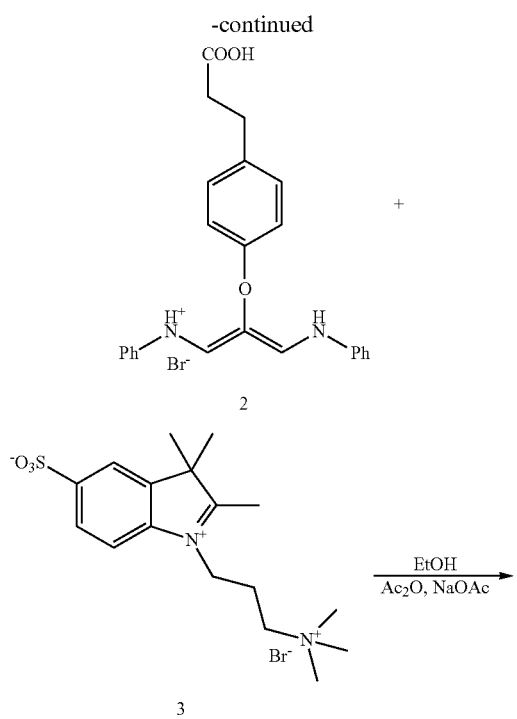
312
-continued
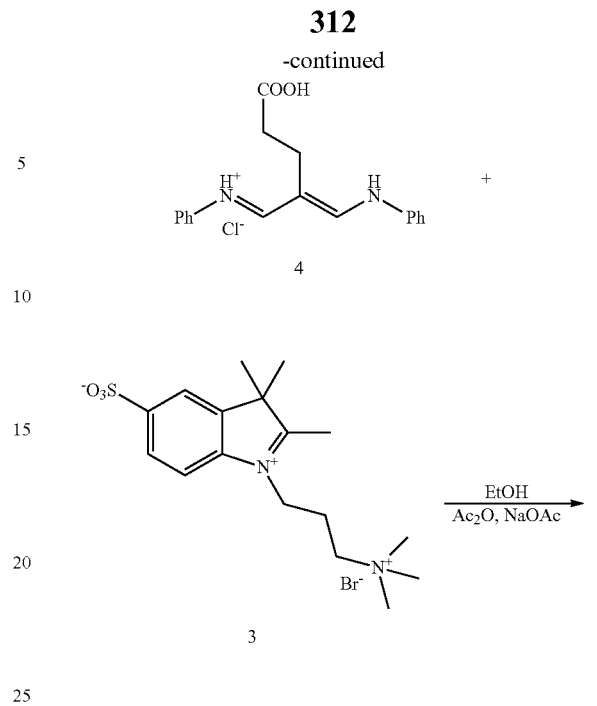
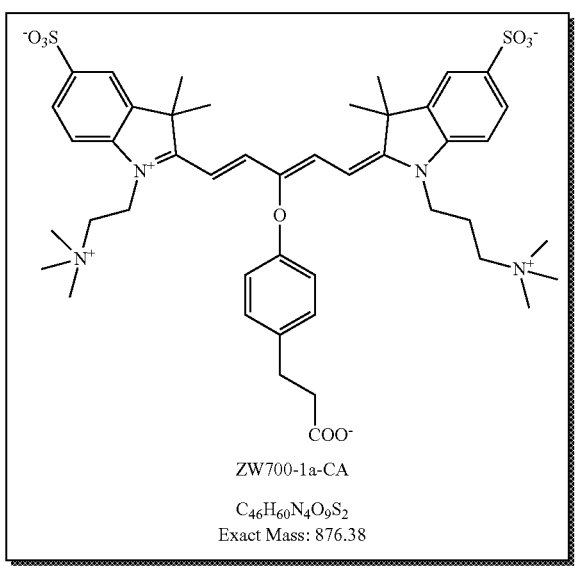
Scheme 7b
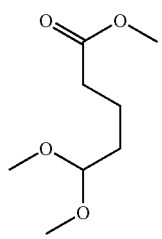
Scheme 7c
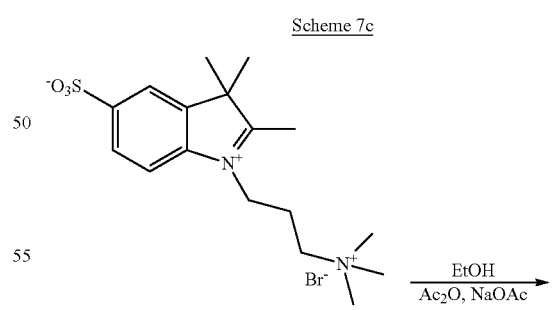

313
-continued

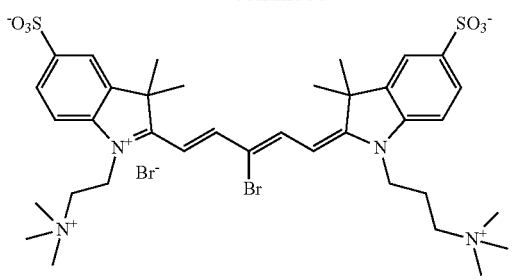

5

314
-continued

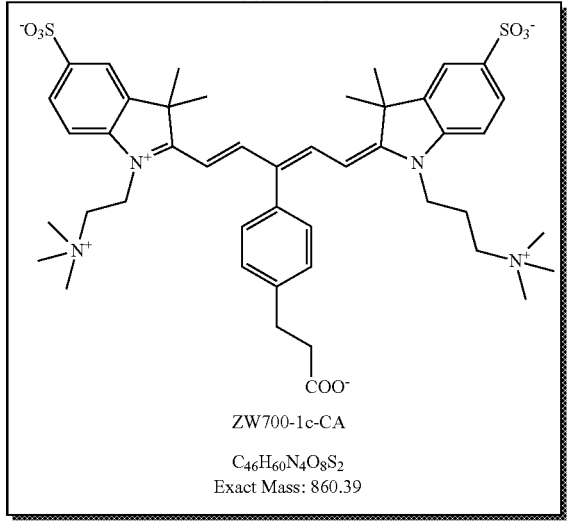

ZW700-1c-CA

C₄₆H₆₀N₄O₈S₂
Exact Mass: 860.39

As shown in Scheme 7a-c, the synthetic routes of 700 nm zwitterionic NIR fluorophore (LN15, A104, TG42) were successfully synthesized through the reaction between quaternary salt 3 and carboxylic acid reagents. LN15 was successfully synthesized by reacting the bromo reagent with disodium salt of 3-(4-hydroxyphenyl)propanoic acid in DMSO at 65° C. Without further purification, the crude product was used to react with the quaternary salt under basic conditions, and LN15 was obtained with very low yield (10%) after reverse phase chromatography purification. A104 was also synthesized with an ethanoic acid moiety added to the central carbon of the polymethine chain. The synthesis begins with methyl 5,5-dimethoxypentanoate reacting with oxalyl chloride followed by a basic workup and treatment with anilinium chloride to form reactive intermediate 4. Reaction with heterocyclic salt 3 proceeds with 4 hours of heating in a mixture of ethanol and acetic anhydride with sodium acetate to yield the final compound A104. TG42 was successfully synthesized through Suzuki-Miyaura cross coupling reaction with an effective 78% yield.

Another methodology as depicted in Scheme 7d may also be utilized

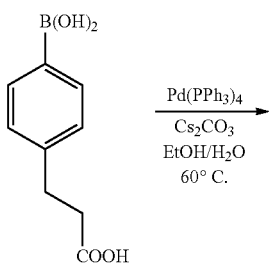

Scheme 7d

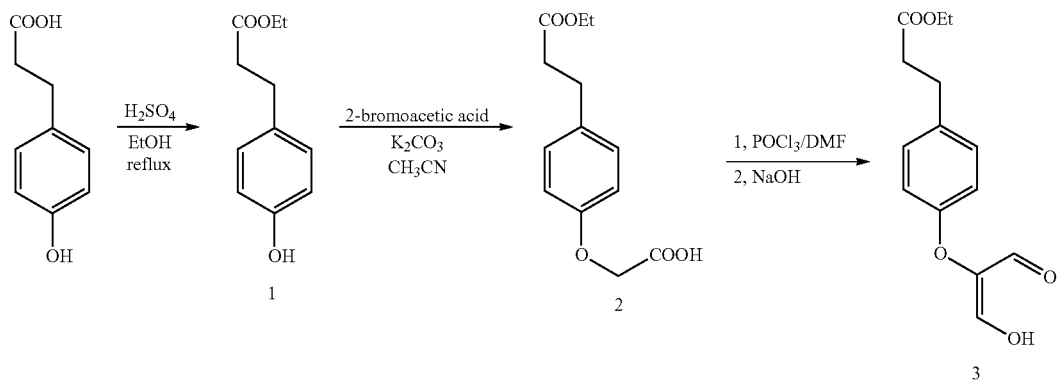

-continued

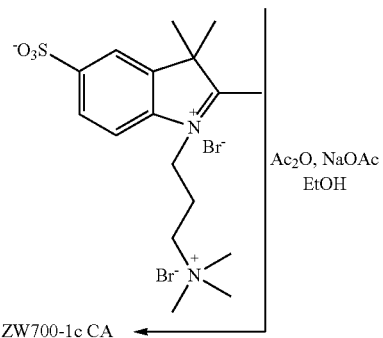

Ac₂O, NaOAc
EtOH

ZW700-1c CA

As outlined in Scheme 7d, a novel methodology was applied to synthesis TG42 in fair yield 40% by reacting the phenolic compound 1 with 2-bromoacetic acid under basic conditions for 6 h to yield compound 2. Vilsmeier formylation using phosphorous oxychloride and DMF was conducted on 2 for 5h followed by basic workup to form the decarboxylated bis-aldehyde 3. Compound 3 was allowed to react with the quaternary salt using sodium acetate in boiling ethanol for around 3-5 h to afford the desired compound.

As such, in another aspect, the invention provides a method of preparing a compound, the method comprising reacting a decarboxylated bis-aldehyde with a quarternary salt to produce the compound.

In certain embodiments, the method comprises reacting a decarboxylated bis-aldehyde of the formula with a quarternary salt of the formula

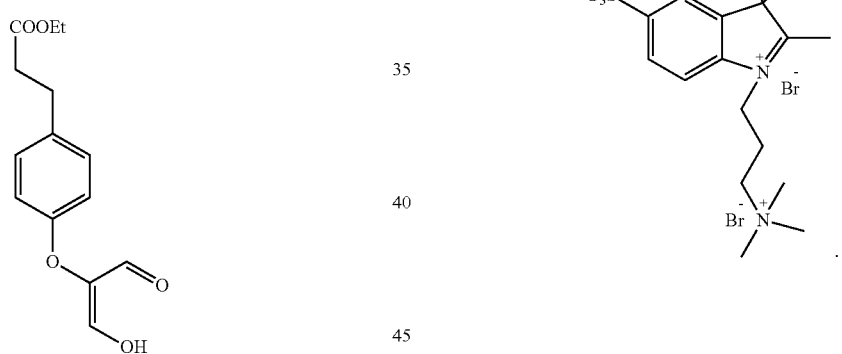

Scheme 7e

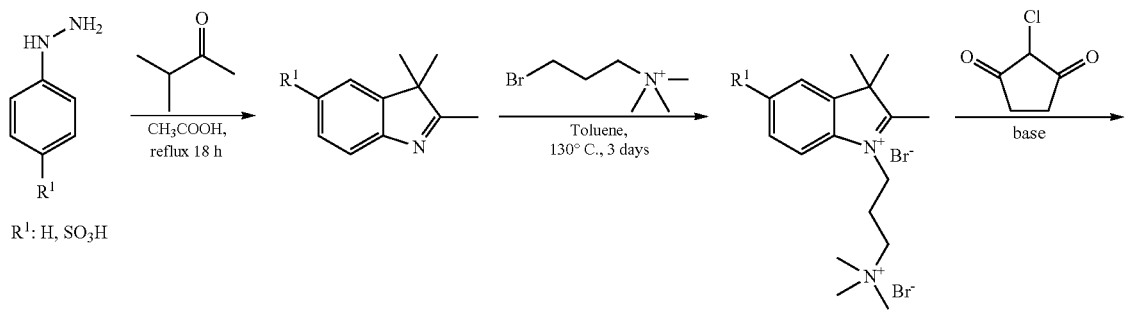

R¹: H, SO₃H

317

318

-continued

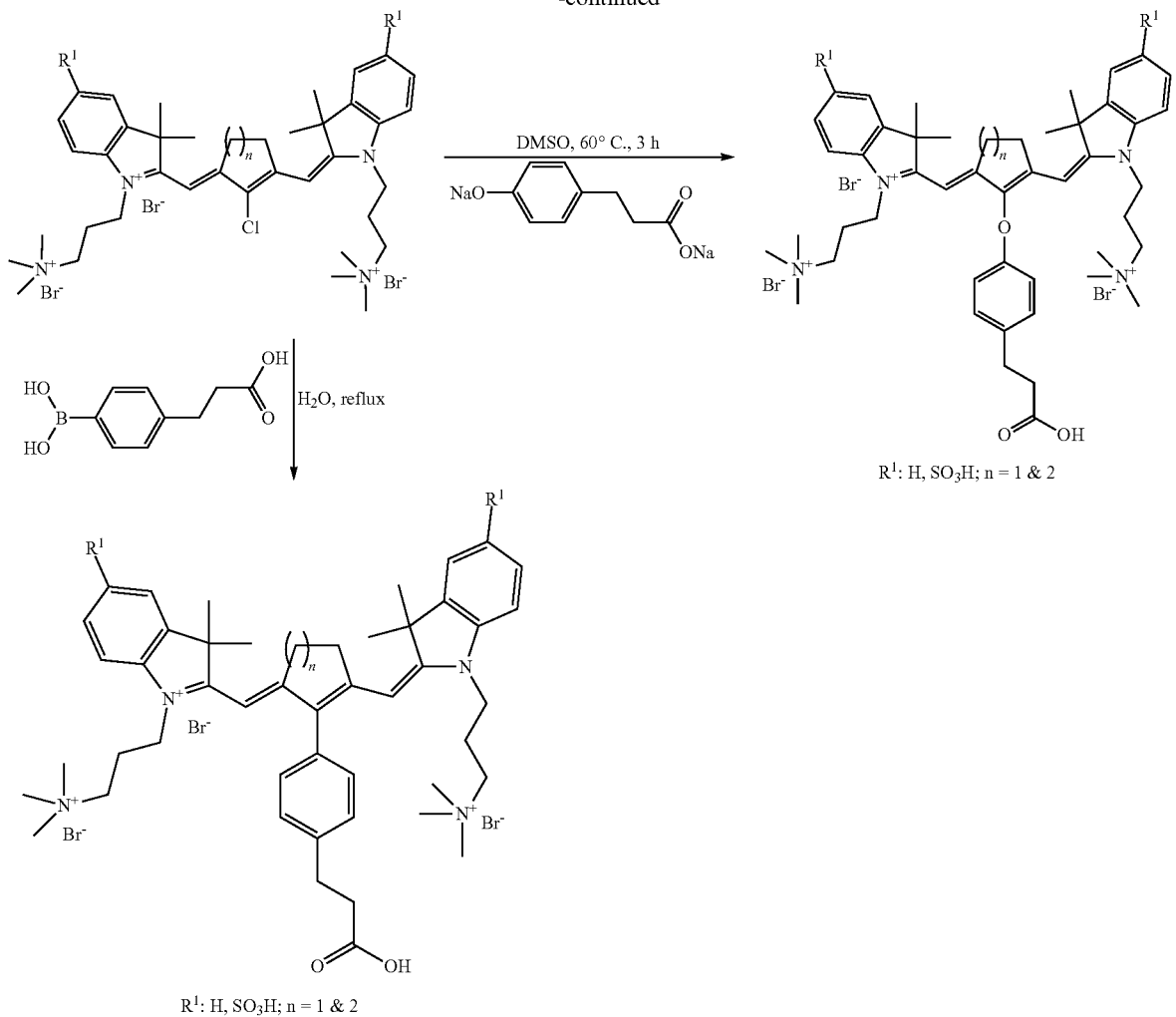

$R^1$: H, SO$_3$H; n = 1 & 2

$R^1$: H, SO$_3$H; n = 1 & 2

To synthesize pentamethine dyes with 5- or 6-membered rings at the dye central position, the chemistry outlined in Scheme 7e is applied to synthesize analogs of LN15, A104, and TG42. In particular, 2-halo 1,3-dicarbonyl pentane or hexane is used as the starting material under ethanol reflux using basic condition to react with activated indolenine derivatives under basic conditions to afford the desired compounds.\

Scheme 8
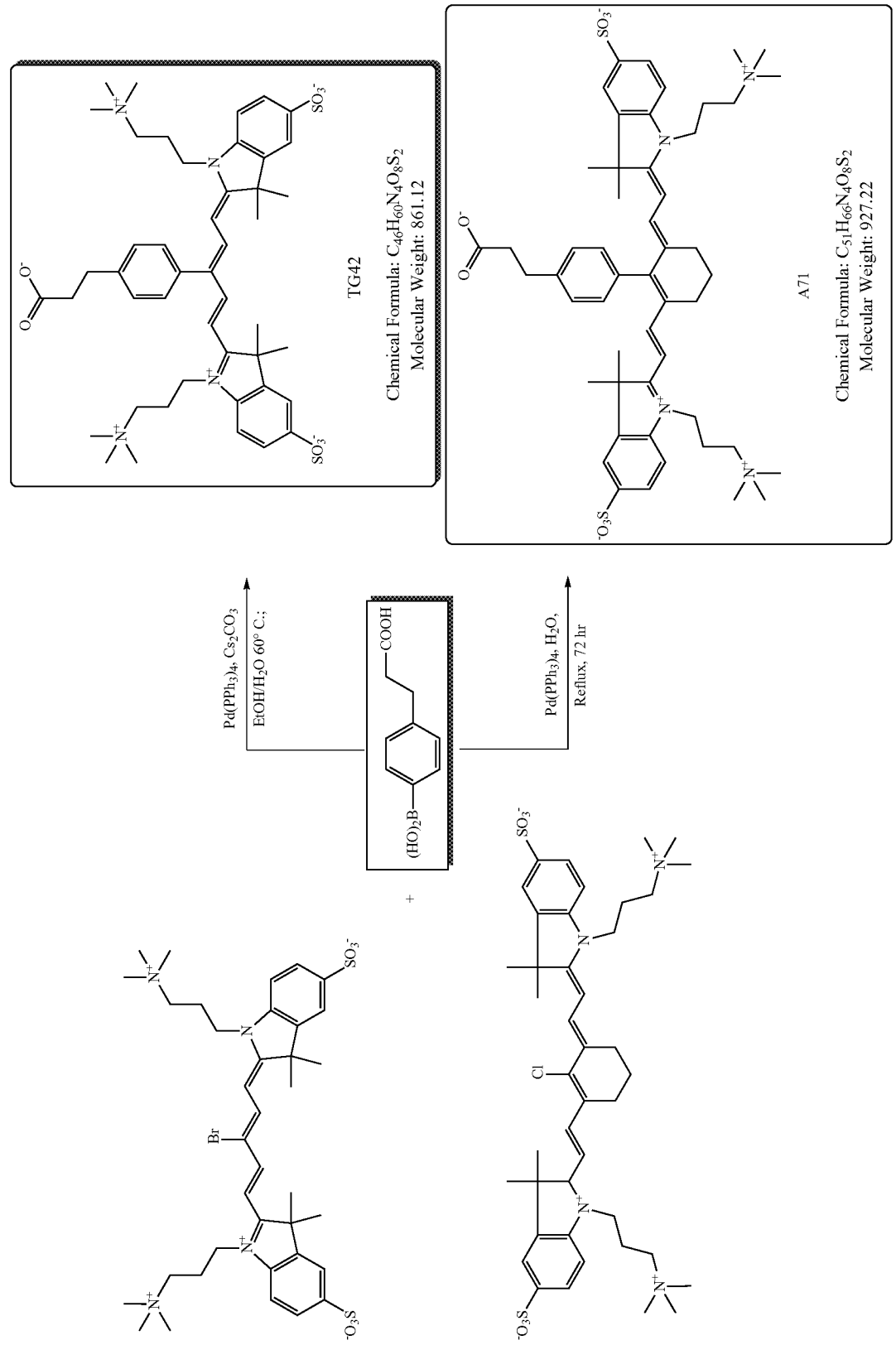

The carbon-carbon bond coupling provides additional stability to the molecule and the compounds TG42 and A71 are synthesized using the palladium mediated Suzuki-coupling reaction. In particular embodiments, the synthesis uses 5 molar percent of tetrakistriphenylphosophine palladium(0) for the coupling reaction and cesium carbonate (3 eq) as the base. This reaction proceeds satisfactorily in water or alcoholic water at elevated temperature using the 3-(4-boronophenyl)propanoic acid and meso-halogenated penta- or heptamethine precursors.

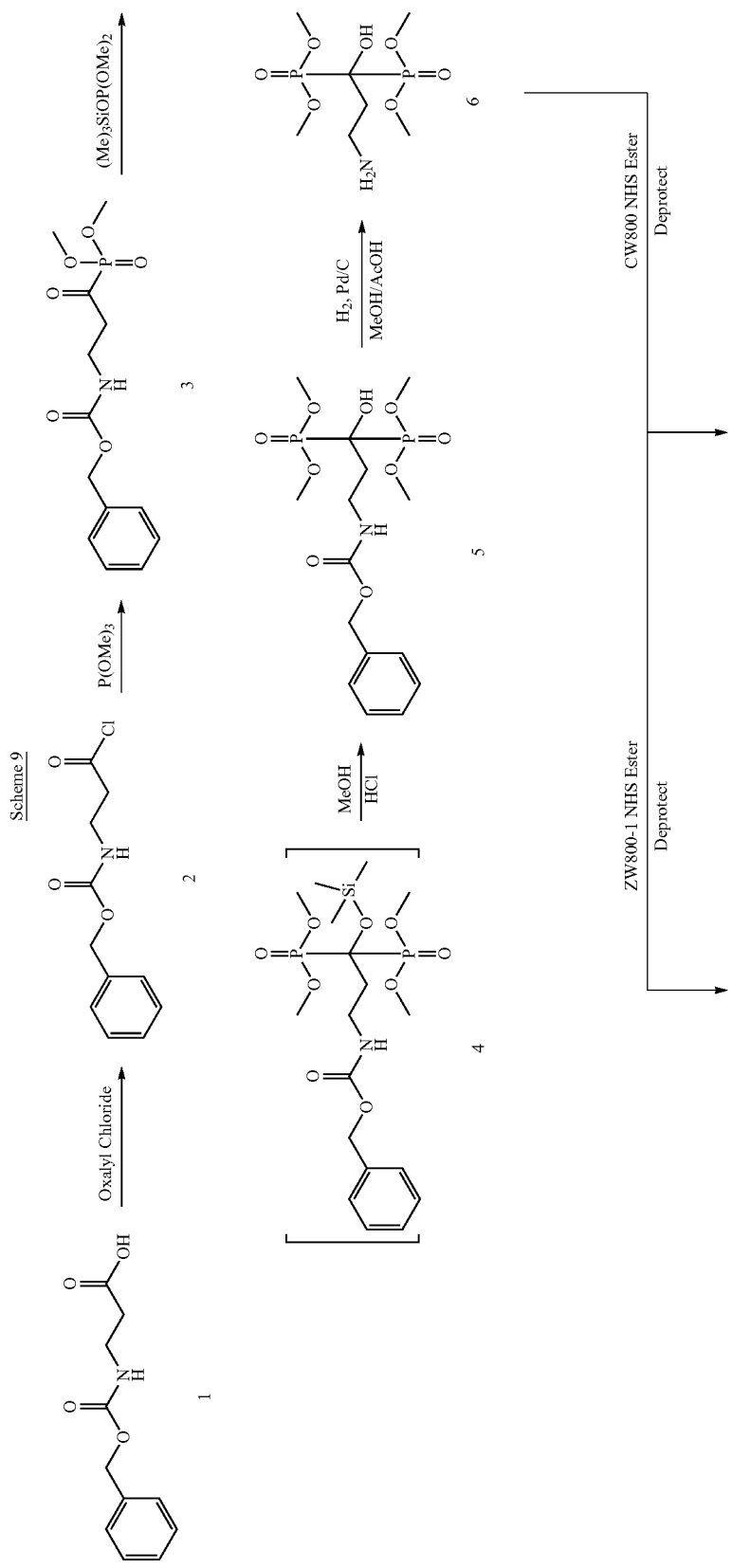

-continued
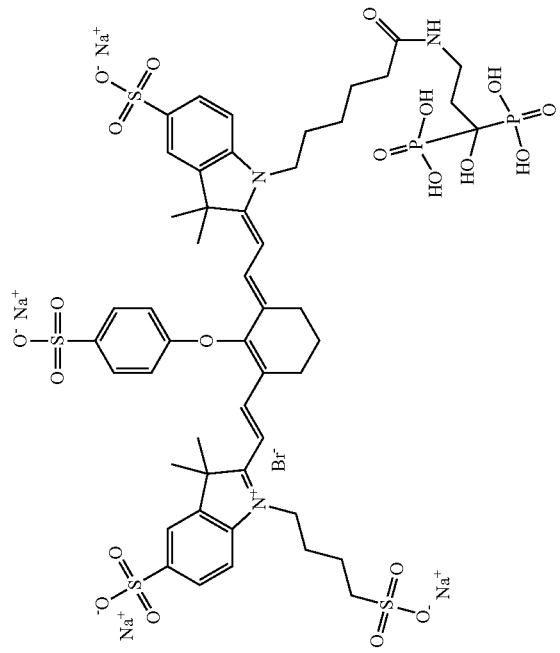
PAM-CW800
Chemical Formula: C₄₉H₆₁BrN₃Na₄O₂₁P₂S₄
Exact Mass: 1388.09
Molecular Weight: 1390.09
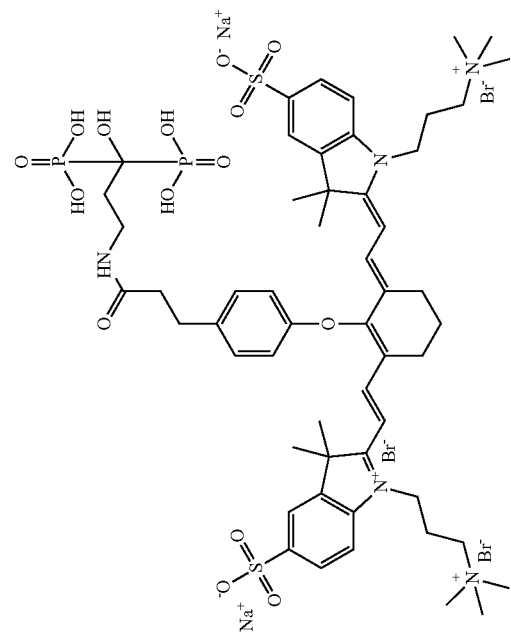
PAM-ZW800-1
Chemical Formula: C₅₄H₇₆Br₃N₅Na₂O₁₅P₂S₂
Exact Mass: 1443.16
Molecular Weight: 1446.97

Pamidronate (PAM)-modified heptamethine fluorophores, PAM-ZW800-1 and PAM-CW800 are prepared originating with protected beta-alanine. Reacting the terminal acid of 3-[(benzyloxycarbonypamino]-propionic acid (20 mmol) with oxalyl chloride 100 mmol at 0° C. in dichloromethane for 30 min and at room temperature for 6 h yields the acyl chloride 2 which undergoes nucleophilic acyl substitution with trimethyl phosphite (22 mmol) which was added drop wise at 0° C. for 5 min. The volatile organic solvent was evaporated under reduced pressure and washed with hexane to give dimethyl [3-(Benzyloxycarbonylamino)-1-(dimethoxyphosphoryl)-1-hydroxypropyl] phosphonate 3 as pale yellow oil (88% yield). Compound 3 is placed in a 500-mL Parr bottle under N2 and dissolved in 50 mL of cold denatured methanol. Palladium on activated carbon (10 wt. %) was added carefully and the Parr shaker apparatus assembled. The reaction is shaken at 50 psi $H_2$ and room temperature until H2 uptake is complete (6-12 hours). The palladium on activated carbon was filtered over a Celite pad; the solvent was evaporated under reduced pressure to give dimethyl [3-amino-1-(dimethoxyphosphoryl)-1-hydroxypropyl] phosphonate as yellow solid (90% yield), the PAM-precursor 6 bearing a primary amine is synthesized and ready for further reactions with NHS-ester modified ZW800-1 and/or CW800. Reacting the precursor 6 with the NHS-ester dyes forms the amide bonds shown in the final compounds symmetrical PAM-ZW800-1 and asymmetrical PAM-CW800.

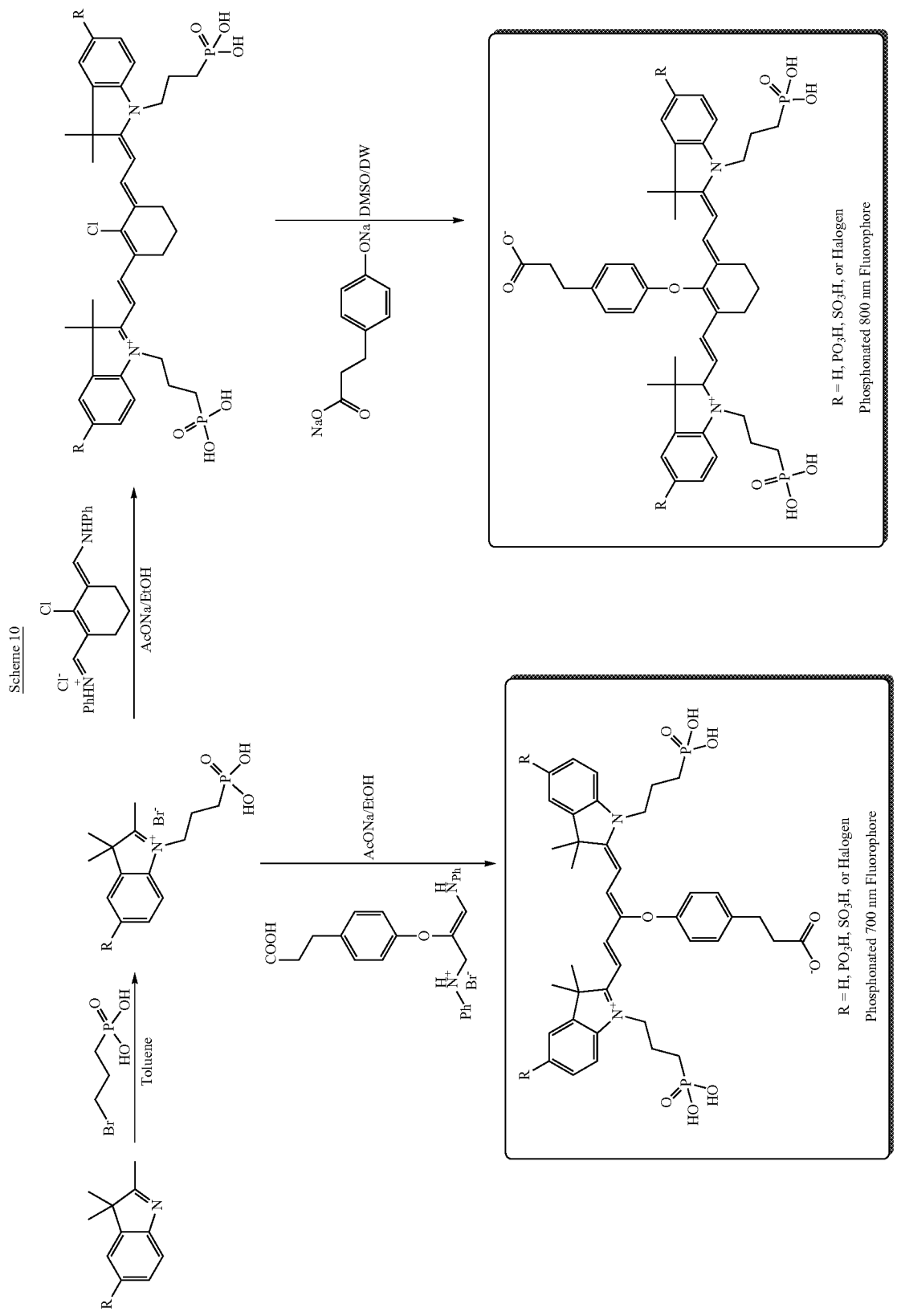

Similar to compounds with a propyltrimethylammonium bromide moiety on the heterocyclic nitrogen, the compounds presented in Scheme 10 contain a phosphonic acid group for molecular targeting. Using identical reaction conditions as discussed above, (3-bromopropyl)phosphonic acid is used in boiling toluene for 18 h to synthesize the quaternized heterocyclic nitrogen in about 3 days. After this step, the dye synthesis proceeds as previously discussed to yield the final Phosphonated 700 nm (P700H and P700SO3) and Phosphonated 800 nm (P800H and P800SO3) Fluorophores.

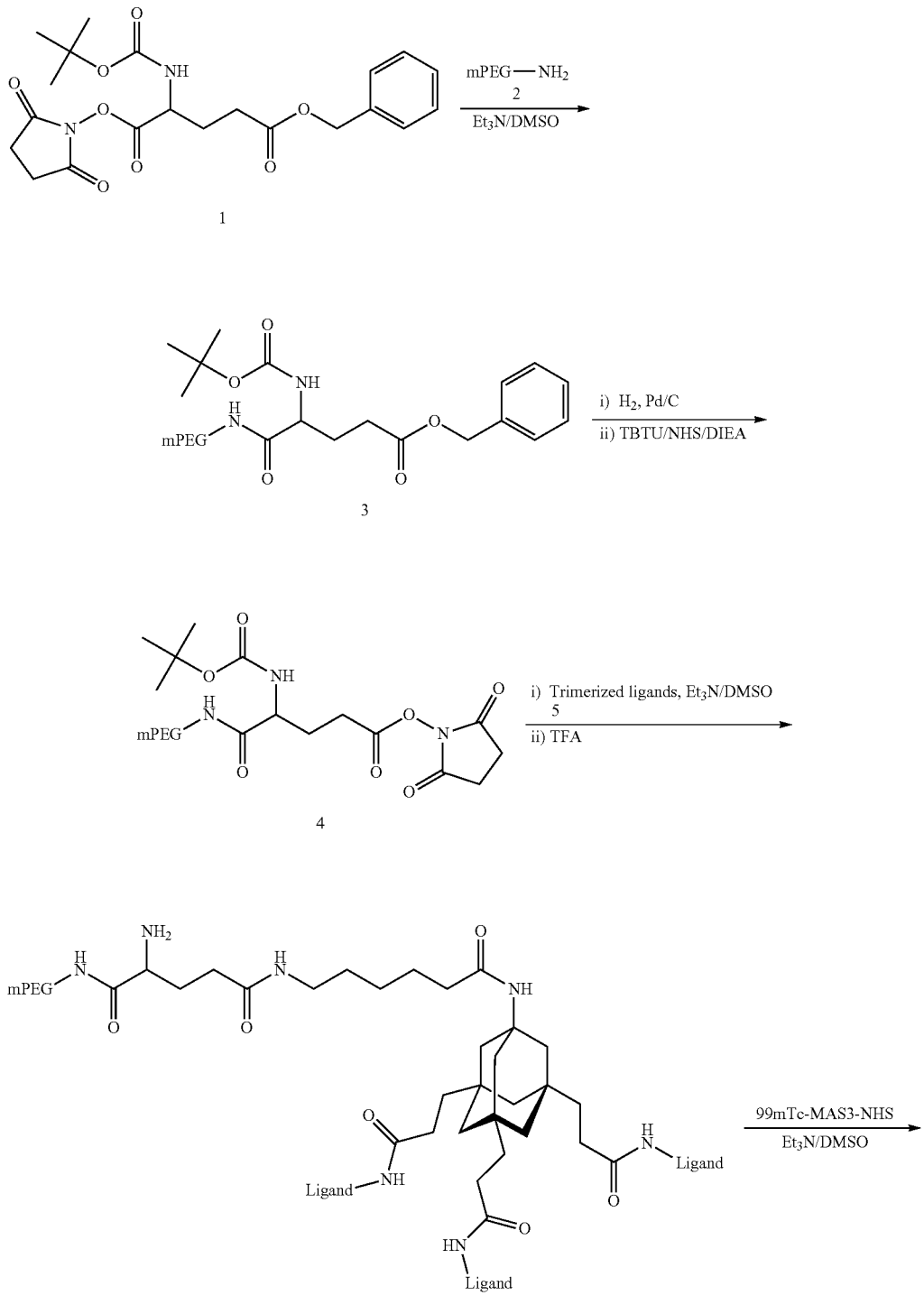

Scheme 11

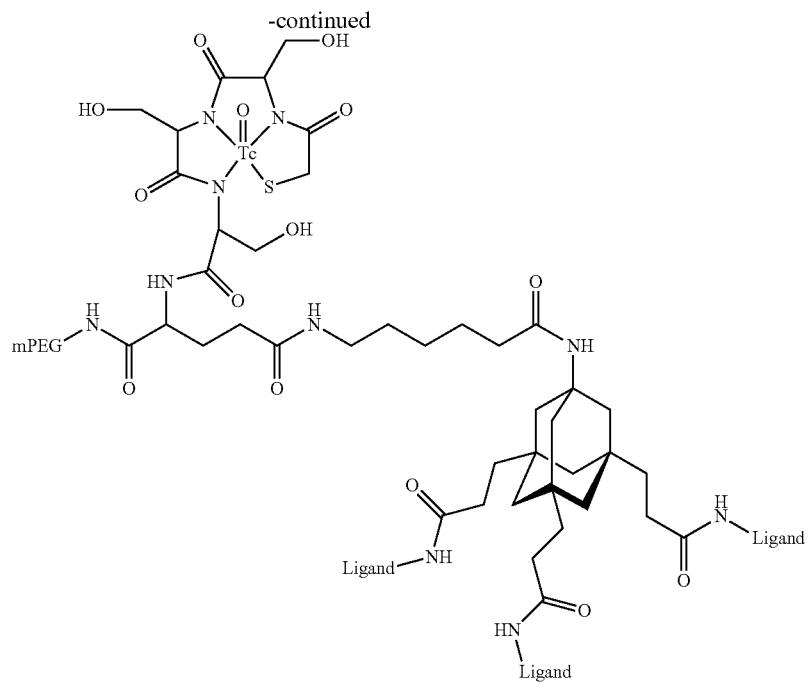

7

Synthesis of PEGylated 99mTc-MAS3 targeting compound begins by dissolving 1 eq.mol mPEG-NH$_2$ (2) in dry DMSO followed by the addition of 1.5 eq.mol Boc-Glu(OBzl)-OSu (5-benzyl-1-(2,5-dioxopyrrolidin-1-yl) (tert-butoxycarbonyl)glutamate) (1) and 0.5 eq.mol triethylamine, stirred at room temperature for 5 h, followed by catalytic hydrogenation to remove the Cbz group. To synthesize the NHS ester (4), compound 3 was dissolved in dry THF followed by the addition of TBTU and NHS. To get compound 6, trimerized ligands (5) were taken in dry DMSO and added to the mPEG-NHS ester (4) followed by deprotection of the Boc-group. Finally, [$^{99}$mTc-MAS$_3$]-NHS was added to compound 6 in DMSO and reacted for 1 hr to yield compound 7.

Scheme 11a

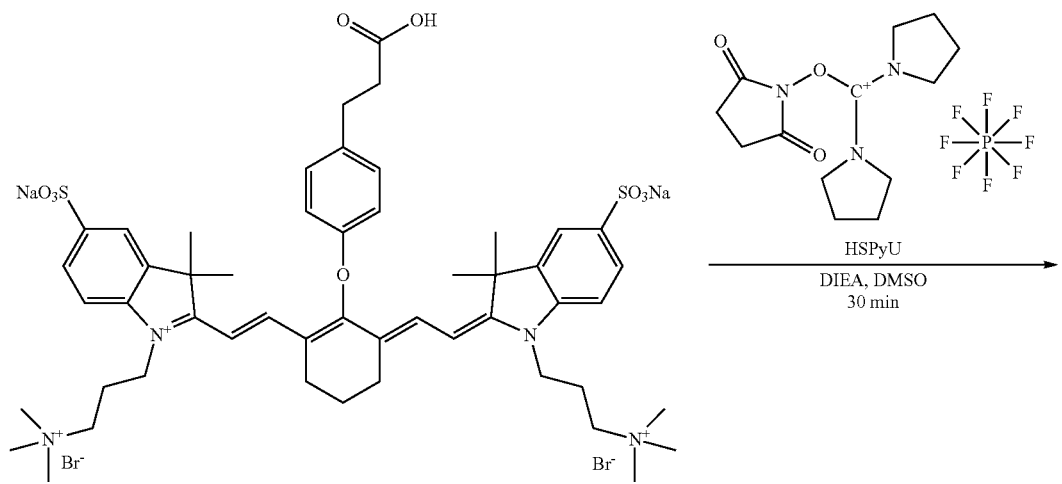

ZW800-1

-continued
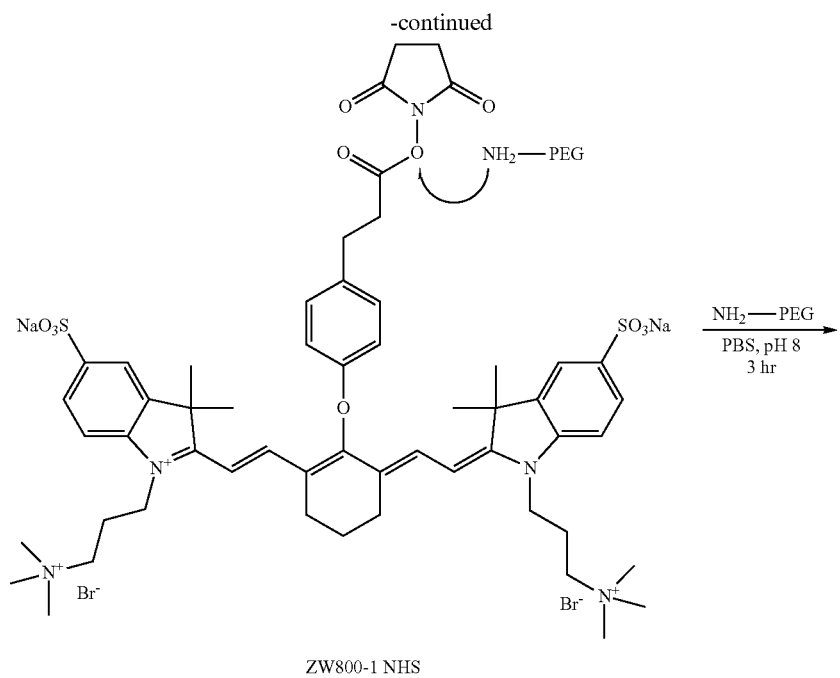
ZW800-1 NHS
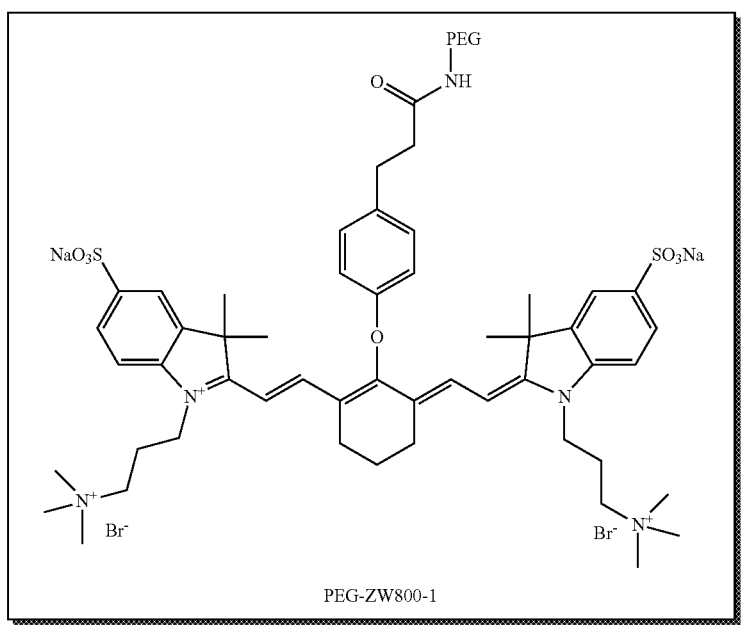
PEG-ZW800-1
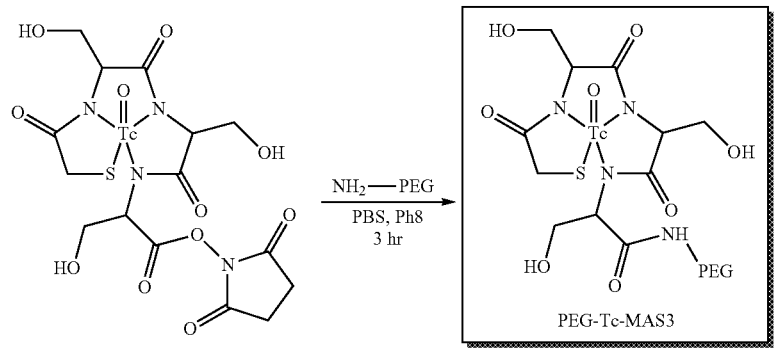
99mTc-MAS3 NHS ester → PEG-Tc-MAS3

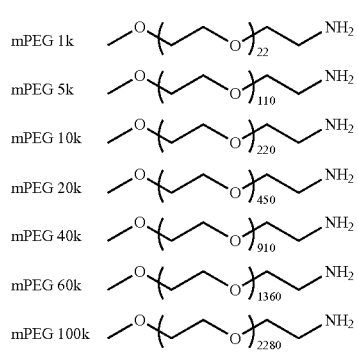

ZW800-1 and 99mTc-MAS3 NHS ester can both be modified with various length units of polyethylene glycol modifications through the NHS-ester linkage. The free primary amine on the polyethylene glycol group can easily react with the NHS-ester of the ZW800-1 NHS in PBS at pH 8.0 for 3 h and form the corresponding amide. ZW800-1 must be modified to form the NHS-ester using our effective coupling method of HSPyU in a mixture of DIPEA and DMSO in 30 minutes. Further modifications with the $NH_2$-PEG are performed in PBS, pH 8.0 for approximately 3 hours.

Scheme 12

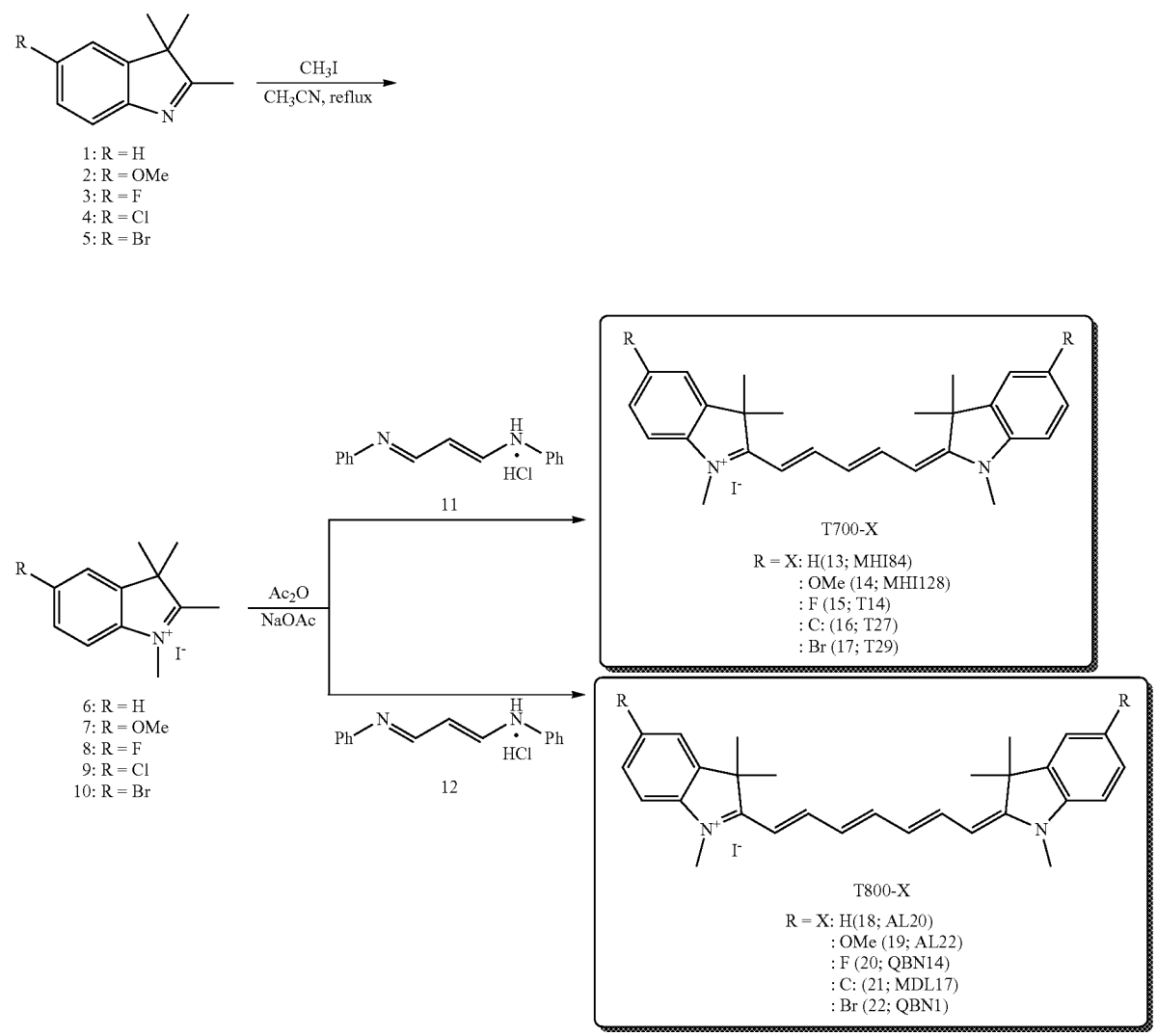

Scheme 12

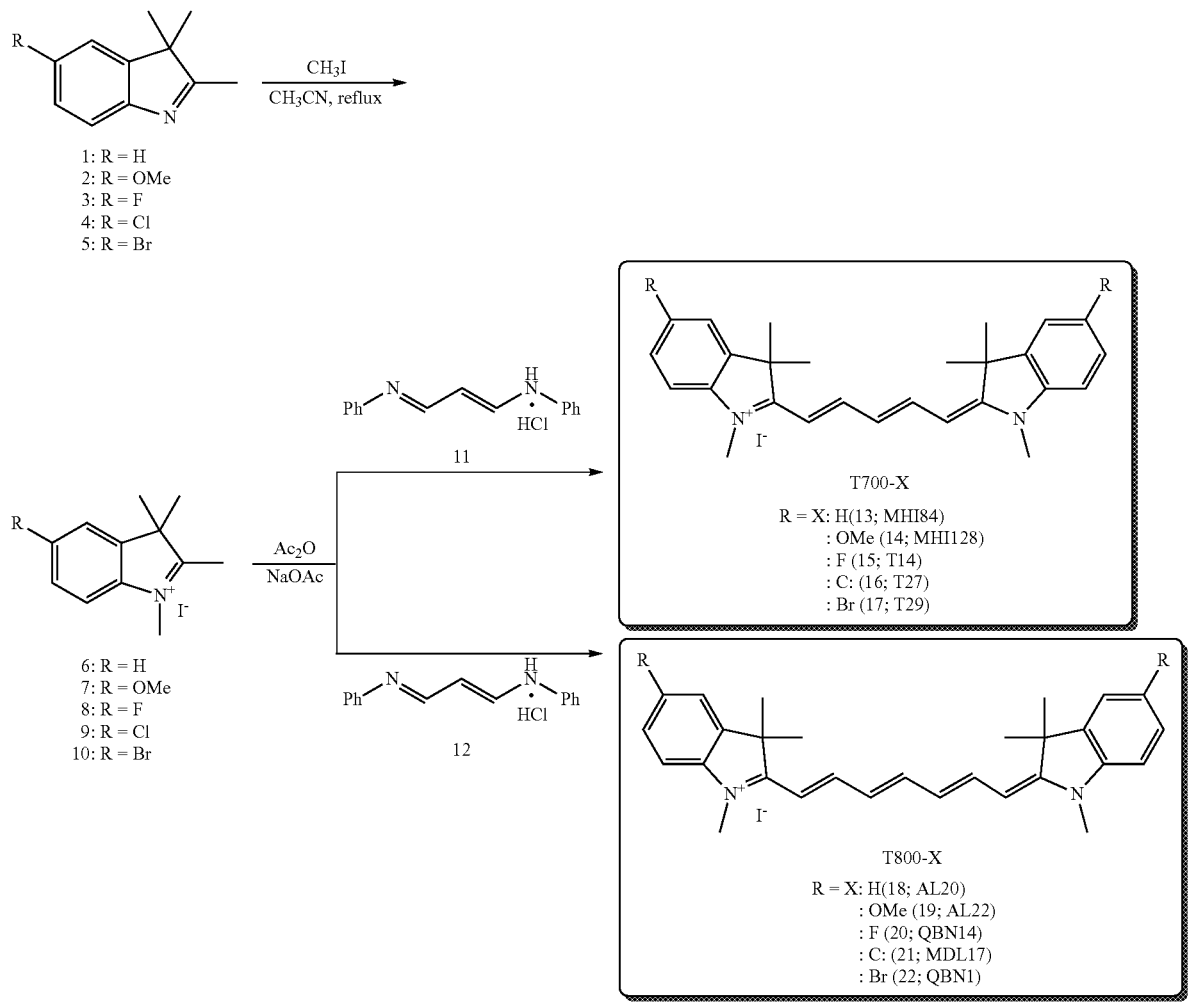

Pentamethine and heptamethine fluorophores bearing heterocyclic modifications (R=H, OMe, F, Cl, Br) are presented in Scheme 12. They have shown excellent promise in delineating the thyroid and parathyroid at 700 nm and 800 nm. They were prepared according to Scheme 12 using our developed methods as previously discussed in Schemes 1 and 2.

All products of Schemes 1-12 have been synthesized and were obtained in high purity (>97%) as indicated by HPLC and TLC analyses using silica gel or C-18 adsorbents. Their high-resolution $^1$HNMR and $^{13}$CNMR spectra are consistent with the indicated structures and confirmed high purity of the samples. Electron-spray mass spectroscopy (ES-MS) was also used to characterize the products and gave the expected peak M+1 as the only peak in the high molecular mass range in each case.

Each of the compounds of the invention can be synthesized using the methods outlined in Schemes 1-12 above upon modification of starting materials and other reagents as will be readily understood by one of ordinary skill in the art.

Compositions

In another aspect, the invention provides pharmaceutical compositions of a compound of the invention.

For the therapeutic uses of compounds provided herein, including compounds of the invention, or pharmaceutically acceptable salts, solvates, N-oxides, prodrugs, or isomers thereof, such compounds are administered in therapeutically effective amounts either alone or as part of a pharmaceutical composition. Accordingly, provided herein are pharmaceutical compositions, which comprise at least one compound provided herein, including at least one compound of the invention, pharmaceutically acceptable salts and/or solvates thereof, and one or more pharmaceutically acceptable carriers, diluents, adjuvant or excipients. The methods of administration of such compounds and compositions include, but are not limited to, intravenous administration, inhalation, oral administration, rectal administration, parenteral, intravitreal administration, subcutaneous administration, intramuscular administration, intranasal administration, dermal administration, topical administration, ophthalmic administration, buccal administration, tracheal administration, bronchial administration, sublingual administration or optic administration. Compounds provided herein are administered by way of known pharmaceutical formulations, including tablets, capsules or elixirs for oral administration, suppositories for rectal administration, sterile solutions or suspensions for parenteral or intramuscular administration, lotions, gels, ointments or creams for topical administration, and the like.

The amount administered will vary depending on, among others, the tissue or organ to be imaged, the age and relative health of the subject, the potency of the compound administered, the mode of administration and the like.

Pharmaceutically acceptable salt forms include pharmaceutically acceptable acidic/anionic or basic/cationic salts. Pharmaceutically acceptable acidic/anionic salts include acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphosphate, polygalacturonate, salicylate, stearate, subacetate, succinate, sulfate, hydrogensulfate, tannate, tartrate, teoclate, tosylate, and triethiodide salts. Pharmaceutically acceptable basic/cationic salts include, the sodium, potassium, calcium, magnesium, diethanolamine, N-methyl-D-glucamine, L-lysine, L-arginine, ammonium, ethanolamine, piperazine and triethanolamine salts.

A pharmaceutically acceptable acid salt is formed by reaction of the free base form of a compound of Formula I-V with a suitable inorganic or organic acid including, but not limited to, hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid. A pharmaceutically acceptable acid addition salt of a compound of Formula I-V can comprise or be, for example, a hydrobromide, hydrochloride, sulfate, nitrate, phosphate, succinate, maleate, formarate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g., 2-naphthalenesulfonate) or hexanoate salt.

The free acid or free base forms of the compounds of the invention may be prepared from the corresponding base addition salt or acid addition salt form, respectively. For example a compound of the invention in an acid addition salt form may be converted to the corresponding free base form by treating with a suitable base (e.g., ammonium hydroxide solution, sodium hydroxide, and the like). A compound of the invention in a base addition salt form may be converted to the corresponding free acid by treating with a suitable acid (e.g., hydrochloric acid, etc.).

Prodrug derivatives of the compounds of the invention may be prepared by methods known to those of ordinary skill in the art (e.g., for further details see Saulnier et al., Bioorg. Med. Chem. Letters, 1994, 4, 1985; the entire teachings of which are incorporated herein by reference).

Protected derivatives of the compounds of the invention may be prepared by means known to those of ordinary skill in the art. A detailed description of techniques applicable to the creation of protecting groups and their removal can be found in T. W. Greene, "Protecting Groups in Organic Chemistry," 3rd edition, John Wiley and Sons, Inc., 1999, the entire teachings of which are incorporated herein by reference.

Compounds of the invention may be prepared as their individual stereoisomers by reaction of a racemic mixture of the compound with an optically active resolving agent to form a pair of diastereoisomeric compounds, separating the diastereomers and recovering the optically pure enantiomers. Resolution of enantiomers may be carried out using covalent diastereomeric derivatives of the compounds of the invention, or by using dissociable complexes (e.g., crystalline diastereomeric salts). Diastereomers have distinct physical properties (e.g., melting points, boiling points, solubility, reactivity, etc.) and may be readily separated by taking advantage of these dissimilarities. The diastereomers may be separated by chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet and Samuel H. Wilen, "Enantiomers, Racemates and Resolutions," John Wiley And Sons, Inc., 1981, the entire teachings of which are incorporated herein by reference.

Suitable pharmaceutically acceptable carriers, diluents, adjuvants, or excipients for use in the pharmaceutical compositions of the invention include tablets (coated tablets) made of for example collidone or shellac, gum Arabic, talc, titanium dioxide or sugar, capsules (gelatin), solutions (aqueous or aqueous-ethanolic solution), syrups containing the active substances, emulsions or inhalable powders (of various saccharides such as lactose or glucose, salts and mixture of these excipients with one another) and aerosols (propellant-containing or -free inhale solutions).

Excipients which may be used include, for example, water, pharmaceutically acceptable organic solvents such as paraffins (e.g., petroleum fractions), vegetable oils (e.g. groundnut or sesame oil), mono- or polyfunctional alcohols (e.g., ethanol or glycerol), carriers such as natural mineral powders (e.g., kaoline, clays, talc, chalk), synthetic mineral powders (e.g., highly dispersed silicic acid and silicates), sugars (e.g., cane sugar, lactose and glucose), emulsifiers (e.g., lignin, spent sulphite liquors, methylcellulose, starch and polyvinylpyrrolidone) and lubricants (e.g., magnesium stearate, talc, stearic acid and sodium lauryl sulphate).

Exemplary methods for preparing the compounds of the invention are described herein, including in the Examples.

Methods

The present invention features various methods using the near-infrared fluorescent biological contrast agents described herein.

In one aspect, the invention provides a method of imaging biological tissue or cells, the method comprising:

(a) contacting the biological tissue cells with a compound of the invention;

(b) irradiating the cells at a wavelength absorbed by the compound;

(c) and detecting a signal from the compound, thereby imaging the biological cells.

The signal may be in the form of absorption, such as occurs during photoacoustic imaging. Alternatively, the imaging agents can have a SBR suitable to permit fluorescence detection. SBR is a measure of the intensity of the fluorescent signal obtained from a target (peak signal) over the measure of the intensity of the fluorescent signal obtained nearby the target (background signal), the target being the tissues, cells, space targeted by the imaging agent. SBR measurements can be readily obtained through routine measurement procedures. For fluorescent imaging systems, and other optical-type systems, digital images recording optical signals of the target facilitate SBR measurement. Higher SBR values are more desirable, resulting in greater resolution of the imaged tissues. In some embodiments, the imaging agents achieve an SBR of at least about 1.1 (i.e., peak signal is at least 10% over background). In further embodiments, the imaging agents achieve an SBR of at least about 1.2, at least about 1.3, at least about 1.4, at least about 1.5, at least about 1.6, at least about 1.7, at least about 1.8, at least about 1.9, or at least about 2.0. In yet further embodiments, the imaging agents achieve an SBR of about 1.1 to about 50, about 1.5 to about 30, about 2.0 to about 20, about 2.0 to about 5.0, or about 5.0 to about 10.

Some of the imaging agents include one or more ionic groups. In some embodiments, the imaging agents include two or more, three or more, four or more, or five or more ionic groups. Ionic groups serve to increase solubility of the generally hydrophobic dye portions of the imaging agent, thus improving biodistribution. They may also contribute to specific targeting. The ionic groups can be located on any portion of the imaging agent.

In certain instances, the imaging agents are hydrophobic agents. In such instances, the hydrophobic agents are capable of conjugating to a hydrophobic compound for imaging, without altering the binding, biodistribution, cell permeation, and/or clearance of the hydrophobic compound. Examples of hydrophobic agents include, but are not limited to L700-1A, L700-1C, L800-1A, and L800-1C.

In certain embodiments, the imaging agents are administered directly to a subject or biological system for the imaging of the targeted cells.

In other embodiments, reactive derivates of the imaging agents of the invention are used to label chemical and biological molecules for further study. Certain molecules which may be labeled using reactive derivatives of the imaging agents of the invention include small molecules (including pharmaceutical, neutraceutical, therapeutic and diagnostic compounds, proteins, peptides, peptidomimetics, antibodies, vaccines, and other chemical and biological molecules which may be of interest in studying by NIR imaging. In such embodiments, the imaging agent of the invention is reacted with the chemical or biological molecule to produce a labeled agent molecule which may then be administered to a subject or biological system for imaging as described herein.

The steps of irradiating the tissue or cells at a wavelength absorbed by the imaging agent, and detecting an optical signal from the irradiated tissue or cells, thereby imaging the tissue or cells, can be performed using an imaging system such as the FLARE™ Image-Guided Surgery System, which is a continuous-wave (CW) intraoperative imaging system that is capable of simultaneous, real-time acquisition and display of color video (i.e., surgical anatomy) and two channels of invisible NIR fluorescent (700 nm and 800 nm) light (see, e.g., Gioux et al., *Mol. Imaging*. 9(5): 237-255 (2010) and U.S. Pat. No. 8,473,035 to Frangioni, for a description of suitable systems). With FLARE™ and other NIR fluorescence imaging systems, contrast agent emission wavelength in the 800-850 nm range (Channel 2 of FLARE™) is preferred whenever possible because of lower autofluorescence and lower attenuation from both absorbance and scatter when compared to emission near 700 nm. Nevertheless, fluorophores emitting within Channel 1 (≈700 nm) of the FLARE™ imaging system still retain the benefits of NIR fluorescence imaging, including detection of nerves and other targets below the surface of blood and tissue.

In some embodiments, the imaging agents can be formulated into pharmaceutically acceptable formulations and administered intravenously to an organism for imaging. The dosed organism can be imaged using, for example, the FLARE™ system. The imaging system can irradiate the dosed organism with radiation absorbed by the imaging agent, and detect optical signals, such as NIR fluorescence, emanating from the targeted portions of the organism containing the imaging agent. The detected signals can be recorded and analyzed by obtaining digital images or video of the subject organism, thereby facilitating diagnostic procedures and image-guided medical techniques.

The invention also provides methods of performing image-guided surgery, the methods comprising imaging cells, tissues, or organs according to a method described herein, and then performing surgery such that the targets are either removed or are preserved, depending on the goals of the surgical intervention. In certain preferred embodiments, the contrast agent is injected intravenously to ensure that all targets are labeled, and imaging is performed after sufficient time has passed for biodistribution to nerves and clearance of surrounding background signal.

In certain embodiments, the targets are biological tissues or organs. In specific embodiments, the targets are lumens, such as the ureters, cartilage, bone cells, bone minerals, thyroid gland, parathyroid gland, adrenal gland, salivary gland, white adipose tissue, brown adipose tissue, ovaries, testes, seminal vesicles, prostate, pancreas, spleen, gallbladder, bile ducts, Peyer's patches, brain grey matter, brain white matter, brain vasculature, choroid plexus, cerebrospinal fluid, nerves, thoracic duct, pan lymph nodes, sentinel lymph nodes, vulnerable plaque, stem cells, or neuroendocrine tumor cells.

It should also be noted that although the examples given below are for in vivo imaging, which represents the most difficult situation because properties such as biodistribution and clearance are dictated in large part by the organism, those skilled in the art will recognize that these same contrast agents can be used for any type of in vitro assay, such as immunohistology, detection of targets in blood or bodily fluid samples, etc. using the same principles of contact with the medium, washout of unbound dose, and detection of a signal derived from absorption, fluorescence emission and/or radioactive emission.

NIR Angiography Agents

A NIR fluorophore injected into the bloodstream can act as an angiographic agent because during the first 8 seconds after intravenous injection there is a rapid arterial flush (≈1 second), a rapid capillary flush (2-3 seconds), a rapid venous flush (≈1-2 seconds), then minutes of clearance from the tissue. The first 8 seconds thus provides a "map" of the circulation in the tissue. NIR angiography is important for imaging the perfusion of skin during plastic and reconstructive surgery and the anastomoses of bowel during gastrointestinal surgery. In general, NIR angiography agents are those that are cleared rapidly from the blood into either urine or bile.

As such, in one aspect, the invention provides a method for imaging tissue perfusion, the method comprising:

(a) contacting the blood with a compound of the invention;

(b) irradiating the blood vessels and surrounding tissue at a wavelength absorbed by the compound;

(c) and detecting a signal from the compound, thereby imaging the distribution and clearance of fluorophore in the tissue over time.

In a particular embodiment, the compound of the invention for angiography is LN15, A104, or TG42; and the irradiating wavelength is in the 660-700 nm range.

In another particular embodiment, the compounds of the invention for use in angiography is A71 or WuA71; and the irradiating wavelength is in the 760-800 nm range.

Ureter Mapping Agents:

Ureter mapping agents are those molecules that are rapidly cleared from the bloodstream by the kidney into urine. As the molecules traverse the ureters towards the bladder, the ureters become highly fluorescent and thus visible. This is useful during Caesarian section, where the ureters are sometimes damaged, as well as many abdominal cancer surgeries where finding the ureters and avoiding them can be difficult.

As such, in one aspect, the invention provides a method for imaging the ureters, the method comprising:

(a) contacting the blood with a compound of the invention;

(b) irradiating the ureters at a wavelength absorbed by the compound;

(c) and detecting a signal from the compound, thereby imaging the ureters.

In a particular embodiment, the compound of the invention for use in ureter imaging is LN15, A104, or TG42; and the irradiating wavelength is in the 660-700 nm range.

In another particular embodiment, the compounds of the invention for use in ureter imaging is A71 or WuA71; and the irradiating wavelength is in the 760-800 nm range.

Cartilage Agents:

Cartilage agents are useful in arthroscopic surgery, general surgery, and non-invasive assessment of neo-cartilage growth during tissue engineering.

As such, in one aspect, the invention provides a method for imaging cartilage cells and/or their products, the method comprising:

(a) contacting the cartilage cells and/or their products with a compound of the invention;

(b) irradiating the tissue at a wavelength absorbed by the compound;

(c) and detecting a signal from the compound, thereby imaging cartilage cells and/or their products.

In a particular embodiment, the compound of the invention for use in cartilage imaging is SP56, E58, YY180, E59, E60, A196, E71, E72 or ZK15; and the irradiating wavelength is in the 660-700 nm range.

In another particular embodiment, the compound of the invention for use in cartilage imaging is LN50, AM, AL30, MM25, MM21, AL31, AL33, SP79, SP99, SP116, SP117, LN65, LN68, LN63, ZK48, CNN3, or CNN4; and the irradiating wavelength is in the 760-800 nm range.

Bone Agents:

Bone agents are useful in the detection of bone metastases, bone growth and tissue microcalcification.

As such, in one aspect, the invention provides a method for imaging bone, the method comprising:

(a) contacting bone cells and/or their products with a compound of the invention;

(b) irradiating the tissue at a wavelength absorbed by the compound;

(c) and detecting a signal from the compound, thereby imaging the bone cells and/or their products.

In a particular embodiment, the compound of the invention for use in bone imaging is P700SO3, P700H, CMI24, E24, E37, E38, E44, or WuA110; and the irradiating wavelength is in the 660-700 nm range.

In another particular embodiment, the compound of the invention for use in bone imaging is P800SO3, P800H, ZK197, or WuA71; and the irradiating wavelength is in the 760-800 nm range.

Thyroid Agents:

In one aspect, the invention provides a method for imaging the thyroid gland, the method comprising:

(a) contacting the thyroid cells and/or their products with a compound of the invention;

(b) irradiating the tissue at a wavelength absorbed by the compound;

(c) and detecting a signal from the compound, thereby imaging the thyroid cells and/or their products.

In a particular embodiment, the compound of the invention for use in thyroid imaging is T14, T27, T29, MHI84, T18, T20, T23, T24, T25, L04, E27, E45, MHI106, MHI128, TP1, NRB3, SP28, SP29, SP30, SP33, SP34, SP51, SP59, SP60, SP72, PTN11, PTN12, ZK26, ZK143, ZK148, or ZK204; and the irradiating wavelength is in the 660-700 nm range.

In another particular embodiment, the compound of the invention for use in thyroid imaging is QBN14, QBN1, AL20, ZK172, ZK185, ZK190, ZK208, MDL17, CNN145, ZK154, or ZK159; and the irradiating wavelength is in the 760-800 nm range.

Parathyroid Agents:

In one aspect, the invention provides a method for imaging the parathyroid gland, the method comprising:

(a) contacting the parathyroid cells and/or their products with a compound of the invention;

(b) irradiating the tissue at a wavelength absorbed by the compound;

(c) and detecting a signal from the compound, thereby imaging the parathyroid cells and/or their products.

In a particular embodiment, the compound of the invention for use in parathyroid imaging is T14, T27, T29, or MHI84; and the irradiating wavelength is in the 660-700 nm range.

In another particular embodiment, the compound of the invention for use in parathyroid imaging is QBN14, MDL17, QBN1, or AL20; and the irradiating wavelength is in the 760-800 nm range.

Adrenal Gland Agents:

Adrenal gland agents are useful to highlight the adrenal gland after an intravenous injection.

As such, in one aspect, the invention provides a method for imaging adrenal medulla and/or adrenal cortex, the method comprising:

(a) contacting the adrenal tissue with a compound of the invention;

(b) irradiating the tissue at a wavelength absorbed by the compound;

(c) and detecting a signal from the compound, thereby imaging the adrenal medulla and/or adrenal cortex.

In a particular embodiment, the compound of the invention for use in adrenal gland imaging is E16, MHI96, MHI97, EAO40, MHI186, LS1, LO3, L04, E24, E27, E36, E37, E43, E45, E50, E51, E77, E79, E80, ZK50, ZK59, ZK106, SP29, SP30, SP33, SP51, SP53, SP60, SP64, YY161, YY163, or YY165; and the irradiating wavelength is in the 60-700 nm range.

In another particular embodiment, the compound of the invention for use in adrenal gland imaging is AL27, AL25, AL29, AL20, ZK190, ZK184, or MDL17; and the irradiating wavelength is in the 760-800 nm range.

Salivary Glands:

Salivary gland agents are useful for targeting salivary gland tumors or for avoiding normal salivary glands during head and neck surgery.

As such, in one aspect, the invention provides a method for imaging salivary glands, the method comprising:

(a) contacting the salivary glands with a compound of the invention;

(b) irradiating the tissue at a wavelength absorbed by the compound;

(c) and detecting a signal from the compound, thereby imaging the salivary glands.

In a particular embodiment, the compound of the invention for use in salivary gland imaging is NRB1, ZK195, ZK135, NRB2, YY163, ZK195, YY161, E79, TP1, SP28, SP29, SP30, SP49, SP72, ZK101, ZK133, ZK134, ZK135, ZK143, ZK150, ZK155, ZK156, ZK159, ZK185, ZK204, T29, or CNN145; and the irradiating wavelength is in the 660-700 nm range.

In another particular embodiment, the compound of the invention for use in salivary gland imaging is ZK211, ZK172, MDL17, ZK198, ZK190, AL22, or AL20; and the irradiating wavelength is in the 760-800 nm range.

White Adipose Tissue:

White adipose tissue agents are useful for highlighting white fat important for certain surgical procedures.

As such, in one aspect, the invention provides a method for imaging white adipose tissue, the method comprising:

(a) contacting the white adipose tissue with a compound of the invention;

(b) irradiating the tissue at a wavelength absorbed by the compound;

(c) and detecting a signal from the compound, thereby imaging the white adipose tissue.

In a particular embodiment, the compound of the invention for use in white adipose imaging is PS31, CMI26, E24, MHI86, ZK240, or ZK244; and the irradiating wavelength is in the 660-700 nm range.

In another particular embodiment, the compound of the invention for use in white adipose imaging is AH34, PS37, or ZK197; and the irradiating wavelength is in the 760-800 n, range.

Brown Adipose Tissue:

Brown adipose tissue agents are useful for highlighting brown fat during surgery and for "imaging" perfusion of the tissue.

As such, in one aspect, the invention provides a method for imaging brown adipose tissue, the method comprising:

(a) contacting the brown adipose tissue with a compound of the invention;

(b) irradiating the tissue at a wavelength absorbed by the compound;

(c) and detecting a signal from the compound, thereby imaging the brown adipose tissue.

In a particular embodiment, the compound of the invention for use in brown adipose tissue imaging is SP60, PS39, SP30, SP29, SP33, SP34, E39, E44, E51, E81, ES17, ZK27, ZK26, SP28, SP27, SP67, PS31, LO1, LO3, YY165, or YY187; and the irradiating wavelength is in the 660-700 nm range.

In another particular embodiment, the compound of the invention for use in brown adipose tissue imaging is QBN1 or PS37; and the irradiating wavelength is in the 760-800 nm range.

Ovaries:

Ovary-specific agents have two major functions. The first is to find and eradicate endometriosis, a painful condition of pre-menopausal women. The second is to find and eradicate ovarian carcinoma.

As such, in one aspect, the invention provides a method for imaging ovaries, the method comprising:

(a) contacting the ovarian cells with a compound of the invention;

(b) irradiating the cells at a wavelength absorbed by the compound;

(c) and detecting a signal from the compound, thereby imaging the ovarian cells.

In a particular embodiment, the compound of the invention for use in ovarian imaging is PS62 or E43; and the irradiating wavelength is in the 660-700 nm range.

In another particular embodiment, the compound of the invention for use in ovarian imaging is AL27 or CNN5; and the irradiating wavelength is in the 760-800 nm range.

Testes:

Testes-specific agents are useful for the highlighting of testicular tumor cells. In certain embodiments, these agents can be used to aid aggressive metastasectomy treatments in advanced Stage IV patients prior to cytotoxic therapy.

As such, in one aspect, the invention provides a method for imaging testicular cells, the method comprising:

(a) contacting the testicular cells with a compound of the invention;

(b) irradiating the cells at a wavelength absorbed by the compound;

(c) and detecting a signal from the compound, thereby imaging the testicular cells.

Seminal Vesicles:

Seminal vesicle agents are useful in assisting a urologist during robotic or open prostatectomy to ensure removal of all seminal vesicles.

As such, in one aspect, the invention provides a method for imaging seminal vesicle cells, the method comprising:

(a) contacting the seminal vesicles with a compound of the invention;

(b) irradiating the cells at a wavelength absorbed by the compound;

(c) and detecting a signal from the compound, thereby imaging the seminal vesicles.

In a particular embodiment, the compound of the invention for use in seminal vesicle imaging is LN65, YY269, or Ox4; and the irradiating wavelength is in the 660-700 nm range.

In another particular embodiment, the-compound of the invention for use in seminal vesicle imaging is CNN2, CNN4, ZK48, LN50, TG66, LN66, AL31, or AL30; and the irradiating wavelength is in the 760-800 nm range.

Prostate:

Prostate gland and/or prostate cancer agents are useful during robotic or open prostatectomy.

As such, in one aspect, the invention provides a method for imaging prostate cells, the method comprising:

(a) contacting the prostate cells with a compound of the invention;

(b) irradiating the cells at a wavelength absorbed by the compound;

(c) and detecting a signal from the compound, thereby imaging the prostate cells.

In a particular embodiment, the compound of the invention for use in prostate imaging is PS62; and the irradiating wavelength is in the 660-700 nm range.

In another particular embodiment, the compounds of the invention for use in prostate imaging is LN66, TG66, CNN4, or CNN10; and the irradiating wavelength is in the 760-800 nm range In certain instances the compounds of the invention can be conjugated to a prostate-specific membrane antigen (PSMA) targeting ligand.

Pancreas:

Prior to the invention, it was very difficult and unusual to find contrast agents that target cells of the exocrine pancreas.

Nevertheless, in one aspect, the invention provides a method for imaging pancreas, the method comprising:

(a) contacting the pancreas cells with a compound of the invention;

(b) irradiating the cells at a wavelength absorbed by the compound;

(c) and detecting a signal from the compound, thereby imaging the pancreas.

In a particular embodiment, the compound of the invention for use in pancreas imaging is T14, PS62, SRA94, SRA89, SP28, SP29, ESS61, or T27; and the irradiating wavelength is in the 660-700 nm range.

In another particular embodiment, the compound of the invention for use in pancreas imaging is AL22, CNN145, Rh800, Ox750, WuA96, or Ox170; and the irradiating wavelength is in the 760-800 nm range.

Spleen:

In one aspect, the invention provides a method for imaging the spleen and accessory splenic tissue, the method comprising:

(a) contacting the spleen or accessory splenic tissue with a compound of the invention;

(b) irradiating the tissue at a wavelength absorbed by the compound;

(c) and detecting a signal from the compound, thereby imaging the spleen or accessory splenic tissue.

In a particular embodiment, the compound of the invention for use in spleen imaging is E24, E44, E37, E38, E39, E43, E50, E51, E78, LO1, PTN1, AL79, SP27, TG5, TP5, EAO42, PS31, SP34, TG115, MHI86, MHI96, or MHI97; and the irradiating wavelength is in the 660-700 nm range.

In another particular embodiment, the compound of the invention for use in spleen imaging is AL29, LS1, AH34, JM1, ZK166, ZK189, ZK197, ZK198, AL27, AL25, MDL16, ZK215, or ZK184; and the irradiating wavelength is in the 760-800 nm range.

Gallbladder:

Many agents that area cleared from blood by liver are excreted into bile and are then concentrated by the gallbladder. Gallbladder contrast agents help localize the gallbladder during laparoscopic surgery and also help highlight the cystic duct.

As such, in one aspect, the invention provides a method for imaging gallbladder, the method comprising:

(a) contacting the gallbladder with a compound of the invention;

(b) irradiating the tissue at a wavelength absorbed by the compound;

(c) and detecting a signal from the compound, thereby imaging the gallbladder.

In a particular embodiment, the compound of the invention for use in gallbladder imaging is PS62, SRA94, SRA89, AC2, ESS61, A106, YY261, SP67, P700H, CNN13, ZK140, or ZK14; and the irradiating wavelength is in the 660-760 nm range.

In another particular embodiment, the compound-of the invention for use in gallbladder imaging is ZK198, ZK208, ZK166, WuA71, or P800H; and the irradiating wavelength is in the 760-800 nm range.

Bile Ducts:

Similarly, in one aspect, the invention provides a method for imaging the bile ducts, the method comprising:

(a) contacting the bile ducts with a compound of the invention;

(b) irradiating the tissue at a wavelength absorbed by the compound;

(c) and detecting a signal from the compound, thereby imaging the bile ducts.

In a particular embodiment, the compound of the invention for use in bile duct imaging is A106, CNN13, ZK140, SRA89, WuA96, Ox170, Ox750, Ox4, ESS61, ZK14, CNN16, CNN145, MHI84, P700H, CNN12, or CNN14; and the irradiating wavelength is in the 660-700 nm range.

In another particular embodiment, the compound of the invention for use in bile duct imaging is ZK198, ZK166, ZK208, P800H, MDL16, or WuA71; and the irradiating wavelength is in the 760-800 nm range.

Peyer's Patches:

Peyer's patches are small collections of lymphatic tissue that protect the mucosal membranes of the GI tract. Prior to the invention, they were extremely difficult to image in living organisms.

As such, in one aspect, the invention provides a method for imaging Peyer's patches the method comprising:

(a) contacting Peyer's patches with a compound of the invention;

(b) irradiating the tissue at a wavelength absorbed by the compound;

(c) and detecting a signal from the compound, thereby imaging Peyer's patches.

In another particular embodiment, the compound of the invention for use in imaging Peyer's patches is AL30; and the irradiating wavelength is in the 760-800 nm range.

Brain Grey Matter Agents:

Brain Grey Matter agents typically have the following features: 1) MW<500 Da, 2) Log D at pH 7.4 between 0.5 and 3, and 3) retained by cell bodies of the brain (grey matter). The low MW and lipophilic (but not too lipophilic) Log D permit crossing of the blood brain barrier. These molecules are important for various types of brain surgery, especially resection of tumors, where highlighting of normal brain is so important.

As such, in one aspect, the invention provides a method for imaging brain grey matter cells, the method comprising:

(a) contacting the brain grey matter with a compound of the invention;

(b) irradiating the tissue at a wavelength absorbed by the compound;

(c) and detecting a signal from the compound, thereby imaging the brain grey matter.

In a particular embodiment, the compound of the invention for use in brain grey matter imaging is WuA96, or ZK104; and the irradiating wavelength is in the 660-700 nm range.

In another particular embodiment, the compound of the invention for use in brain grey matter imaging is ZK189; and the irradiating wavelength is in the 760-800 nm range.

Brain White Matter Agents:

In another aspect, the invention provides a method for imaging brain white matter, comprised of nerve axons and associated glia, the method comprising:

(a) contacting the brain white matter with a compound of the invention;

(b) irradiating the tissue at a wavelength absorbed by the compound;

(c) and detecting a signal from the compound, thereby imaging the brain white matter.

Brain Vasculature Agents:

Brain Vasculature Agents bind to either the arterial tree or vascular tree of the brain.

As such, in one aspect, the invention provides a method for imaging brain vasculature, the method comprising:

(a) contacting the brain vasculature with a compound of the invention;

(b) irradiating the tissue at a wavelength absorbed by the compound;

(c) and detecting a signal from the compound, thereby imaging the brain vasculature.

In a particular embodiment, the compound of the invention for use in brain vasculature imaging is ZK214, or ZK104; and the irradiating wavelength is in the 660-700 nm range.

Choroid Plexus:

The choroid plexus is the tissue that filters blood to produce cerebrospinal fluid (CSF). Several agents enter the choroid plexus but get trapped in this tissue while attempting to traverse the blood brain barrier.

As such, in one aspect, the invention provides a method for imaging choroid plexus, the method comprising:

(a) contacting the choroid plexus with a compound of the invention;

(b) irradiating the tissue at a wavelength absorbed by the compound;

(c) and detecting a signal from the compound, thereby imaging the choroid plexus.

In a particular embodiment, the compound of the invention for use in choroid plexus imaging is SP28, ZK135, SP66, ZK195, SP29, SP30, SP33, SP49, SP51, ZK78, ZK134, ZK135, ZK143, ZK140, ZK26, ZK78, ZK79, ZK133, ZK23, ZK101, SP66, SP72, MHI84, T14, T18, T20, or T23; and the irradiating wavelength is in the 660-700 nm range.

In another particular embodiment, the compound of the invention for use in choroid plexus imaging is ZK208, ZK185, AL22, ZK172, MDL16, ZK211, ZK153, ZK155, or ZK169; and the irradiating wavelength is in the 760-800 nm range.

Cerebrospinal Fluid:

Certain molecules of the invention can completely traverse the choroid plexus and enter the CSF. They are particularly useful for finding CSF before accidentally puncturing the meninges, or for finding and repairing tears in the meninges.

As such, in one aspect, the invention provides a method for imaging cerebrospinal fluid, the method comprising:

(a) contacting the cerebrospinal fluid with a compound of the invention;

(b) irradiating the tissue at a wavelength absorbed by the compound;

(c) and detecting a signal from the compound, thereby imaging the cerebrospinal fluid.

In a particular embodiment, the compound of the invention for use in cerebrospinal fluid imaging is SP66, SP43, SP72, SP28, MHI84, YY161, or YY163; and the irradiating wavelength is in the 660-700 nm range.

In another particular embodiment, the compound of the invention for use in cerebrospinal fluid imaging is AL20, ZK189, or ZK208; and the irradiating wavelength is in the 760-800 nm range.

Pituitary Gland:

Several molecules of the invention appear to highlight either the anterior pituitary, posterior pituitary, or both after a single intravenous injection.

As such, in one aspect, the invention provides a method for imaging the pituitary gland, the method comprising:

(a) contacting the pituitary gland with a compound of the invention;

(b) irradiating the tissue at a wavelength absorbed by the compound;

(c) and detecting a signal from the compound, thereby imaging the pituitary gland.

In a particular embodiment, the compound of the invention for use in pituitary imaging is SP60, SP64, SP28, SP29, SP30, SP33, SP34, SP43, SP51, SP53, ZK159, MHI84, YY187, SP59, SP67, ZK23, ZK204, ZK106, AL11, SP66, E79, E80, ES21, or LO3; and the irradiating wavelength is in the 660-700 nm range.

In another particular embodiment, the compounds of the invention for use in pituitary imaging is AL22, ZK185, ZK208, ZK172, ZK190, QBN1, QBN14, ZK153, ZK156, AL25, AL29, AL20, MDL17, or MDL16; and the irradiating wavelength is in the 760-800 nm range.

Thoracic Duct Agents:

Agents injected into the lower lymphatics will eventually concentrate in the thoracic duct as lymph traverse from below the diaphragm to above the diaphragm, and prior to efflux into the left brachiocephalic vein. These agents are particularly valuable during several types of thoracic surgery because the thoracic duct is otherwise extremely difficult to find, and if lacerated, difficult to repair because lymph is clear.

As such, in one aspect, the invention provides a method for imaging the thoracic duct, the method comprising:

(a) contacting the thoracic duct with a compound of the invention;

(b) irradiating the tissue at a wavelength absorbed by the compound;

(c) and detecting a signal from the compound, thereby imaging the thoracic duct.

In a particular embodiment, the compound of the invention for use in thoracic duct imaging is LN15, A104, or TG42; and the irradiating wavelength is in the 660-700 nm range. in thoracic duct imaging is A71, ZW800-1, or WuA71; and the irradiating wavelength is in the 760-800 nm range.

Pan-Lymph Node Agents:

Sentinel lymph node mapping has revolutionized the treatment of breast cancer and melanoma. However, 20-25% of patients are found to have tumor cells in their sentinel lymph node and therefore require a completion lymphadenectomy, i.e., removal of all the lymph nodes in the basin. Finding all lymph nodes in an area of the body is extremely difficult to do.

Pan-lymph node mapping agents that highlight all lymph nodes after a single intravenous injection are useful during many types of surgery. They can also be used in conjunction with a sentinel lymph node agent to find both sentinel lymph nodes and all lymph nodes in a particular basin.

As such, in one aspect, the invention provides a method for imaging lymph nodes, the method comprising:

(a) contacting the lymph nodes with a compound of the invention;

(b) irradiating the tissue at a wavelength absorbed by the compound;

(c) and detecting a signal from the compound, thereby imaging the lymph nodes.

In a particular embodiment, the compound of the invention for use in lymph node imaging is A150, A146, A149, A148, A160, A161, A20, SP27, SP43, SP117, ZK197, ZK134, ZK46, ZK101, AL11, AL12, EAO42, ZK148, E16, E50, E51, E77, E78, E58, E59, E60, E70, E72, LO1, LO2, PTN11, ZK143, ZK140, ZK29, WuA108, MHI86, MHI96, or MHI97; and the irradiating wavelength is in the 660-700 nm range.

In another particular embodiment, the compounds of the invention for use in lymph node imaging is MM25, A64, AL30, AL33, PTN6, AH34, CNN10, MM21, CNN5, A71, MDL16, ZK172, LN63, ZK154, or ZK155; and the irradiating wavelength is in the 760-800 nm range.

Sentinel Lymph Node Agents:

Sentinal lymph node agents are injected in and around a tumor and quickly flow to the first lymph node that drains the tumor, called the sentinel lymph node (SLN).

As such, in one aspect, the invention provides a method for imaging sentinel lymph nodes, the method comprising:

(a) contacting the sentinel lymph node with a compound of the invention;

(b) irradiating the tissue at a wavelength absorbed by the compound;

(c) and detecting a signal from the compound, thereby imaging the sentinel lymph node.

In a particular embodiment, the compound of the invention for use in sentinel lymph imaging is MHI86, MHI96, MHI97, A150, A146, A149, A148, A160, A161, A20, E37, or E78; and the irradiating wavelength is in the 660-700 nm range.

In another particular embodiment, the compound of the invention for use in sentinel lymph node imaging is MM25, A64, AL30, or AL33; and the irradiating wavelength is in the 760-800 nm range.

Vulnerable Plaque Agents:

By virtue of their lipophilicity, certain compounds of the invention may be taken up by vulnerable plaque and therefore highlight areas of intima that are at a higher risk for rupture.

As such, in one aspect, the invention provides a method for imaging vulnerable plaque cells, the method comprising:

(a) contacting the vulnerable plaque with a compound of the invention;

(b) irradiating the tissue at a wavelength absorbed by the compound;

(c) and detecting a signal from the compound, thereby imaging the vulnerable plaque.

Stem Cell Tracking and Viability Agents:

Longitudinal monitoring of cell migration, division, and differentiation is of paramount importance in stem cell-based medical treatment. Many lipophilic cationic NIR fluorophores with a Log D at pH 7.4 within a narrow range will partition into living cells and thus serve as tracking and/or viability indicators.

As such, in one aspect, the invention provides a method for imaging stem cells, the method comprising:

(a) contacting the stem cells with a compound of the invention;

(b) irradiating the cells at a wavelength absorbed by the compound;

(c) and detecting a signal from the compound, thereby imaging the stem cells.

In a particular embodiment, the compound of the invention for use in stem cell imaging is PS127, PS129, PS131, PS133, CNN12, CNN13, CNN14, CNN16, CNN17, Ox4, Ox170, ZK126, ZK211, ZK214, or EAO40; and the irradiating wavelength is in the 660-700 nm range.

In another particular embodiment, the compound of the invention for use in stem cell imaging is PS126, PS128, PS130, or PS132; and the irradiating wavelength is in the 760-800 nm range.

In certain embodiments, the compounds of the invention for use in stem cell imaging have primary or secondary amines as part of their structure, which permit covalent fixation in place after treatment with paraformaldehyde (Mannich reaction) or other amine-reactive fixatives.

Tissue Engineering Agents:

Biodegradable scaffolds have been extensively used in the field of tissue engineering and regenerative medicine. Tissue Engineering Agents provide noninvasive monitoring of in vivo scaffold degradation or product formation.

As such, in one aspect, the invention provides a method for imaging biodegradable scaffolds, the method comprising:

(a) contacting the biodegradable scaffold with a compound of the invention;

(b) irradiating the scaffold at a wavelength absorbed by the compound;

(c) and detecting a signal from the compound, thereby imaging the biodegradable scaffold.

In a particular embodiment, the compound of the invention for use in imaging biodegradable scaffolds is A71-NHS ester, MHI103, CNN12, CNN13, CNN14, CNN16, CNN17, Ox4, Ox170, ZK126, ZK211, ZK214, EAO40, E59, EAO42, PTN12, E72, E24, E27, E50, E51, E79, E80, E81, ES17, ES21, LO1, LO2, T17, T23, T25, A106, A148, A150, A161, or AC8; and the irradiating wavelength is in the 660-700 nm range.

In another particular embodiment, the compound of the invention for use in imaging biodegradable scaffolds is LN15-NHS ester, LN68, LN50, CNN3, LN65, LN63, or ZK166; and the irradiating wavelength is in the 760-800 nm range.

In certain embodiments, the compounds of the invention are amine-containing or meso-brominated compounds which are conjugated to biodegradable scaffolds.

Neuroendocrine Tumors:

Neuroendocrine tumors are a group of rare tumors that show similar growth patterns and resistance to chemotherapy. They occur throughout the body and, although primary tumors are often curable by surgery, they are difficult to find when they are small. A particularly vexing group of neuroendocrine tumors are the pancreatic endocrine tumors, comprised of gastrinoma, insulinoma, glucagonoma, VIPoma, and somatostatinoma. Fluorophores targeted to pancreatic endocrine tumors provide surgeons with sensitive, specific and real-time image guidance after a single preoperative, intravenous injection.

As such, in one aspect, the invention provides a method for imaging neuroendocrine tumors, the method comprising:

(a) contacting the neuroendocrine tumor with a compound of the invention;

(b) irradiating the tissue at a wavelength absorbed by the compound;

(c) and detecting a signal from the compound, thereby imaging the Neuroendocrine tumor.

In a particular embodiment, the compound of the invention for use in neuroendocrine tumor imaging is ESS61, SRA89, SRA94, CNN145, MHI84, Ox4, Ox170, Ox750, WuA96, CNN16, CNN12, or CNN14; and the irradiating wavelength is in the 660-700 nm range.

In another particular embodiment, the compound of the invention for use in neuroendocrine tumor imaging is AL20, AL22, AL33, or AL30; and the irradiating wavelength is in the 760-800 nm range.

Hydrophobic Molecules Tumors:

Hydrophobic molecules are often administered to a subject for various therapeutic and diagnostic purposes. Hydrophobic Fluorophores can conjugate to such molecules and allow for the imaging and study of the distribution of such molecules.

As such, in one aspect, the invention provides a method for imaging a hydrophobic molecule in a biological system, the method comprising:

(a) conjugating an imaging agent of the invention to a hydrophobic molecule to form a conjugated agent molecule;

(b) contacting a subject biological system with the conjugated agent molecule;

(c) irradiating the conjugated agent molecule at a wavelength absorbed by the imaging agent;

(c) and detecting a signal from the conjugated agent molecule, thereby imaging the hydrophobic molecule.

In a particular embodiment, the compound of the invention for use with hydrophobic molecules is L700-1A and L700-1C; and the irradiating wavelength is in the 660-700 nm range.

In another particular embodiment, the compound of the invention for use with hydrophobic molecules is L800-1A and L800-1C; and the irradiating wavelength is in the 760-800 nm range.

Agents for Intravital Microscopy and PEGylated Agents:

Vascular functions rely on the endothelial cells lining the vasculature to provide a semi-permeable barrier between blood contents and the tissue interstitium. For intravital microscopy, fluorophores should be large to circulate longer in the bloodstream. PEGylation or bulky dextran conjugation may be used to increase the blood half-life of bioactive small molecules and peptides.

Specifically, certain sized, linear polyethylene glycol (PEG) molecules, in the range of 20 kDa to 60 kDa, get retained at sites of abnormal vasculature, like tumors. Because PEG molecules show low non-specific binding to normal tissues and organs, the SBR is high. PEG molecules that are smaller than 20 kDa are filtered by the kidney and do not show uptakes in abnormal tissue/tumors while molecules larger than 60 kDa are not efficiently removed from the body by renal filtration and lead to high background.

As such, in certain embodiments, the compounds of the invention may be modified to include a polyethylene glycol group. Such PEGylated compounds may be branched or linear. In certain embodiments, the linear PEGylated compounds are in the range of about 20 kDa to about 60 kDa.

In a particular embodiment, the compound of the invention is LN15, A104, or TG42; each of which is conjugated with linear or branched PEG of 60 kDa, 40 kDa, 20 kDa, or 100 kDa, or Dextran of 70 kDa, 100 kDa, or 150 kDa.

In another particular embodiment, the compounds of the invention is ZW800-1-, A71-, or WuA71 each of which is conjugated with linear or branched PEG of 60 kDa, 40 kDa, 20 kDa, or 100 kDa, or Dextran of 70 kDa, 100 kDa, or 150 kDa.

Dual-Modality Optical/Nuclear Agents:

In some embodiments, the compounds of the invention can be conjugated to a metal chelator agent for use in single-photon emission computed tomography (SPECT), positron emission tomography (PET), and/or magnetic resonance imaging (MRI). In certain embodiments, the metal chelator agent is a DOTA, DTPA, hydrazinonicotinic acid (HYNIC), or desferoxime, or a derivative thereof. In particular embodiments, the metal atom is selected from the group consisting of Zr-89, Ga-68 and Rb-82, and the signal is detected by positron emission tomography; the metal atom is selected from the group consisting of Tc-99m and In-111, and the signal is detected by single-photon emission computed tomography; or the metal atom is a lanthanide selected from the group consisting of Gd, Dy and Yb, and the signal is detected by magnetic resonance imaging.

In a particular embodiment, the compound of the invention is ZW800-1, A71, or LN15, conjugated to either DOTA, DTPA, or deferoxamine.

The following examples are put forth so as to provide those of ordinary skill in the art with a complete disclosure and description of how to make and use the assay, screening, and therapeutic methods of the invention, and are not intended to limit the scope of what the inventors regard as their invention.

Examples

Optical Property Measurements

Absorbance and fluorescence emission spectra were measured using fiber optic HR2000 absorbance (200-1100 nm) and USB2000FL fluorescence (350-1000 nm) spectrometers (Ocean Optics, Dunedin, Fla.). Excitation was provided by a 532 nm green laser pointer (Opcom Inc., Xiamen, China) set to 5 mW, a 655 nm red laser pointer (Opcom Inc., Xiamen, China) set to 5 mW, or a 770 nm NIR laser diode light source (Electro Optical Components, Santa Rosa, Calif.) set to 10 mW and coupled through a 300 µm core diameter, NA 0.22 fiber (Fiberguide Industries, Stirling, N.J.). In silico calculations of the partition coefficient (log D at pH 7.4) and surface molecular charge and hydrophobicity were calculated using MarvinSketch 5.2.1 by taking major microspecies at pH 7.4 (ChemAxon, Budapest, Hungary).

NIR Fluorescence Imaging System

The dual-NIR channel FLARE' imaging system has been described in detail previously (26-28). It provides simultaneous illumination with white light (400-650 nm) at 40,000 lx, 660 nm NIR Channel 1 excitation at 4 mW/cm$^2$ and 760 bmm NIR Channel 2 excitation at 10 mW/cm$^2$. Color and two independent NIR fluorescence emission images (≈700 nm for Channel 1 and ≈800 nm for Channel 2) were acquired simultaneously with custom software at rates up to 15 Hz over a 15 cm diameter field of view. NIR fluorescence from Channel 1 was pseudo-colored in red and NIR fluorescence from Channel 2 was pseudo-colored in lime green prior to merger with the color video image. The imaging system was positioned at a distance of 18 inches from the surgical field.

Animal Models and Intraoperative NIR Fluorescence Imaging

Animals were housed in an AAALAC-certified facility. Animal studies were performed under the supervision of Beth Israel Deaconess Medical Center's Institutional Animal Care and Use Committee (IACUC) in accordance with approved institutional protocols (#101-2011 for rodents and #046-2010 for pigs).

Initial in vivo screening occurred in mice, rats, and pigs In the animal studies described below, either sex of 25 g CD-1 mice (Charles River Laboratories, Wilmington, Mass.) and either sex of 250 g Sprague-Dawley (SD) rats (Taconic Farms, Germantown, N.Y.) were used after anesthetizing with 100 mg/kg ketamine and 10 mg/kg xylazine intraperitoneally (Webster Veterinary, Fort Devens, Mass.). Either sex of Yorkshire pigs (E. M. Parsons and Sons, Hadley, Mass.) averaging 35 kg were induced with 4.4 mg/kg intramuscular Telazol™ (Fort Dodge Labs, Fort Dodge, Iowa), intubated, and maintained with 2% isoflurane (Baxter Healthcare Corp., Deerfield, Ill.). Following anesthesia, a 16G central venous catheter was inserted into the external jugular vein, and saline was administered as needed. Electrocardiogram, heart rate, pulse oximetry, and body temperature were monitored throughout surgery.

To screen the optimum targeted contrast agent, 2-200 nmol of each NIR fluorophore was injected intravenously in CD-1 mice and sacrificed animals 1-4 h post-injection (n>3). Target tissues/organs were observed at indicated time points such as 0, 5, 10, 15, 30, 60, 120, 180, and 240 min with the FLARE™ imaging system. After intraoperative imaging, animals were sacrificed, and the target tissue and other major organs including heart, lung, liver, spleen, pancreas, kidneys, duodenum, intestine, and muscle were resected to quantify biodistribution and clearance. For rats, an optimized dose (10-1000 nmol) was injected depending on the targeting purpose, and targeting and biodistribution were observed 4 h post-injection (n>3). For the large animal study, the appropriate dose was calculated based on the previous dose dependence study in the small animal study. To confirm the drug kinetics in large animals, 0.5-10 µmol of the NIR fluorescence was injected through the external jugular vein (n>3). Then the target tissue and surrounding organ were imaged at the indicated time points (0, 1, 5, 10, 15, 30, 60, 90, 120, 180, and 240 min).

Results

Ureters: A 35 kg female pig was injected intravenously at time zero with 5 µmol of compound LN15 (700 nm) or A71 (800 nm) dissolved in saline or D5W. After a waiting period of 30 min the animal was surgically exposed and the ureters were imaged for NIR fluorescence using Channel 1 (700 nm) or Channel 2 (800 nm) of the FLARE imaging system, respectively over the next 4 hours. As shown in FIGS. 1 and 2, the ureter is highlighted with high contrast using this compound.

Pan LN: A 250 g male rat was injected intravenously at time zero with 20 nmol of compound A150 (700 nm) or MM25 (800 nm) dissolved in saline or D5W. After a waiting period of 4 hours, the animal was surgically exposed and the pan lymph nodes were imaged for NIR fluorescence using Channel 1 (700 nm) or Channel 2 (800 nm) of the FLARE imaging system, respectively. As shown in FIGS. 3 and 4, all lymph nodes are highlighted with high contrast using this compound.

SLN: A 35 kg female pig was injected subcutaneously into bowel at time zero with 5 nmol of compound MHI86 (700 nm) or MM25 (800 nm) dissolved in saline or D5W. After a waiting period of 5 min, the target tissue was exposed and the SLN was imaged for NIR fluorescence using Channel 1 (700 nm) or Channel 2 (800 nm) of the FLARE imaging system, respectively. As shown in FIGS. 5 and 6, the SLN is highlighted with high contrast using this compound.

Figure 7:
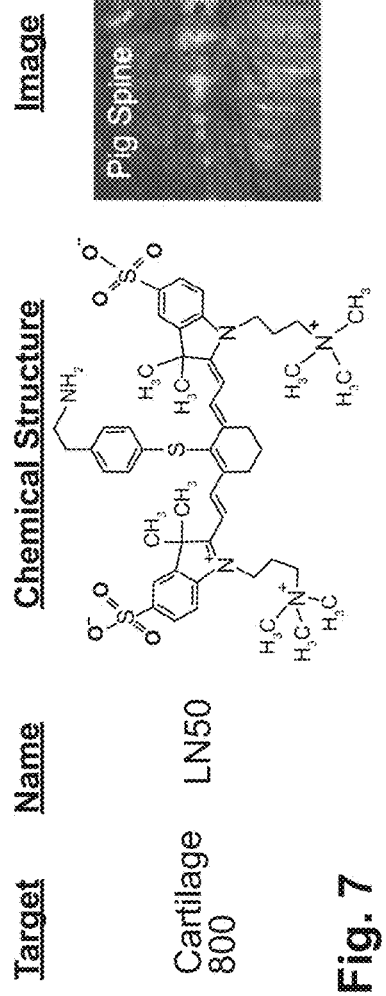
FIG. 7—depicts the imaging of Cartilage at 800 nm using LN50 (Image without irradiation, NIR irradiated image, overlay of both)
Figure 7:
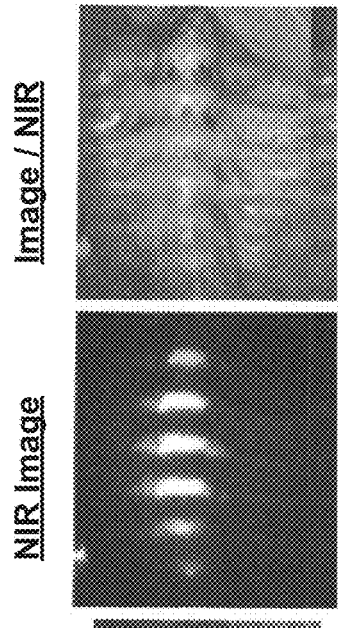
Figure 8:
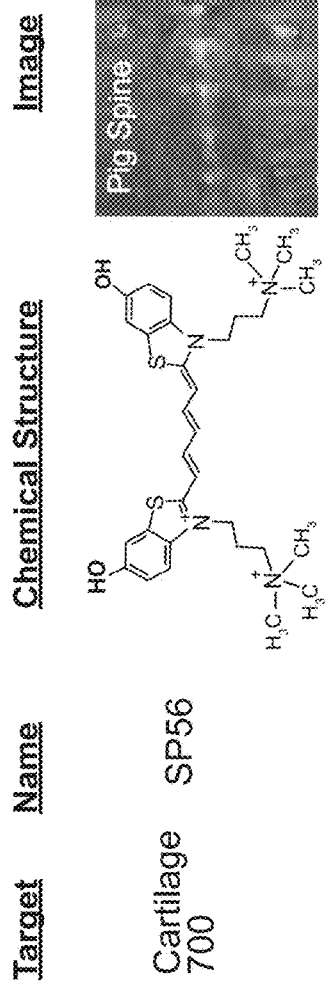
FIG. 8—depicts the imaging of Cartilage at 700 nm using SP56 (Image without irradiation, NIR irradiated image, overlay of both)
Figure 8:
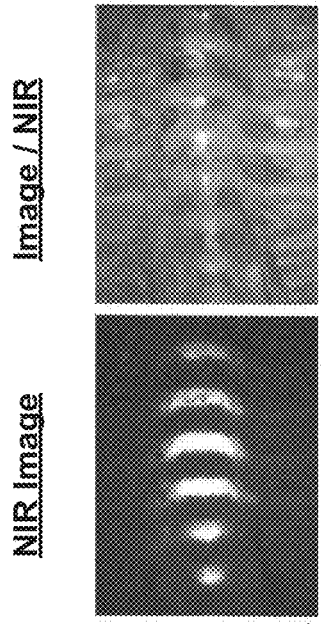

Cartilage: A 35 kg female pig was injected intravenously at time zero with 5 µmol of compound SP56 (700 nm) or LN50 (800 nm) dissolved in saline or D5W. After a waiting period of 4 hours, the animal was surgically exposed and the spinal cartilage was imaged for NIR fluorescence using Channel 1 (700 nm) or Channel 2 (800 nm) of the FLARE imaging system, respectively. As shown in FIGS. 7 and 8, the cartilage is highlighted with high contrast using this compound.

Figure 9:
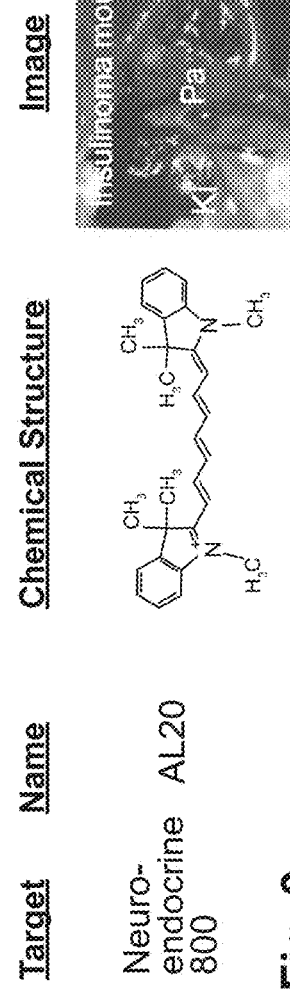
FIG. 9—depicts the imaging of neuroendocrine tumors at 800 nm using AL20 (Image without irradiation, NIR irradiated image, overlay of both)
Figure 9:
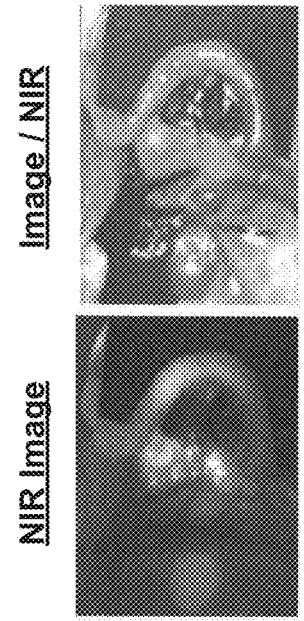

Neuroendocrine Tumors: A 25 g male insulinoma-bearing mouse was injected intravenously at time zero with 140 nmol of compound ESS61 (700 nm) or AL20 (800 nm) dissolved in saline or D5W. After a waiting period of 1 hour, the animal was surgically exposed and the pancreas was imaged for NIR fluorescence using Channel 1 (700 nm) or Channel 2 (800 nm) of the FLARE imaging system, respectively. As shown in FIGS. 9 and 10, the tumors are highlighted with high contrast using this compound.

Bone: A 35 kg female pig was injected intravenously at time zero with 5 µmol of compound P700SO3 (700 nm) or P800SO3 (800 nm) dissolved in saline or D5W. After a waiting period of 4 hours, the animal was surgically exposed and the rib cage was imaged for NIR fluorescence using Channel 1 (700 nm) or Channel 2 (800 nm) of the FLARE imaging system, respectively. As shown in FIGS. 10 and 11, the bone is highlighted with high contrast using this compound.

Figure 13:
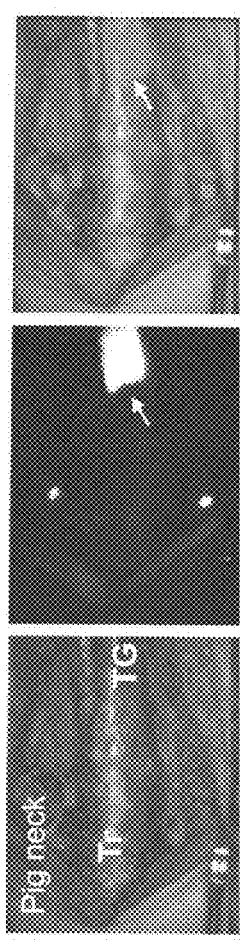
FIG. 13—depicts the imaging of the thyroid gland at 800 nm using QBN14 (Image without irradiation, NIR irradiated image, overlay of both)
Figure 13:
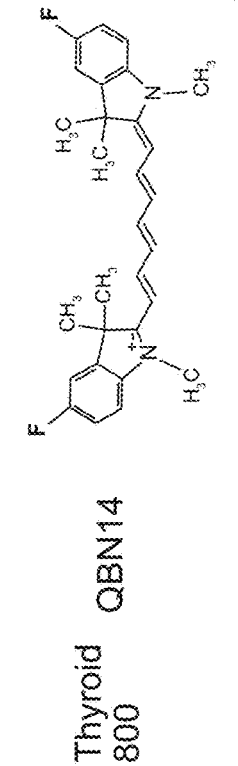

Thyroid: A 35 kg female pig was injected intravenously at time zero with 5 µmol of compound T14 (700 nm) or QBN14 (800 nm) dissolved in saline or D5W. After a waiting period of 4 hours, the animal was surgically exposed and the thyroid was imaged for NIR fluorescence using Channel 1 (700 nm) or Channel 2 (800 nm) of the FLARE imaging system, respectively. As shown in FIGS. 12 and 13, the thyroid is highlighted with high contrast using this compound.

Figure 14:
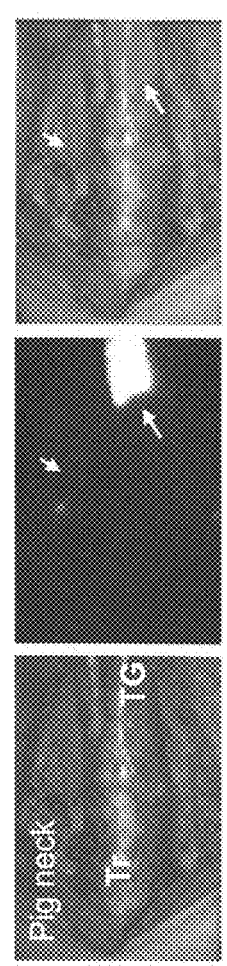
FIG. 14—depicts the imaging of the thyroid gland at 700 nm using T14 (Image without irradiation, NIR irradiated image, overlay of both)
Figure 14:
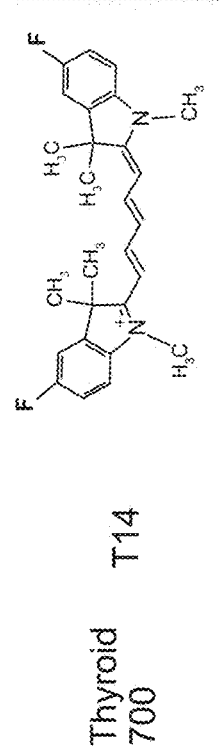
Figure 15:
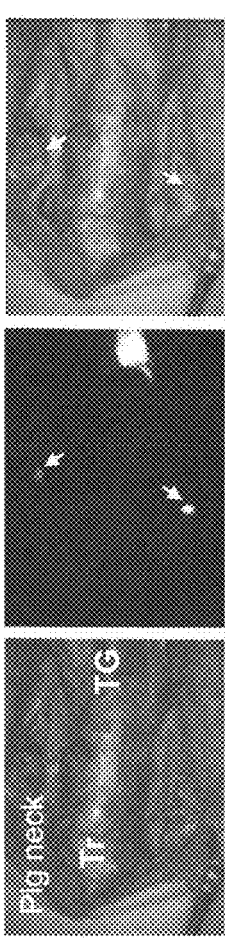
FIG. 15—depicts the imaging of parathyroid gland at 800 nm using QBN14 (Image without irradiation, NIR irradiated image, overlay of both)
Figure 15:
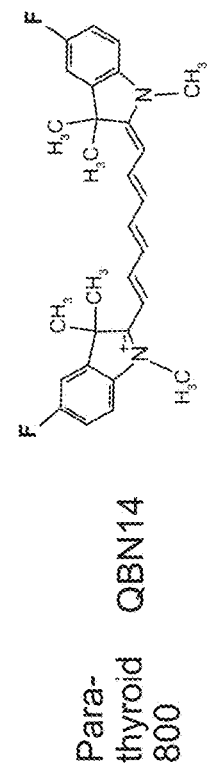
Figure 16:
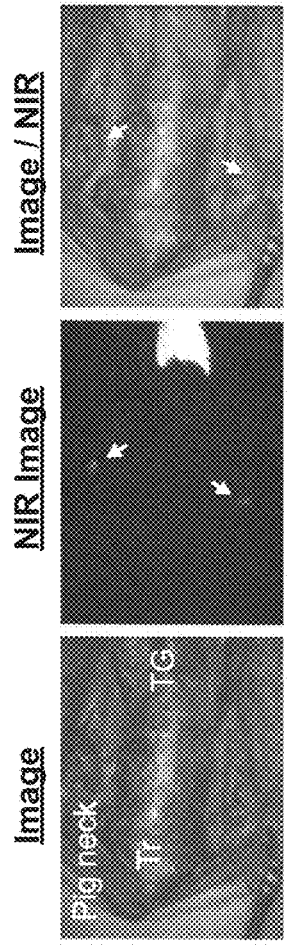
FIG. 16—depicts the imaging of parathyroid gland at 700 nm using T14 (Image without irradiation, NIR irradiated image, overlay of both)

Parathyroid: A 35 kg female pig was injected intravenously at time zero with 5 µmol of compound T14 (700 nm) or QBN14 (800 nm) dissolved in saline or D5W. After a waiting period of 4 hours, the animal was surgically exposed and the parathyroid was imaged for NIR fluorescence using Channel 1 (700 nm) or Channel 2 (800 nm) of the FLARE imaging system, respectively. As shown in FIGS. 14 and 16; the parathyroid is highlighted with high contrast using this compound.

Figure 17:
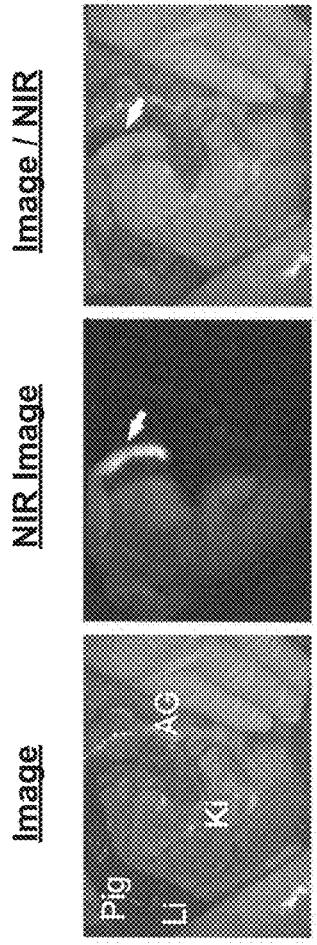
FIG. 17—depicts the imaging of the adrenal gland at 800 nm using AL27 (Image without irradiation, NIR irradiated image, overlay of both)
Figure 18:
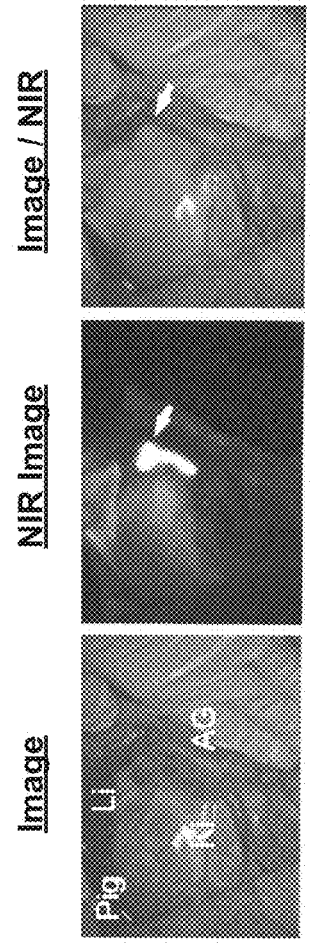
FIG. 18—depicts the imaging of adrenal gland at 700 nm using E16 (Image without irradiation, NIR irradiated image, overlay of both)

Adrenal: A 35 kg female pig was injected intravenously at time zero with 5 µmol of compound E16 (700 nm) or AL27 (800 nm) dissolved in saline or D5W. After a waiting period of 4 hours, the animal was surgically exposed and the adrenal was imaged for NIR fluorescence using Channel 1 (700 nm) or Channel 2 (800 nm) of the FLARE imaging system, respectively. As shown in the FIGS. 17 and 18, the adrenal is highlighted with high contrast using this compound.

Figure 19:
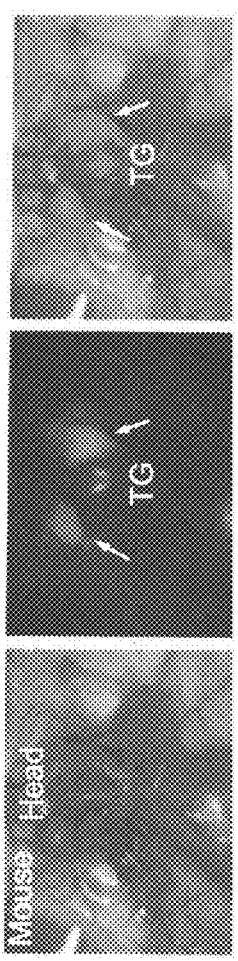
FIG. 19—depicts the imaging of salivary glands at 800 nm using ZK211 (Image without irradiation, NIR irradiated image, overlay of both)
Figure 19:
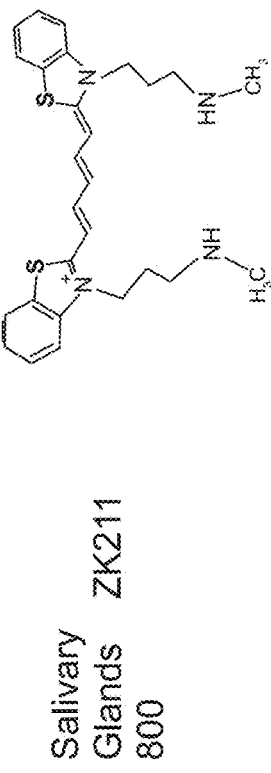
Figure 20:
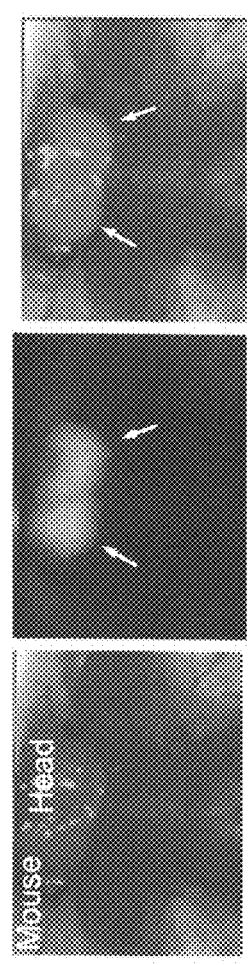
FIG. 20—depicts the imaging of salivary glands at 700 nm using NRB1 (Image without irradiation, NIR irradiated image, overlay of both)
Figure 20:
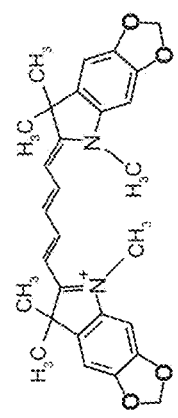

Salivary glands: A 25 g male mouse was injected intravenously at time zero with 25 nmol of compound NRB1 (700 nm) or ZK211 (800 nm) dissolved in saline or D5W. After a waiting period of 4 hours, the animal was surgically exposed and the salivary glands were imaged for NIR fluorescence using Channel 1 (700 nm) or Channel 2 (800 nm) of the FLARE imaging system, respectively. As shown in FIGS. 19 and 20, the salivary glands are highlighted with high contrast using this compound.

Figure 21:
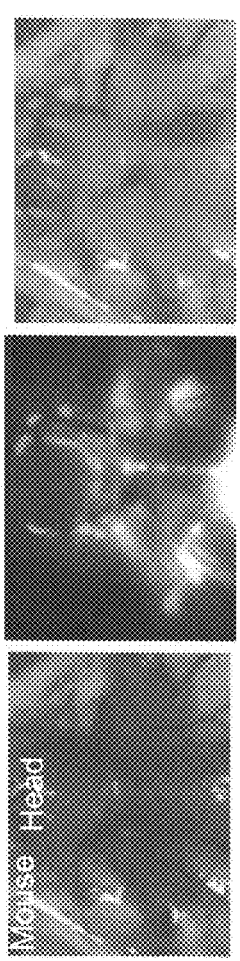
FIG. 21—depicts the imaging of white adipose tissue at 800 nm using AH34 (Image without irradiation, NIR irradiated image, overlay of both)
Figure 21:
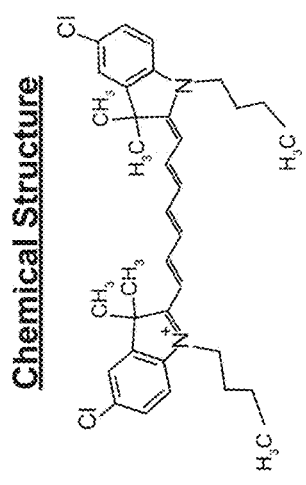
Figure 22:
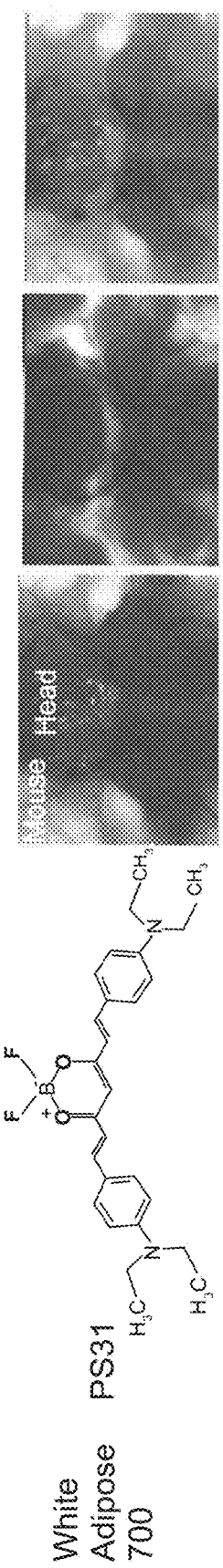
FIG. 22—depicts the imaging of white adipose tissue at 700 nm using PS31 (Image without irradiation, NIR irradiated image; overlay of both)

White adipose tissue: A 25 g male mouse was injected intravenously at time zero with 25 nmol of compound PS31 (700 nm) or AH34 (800 nm) dissolved in saline or D5W. After a waiting period of 4 hours, the animal was surgically exposed and the white adipose tissue was imaged for NIR fluorescence using Channel 1 (700 nm) or Channel 2 (800 nm) of the FLARE imaging system, respectively. As shown in FIGS. 21 and 22, the white adipose tissue is highlighted with high contrast using this compound.

Figure 23:
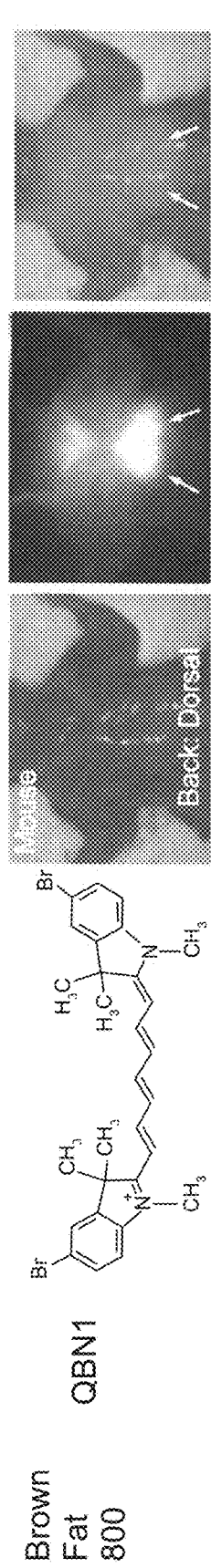
FIG. 23—depicts the imaging of brown adipose tissue at 800 nm using QBN1 (Image without irradiation, NIR irradiated image, overlay of both)
Figure 24:
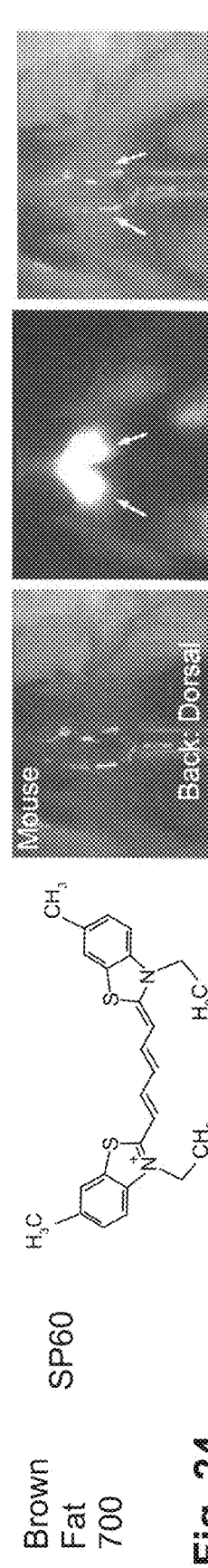
FIG. 24—depicts the imaging of brown adipose tissue at 700 nm using SP60 (Image without irradiation, NIR irradiated image, overlay of both)

Brown adipose tissue: A 25 g male mouse was injected intravenously at time zero with 25 nmol of compound SP30 (700 nm) or QBN1 (800 nm) dissolved in saline or D5W. After a waiting period of 4 hours, the animal was surgically exposed and the brown fat was imaged for NIR fluorescence using Channel 1 (700 nm) or Channel 2 (800 nm) of the FLARE imaging system, respectively. As shown in FIGS. 23 and 24, the brown fat is highlighted with high contrast using this compound.

Ovaries: A 25 g female mouse was injected intravenously at time zero with 25 nmol of compound PS62 (700 nm) or AL27 (800 nm) dissolved in saline or D5W. After a waiting period of 4 hours, the animal was surgically exposed and the ovaries were imaged for NIR fluorescence using Channel 1 (700 nm) or Channel 2 (800 nm) of the FLARE imaging system, respectively. As shown in FIGS. 25 and 26, the ovaries are highlighted with high contrast using this compound.

Figures 28, 29, 30:
FIG. 28—depicts the imaging of the seminal vesicles at 700 nm using LN65 (Image without irradiation, NIR irradiated image, overlay of both)
FIG. 29—depicts the imaging of the prostate gland at 800 nm using LN66 (Image without irradiation, NIR irradiated image, overlay of both)
FIG. 30—depicts the imaging of the prostate gland at 700 nm using PS62 (Image without irradiation, NIR irradiated image, overlay of both)

Seminal vesicles: A 25 g male mouse was injected intravenously at time zero with 25 nmol of compound LN65 (700 nm) or CNN2 (800 nm) dissolved in saline or D5W. After a waiting period of 4 hours, the animal was surgically exposed and the seminal vesicle was imaged for NIR fluorescence using Channel 1 (700 nm) or Channel 2 (800 nm) of the FLARE imaging system, respectively. As shown in FIGS. 27 and 28, the seminal vesicle is highlighted with high contrast using this compound.

Prostate: A 25 g male mouse was injected intravenously at time zero with 25 nmol of compound PS62 (700 nm) or LN66 (800 nm) dissolved in saline or D5W. After a waiting period of 4 hours, the animal was surgically exposed and the prostate was imaged for NIR fluorescence using Channel 1 (700 nm) or Channel 2 (800 nm) of the FLARE imaging system, respectively. As shown in FIGS. 29 and 30, the prostate is highlighted with high contrast using this compound.

Figure 31:
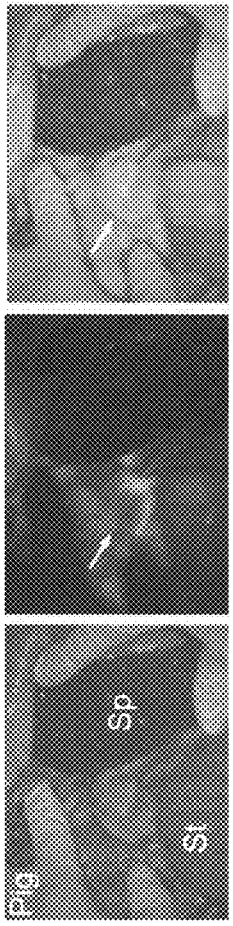
FIG. 31—depicts the imaging of the pancreas at 800 nm using AL22 (Image without irradiation, NIR irradiated image, overlay of both)
Figure 32:
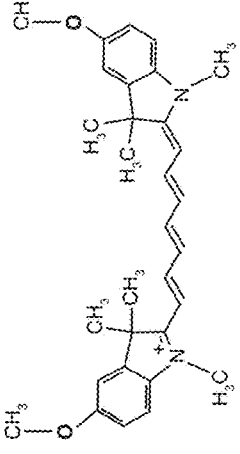
FIG. 32—depicts the imaging of the pancreas at 700 nm using T14 (Image without irradiation, NIR irradiated image, overlay of both)

Pancreas: A 35 kg female pig was injected intravenously at time zero with 5 µmol of compound T14 (700 nm) or AL22 (800 nm) dissolved in saline or D5W. After a waiting period of 4 hours, the animal was surgically exposed and the pancreas was imaged for NIR fluorescence using Channel 1 (700 nm) or Channel 2 (800 nm) of the FLARE imaging system, respectively. As shown in FIGS. 31 and 32, the pancreas is highlighted with high contrast using this compound.

Figure 33:
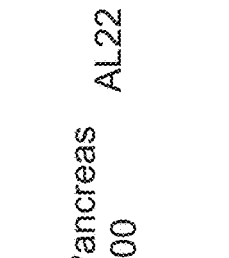
FIG. 33—depicts the imaging of the spleen at 800 nm using AL29 (Image without irradiation, NIR irradiated image, overlay of both)
Figure 34:
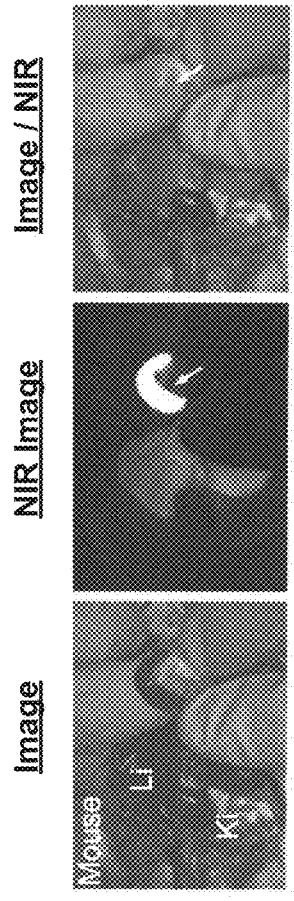
FIG. 34—depicts the imaging of the spleen at 700 nm using E24 (Image without irradiation, NIR irradiated image, overlay of both)

Spleen: A 25 g male mouse was injected intravenously at time zero with 25 nmol of compound E24 (700 nm) or AL29 (800 nm) dissolved in saline or D5W. After a waiting period of 4 hours, the animal was surgically exposed and the spleen was imaged for NIR fluorescence using Channel 1 (700 nm) or Channel 2 (800 nm) of the FLARE imaging system, respectively. As shown in FIGS. 33 and 34, the spleen is highlighted with high contrast using this compound.

Figure 35:
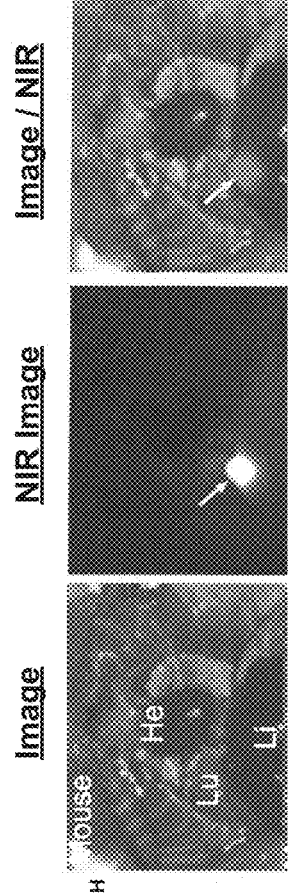
FIG. 35—depicts the imaging of the gallbladder at 800 nm using ZK198 (Image without irradiation, NIR irradiated image, overlay of both)
Figure 36:
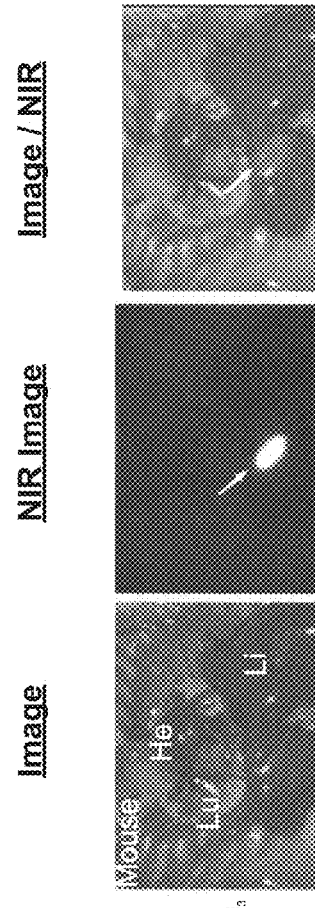
FIG. 36—depicts the imaging of the gallbladder at 700 nm using PS62 (Image without irradiation, NIR irradiated image, overlay of both)

Gallbladder: A 25 g male mouse was injected intravenously at time zero with 25 nmol of compound PS62 (700 nm) or ZK198 (800 nm) dissolved in saline or D5W. After a waiting period of 4 hours, the animal was surgically exposed and the gallbladder was imaged for NIR fluorescence using Channel 1 (700 nm) or Channel 2 (800 nm) of the FLARE imaging system, respectively. As shown in FIGS. 35 and 36, gallbladder is highlighted with high contrast using this compound.

Bile ducts: A 35 kg female pig was injected intravenously at time zero with 5 µmol of compound A106 (700 nm) or ZK198 (800 nm) dissolved in saline or D5W. After a waiting period of 4 hours, the animal was surgically exposed and the bile duct was imaged for NIR fluorescence using Channel 1 (700 nm) or Channel 2 (800 nm) of the FLARE imaging system, respectively. As shown in FIGS. 37 and 38, the bile duct is highlighted with high contrast using this compound.

Peyer's patches: A 250 g male rat was injected intravenously at time zero with 100 nmol of compound AL30 (800 nm) dissolved in saline or D5W. After a waiting period of 4 hours, the animal was surgically exposed and the Peyer's patches were imaged for NIR fluorescence using Channel 2 (800 nm) of the FLARE imaging system. As shown in FIG. 39, the Peyer's patches are highlighted with high contrast using this compound.

Figures 40, 41, 42:
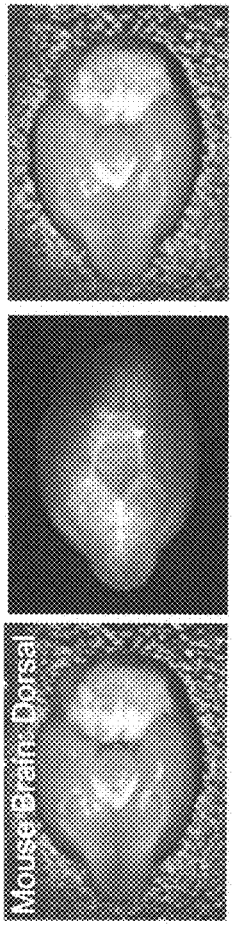
FIG. 40—depicts the imaging of the brain vasculature at 700 nm using ZK214 (Image without irradiation, NIR irradiated image, overlay of both)
FIG. 41—depicts the imaging of brain grey matter at 800 nm using ZK189 (Image without irradiation, NIR irradiated image, overlay of both)
FIG. 42—depicts the imaging of brain grey matter at 700 nm using WuA96 (Image without irradiation, NIR irradiated image, overlay of both)

Brain vasculature: A 25 g male mouse was injected intravenously at time zero with 25 nmol of compound ZK214 (700 nm) dissolved in saline or D5W. After a waiting period of 4 hours, the animal was surgically exposed and the brain vasculature was imaged for NIR fluorescence using Channel 1 (700 nm) of the FLARE imaging system. As shown in FIG. 40, the brain vasculature is highlighted with high contrast using this compound.

Brain grey matter: A 25 g male mouse was injected intravenously at time zero with 25 nmol of compound WuA96 (700 nm) or ZK189 (800 nm) dissolved in saline or D5W. After a waiting period of 4 hours, the animal was surgically exposed and the brain grey matter was imaged for NIR fluorescence using Channel 1 (700 nm) or Channel 2 (800 nm) of the FLARE imaging system, respectively. As shown in FIGS. 41 and 42, the brain grey matter is highlighted with high contrast using this compound.

Figure 43:
FIG. 43—depicts the imaging of the choroid plexus at 800 nm using ZK208 (Image without irradiation, NIR irradiated image, overlay of both)
Figure 43:
Figure 43:
Figure 43:
Figure 44:
FIG. 44—depicts the imaging of the choroid plexus at 700 nm using SP28 (Image without irradiation, NIR irradiated image, overlay of both)
Figure 44:
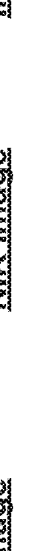
Figure 44:
Figure 44:

Choroid plexus: A 25 g male mouse was injected intravenously at time zero with 25 nmol of compound SP28 (700 nm) or ZK208 (800 nm) dissolved in saline or D5W. After a waiting period of 4 hours, the animal was surgically exposed and the choroid plexus was imaged for NIR fluorescence using Channel 1 (700 nm) or Channel 2 (800 nm) of the FLARE imaging system, respectively. As shown in FIGS. 43 and 44, the choroid plexus is highlighted with high contrast using this compound.

Figure 45:
FIG. 45—depicts the imaging of the cerebrospinal fluid at 800 nm using AL20 (Image without irradiation, NIR irradiated image, overlay of both)
Figure 45:
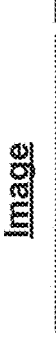
Figure 45:
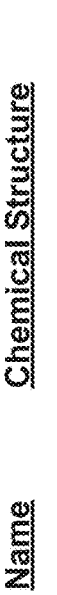
Figure 46:
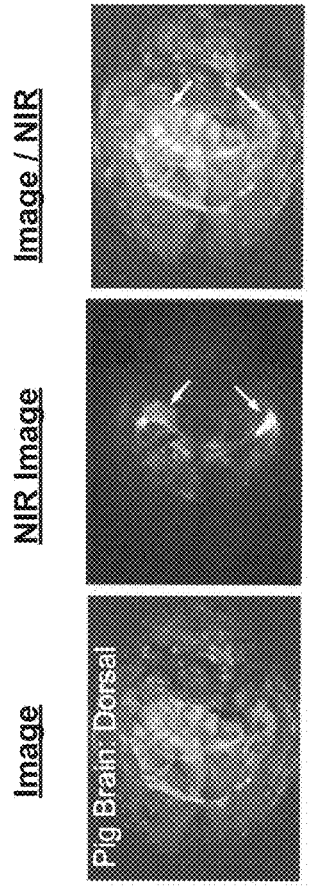
FIG. 46—depicts the imaging of the cerebrospinal fluid at 700 nm using SP66 (Image without irradiation, NIR irradiated image, overlay of both)

CSF: A 35 kg female pig was injected intravenously at time zero with 5 µmol of compound SP66 (700 nm) or AL20 (800 nm) dissolved in saline or D5W. After a waiting period of 4 hours, the animal was surgically exposed and the CSF was imaged for NIR fluorescence using Channel 1 (700 nm) or Channel 2 (800 nm) of the FLARE imaging system, respectively. As shown in FIGS. 45 and 46, the CSF is highlighted with high contrast using this compound.

Figure 47:
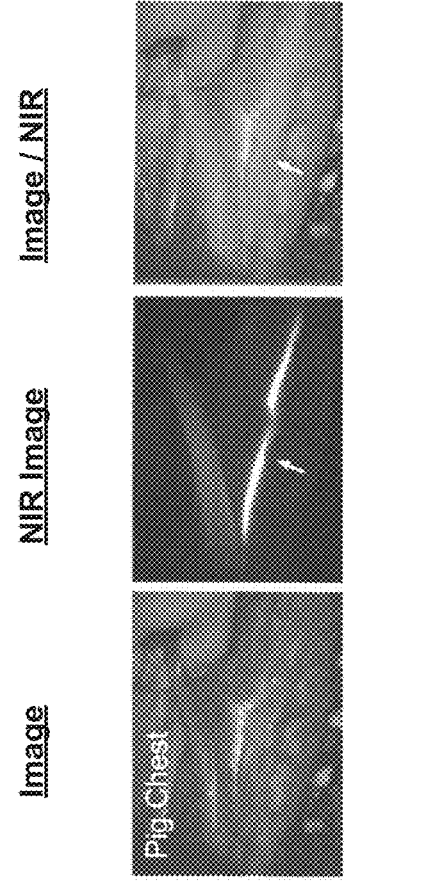
FIG. 47—depicts the imaging of the thoracic duct at 800 nm using A71 (Image without irradiation, NIR irradiated image, overlay of both)
Figure 48:
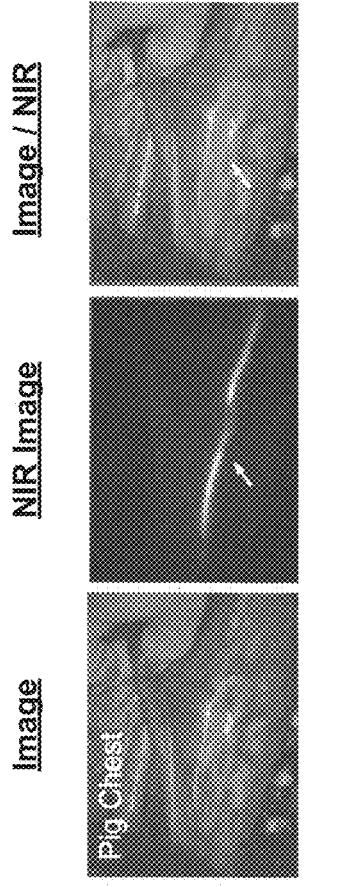
FIG. 48—depicts the imaging of thoracic duct at 700 nm using LN15 (Image without irradiation, NW irradiated image, overlay of both)

Thoracic duct: A 35 kg female pig was injected subcutaneously into the lower leg at time zero with 5 µmol of compound A106 (700 nm) or ZK198 (800 nm) dissolved in saline or D5W. After a waiting period of 30 minutes, the animal was surgically exposed and the thoracic duct was imaged for NIR fluorescence using Channel 1 (700 nm) or Channel 2 (800 nm) of the FLARE imaging system, respectively. As shown in FIGS. 47 and 48, the thoracic duct is highlighted with high contrast using this compound.

PEGylated agents: A 25 g female xenograft tumor-bearing mouse was injected intravenously at time zero with 10 nmol of compound PEG60k-LN15 (700 nm) or PEG60k-ZW800-1 (800 nm) dissolved in saline or D5W. After a waiting period of 4 hour, the tumor was imaged for NIR fluorescence using Channel 1 (700 nm) or Channel 2 (800 nm) of the FLARE imaging system, respectively. As shown in the FIGS. 49 and 50, the tumor is highlighted with high contrast using this compound.

Figure 52:
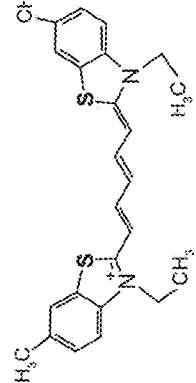
FIG. 52—depicts the imaging of pituitary gland at 700 nm using SP60 (Image without irradiation, NIR irradiated image, overlay of both)
Figure 52:
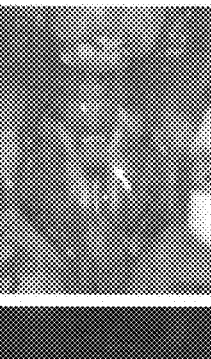
Figure 52:
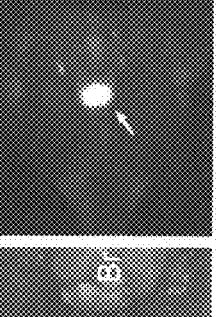
Figure 52:
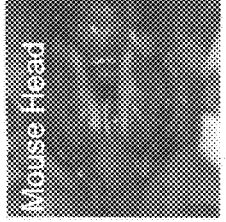

Pituitary gland: A 25 g male mouse was injected intravenously at time zero with 25 nmol of compound SP60 (700 nm) or AL22 (800 nm) dissolved in saline or D5W. After a waiting period of 4 hours, the animal was surgically exposed and the pituitary gland was imaged for NIR fluorescence using Channel 1 (700 nm) or Channel 2 (800 nm) of the FLARE imaging system, respectively. As shown in FIGS. 51 and 52, the pituitary gland is highlighted with high contrast using this compound.

Figure 53:
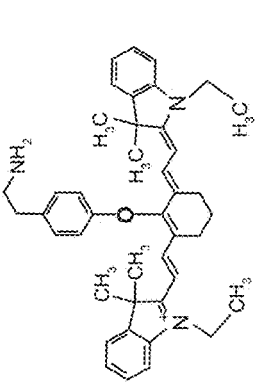
FIG. 53—depicts the imaging of stem cellsat 800 nm using PS126 (Image without irradiation, NIR irradiated image, overlay of both)
Figure 53:
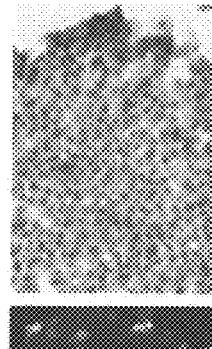
Figure 53:
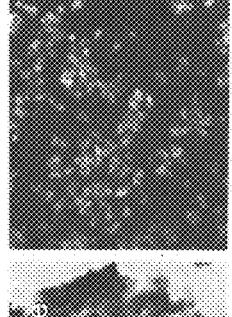
Figure 53:
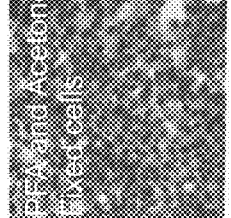
Figure 54:
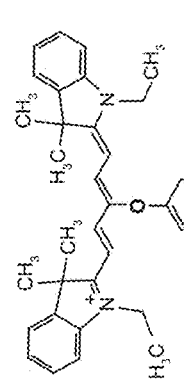
FIG. 54—depicts the imaging of stem cells at 700 nm using PS127 (Image without irradiation, NIR irradiated image, overlay of both)

Stem cell tracking: Cells grown in 35 mm or 60 mm plates at 70% confluence were incubated in cell culture media with 2 µM compound PS127 (700 nm) or PS126 (800 nm) in the 37° C. incubator with 5% $CO_2$. After an incubation time of 30 min, cells were washed 3 times with warm media, followed by fixing in 2% paraformaldehyde for 30 min. After centrifuge, cell pellets were frozen in OCT, and tested after washing with acetone. Cell pellets were cut to a 10 µm thickness and imaged for NIR fluorescence using Channel 1 (700 nm) or Channel 2 (800 nm) of fluorescence microscope, respectively. As shown in FIGS. 53 and 54, the cytoplasm of cell is highlighted with high contrast using this compound.

Figure 55:
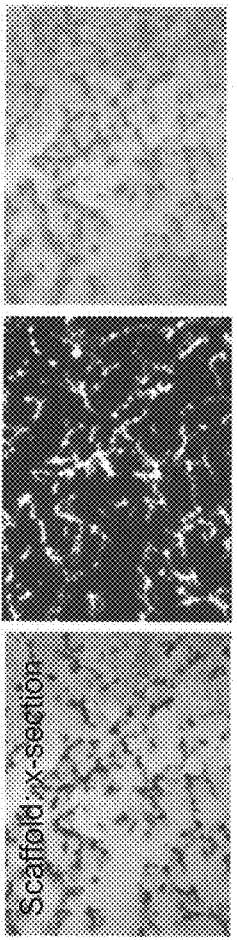
FIG. 55—depicts the imaging of engineered tissue scaffolds and cells at 800 nm using A71-NHS (Image without irradiation, NIR irradiated image, overlay of both)
Figure 55:
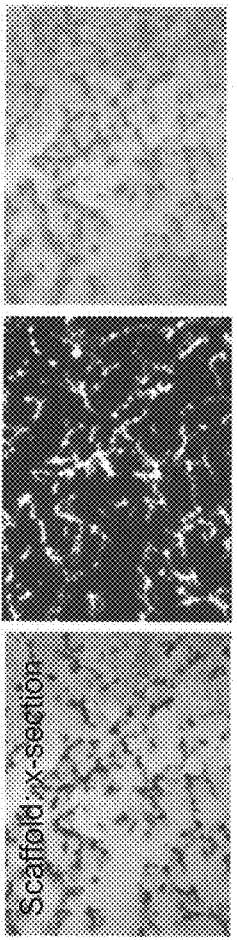
Figure 56:
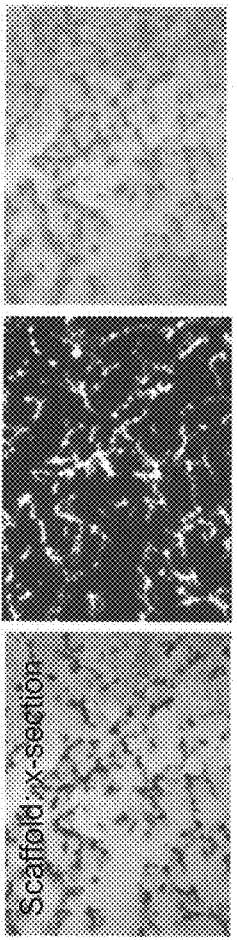
FIG. 56—depicts the imaging of engineered tissue scaffolds and cells at 700 nm using LN15-NHS (Image without irradiation, NIR irradiated image, overlay of both)
Figure 56:
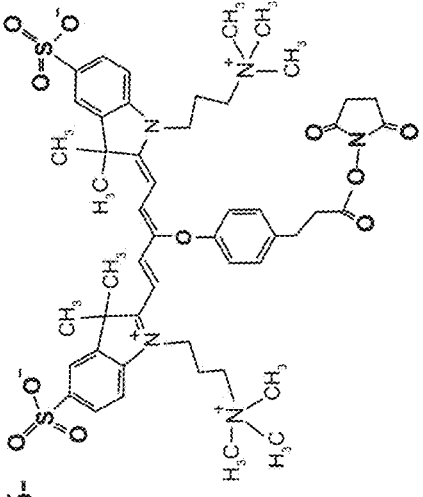

Tissue engineering: A biodegradable scaffold (1 cm×1 cm×0.5 cm) was conjugated with 50 nmol of LN15-NHS (700 nm) or A71-NHS (800 nm) dissolved in DMSO through the NHS ester-amine reaction. The NIR scaffold was washed with water and ethanol 5 times, respectively, followed by freeze-drying. The scaffold was implanted into the subcutaneous pocket of athymic nude mouse 30 days prior to imaging. The extracted scaffold was frozen, cut to a 20 μm thickness, and imaged for NIR fluorescence using Channel 1 (700 nm) or Channel 2 (800 nm) of fluorescence microscope, respectively. As shown in FIGS. 55 and 56, the cross-section of scaffold is highlighted with high contrast using this compound.

Intravital microscopy: A 25 g male insulinoma-bearing mouse was injected intravenously at time zero with 25 nmol of compound Dex70k-LN15 (700 nm) or Dex70k-ZW800-1 (800 nm) dissolved in saline or D5W. After a waiting period of 1 min, the animal was surgically exposed and the tumor vasculature was imaged for NIR fluorescence using Channel 1 (700 nm) or Channel 2 (800 nm) of the FLARE imaging system, respectively. As shown in FIGS. 57 and 58, the tumor vasculature is highlighted with high contrast using this compound.

EQUIVALENTS

Those skilled in the art will recognize, or be able to ascertain using no more than routine experimentation, many equivalents to the specific embodiments of the invention described herein.

Such equivalents are intended to be encompassed by the following claims.

REFERENCES

1. Gerowska, M. et al. Tetrahedron 68 857-864 (2012)
2. Halder, S. et al. Eur. J. of Med. Chem. 54, 647-59 (2012)
3. Sakiko, A. et al. Chem.-A Eur. J., 15, 9191-9200 (2009)
4. Chang, Y-T. et al. Chem. Commun., 47, 3514-3516 (2011)
5. (II) Chang, Y-T. et al. Chem. Commun., 46, 7406-7408 (2010)
6. Briza, T. et al. Chem. Commun. 16, 1901-1903 (2008)
7. Lynch, D. E. et al. Dyes and Pigments 96, 116-124 (2013)
8. Prostota, Y. et al. Dyes and Pigments 96, 554-562 (2013)
9. Kalliat, A. T. et al. Org. Lett., 6, 3965-3968 (2004)
10. Park, J. et al. Chem. Commun., 48, 2782-2784 (2012)
11. Matsui, M. et al. Tetrahedron 68 1931-1935 (2012)
12. Leventis, N. et al. Tetrahedron, 53, 10083-10092. (1997)
13. Dai, C. et al. Chem. Commun., 48, 5367-5369 (2012)
14. Lu, Y.-T. et al. Dyes and Pigments 89, 44-48, (2011)
15. Takacs, D, et al. Tetrahedron Lett. 53, 5585-5588 (2012)
16. Wainwright, M. et al. Dyes and Pigments 73, 7-12 (2007)
17. Gloster, D. F. et al. J. Heterocycl. Chem, 36, 25-32 (1999)
18. Garipova I. Yu. et al. Molecules 8, 505-519 (2003)
19. Singh, P. et al. J. Org. Chem 76, 6134-6145 (2011)
20. Ge, J-F. et al. Dyes and Pigments 79 33-39, (2008)
21. Pauff, S. M. et al. Org. Lett. 13, 6196-6199 (2011)
22. Ge, J-F. et al. J. Med. Chem. 51, 3654-3658 (2008)
23. Link, M. et al. Eur. J. Org. Chem. 36, 6922-6927 (2010)
24. Killoran, J., et al. Chem Commun. 7(17), 1862-3 (2002)
25. Killoran, J. et al. New J. Chem. 32 (3), 483-489 (2008)
26. McDonnell, S. O. et al. Org. Lett. 8 (16), 3493-6 (2006)
27. A. J. Cohen et al., Phrenic nerve injury after coronary artery grafting: is it always benign? Ann Thorac Surg 64, 148 (July 1997).
28. I. A. Chaudhary, Samiullah, R. Masood, M. A. Majrooh, A. A. Mallhi, Recurrent laryngeal nerve injury: an experience with 310 thyroidectomies. J Ayub Med Coll Abbottabad 19, 46 (July-September 2007).
29. R. W. Clough et al., Cortical edema in moderate fluid percussion brain injury is attenuated by vagus nerve stimulation. Neuroscience 147, 286 (Jun. 29, 2007).
30. C. Shi, S. R. Flanagan, U. Samadani, Vagus nerve stimulation to augment recovery from severe traumatic brain injury impeding consciousness: a prospective pilot clinical trial. Neurol Res 35, 263 (April 2013).
31. B. H. Lang, C. Y. Lo, W. F. Chan, K. Y. Lam, K. Y. Wan, Staging systems for papillary thyroid carcinoma: a review and comparison. Ann Surg 245, 366 (March 2007).
32. S. K. Snyder, T. C. Lairmore, J. C. Hendricks, J. W. Roberts, Elucidating mechanisms of recurrent laryngeal nerve injury during thyroidectomy and parathyroidectomy. J Am Coll Surg 206, 123 (January 2008).
33. D. Myssiorek, Recurrent laryngeal nerve paralysis: anatomy and etiology. Otolaryngol Clin North Am 37, 25 (February 2004).
34. C. Wu et al., Molecular probes for imaging myelinated white matter in CNS. J Med Chem 51, 6682 (Nov. 13, 2008).
35. C. Wu et al., A novel fluorescent probe that is brain permeable and selectively binds to myelin. J Histochem Cytochem 54, 997 (September 2006).
36. B. Stankoff et al., Imaging of CNS myelin by positron-emission tomography. Proc Natl Acad Sci USA 103, 9304 (Jun. 13, 2006).
37. J. R. Meyers et al., Lighting up the senses: FM1-43 loading of sensory cells through nonselective ion channels. J Neurosci 23, 4054 (May 15, 2003).
38. S. L. Gibbs-Strauss et al., Molecular imaging agents specific for the annulus fibrosus of the intervertebral disk. Mol Imaging 9, 128 (June 2010).
39. S. L. Gibbs et al., Structure-activity relationship of nerve-highlighting fluorophores. PLoS One 8, e73493 (2013).
40. V. E. Cotero et al., Intraoperative fluorescence imaging of peripheral and central nerves through a myelin-selective contrast agent. Mol Imaging Biol 14, 708 (December 2012).
41. A. Nakayama, A. C. Bianco, C. Y. Zhang, B. B. Lowell, J. V. Frangioni, Quantitation of brown adipose tissue perfusion in transgenic mice using near-infrared fluorescence imaging. Mol Imaging 2, 37 (January 2003).
42. M. A. Whitney et al., Fluorescent peptides highlight peripheral nerves during surgery in mice. Nat Biotechnol 29, 352 (April 2011).
43. A. P. Wu et al., Improved facial nerve identification with novel fluorescently labeled probe. The Laryngoscope 121, 805 (April 2011).
44. H. S. Choi et al., Targeted zwitterionic near-infrared fluorophores for improved optical imaging. Nat Biotechnol 31, 148 (February 2013).
45. Y. Ashitate et al., Two-wavelength near-infrared fluorescence for the quantitation of drug antiplatelet effects in large animal model systems. J Vasc Surg 56, 171 (July 2012).
46. H. S. Choi et al., Rapid translocation of nanoparticles from the lung airspaces to the body. Nat Biotechnol 28, 1300 (December 2010).

47. B. Trojanowicz et al., Retinoic acid-mediated down-regulation of ENO1/MBP-1 gene products caused decreased invasiveness of the follicular thyroid carcinoma cell lines. J Mol Endocrinol 42, 249 (March 2009).
48. H. Pajouhesh, G. R. Lenz, Medicinal chemical properties of successful central nervous system drugs. NeuroRx 2, 541 (October 2005).
49. U. Fagerholm, The highly permeable blood-brain barrier: an evaluation of current opinions about brain uptake capacity. Drug Discov Today 12, 1076 (December 2007).
50. R. N. Waterhouse, Determination of lipophilicity and its use as a predictor of blood-brain barrier penetration of molecular imaging agents. Mol Imaging Biol 5, 376 (November-December 2003).
51. S. L. Gibbs-Strauss et al., Nerve-highlighting fluorescent contrast agents for image-guided surgery. Mol Imaging 10, 91 (April 2011).
52. S. L. Troyan et al., The FLARE intraoperative near-infrared fluorescence imaging system: a first-in-human clinical trial in breast cancer sentinel lymph node mapping. Ann Surg Oncol 16, 2943 (October 2009).
53. S. Gioux et al., High-power, computer-controlled, light-emitting diode-based light sources for fluorescence imaging and image-guided surgery. Mol Imaging 8, 156 (May-June 2009).
54. Y. Ashitate, A. Stockdale, H. S. Choi, R. G. Laurence, J. V. Frangioni, Real-time simultaneous-near-infrared fluorescence imaging of bile duct and arterial anatomy. J Surg Res 176, 7 (July 2012).
55. K. W. Kelley, S. E. Curtis, G. T. Marzan, H. M. Karara, C. R. Anderson, Body surface area of female swine. J Anim Sci 36, 927 (May 1973).
56. S. Reagan-Shaw, M. Nihal, N. Ahmad, Dose translation from animal to human studies revisited. Faseb J 22, 659 (March 2008).

The contents of all patent, patent applications, and publications cited herein are incorporated herein by reference in their entireties.

What is claimed is:

1. A method of imaging tissue, lumens, or cells, the method comprising:
   (a) intravenously administering an imaging composition to an organism comprising the tissue, lumen, or cells wherein the imaging composition consists essentially of an imaging agent, wherein intravenously administering the imaging composition comprises contacting the tissue, lumen or cells with the imaging agent, wherein the imaging agent is ESS 61:

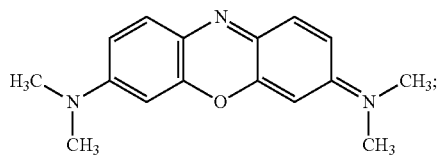

(ESS61)

(b) irradiating the tissue, lumen, or cells at a wavelength absorbed by the imaging agent;
   (c) and detecting a signal from the imaging agent, thereby imaging the tissue, lumen, or cells.

2. The method of claim 1, wherein the tissue or cells are blood vessels, lumens, ureters, blood vessel lumens, endothelial cells lining blood vessels, cartilage cells, bone cells, thyroid cells, thyroid glands, parathyroids cells, parathyroid glands, adrenal gland cells, adrenal glands, salivary gland cells, salivary glands, white adipose tissue, brown adipose tissue, ovarian cells, testicular cells, seminal vesicles, prostate cells, pancreas cells, spleen cells, gallbladder lumens, gallbladder cells, bile duct lumens, bile duct cells, Peyer's patches, brain grey matter, brain white matter, brain vasculature cells, choroid plexus tissue and fluid, cerebrospinal fluid, nerves, lymph nodes, sentinel lymph nodes, vulnerable plaque, stem cells, breast cancer cells, or neuroendocrine tumors.

3. The method of claim 1, wherein the organism is human.

4. The method of claim 1, wherein the imaging agent has peak absorbance at about 600 nm to 850 nm.

5. The method of claim 1, wherein the tissue or cells is imaged ex vivo.

6. A method of imaging neuroendocrine tumor cells, the method comprising:
   (a) intravenously administering an imaging composition to an organism comprising the neuroendocrine tumor cells, wherein the imaging composition consists essentially of an imaging agent, and wherein the intravenously administering comprises contacting the neuroendocrine tumor cells with the imaging agent, wherein the imaging agent is ESS 61:

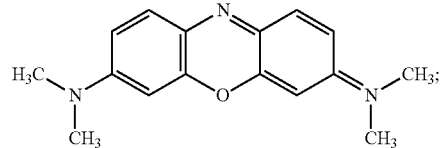

(ESS61)

(b) irradiating the neuroendocrine tumor cells at a wavelength absorbed by the imaging agent;
   (c) and detecting a signal from the imaging agent, thereby imaging the neuroendocrine tumor cells.

7. A method of imaging breast cancer cells, the method comprising:
   (a) intravenously administering an imaging agent to an organism comprising the breast cancer cells, wherein the imaging composition consists essentially of an imaging agent, and wherein the intravenously administering comprises contacting the breast cancer cells with the imaging agent, wherein the imaging agent is ESS 61:

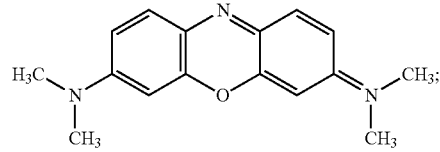

(ESS61)

(b) irradiating the neuroendocrine tumor cells at a wavelength absorbed by the imaging agent;
   (c) and detecting a signal from the imaging agent, thereby imaging the breast cancer cells.

* * * * *

UNITED STATES PATENT AND TRADEMARK OFFICE
CERTIFICATE OF CORRECTION

PATENT NO. : 11,077,210 B2
APPLICATION NO. : 15/033337
DATED : August 3, 2021
INVENTOR(S) : Frangioni et al.

Page 1 of 1

It is certified that error appears in the above-identified patent and that said Letters Patent is hereby corrected as shown below:

In the Specification

At Column 1, Lines 17-19:
Delete:
"This invention was made with government support under CA115296, EB010022, and EB011523 awarded by NIH. The Government has certain rights in the invention."

Insert:
--This invention was made with government support under grant numbers CA115296, EB010022, and EB011523 awarded by the National Institutes of Health. The Government has certain rights in the invention.--

Signed and Sealed this
Tenth Day of February, 2026

John A. Squires
*Director of the United States Patent and Trademark Office*